(12) United States Patent
Shahaf et al.

(10) Patent No.: US 11,278,682 B2
(45) Date of Patent: Mar. 22, 2022

(54) DEVICE AND METHOD FOR AEROSOLIZED DELIVERY OF SUBSTANCE TO A NATURAL ORIFICE OF THE BODY

(71) Applicant: SIPNOSE LTD., Yokne'am Ilit (IL)

(72) Inventors: Daniel Shahaf, M.P. Emek Ha-Yarden (IL); Iris Shichor, Zichron Yaakov (IL)

(73) Assignee: SIPNOSE LTD., Yokne'am Ilit (IL)

( * ) Notice: Subject to any disclaimer, the term of this patent is extended or adjusted under 35 U.S.C. 154(b) by 87 days.

(21) Appl. No.: 15/982,630

(22) Filed: May 17, 2018

(65) Prior Publication Data

US 2018/0344951 A1 Dec. 6, 2018

Related U.S. Application Data

(63) Continuation-in-part of application No. 14/733,143, filed on Jun. 8, 2015.
(Continued)

(51) Int. Cl.
*A61M 11/00* (2006.01)
*A61M 15/00* (2006.01)
(Continued)

(52) U.S. Cl.
CPC ......... *A61M 11/006* (2014.02); *A61M 11/007* (2014.02); *A61M 11/02* (2013.01);
(Continued)

(58) Field of Classification Search
CPC .. A61M 11/00; A61M 11/001; A61M 11/006; A61M 11/007; A61M 11/008;
(Continued)

(56) References Cited

U.S. PATENT DOCUMENTS

| 462,990 A | 11/1891 | Oppenheimer |
| 3,921,637 A | 11/1975 | Bennie et al. |

(Continued)

FOREIGN PATENT DOCUMENTS

| DE | 20 2013 105 715 U1 | 2/2014 |
| EP | 1 023 098 B1 | 9/2004 |

(Continued)

OTHER PUBLICATIONS

Damm et al., "Intranasal Volume and Olfactory Function", Chemical Senses, 2002, pp. 831-839, vol. 27, Oxford University Press.
(Continued)

*Primary Examiner* — Colin W Stuart
(74) *Attorney, Agent, or Firm* — Foley & Lardner LLP

(57) ABSTRACT

A device for delivering a predetermined amount of a substance within at least one body cavity of a subject, where the predetermined amount is at an effective amount for treatment of obesity or binge eating disorder. The device includes (a) A volume to contain the predetermined amount of the substance. (b) A delivery end placeable in proximity to the body cavity. The delivery end is in fluid communication with the volume and comprises at least one orifice. (c) A valve mechanically connected to the volume, with at least two configurations: (i) an active configuration configured to deliver the predetermined amount of the substance; and, (ii) an inactive configuration, in which the valve prevents delivery of the predetermined amount of the substance. (d) A fluid tight chamber configured to contain a predetermined volume of pressurized gas at a predetermined pressure.

58 Claims, 87 Drawing Sheets

Related U.S. Application Data

(60) Provisional application No. 62/117,986, filed on Feb. 19, 2015, provisional application No. 62/077,246, filed on Nov. 9, 2014, provisional application No. 62/507,816, filed on May 18, 2017.

(51) Int. Cl.

| | | |
|---|---|---|
| *A61M 15/08* | (2006.01) | |
| *A61M 31/00* | (2006.01) | |
| *A61M 11/02* | (2006.01) | |
| A61M 21/02 | (2006.01) | |
| A61K 9/00 | (2006.01) | |
| A61M 21/00 | (2006.01) | |
| B05B 7/14 | (2006.01) | |
| B05B 11/00 | (2006.01) | |
| B05B 7/04 | (2006.01) | |

(52) U.S. Cl.
CPC ...... *A61M 15/009* (2013.01); *A61M 15/0045* (2013.01); *A61M 15/0065* (2013.01); *A61M 15/0098* (2014.02); *A61M 15/08* (2013.01); *A61M 31/00* (2013.01); A61K 9/0043 (2013.01); A61M 15/0003 (2014.02); A61M 15/003 (2014.02); A61M 15/0021 (2014.02); A61M 21/02 (2013.01); A61M 2021/0016 (2013.01); A61M 2202/064 (2013.01); A61M 2202/30 (2013.01); A61M 2205/073 (2013.01); A61M 2205/3331 (2013.01); A61M 2205/3379 (2013.01); A61M 2205/7545 (2013.01); A61M 2206/16 (2013.01); A61M 2209/045 (2013.01); A61M 2210/065 (2013.01); A61M 2210/0618 (2013.01); A61M 2210/0625 (2013.01); A61M 2210/0662 (2013.01); A61M 2210/1067 (2013.01); A61M 2210/1089 (2013.01); A61M 2210/1475 (2013.01); B05B 7/0416 (2013.01); B05B 7/1486 (2013.01); B05B 11/3091 (2013.01)

(58) Field of Classification Search
CPC ...... A61M 11/02; A61M 11/06; A61M 15/00; A61M 15/0001; A61M 15/002; A61M 15/0028; A61M 15/003; A61M 15/0003; A61M 15/0031; A61M 15/0043; A61M 15/0061; A61M 15/0063; A61M 15/0091; A61M 15/0093; A61M 15/0095; A61M 15/08; A61M 31/00; A61M 2202/04; A61M 2202/064; A61M 2205/073; A61M 2206/16; A61M 2209/02; A61M 2210/0618; A61M 2210/0625; A61M 2210/065; A61M 2210/0662

See application file for complete search history.

(56) References Cited

U.S. PATENT DOCUMENTS

| | | |
|---|---|---|
| 4,114,615 A | 9/1978 | Wetterlin |
| 4,620,670 A | 11/1986 | Hughes |
| 5,740,794 A | 4/1998 | Smith et al. |
| 6,398,074 B1 | 6/2002 | Bruna et al. |
| 7,497,390 B2 | 3/2009 | Beller |
| 7,726,308 B1 | 6/2010 | Flora |
| 7,802,569 B2 | 9/2010 | Yeates et al. |
| 7,900,659 B2 | 3/2011 | Whitley et al. |
| 2002/0023641 A1 | 2/2002 | Stadelhofer |
| 2002/0092520 A1 | 7/2002 | Casper et al. |
| 2003/0079743 A1 | 5/2003 | Genova et al. |
| 2003/0187404 A1 | 10/2003 | Waldenburg |
| 2003/0209455 A1 | 11/2003 | Pynson et al. |
| 2005/0028812 A1 | 2/2005 | Djupesland |
| 2006/0067911 A1* | 3/2006 | Nilsson ............ A61M 15/0045 424/85.1 |
| 2006/0107957 A1* | 5/2006 | Djupesland ............ A61M 11/00 128/206.11 |
| 2006/0151629 A1 | 7/2006 | Vedrine et al. |
| 2006/0213514 A1* | 9/2006 | Price ................. A61M 15/0043 128/203.15 |
| 2007/0060868 A1 | 3/2007 | Tsutsui |
| 2007/0125371 A1* | 6/2007 | Djupesland ........... A61M 15/00 128/200.14 |
| 2007/0151562 A1 | 7/2007 | Jones et al. |
| 2007/0154407 A1 | 7/2007 | Peters et al. |
| 2008/0092887 A1 | 4/2008 | Hodson et al. |
| 2008/0210229 A1 | 9/2008 | Corbacho |
| 2009/0285849 A1 | 11/2009 | Barsanti et al. |
| 2009/0314293 A1* | 12/2009 | Djupesland ............ A61M 11/00 128/203.18 |
| 2010/0282246 A1 | 11/2010 | Djupesland et al. |
| 2011/0048414 A1 | 3/2011 | Hoekman et al. |
| 2011/0088690 A1 | 4/2011 | Djupesland et al. |
| 2011/0168172 A1 | 7/2011 | Patton et al. |
| 2011/0283996 A1 | 11/2011 | Abrams |
| 2012/0291779 A1 | 11/2012 | Haartsen et al. |
| 2013/0096495 A1 | 4/2013 | Holmqvist et al. |
| 2013/0180524 A1* | 7/2013 | Shahaf .................. A61M 11/00 128/203.12 |
| 2013/0267864 A1 | 10/2013 | Addington et al. |
| 2013/0299607 A1 | 11/2013 | Wilkerson et al. |
| 2013/0345673 A1 | 12/2013 | Ferreri et al. |
| 2014/0060532 A1 | 3/2014 | Hodges et al. |
| 2015/0122257 A1 | 5/2015 | Winkler et al. |
| 2015/0144129 A1* | 5/2015 | Djupesland ............ A61M 16/14 128/200.23 |
| 2015/0174343 A1 | 6/2015 | Muellinger et al. |
| 2015/0209325 A1 | 7/2015 | Najarian et al. |
| 2015/0297845 A1 | 10/2015 | Shahaf et al. |
| 2016/0129205 A1 | 5/2016 | Shahaf et al. |
| 2018/0072480 A1 | 3/2018 | Genosar |
| 2018/0110922 A1 | 4/2018 | Dunki-Jacobs et al. |
| 2019/0015613 A1 | 1/2019 | Shahaf et al. |
| 2019/0060168 A1 | 2/2019 | Koska |
| 2020/0197631 A1 | 6/2020 | Stedman et al. |
| 2020/0289768 A1 | 9/2020 | Shahaf et al. |
| 2020/0306463 A1 | 10/2020 | Shahaf et al. |

FOREIGN PATENT DOCUMENTS

| | | | |
|---|---|---|---|
| EP | 1 752 176 A1 | 2/2007 | |
| EP | 2 030 645 A1 | 3/2009 | |
| GB | 0 724 974 A | 2/1955 | |
| GB | 2 415 376 A | 12/2005 | |
| WO | WO-90/12567 A1 | 11/1990 | |
| WO | WO-2012/029064 A1 | 3/2012 | |
| WO | WO-2013128447 A1 * | 9/2013 | ............ A61M 11/02 |
| WO | WO-2015/025324 A1 | 2/2015 | |
| WO | WO-2016/199135 A1 | 12/2016 | |
| WO | WO-2019/003216 A1 | 1/2019 | |
| WO | WO-2019/079335 A1 | 4/2019 | |
| WO | WO-2019/220443 A1 | 11/2019 | |

OTHER PUBLICATIONS

Derendorf et al., "Molecular and clinical pharmacology of intranasal corticosteroids: clinical and therapeutic implications", Allergy, 2008, pp. 1292-1300, vol. 63, 2008 Blackwell Munksgaard.

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

International Preliminary Reporton Patentability for International Application No. PCT/IL2014/050752, dated Feb. 23, 2016.

International Search Report & International Written Opinion of the International Searching Authority issued in International Application No. PCT/IL2014/050752, dated Dec. 18, 2014.

(56) References Cited

OTHER PUBLICATIONS

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology-Lung Cellular and Molecular Physiology, 2016, pp. L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure over time", International Journal of Obesity, 2014, pp. 650-656, vol. 38, 2014 Macmillan Publishers Limited.

Scheibe et al., "Intranasal Administration of Drugs", Archives of Otolaryngology-Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

\* cited by examiner

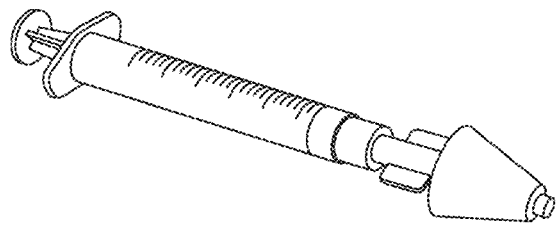
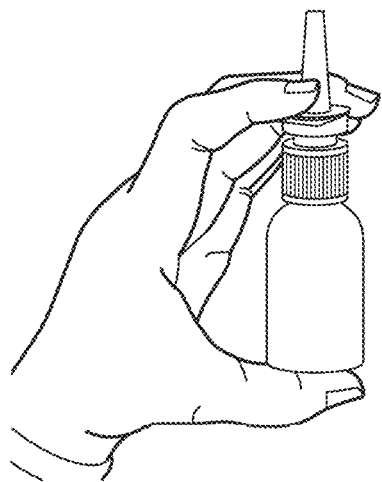
Prior Art Fig. 1A
Prior Art Fig. 1B
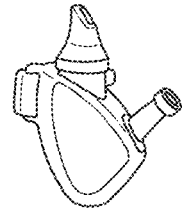
Prior Art Fig. 1C
Prior Art Fig. 1D

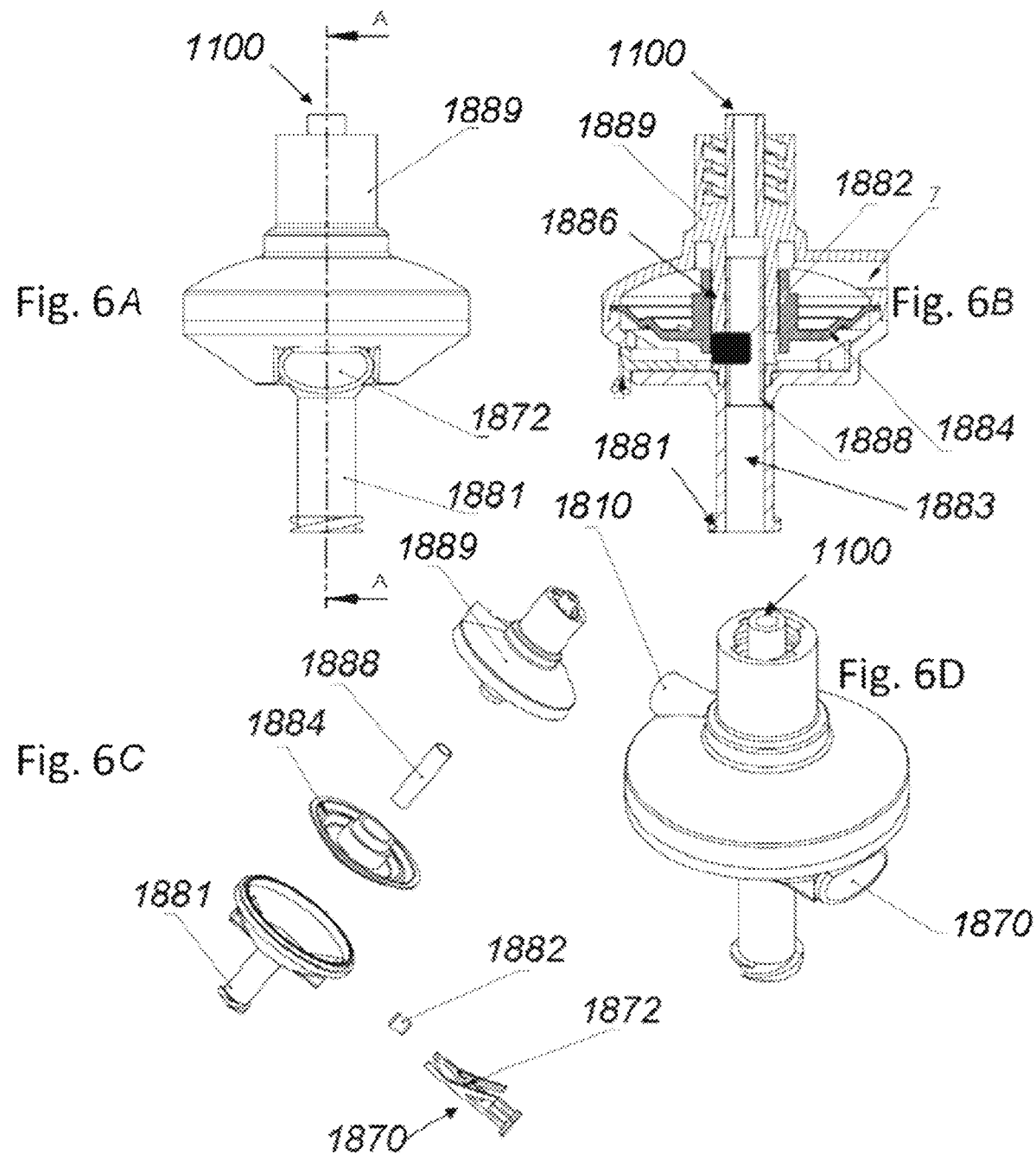

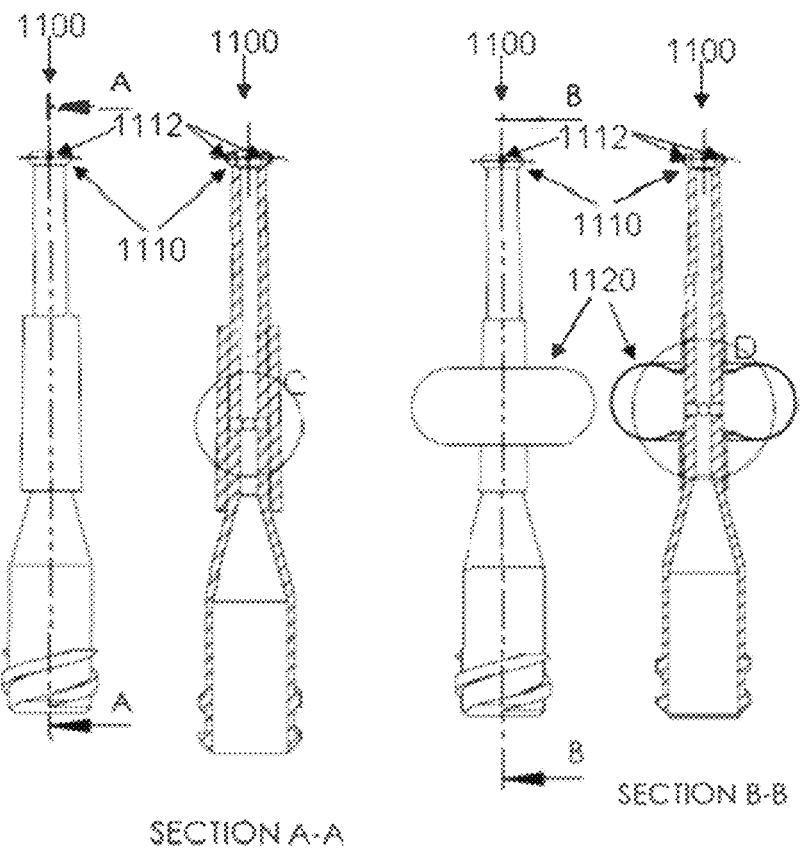
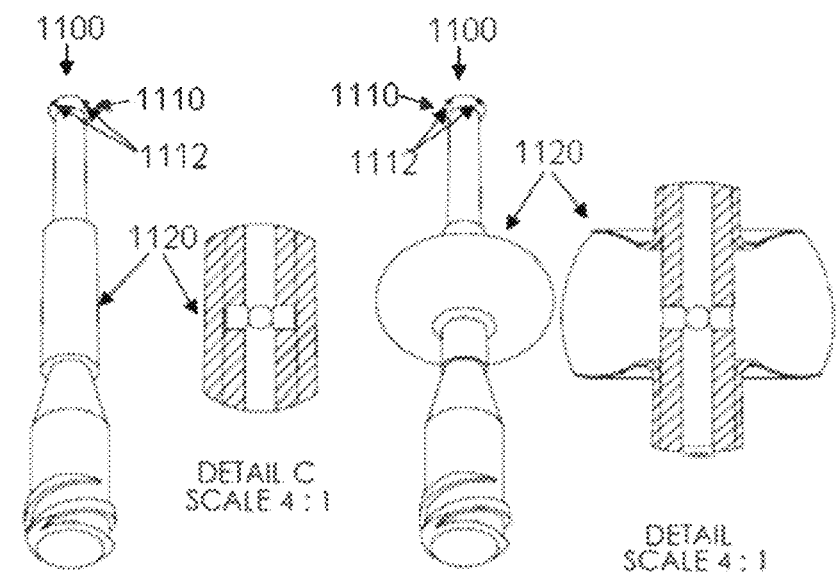
Fig. 9A  Fig. 9B  Fig. 9C  Fig. 9D
Fig. 9E  Fig. 9F  Fig. 9G  Fig. 9H

SECTION A-A
SCALE 2:1

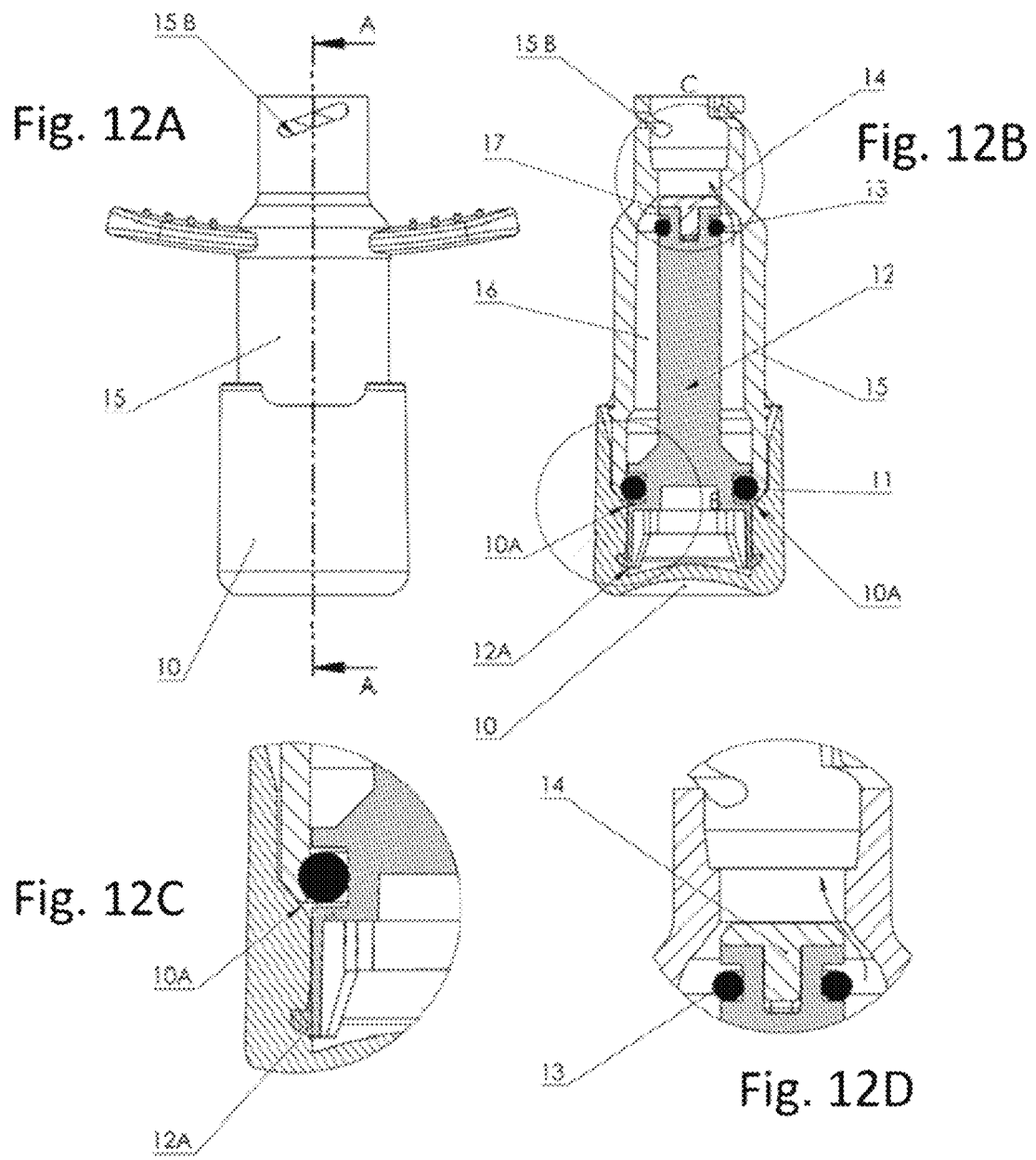

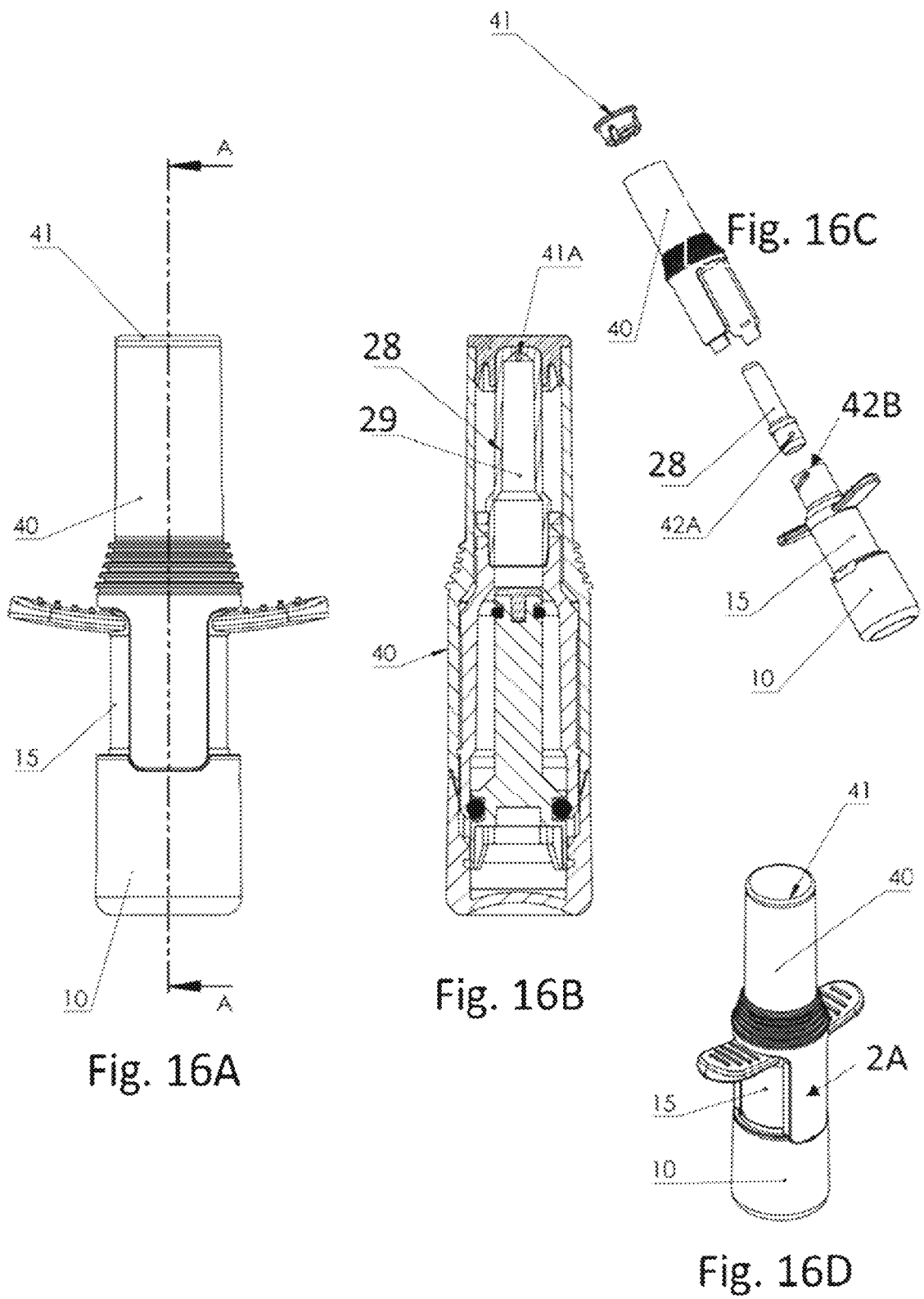

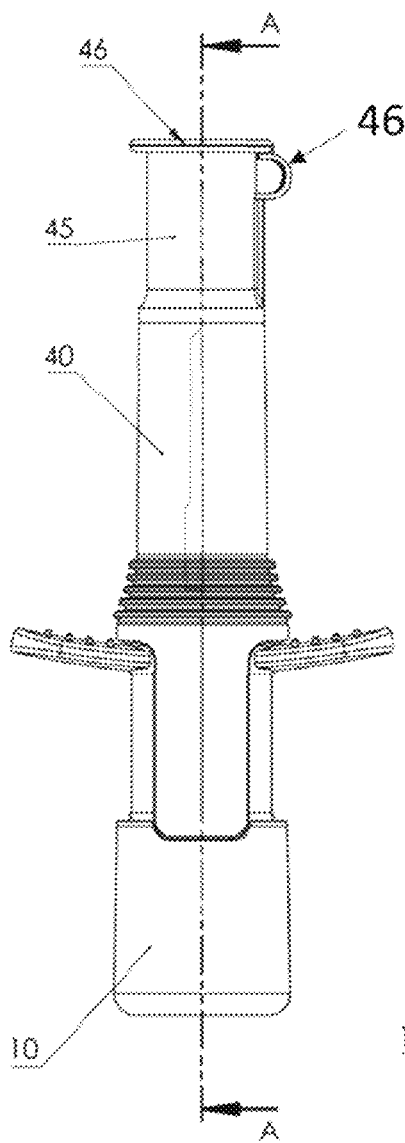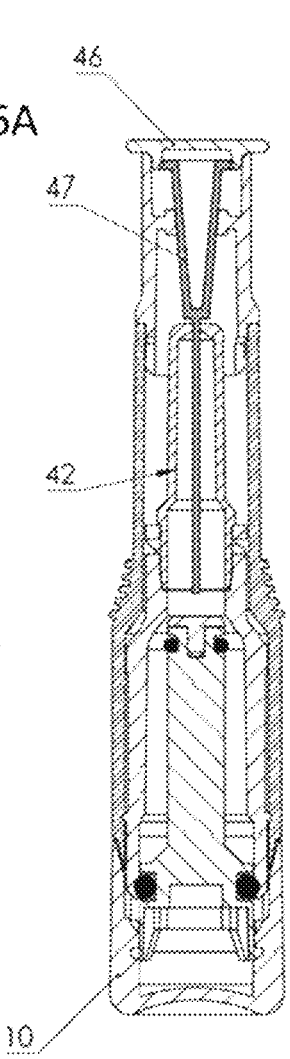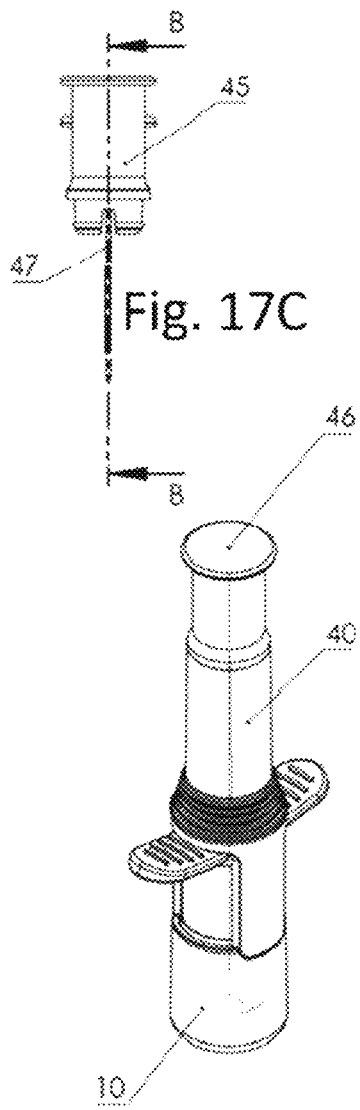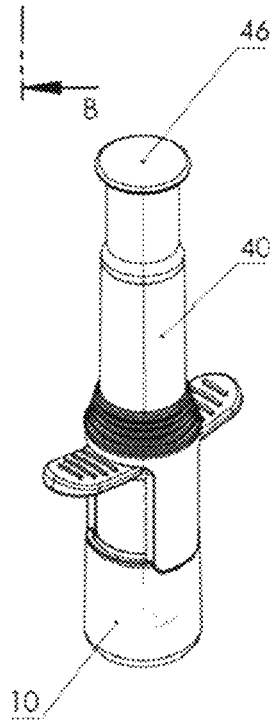
Fig. 17A   Fig. 17B   Fig. 17D

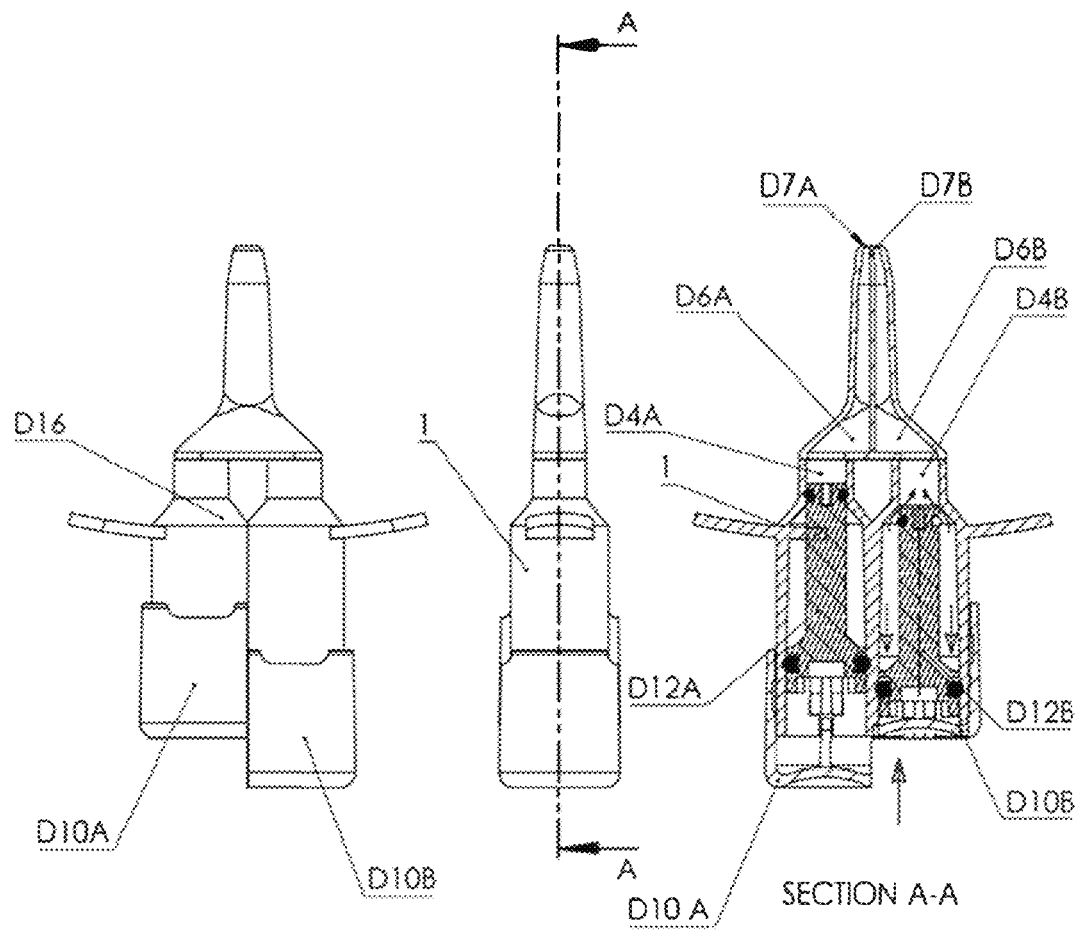
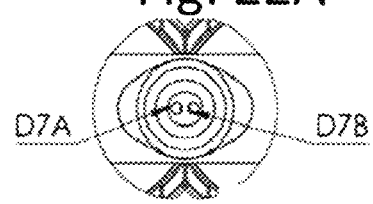
Fig. 22F
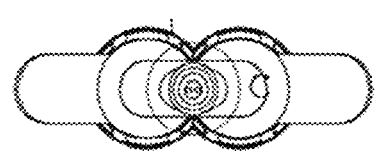
Fig. 22D
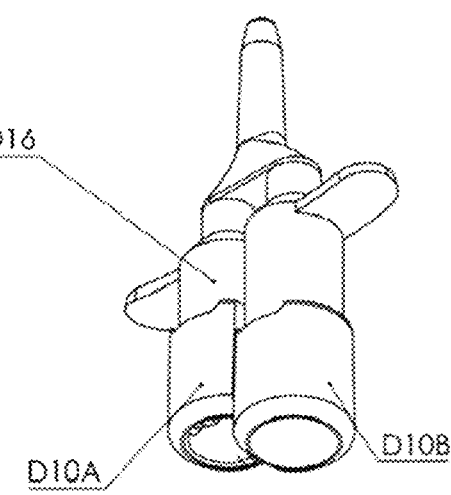
Fig. 22E

| Operating Conditions | Before Activation | After Activation |
|---|---|---|
| 1 | | |
| 2 | | |
| 3 | | |

Fig. 27A
Fig. 27B
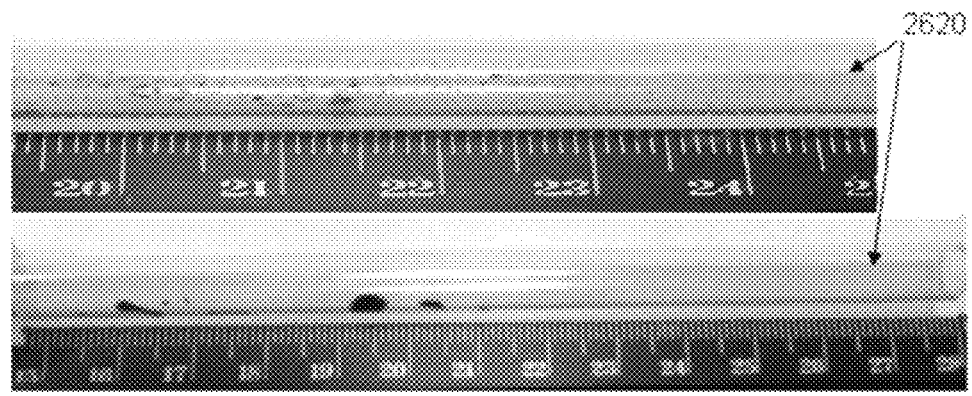
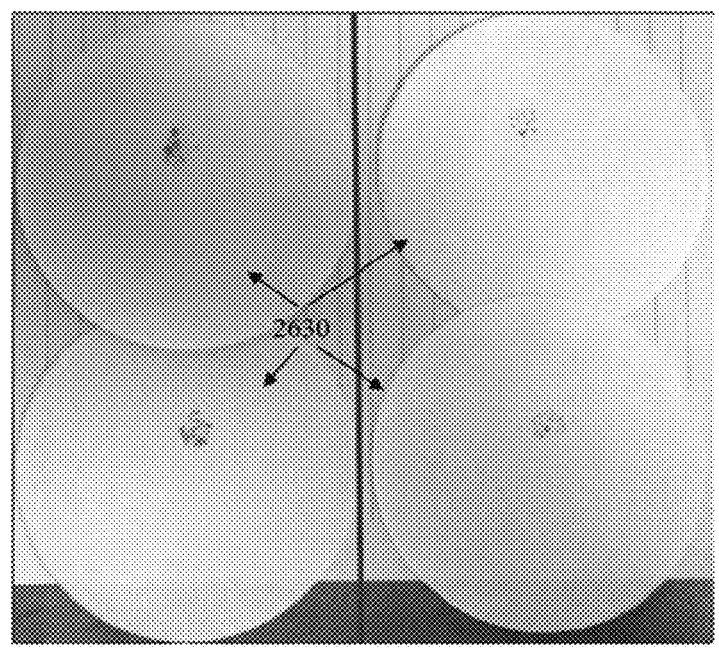
Fig. 28A    Fig. 28B

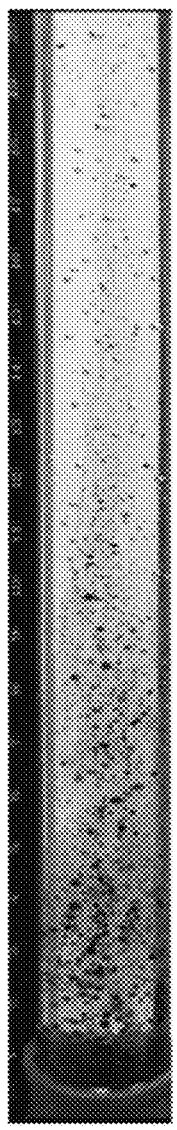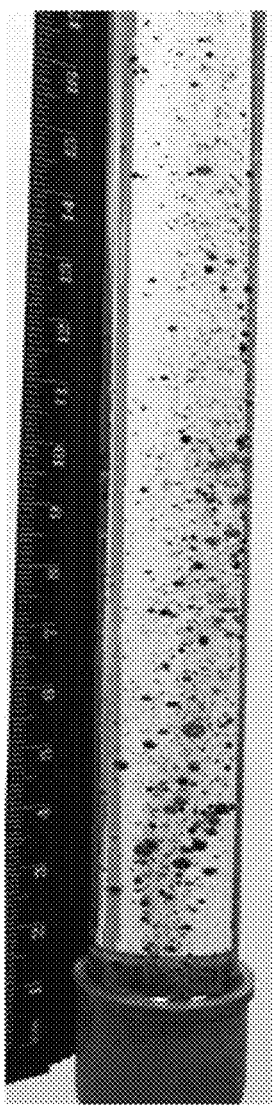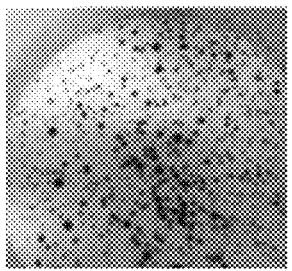
Fig. 34A    Fig. 34B    Fig. 34C    Fig. 34D

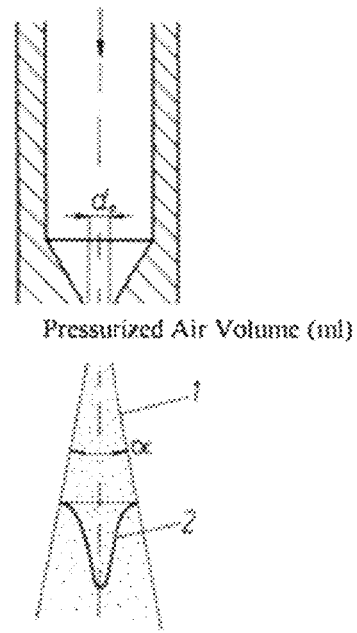
Fig. 48
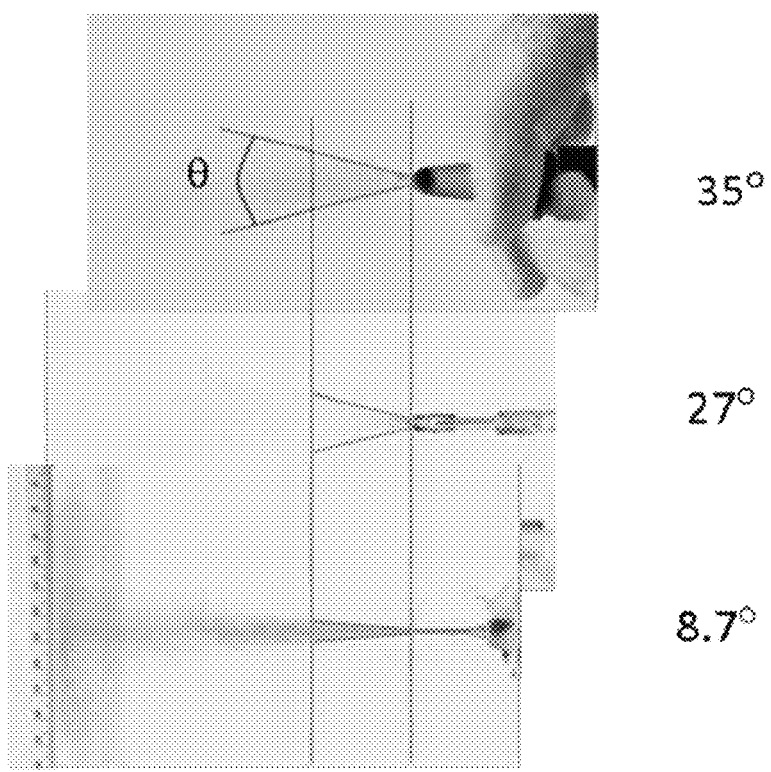
Fig. 49A   35°
Fig. 49B   27°
Fig. 49C   8.7°

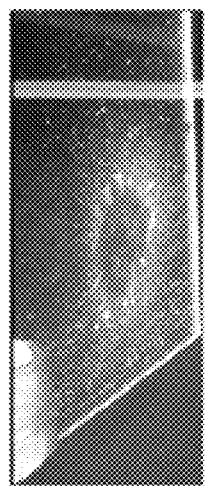 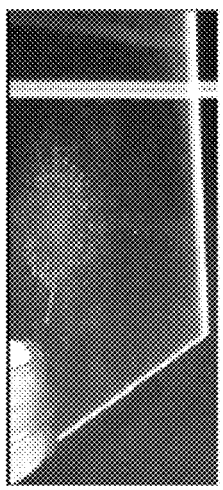 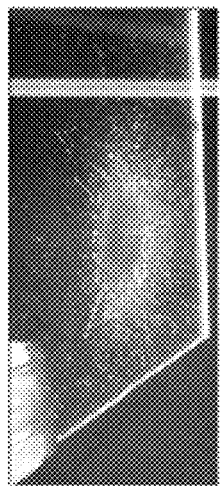 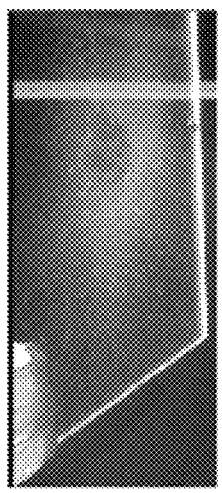 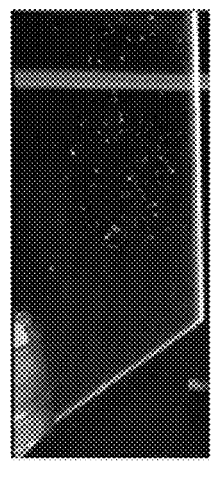
Fig. 52A    Fig. 52B    Fig. 52C    Fig. 52D    Fig. 52E
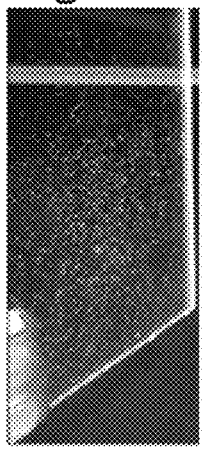 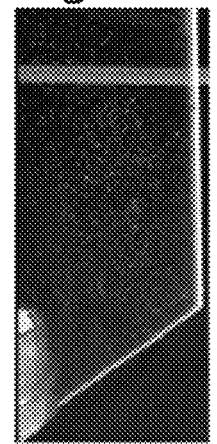 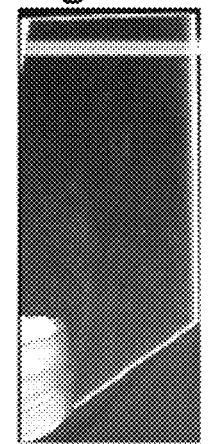 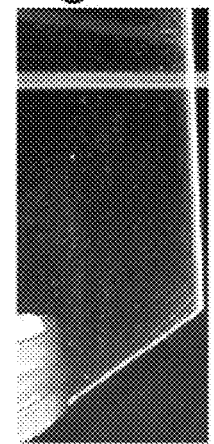 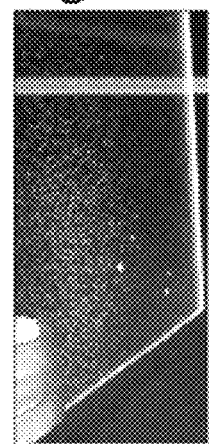
Fig. 52F    Fig. 52G    Fig. 52H    Fig. 52I    Fig. 52J

Effect of Pressure on Release Time

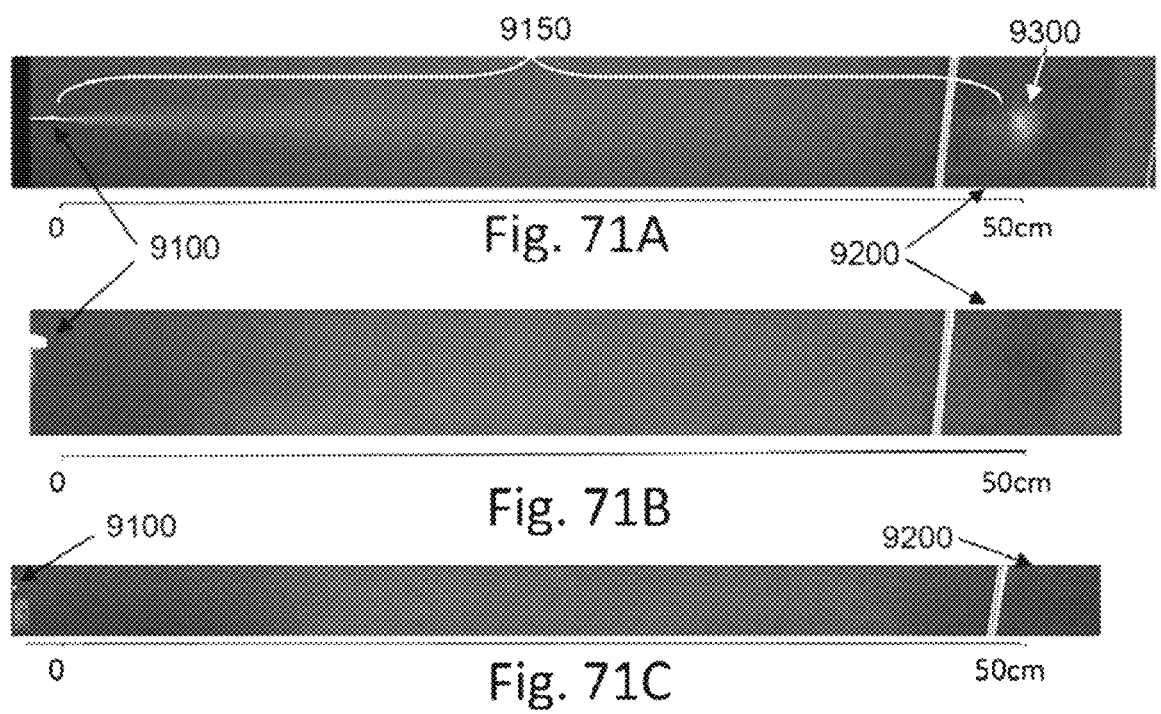

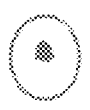

Plasma Concentration

Brain Concentration

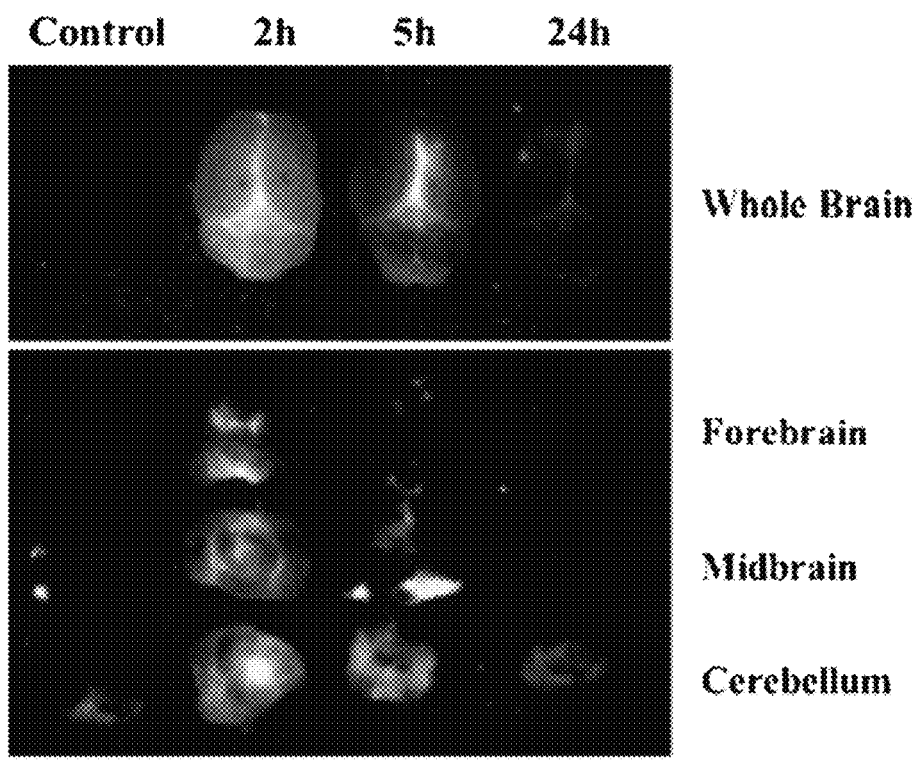
Fig. 110A
Fig. 110B
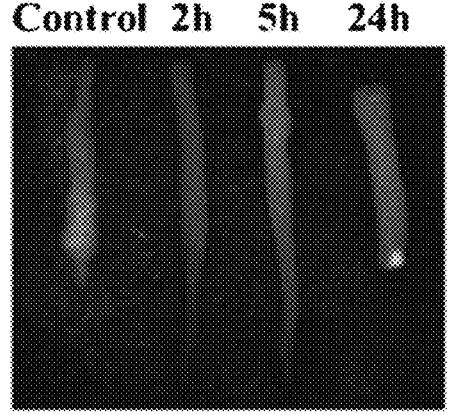
Fig. 110C

DEVICE AND METHOD FOR AEROSOLIZED DELIVERY OF SUBSTANCE TO A NATURAL ORIFICE OF THE BODY

CROSS-REFERENCES TO RELATED APPLICATIONS

The present application is a continuation-in-part application of U.S. patent application Ser. No. 14/733,143 filed on Jun. 8, 2015, which claims the benefit of priority of U.S. provisional patent application No. 62/117,986 filed on Feb. 19, 2015 and of U.S. provisional patent application No. 62/077,246 filed on Nov. 9, 2014. The present application also claims the benefit of priority of U.S. provisional patent application No. 62/507,816 filed on May 18, 2017. All of said applications being incorporated by reference herein in their entirety.

FIELD OF THE INVENTION

The present invention generally pertains to a system for delivering aerosolized substance to a natural orifice of the body.

BACKGROUND OF THE INVENTION

In the pharmaceutical and therapeutic areas, nasal delivery is a known and acceptable delivery route that can provide a solution for a wide range of therapeutics and medical indications.

Prior art nasal delivery devices suffer from difficulties in: dose control, delivery accuracy, drug storage, and treatment with multiple medications. Metered dose delivery, where a fixed dose is released in every activation is common in nasal and aerosol delivery of pharmaceuticals. For metered dose delivery, each delivery device is designed to deliver a specific, unchangeable dose per activation. In some therapeutics areas, there is a need for a different dose for each patient, sometimes even for each therapeutic treatment for the same patient. For example: for the pediatric population, the dose often must depend on the weight of the patient. In other cases, such as acute treatment in cases of breakthrough seizures, breakthrough pain, or Parkinson's "off stage", the treatment should reflect the patient's medical condition.

Loading of a desirable dose to fit a specific need is not common in nasal delivery applications, moreover, one of the main obstacles to providing an adjustable dose in nasal delivery devices, especially when released in the form of an aerosol, is maintaining, over a wide range of dose sizes, reproducible aerosol characteristics in terms of dose released, residual volume, droplet diameter, droplet size distribution and plume geometry.

In many therapeutic areas there is a need to provide the patient with a number of medications during the same treatment. With oral delivery, a patient can consume different pills one after the other, or consume one pill that contains more than one active ingredient/drug (For example: L-Dopa+Carbidopa; Topiramate+Phentermine (like in Qsymia) and more. In injectable and nasal delivery, the ability to mix compounds before or at the time of administration is less common.

In some cases there is a need to store compounds and materials separately in order to maintain stability and functionality. This can conflict with a need to deliver the compounds in a specialized formulation for better user experience and/or better absorption. For example, a drug which is a biologic or protein or an active compound that is not stable in solution can be highly stable as a dry powder. For such drugs, mixture of the dry powder drug with a liquid formations at the time of administration, could provide a homogenous solution to be delivered efficiently to the target tissue. User compliance could be high, since it is effective and provides a positive user experience. Another example is an insoluble compound that is stored in one compartment and is released with, slightly before or slightly after a formulation that will either affect the spread of the compound in the target tissue, or improve the absorption of the compound via the mucosal tissue, or change the adhesion of the compound to the mucosal tissue (to lengthen or shorten the exposure of the mucosal tissue to the compound, or, the formulation can protect the active compound from degradation and/or clearance. However, in the prior art there is no way to provide both long-term separate storage for components of a formulation and automatic mixing of the components at the time of administration.

Obesity and other conditions related to inappropriate intake of food are a common and growing problem. Appetite-suppressant drugs are well known in the art. However, appetite-suppressant drugs given orally has the limitations of first pass metabolism and thus are given in high doses in order to allow sufficient doses to be delivered to the target area (mostly in the brain). This leads to high systemic distribution of the drug that can cause unwanted side effects. Appetite suppressant drugs given parenterally pass to the brain through the blood stream and therefore can also have systematic effects other than the desired suppression of appetite. Furthermore, either with orally or with parenterally delivered drugs, the blood-brain barrier can limit the uptake of the drug to the brain. Appetite-suppressant drugs, as given nasally in the prior art also pass through the blood stream before reaching the brain so that traditional nasal administration can suffer from the same flaws as parenteral and/or oral administration. On top of that, all commercial BED/ obesity treatments are chronically administrated, while Sip-Nose's suggested solution is administrated upon demand, for example at the time of the binge. Given the many unwanted side effects of drugs such as topiramate, a solution that enables using a lower dose than the normal one in the field, that will be fast acting and will result in relatively fast clearance upon demand only will increase the safety profile and improve user compliance.

Therefore, a device that can deliver to the brain via the nasal cavity an efficient amount of a drug such as an appetite suppressant can be a valuable adjunct to the treatment of obesity, weight loss and binge eating disorder (BED). As shown below, administration of an odorant in conjunction with the appetite suppressant can enhance the efficacy of the treatment by inducing feelings of satiety in a patient, making the treatment a positive experience to enhance user compliance which is very low in the target populations treated for obesity and BED.

Ramaekers et al. (M G Ramaekers, S Boesveldt, "*Odors: appetizing or satiating? Development of appetite during odor exposure over time*", International Journal of Obesity, 2014, nature.com) relates that it is known that exposure to palatable food odors influences appetite responses, either promoting or inhibiting food intake. It is suggested that food odors can be appetizing after a short exposure (of circa 1-3 min), but can become satiating over time (circa 10-20 min). Therefore, the effect of odor exposure on general appetite and sensory-specific appetite (SSA) over time was investigated. In a cross-over study, 21 unrestrained women (age: 18-45 years; BMI: 18.5-25 kg m-2) were exposed for 20 min to eight different odor types: five food odors, two nonfood odors and no-odor. All odors were distributed in a test room at suprathreshold levels. General appetite, SSA and salivation were measured over time. All food odors significantly increased general appetite and SSA, compared with the no-odor condition. The nonfood odors decreased general appetite. All effects did not change over time during odor exposure. Savory odors increased the appetite for savory foods, but decreased appetite for sweet foods, and vice versa after exposure to sweet odors. Neither food odors nor nonfood odors affected salivation. Palatable food odors were appetizing during and after odor exposure and did not become satiating over a 20-min period. Food odors had a large impact on SSA and a small impact on general appetite. Moreover, exposure to food odors increased the appetite for congruent foods, but decreased the appetite for incongruent foods. It may be hypothesized that, once the body is prepared for intake of a certain food with a particular macronutrient composition, it is unfavorable to consume foods that are very different from the cued food.

Yeomans finds (M R Yeomans, "*Olfactory influences on appetite and satiety in humans*", *Physiology & Behavior.* 2006—Elsevier) that odor stimuli play a major role in perception of food flavor. Odor stimuli such as food-related odors have also been shown to increase rated appetite, and induce salivation and release of gastric acid and insulin. However, the ability to identify an odor as food-related and a liking for a food-related odor are both learned responses. In conditioning studies, repeated experience of odors with sweet and sour tastes results in enhanced ratings of sensory quality of the paired taste for the odor on its own. Studies also report increased pleasantness ratings for odors paired with sucrose for participants who like sweet tastes, and conversely decreased liking and increased bitterness for quinine-paired odors. When odors were experienced in combination with sucrose when hungry, liking was not increased if tested sated, suggesting that expression of acquired liking for odors depends on current motivational state. Other studies report sensory-specific satiety is seen with food-related odors. Overall, these studies suggest that once an odor is experienced in a food-related context, that odor acquires the ability to modify both preparatory and satiety-related components of ingestion.

Eseke et al. (E T Massolt, P M van Haard, J F Rehfeld, E F Posthuma, "*Appetite suppression through smelling of dark chocolate correlates with changes in ghrelin in young women*", *Regulatory peptides,* 2010, Elsevier) find that cephalic effects on appetite are mediated by vagal tone and altered gastrointestinal hormones. The study explores the relationship between appetite and levels of gastrointestinal hormones after smelling chocolate and after melt-and-swallow 30 g of chocolate (1.059 oz, 85% cocoa, 12.5 g of sugar per 100 g product). Twelve females (BMI between 18 and 25 kg/m$^2$) participated in two 60-minute study sessions. In the first session, all 12 women ate chocolate; for the second session, they were randomized either to smell chocolate (n=6) or to serve as a control (no eating or smelling; n=6). At the start of the sessions, levels of insulin, glucagon-like peptide-1 (GLP-1) and cholecystokinin (CCK), but not glucose, correlated with appetite scored on a visual analogue scale (VAS). In contrast, ghrelin levels correlated inversely with scored appetite. Chocolate eating and smelling both induced a similar appetite suppression with a disappearance of correlations between VAS scores and insulin, GLP-1 and CCK levels. However, while the correlation between VAS score and ghrelin disappeared completely after chocolate eating, it reversed after chocolate smelling, that is, olfactory stimulation with dark chocolate (85%) resulted in a satiation response that correlated inversely with ghrelin levels.

Schiffman and Graham find (S S Schiffman and B G Graham, "*Taste and smell perception affect appetite and Immunity in the elderly*", *European Journal of Clinical Nutrition* (2000) 54, Suppl 3, S54-S63) that the losses in taste and smell that occur with advancing age can lead to poor appetite, inappropriate food choices, as well as decreased energy consumption. Decreased energy consumption can be associated with impaired protein and micronutrient status and may induce subclinical deficiencies that directly affect function. Most nutritional interventions in the elderly do not compensate for taste and smell losses and complaints. For example, cancer is a medical condition in which conventional nutritional interventions (that do not compensate for taste and smell losses) are ineffective. Evidence is now emerging that suggests compensation for taste and smell losses with flavor-enhanced food can improve palatability and/or intake, increase salivary flow and immunity, reduce chemosensory complaints in both healthy and sick elderly, and lessen the need for table salt.

Therefore, odorants can be used to enhance a response to appetitive cues so that delivery of an odorant in addition to an appetite suppressant can increase the efficacy of the appetite suppressant.

It is therefore a long felt need to provide a system for the treatment of conditions such as obesity, weight loss and binge eating disorder which can be optimized for efficient delivery of a substance to a target site, said optimization bringing sufficient material to the target site, ensuring adequate absorption into and through the mucosal layer while minimizing unwanted side effects.

SUMMARY OF THE INVENTION

It is an object of the present invention to disclose a system and method for delivering an aerosolized substance to a natural orifice of the body. It is another object of the present invention to disclose a device for delivering a predetermined amount $V_{sub}$ of at least one substance, within at least one body cavity of a subject, said device comprising:
- at least one predetermined volume sized and shaped for containing said predetermined amount $V_{sub}$ of said at least one substance;
- a delivery end for placement in proximity to said body cavity, said delivery end being in fluid communication with said at least one predetermined volume; said delivery end comprises at least one orifice of diameter D [mm];
- at least one valve mechanically connectable to said volume, characterized by at least two configurations: (i) an active configuration in which said valve enables delivery of predetermined amount $V_{sub}$ of said at least one substance from said volume to said body cavity via said delivery end; and, (ii) an inactive configuration, in which said valve prevents delivery of said predetermined amount $V_{sub}$ of said at least one substance from said volume to said body cavity;
- said valve is reconfigurable from said inactive configuration to said active configuration within a predetermined period of time, dt, in response to activation of the same; and
- a fluid tight chamber configured to contain a predetermined volume $V_{gas}$ [ml] of a pressurized gas at a predetermined pressure, $P_{gas}$ [barg];
- said pressurized gas, once said valve is reconfigured from said inactive configuration to said active configuration, is configured to entrain said at least one substance and deliver the same via said orifice in said delivery end within said body cavity; and said device is configured to deliver said predetermined amount $V_{sub}$ of said at least one substance and said predetermined volume $V_{gas}$ of said pressurized gas through said at least one orifice within a predetermined time $dt_{deliver}$;

wherein said predetermined amount $V_{sub}$ of said at least one substance is at an effective amount for treatment of at least one condition selected from a group consisting of: obesity, binge eating disorder, pain management, epilepsy and any combination thereof;

further wherein said substance is selected from a group consisting of Midazolam, Topiramate and at least one *cannabis* derivative.

It is another object of the present invention to disclose the device of claim 1, wherein sat least one of the following is true:

said pain management manages pain selected from a group consisting of: chronic pain; neuropathic pain; cancer pain, breakthrough pain, migraines and any combination thereof;

said predetermined amount $V_{sub}$ of said at least one substance is at an effective amount for emergency treatment of drug overdose;

said epilepsy treatment is selected from a group consisting of: a chronic treatment for prevention of epileptic seizures, a chronic treatment for reduction in occurrence of epileptic seizures, a chronic treatment for reduction of strength of epileptic seizures, a rescue treatment at the time of occurrence of an epileptic seizure, and any combination thereof;

said predetermined amount $V_{sub}$ of said at least one substance is at an effective amount for treatment of brain cancer; said brain cancer selected from a group consisting of: Glioblastoma, secondary tumor, brain stem cancer and any combination thereof said treatment is selected from a group consisting of: direct treatment of a brain cancer in order to reduce a tumor; treatment of a patient with a non-brain cancer in order to prevent metastasis of the non-brain cancer to the brain; and any combination thereof;

said *cannabis* derivative is selected from a group consisting of: tetrahydrocannabinol (THC); cannabidiol (CBD), cannabinol (CBN), tetrahydrocannabivarin (THCV), natural or synthetic *cannabis* extract, and any combination thereof; and said predetermined amount $V_{sub}$ is measurable as a volume [ml] or a mass [mg].

It is another object of the present invention to disclose a device, wherein at least one of the following is true:

said at least one substance is selected from a group consisting of: Phentamine, GLP-1, a GLP-1 analog, a GLP-1 derivative and any combination thereof;

said at least one substance is Naloxone;

said at least one substance is selected from a group consisting of: a chemotherapy drug, a biologic, an antibody, and any combination thereof;

said predetermined amount $V_{sub}$ of said at least one substance is at an effective amount for vaccination;

said vaccination is configured to provide a vaccine selected from a group consisting of: anthrax vaccine, Hepatitis B vaccine, Tetanus vaccine, Influenza vaccine and any combination thereof;

said predetermined amount $V_{sub}$ of said at least one substance is at an effective amount for enhancement of an immune system;

at least one central nervous system disorder is treatable via said enhancement of the immune system;

said at least one central nervous system disorder is selected from a group consisting of: Alzheimer's disease, Parkinson's disease and any combination thereof;

said at least one substance is selected from a group consisting of: a pharmaceutical, a natural compound, a biologic, a hormone, a peptide, a protein, a virus, a cell, a stem cell and any combination thereof; and at least one odorant is deliverable at the time of delivery of said at least one substance; an odor of said at least one odorant is selected from a group consisting of: grapefruit, lemon, vanilla, green apple, banana, peppermint, fennel, patchouli, bergamot and any combination thereof: a component of said at least one odorant is selected from a group consisting of: a natural smell molecule, a synthetic smell molecule and any combination thereof; and before delivery, said odorant is held in a manner selected from a group consisting of: stored in said pressurized gas, stored in at least one of said at least one substance, stored in a device material, and any combination thereof.

It is another object of the present invention to disclose a device, wherein at least one of the following is true:

said delivery occurs at a pressure rate of $dP_{gas}/dt_{deliver}$; a volume rate of $dV_{gas}/dt_{deliver}$; and an amount rate of $dV_{sub}/dt_{deliver}$;

said body cavity is selected from a group consisting of: a nasal cavity, the mouth, the throat, an ear, the vagina, the rectum, and the urethra;

said at least one substance is selected from a group consisting of a gas, a liquid, a powder, an aerosol, a slurry, a gel, a suspension and any combination thereof;

said device is configured to deliver a plurality of amounts of said substance; each of said plurality of amounts separated in time from all other of said plurality of amounts, each of said plurality of amounts being predetermined; said predetermination selected from a group consisting of: each of said plurality of amounts being an unchangeable amount fixed before first use of the device; each of said plurality of amounts being a selectable adjustable amount and, after selection of a size for said amount, said selected amount being automatically deliverable; and said predetermined amount of said substance is introducible into said device via a syringe.

It is another object of the present invention to disclose a device, wherein at least one of the following is true:

said valve is reconfigurable from said active configuration to said inactive configuration;

said valve is single use;

said valve is selected from a group consisting of a frangible membrane, a mechanical valve and any combination thereof.

It is another object of the present invention to disclose a device, wherein at least one of the following is true:

$P_{gas}$ is in a range of about 1-10 barg;

$V_{gas}$ is in a range of about 1-21 ml;

$V_{sub}$ is in a range of about 0.01-7 ml or in a range of about 0.01-1000 mg;
D is in a range of 0.2-6 mm;
said pressure rate $$\frac{dP_{gas}}{dt_{deliver}} \to \infty;$$

said pressure velocity $dP_{gas}/dt_{deliver}$ is greater than about 0.001 barg/ms;
said amount rate $dV_{sub}/dt_{deliver}$ is greater than about 0.0001 ml/ms or greater than about 0.0001 mg/ms;
said volume rate $dV_{gas}/dt_{deliver}$ is greater than about 0.001 ml/ms;
said predetermined period of time, $dt \to 0$;
$dt_{deliver}$ is in a range of about 0 to 500 ms;
viscosity $\eta$ of said at least one substance is in a range of about $1 \times 10^{-3}$ poise to about 1 poise; and
any combination thereof.

It is another object of the present invention to disclose a device, wherein at least one of the following is true:
DV50 diameter of particles of said at least one substance, after exit from said device, is less than about 100 μm;
DV90 diameter of said particles of said at least one substance is less than about 1000 μm;
a full width of a plume of aerosol comprising said at least one substance and said pressurized gas subtends an angle θ of less than about 25°;

particles in said plume of aerosol have velocities in a range of about 5 m/s to 50 m/s;

said pressurized gas comprises air, nitrogen, oxygen, carbon dioxide, helium, neon, xenon and any combination thereof;

during dispensing of said at least one substance, a mixture of said predetermined volume $V_{gas}$ [ml] of said pressurized gas with said predetermined amount $V_{sub}$ of said at least one substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume $V_{gas}$ of said pressurized gas, said predetermined amount $V_{sub}$ of said at least one substance, said predetermined pressure $P_{gas}$ of said pressurized gas, said predetermined orifice diameter D, and any combination thereof;

said at least one substance is stored under either an inert atmosphere or under vacuum to prevent reactions during storage;

a dose-response curve is substantially linear for brain concentration of said at least one substance when administered nasally via said device; and a dose-response curve for brain concentration of said at least one substance when administered nasally via said device selected from a group consisting of logarithmic, parabolic, exponential, sigmoid, power-law, and any combination thereof.

It is another object of the present invention to disclose a device, wherein at least one of the following is true:

said predetermined volume is selected from a group consisting of: a container fluidly connectable to said device, a predetermined volume within said device and any combination thereof;

said predetermined volume comprises a port fluidly connectable to the exterior of said device, said port configured such that said at least one substance is insertable into said container via said port;

said device comprises a port cover configured to provide an air-tight closure for said predetermined volume, said port cover slideable along said device, rotatable around said device, rotatable around a hinge on the exterior of said device and any combination thereof; and said container is insertable into said device.

It is another object of the present invention to disclose a device, wherein said predetermined volume has a main longitudinal axis, said predetermined volume comprising a number n of compartments, said predetermined volume configured to contain at least a portion of said predetermined amount $V_{sub}$ of said at least one substance, said amount $V_{sub}$ of said at least one substance containable in at least one of said compartments; at least one of the following being true:

said predetermined volume is a capsule;

the number n of said compartments is an integer greater than or equal to 1; at least one said compartment has cross-section with shape selected from a group consisting of: wedge shaped, circular, oval, elliptical, polygonal, annular, and any combination thereof;

for said number n of compartments being an integer greater than 1, at least two said compartments have different volumes;

for said number n of compartments being an integer greater than 1, at least two said compartments have the same volume;

for said number n of compartments being an integer greater than 1, at least two said compartments have different cross-sectional areas;

for said number n of compartments being an integer greater than 1, at least two said compartments have the same cross-sectional area;

for said number n of compartments being an integer greater than 1, at least two said compartments contain different substances;

for said number n of compartments being an integer greater than 1, at least two said compartments contain the same substance;

for said number n of compartments being an integer greater than 1, at least two said compartments are disposed coaxially around said main longitudinal axis of said capsule;

for said number n of compartments being an integer greater than 1, at least two said compartments are disposed sequentially along said main longitudinal axis of said capsule;

for said number n of compartments greater than 1, said plurality of substances mix during said dispensing; and for said number n of compartments greater than 1, said plurality of substances react during said dispensing.

It is another object of the present invention to disclose a device, wherein, when said substance is delivered into a tube, at least one of the following is true:

the distance traveled down the tube is L. and L is substantially independent of said viscosity η of said substance;

the distance traveled down the tube is L, where $L=a_{6a} P+b_{6a}$; the units of L are cm and the units of P are barg, $a_{6a}$ is in a range of about 0 to about 116 and $b_{6a}$ is in a range of about 0 to about 306;

the distance traveled down the tube is L, where $L=a_{6b} P^3-b_{6b} P^2+c_{6b} P$; the units of L are cm and the units of P are barg, $a_{6b}$ is in a range of about 6.5 to about 9.75, $b_{6b}$ is in a range of about −65 to about −97.5 and $c_{6b}$ is in a range of about 202 to about 303;

the distance traveled down the tube is L, where $L=a_{6c} P^{b6c}$; the units of L are cm and the units of P are barg, $a_{6c}$ is in a range of about 0 to about 902 and $b_{6c}$ is in a range of about 0 to about 3.72;

the distance traveled down the tube is L, where $L=a_{7a} V_{gas}+b_{7a}$; the units of L are cm and the units of P are barg, $a_{7a}$ is in a range of about 0 to about 10 and $b_{7a}$ is in a range of about 165 to about 282;

the distance traveled down the tube is L, where $L=: b_{7b} V_{gas}/(a_{7b}+V_{gas})$; the units of L are cm and the units of P are barg, $a_{7b}$ is in a range of about −0.26 to about 2.05 and bb is in a range of about 235 to about 350; and the distance traveled down the tube is L, where $L=a_{7c} V_{gas}^{b7c}$; the units of L are cm and the units of P are barg, $a_{7c}$ is in a range of about 0 to about 320 and $b_{7c}$ is in a range of about 0 to about 0.96.

It is another object of the present invention to disclose a method of delivering a predetermined volume $V_{sub}$ [ml] of at least one substance within at least one body cavity of a subject, comprising:

providing a device comprising:

at least one predetermined volume sized and shaped for containing said predetermined amount $V_{sub}$ of said at least one substance;

a delivery end for placement in proximity to said body cavity, said delivery end being in fluid communication with said predetermined volume; said delivery end comprising at least one orifice of diameter D [mm];

at least one valve mechanically connected to said volume, characterized by at least two configurations: (i) an active configuration in which said valve enables delivery of said predetermined amount $V_{sub}$ of said at least one substance from said volume to said body cavity via said delivery end; and, (ii) an inactive configuration, in which said valve prevents delivery of said predetermined amount $V_{sub}$ of said substance from said volume to said body cavity;

said valve is reconfigurable from said Inactive configuration to said active configuration within a predetermined period of time, dt, in response to activation of the same; and a fluid tight chamber configured to contain predetermined volume $V_{gas}$ [ml] of pressurized gas at a predetermined pressure, $P_{gas}$ [barg];

emplacing said substance in said predetermined volume;

setting said valve in said inactive configuration;

pressurizing said fluid-tight chamber with said gas to said predetermined pressure;

placing said delivery end in proximity to said body cavity;

reconfiguring said valve from said inactive configuration to said active configuration thereby entraining said substance in said predetermined volume $V_{gas}$ of said pressurized gas; thereby delivering said predetermined amount $V_{sub}$ of said substance and said predetermined volume $V_{gas}$ of said pressurized gas through said at least one orifice within a predetermined time $dt_{deliver}$;

wherein said predetermined amount $V_{sub}$ of said at least one substance is at an effective amount for treatment of at least one disease selected from a group consisting of: obesity, binge eating disorder and any combination thereof further wherein said substance is selected from a group consisting of Midazolam, Topiramate and at least one *cannabis* derivative.

It is another object of the present invention to disclose the method, additionally comprising at least one of the following steps:

selecting a pain managed by said pain management from a group consisting of: chronic pain; neuropathic pain; cancer pain, breakthrough pain, migraines and any combination thereof;

selecting said predetermined amount $V_{sub}$ of said at least one substance to be at an effective amount for emergency treatment of drug overdose;

selecting said epilepsy treatment from a group consisting of: a chronic treatment for prevention of epileptic seizures, a chronic treatment for reduction in occurrence of epileptic seizures, a chronic treatment for reduction of strength of epileptic seizures; a rescue treatment at the time of occurrence of an epileptic seizure, and any combination thereof;

providing said predetermined amount $V_{sub}$ of said at least one substance to be at an effective amount for treatment of brain cancer; said brain cancer selected from a group consisting of: Glioblastoma, secondary tumor, brain stem cancer and any combination thereof;

selecting said treatment from a group consisting of: direct treatment of a brain cancer in order to reduce a tumor: treatment of a patient with a non-brain cancer in order to prevent metastasis of the non-brain cancer to the brain; and any combination thereof;

selecting said *cannabis* derivative from a group consisting of: tetrahydrocannabinol (THC); cannabidiol (CBD), cannabinol (CBN), tetrahydrocannabivarin (THCV), natural or synthetic *cannabis* extract, and any combination thereof; and measuring said predetermined amount $V_{sub}$ as a volume [ml] or a mass [mg].

It is another object of the present invention to disclose the method, additionally comprising at least one of the following steps:

selecting said at least one substance from a group consisting of: Phentamine, GLP-1, a GLP-1 analog, a GLP-1 derivative and any combination thereof;

selecting said at least one substance to be Naloxone;

selecting said at least one substance from a group consisting of: a chemotherapy drug, a biologic, an antibody, and any combination thereof;

selecting said predetermined amount $V_{sub}$ of said at least one substance to be at an effective amount for vaccination;

selecting a vaccine to provide said vaccination from a group consisting of: anthrax vaccine, Hepatitis B vaccine, Tetanus vaccine, Influenza vaccine and any combination thereof;

selecting said predetermined amount $V_{sub}$ of said at least one substance to be an effective amount for enhancement of an immune system;

treating at least one central nervous system disorder via enhancement of the immune system;

selecting aid at least one central nervous system disorder from a group consisting of: Alzheimer's disease, Parkinson's disease and any combination thereof;

selecting said at least one substance from a group consisting of: a pharmaceutical, a natural compound, a biologic, a hormone, a peptide, a protein, a virus, a cell, a stem cell and any combination thereof; and delivering at least one odorant at the time of delivery of said at least one substance; an odor of said at least one odorant is selected from a group consisting of: grapefruit, lemon, vanilla, green apple, banana, peppermint, fennel, patchouli, bergamot and any combination thereof; a component of said at least one odorant is selected from a group consisting of: a natural smell molecule, a synthetic smell molecule and any combination thereof; and before delivery, said odorant is held in a manner selected from a group consisting of: stored in said pressurized gas, stored in at least one of said at least one substance, stored in a device material, and any combination thereof.

It is another object of the present invention to disclose the method, additionally comprising at least one of the following steps:

delivering at a pressure rate of $dP_{gas}/dt_{deliver}$; a volume rate of $dV_{gas}/dt_{deliver}$; and an amount rate of $dV_{sub}/dt_{deliver}$;

selecting said body cavity from a group consisting of: a nasal cavity, the mouth, the throat, an ear, the vagina, the rectum, and the urethra; and selecting said at least one substance from a group consisting of a gas, a liquid, a powder, an aerosol, a slurry, a gel, a suspension and any combination thereof delivering a plurality of amounts of said substance; each of said plurality of amounts separated in time from all other of said plurality of amounts, each of said plurality of amounts being predetermined; said predetermination selected from a group consisting of: each of said plurality of amounts being an unchangeable amount fixed before first use of the device; each of said plurality of amounts being a selectable adjustable amount and, after selection of a size for said amount, said selected amount being automatically deliverable; and introducing said predetermined amount of said substance into said device via a syringe It is another object of the present invention to disclose the method, additionally comprising at least one of the following steps:

reconfiguring said valve from said active configuration to said inactive configuration;

providing said valve as a single use valve; and selecting said valve is selected from a group consisting of a frangible membrane, a mechanical valve and any combination thereof.

It is another object of the present invention to disclose the method, wherein at least one of the following is true:

$P_{gas}$ is in a range of about 1-10 barg;

$V_{gas}$ is in a range of about 1-21 ml;

$V_{gas}$ is in a range of about 0.01-7 ml or in a range of about 0.01-1000 mg;

D is in a range of 0.2-6 mm;

said pressure rate $$\frac{dP_{gas}}{dt_{deliver}} \to \infty;$$

said pressure velocity $dP_{gas}/dt_{deliver}$ is greater than about 0.001 barg/ms;

said amount rate $dV_{sub}/dt_{deliver}$ is greater than about 0.0001 ml/ms or greater than about 0.0001 mg/ms;

said volume rate $dV_{gas}/dt_{deliver}$ is greater than about 0.001 ml/ms;

said predetermined period of time, dt→0;

$dt_{deliver}$ is in a range of about 0 to 500 ms;

viscosity η of said at least one substance is in a range of about $1\times10^{-3}$ poise to about 1 poise; and any combination thereof.

It is another object of the present invention to disclose the method, wherein at least one of the following is true:

DV50 diameter of particles of said at least one substance, after exit from said device, is less than about 100 μm;

DV90 diameter of said particles of said at least one substance is less than about 1000 μm;

a full width of a plume of aerosol comprising said at least one substance and said pressurized gas subtends an angle θ of less than about 25°;

particles in said plume of aerosol have velocities in a range of about 5 m/s to 50 m/s;

said pressurized gas comprises air, nitrogen, oxygen, carbon dioxide, helium, neon, xenon and any combination thereof;

during dispensing of said at least one substance, a mixture of said predetermined volume $V_{gas}$ [ml] of said pressurized gas with said predetermined amount $V_{sub}$ of said at least one substance entrained within it forms a plume of aerosol: said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume $V_{gas}$ of said pressurized gas, said predetermined amount $V_{sub}$ of said at least one substance, said predetermined pressure $P_{gas}$ of said pressurized gas, said predetermined orifice diameter D, and any combination thereof;

said at least one substance is stored under either an inert atmosphere or under vacuum to prevent reactions during storage;

a dose-response curve is substantially linear for brain concentration of said at least one substance when administered nasally via said device; and a dose-response curve for brain concentration of said at least one substance when administered nasally via said device selected from a group consisting of logarithmic, parabolic, exponential, sigmoid, power-law, and any combination thereof.

It is another object of the present invention to disclose the method, additionally comprising at least one of the following steps:

selecting said predetermined volume from a group consisting of: a container fluidly connectable to said device, a predetermined volume within said device and any combination thereof providing said predetermined volume with a port fluidly connectable to the exterior of said device, said port configured such that said at least one substance is insertable into said container via said port;

providing said device with a port cover; said port cover providing an air-tight closure for said predetermined volume by at least one member of a group consisting of: sliding said port cover along said device, rotating said port cover around said device, rotating said port cover around a hinge on the exterior of said device and any combination thereof; and inserting said container into said device.

It is another object of the present invention to disclose the method, wherein said predetermined volume has a main longitudinal axis, said predetermined volume comprising a number n of compartments, said predetermined volume configured to contain at least a portion of said predetermined amount $V_{sub}$ of said at least one substance, said amount $V_{sub}$ of said at least one substance containable in at least one of said compartments; at least one of the following being true:

said predetermined volume is a capsule;

the number n of said compartments is an integer greater than or equal to 1; at least one said compartment has cross-section with shape selected from a group consisting of: wedge shaped, circular, oval, elliptical, polygonal, annular, and any combination thereof;

for said number n of compartments being an integer greater than 1, at least two said compartments have different volumes;

for said number n of compartments being an integer greater than 1, at least two said compartments have the same volume;

for said number n of compartments being an integer greater than 1, at least two said compartments have different cross-sectional areas;

for said number n of compartments being an integer greater than 1, at least two said compartments have the same cross-sectional area;

for said number n of compartments being an integer greater than 1, at least two said compartments contain different substances;

for said number n of compartments being an integer greater than 1, at least two said compartments contain the same substance;

for said number n of compartments being an integer greater than 1, at least two said compartments are disposed coaxially around said main longitudinal axis of said capsule;

for said number n of compartments being an integer greater than 1, at least two said compartments are disposed sequentially along said main longitudinal axis of said capsule;

for said number n of compartments greater than 1, said plurality of substances mix during said dispensing; and for said number n of compartments greater than 1, said plurality of substances react during said dispensing.

It is another object of the present invention to disclose the method wherein, when said substance is delivered into a tube, at least one of the following is true:

the distance traveled down the tube is L and L is substantially independent of said viscosity η of said substance;

the distance traveled down the tube is L, where $L=a_{6a} P+b_{6a}$; the units of L are cm and the units of P are barg, $a_{6a}$ is in a range of about 0 to about 16 and $b_{6a}$ is in a range of about 0 to about 306;

the distance traveled down the tube is L, where $L=a_{6b} P^3 - b_{6b} P^2 + c_{6b} P$; the units of L are cm and the units of P are barg, $a_{6b}$ is in a range of about 6.5 to about 9.75, $b_{6b}$ is in a range of about −65 to about −97.5 and $c_{6b}$ is in a range of about 202 to about 303;

the distance traveled down the tube is L, where $L=a_{6c} P^{b6c}$; the units of L are cm and the units of P are barg, $a_{6c}$ is in a range of about 0 to about 902 and $b_{6c}$ is in a range of about 0 to about 3.72;

the distance traveled down the tube is L, where $L=a_{7a} V_{gas}+b_{7a}$; the units of L are cm and the units of P are barg, $a_{7a}$ is in a range of about 0 to about 10 and $b_{7a}$ is in a range of about 165 to about 282;

the distance traveled down the tube is L, where $L=b_{7b} V_{gas}/(a_{7b}+V_{gas})$; the units of L are cm and the units of P are barg, $a_{7b}$ is in a range of about −0.26 to about 2.05 and $b_{7b}$ is in a range of about 235 to about 350; and the distance traveled down the tube is L, where $L=a_{7c} V_{gas}^{b7c}$; the units of L are cm and the units of P are barg, $a_{7c}$ is in a range of about 0 to about 320 and $b_{7c}$ is in a range of about 0 to about 0.96.

BRIEF DESCRIPTION OF THE DRAWINGS

The invention is herein described, by way of example only, with reference to the accompanying drawings, wherein:

FIG. 1A-D shows examples of the prior art;

FIGS. 6A-D shows a preferred embodiment of the loading portion of the device with a pinch triggering mechanism.

FIGS. 9A-9H shows an embodiment of a nozzle with a tip extension and an expandable portion

FIGS. 12A-D shows an embodiment of the body of the nasal delivery device as assembled, after activation

FIGS. 16A-D illustrate a device with a replaceable nose piece preloaded with a single dose of a medicament.

FIGS. 17A-D illustrate a device which can be loaded with a medicament, drug or substance via a syringe.

FIGS. 18A-D show the device which can be loaded with a medicament, drug, or substance via a syringe with a syringe in place.

FIGS. 22A-F show an embodiment of the device with a single nose piece.

FIGS. 27A-B shows the results of droplet penetration on the inner tube surface.

FIGS. 28A-B shows the results of droplet penetration through a tube with a pressure of 2 barg on the absorbent.

FIGS. 33A-E show the effect of orifice size on droplet size and droplet distribution in a device of the present invention after droplet penetration through a liquid filled tube with a pressure of 7 barg.

FIGS. 34A-D show the effect of orifice size on droplet size and droplet distribution in a device of the present invention after droplet penetration through a liquid filled tube with a pressure of 4 barg.

FIG. 48 illustrates measurement of plume angle;

FIG. 49A-C illustrates plume angle for various devices;

FIGS. 52A-J show examples of spray coverage for different devices, with FIGS. 52A-D showing coverage and droplet distribution for the SipNose device for different device parameters, while FIGS. 52E-J show coverage and droplet distribution for a number of different commercial devices;

FIG. 71A-C illustrate carrying distance and spread area for various devices;

FIG. 110A-C shows histopathological images of rats after administration of Fluorescein.

DETAILED DESCRIPTION OF THE PREFERRED EMBODIMENTS

Figure 2:
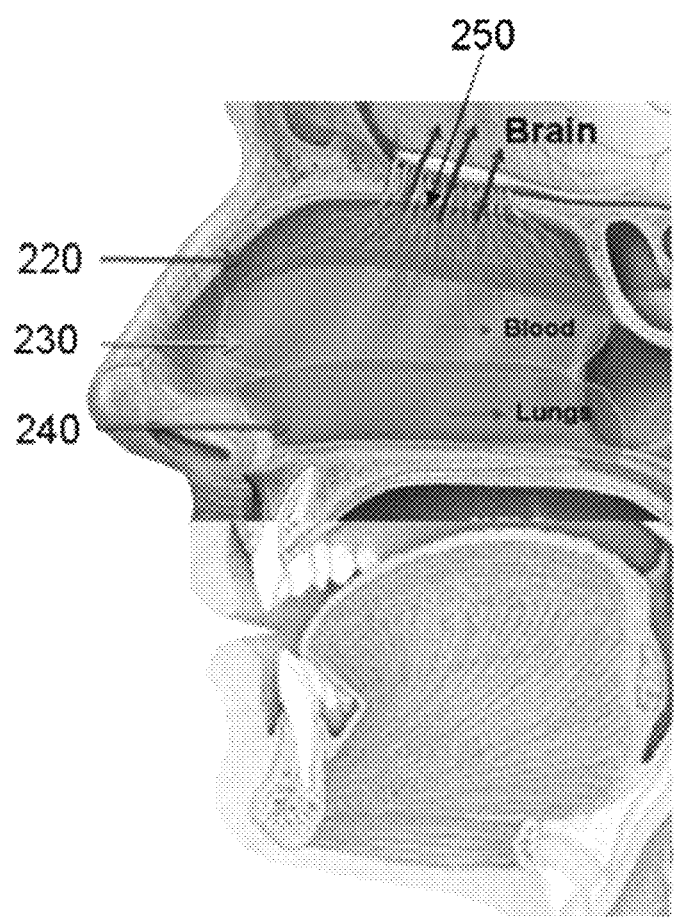
FIG. 2 shows a cross-section of the face, illustrating zones in the nose from which material therein transfers to different parts of the body.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume orifice diameter enable the formation of optimized aerosol characteristics for both improved delivery of aerosol to the target area (such as the olfactory epithelium in the nasal cavity) and enhanced absorption at that area for better delivery to a desired tissue (such as the brain).

The term 'μl' or 'μm' hereinafter refers to the unit micro liters.

The term 'capsule' or 'container' hereinafter refers to a container configured to contain a flowable substance. The term flowable refers hereinafter to any liquid, gas, aerosol, powder and any combination thereof. It should be emphasized that the term capsule can also refer to a predetermined volume within the same in which a flowable substance is placed. In other words, the predetermined volume is sized and shaped to enclose a predetermined volume of said substance.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon, xenon and any combination thereof. Devices charged by hand will typically use air as the carrier gas.

The term 'channel' hereinafter refers to a passageway allowing passage of a fluid through at least a portion of a mixing mechanism. The channel can be disposed within a portion of the mixing mechanism, forming a closed bore; it can be on an exterior of a portion of the mixing mechanism, forming a groove on the portion of the mixing mechanism, and any combination thereof.

The term 'about' refers hereinafter to a range of 25% below or above the referred value.

The term 'biologic' or 'biologic response modifier' hereinafter refers to material manufactured in or extracted from biological sources such as a genetically engineered protein derived from human genes, or a biologically effective combination of such proteins.

All pressures herein are gauge pressures, relative to atmospheric pressure. Pressure units will be written herein using the standard abbreviation for "gauge', namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the activation time and reflects the time for the device to reconfigure from the active configuration to the inactive configuration or vice versa.

The term 'valve' refers hereinafter to a device with an inactive configuration and an active configuration. In the inactive configuration, a valve prevents passage of fluid from a container, whereas in the active configuration, the fluid can exit the container. As used herein, the term valve includes both a mechanical valve and a frangible membrane which, when whole, seals a container but which, when broken, allows passage of fluid from the container.

The terms 'the device', 'the present device', 'the SipNose device' and 'SipNose' will be used interchangeably to refer to the device of the present invention.

In all of the embodiments of the device shown hereinbelow, identical numbers refer to identical functions.

All figures shown herein are illustrative and none is to scale.

The present invention teaches a device for delivering a predetermined amount of a substance, preferably comprising a medication or combination of medications, into a body orifice of a subject, preferably at least one nasal cavity, although the orifice can comprise any of the body's natural orifices, including a nostril, the mouth, the ear, the throat, the urethra, the vagina, the rectum and any combination thereof.

The device comprises a delivery mechanism. The medicament can be supplied to the device by means of an insertable medicament capsule configured to contain the medicament; at least one integral medicament storage area configured to contain the medicament, an injection port in communication with an integral medicament holding area so that medicament can be injected into the device, and any combination thereof. The device can apply a broad range of drugs and materials to a nasal cavity for local effect, deliver a broad range of drugs and materials through the nasal cavity to the systemic circulation, deliver a broad range of drugs and materials through the nasal cavity to the central nervous system (CNS) (the brain, spinal cord and associated nerves), and any combination thereof.

In some embodiments, the device can deliver a drug such as, but not limited to, Topiramate, Phentamine, GLP-1 and GLP-1 analogs and derivatives and any combination thereof to the nasal passages, preferably for the treatment of at least one of obesity and binge eating disorder. In variants of these embodiments, intranasal delivery of Topiramate, with or without Phentamine, GLP-1 and GLP-1 analogs, provides a treatment when the urge to binge occurs.

Other indications for Topiramate include as an anticonvulsant, treatment of epilepsy, treatment of Lennox-Gastaut syndrome and prevention of migraine.

Topiramate has been in commercial use since 1996 (generic since 2006. It works by affecting the brain and helps to reduce seizure activity, prevent migraine headaches from occurring and was approved by the FDA in combination with phentermine for weight loss. Its immediate delivery to the central nervous system and potential to be effective in low doses to reduce side effects such as somnolence, fatigue and dizziness in over 10% of patients is of great importance, which fits perfectly the intranasal route.

In some embodiments, the device can deliver a drug such as, but not limited to, Midazolam, typically for control of epilepsy and for sedation.

In some embodiments, the device can deliver a drug such as, but not limited to, *cannabis*, or a *cannabis* derivative such as, but not limited to, cannabinoids, Cannabidiol and any combination thereof. *Cannabis* and its derivatives can be used for pain management, especially cancer pain; and for treatment of schizophrenia; eating disorders such as obesity and binge eating disorders; dementia; diabetes; nausea; obsessive compulsive disorder, anxiety, depression. Psychosis and bipolar disorder, Addiction, immune diseases such as multiple sclerosis, arthritis, cancer, obesity, diabetes: Alzheimer's disease; epilepsy, Parkinson's disease; Huntington's disease; graft vs. host disease (GVHD); traumatic brain injury; and inflammation. Other studies indicate that it can be used for neuroprotection and neurogenesis.

*Cannabis* has a range of therapeutic benefits including as an analgesic for pain, antispasm for multiple sclerosis, anticonvulsive for epilepsy, nausea suppressant for chemotherapy, and appetite stimulant for wasting in HIV/AIDS patients.

There are a variety of ways to consume *cannabis*. The three most common methods are inhalation via smoking, inhalation via vaporization (vaping), and ingestion of edible products. The mode of administration can impact the onset, intensity, and duration of psychoactive effects, effects on organ systems, and the addictive potential and negative consequences associated with use. Although most medical *cannabis* users report trying multiple modes, smoking has been the dominant mode of delivery. With smoked *cannabis*, the psychoactive effects and peak THC blood levels occur in minutes, and the effects last approximately one to four hours.

Smoking users report several advantages for smoked modes of delivery, including greater enjoyment, convenience and ease of use, more immediate and effective relief of symptoms, greater control over dosage, lower dose for desired effect, and whole-body euphoria.

Despite the appeal among users, smoked modes of delivery have several disadvantages. These include social disapproval for smoking and smell, as well as concerns about increased health risks from smoke inhalation. Studies have consistently shown that *cannabis* smokers report a higher frequency of cough and sputum production, wheezing, and bronchitis compared with non-smokers, as a result of airway inflammation and infection. In addition, some literature reports the presence of lung cancer among heavy *cannabis* smokers, as well as bullous lung disease and emphysema. Evidence on the long-term respiratory effects of *cannabis* smoking is complicated by the co-morbidity of *cannabis* and cigarette smoking (including mixing tobacco and *cannabis*), as well as time lag in the onset of chronic respiratory diseases. Nevertheless, chronic smoke inhalation from *cannabis* smoke is likely to reduce respiratory health. Furthermore, smoking allows the user to more effectively self-titrate the dose and desired level of intoxication but portends inhalation of carcinogenic materials and adverse effects on respiratory health Vaping, defined as "using electricity to heat *cannabis* products so that the *cannabis* resin is released as a vapor that is inhaled." has a similar onset, peak, and duration as smoking and produces a similar "high" feeling.

Vaporization provides delivery characteristics that are similar to smoking, with respect to the time to onset and some sensory effects. However, vaporizers do not heat marijuana to the point of combustion and, therefore, expose users to significantly lower levels of toxicants that are only present in smoke. Chemical analysis, self-reported data, and spirometry testing demonstrate that vaporization of *cannabis* is less harmful and reduces respiratory effects compared to smoking. Users perceive vaporization similar to smoking in terms of ease of dose titration and fast onset of action, but with fewer side effects. Vaporizing has also been reported to taste better, has no smoke smell, and is more discreet. Therefore, users may prefer vaping instead of smoking as their primary method of administration. These "positive" aspects of vaping and the perception of reduced respiratory system harm could conceivably lead to more frequent consumption or earlier initiation of *cannabis*, and a concomitant increased risk of developing problematic use or addiction. Common disadvantages associated with vaporizers include greater inconvenience, the difficulty of using vaporizers, and the higher cost.

The long-term health consequences of regularly vaping *cannabis* are not known but vaping may minimize impact on respiratory function compared with smoking *cannabis* by reducing the inhalation of combustible smoke and its carcinogenic constituents.

Alternative modes of delivery have the potential to reduce the negative respiratory health risks associated with smoking *cannabis*. *Cannabis* can be consumed orally in edibles and oro-mucosally in sprays or tinctures. Eating *cannabis* (edibles) produces a different pharmacokinetic profile than smoking or vaping. Onset of the effect is delayed to approximately 30 to 60 minutes, peak blood levels of THC occur approximately three hours later, and the effects can last over six hours.

Edibles also allow the user to avoid inhaling smoke; however, it is harder to titrate the intoxicating effects due to the delayed and variable onset of effects. Consequently edibles have recently been tied to *cannabis* "overdose" following ingestion of additional doses because of the misperception that the initial dose had not produced the desired effect. Availability of edibles has also been associated with increased rates of accidental pediatric ingestion of *cannabis* and associated adverse effects.

Oral modes of delivery are perceived by users as healthier than smoking, less obvious than smoking since there is no smell, more convenient, and to have longer lasting effects. On the other hand, medical *cannabis* users have reported that edibles do not provide the same euphoria, are more expensive, difficult to titrate dose and prepare, and have a slow onset of effect.

Advantages of delivery of the above drugs via the Sip-Nose device include: the system is fast acting, with a fast clearance. It provides high efficacy with low doses and has a high efficiency with low side effects. Effectively, this method of treatment functions as an "acute use" treatment rather than a "chronic use" treatment.

In addition, at least one odorant (smellable molecule) can be provided. Delivery of the drug can be combined with delivery of the at least one odorant in order to:
Reduce appetite
Create a good patient experience for better compliance or both.
Other functions of an odorant, in addition to or in place of the above, are given hereinbelow.

An odorant for assistance in the treatment of obesity and binge eating disorder can include, but is not limited to: grapefruit, lemon, vanilla, green apple, banana, peppermint, fennel, patchouli, bergamot and any combination thereof.

The odorant can be:
stored in the compressed gas
stored in the drug formulation
stored in a device material such as a nose piece material and released therefrom either continuously or at the time of delivery and
any combination thereof.

The odorant can be, as disclosed below, a natural smell molecule, a synthetic smell molecule and any combination thereof.

The medicament can comprise a dry powder, a liquid formulation, or a mixture thereof. As disclosed below, any combination of components of the medicament can be stored in any combination of compartments in a container or capsule.

In some embodiments, *Cannabis* based therapeutics can be delivered, for:
Pain management: chronic pain; neuropathic pain; cancer pain, breakthrough pain, migraines and any combination thereof and
Epilepsy
as a chronic treatment for prevention/reduction of epileptic seizure occurrence and strength
as rescue treatment when seizures occur and
any combination thereof.

The *Cannabis* based therapeutic can be a *Cannabis* based extract, a synthetic compound that includes active ingredients, a derivative of the above. Non-limiting examples include: tetrahydrocannabinol (THC); cannabinoids, such as cannabidiol (CBD), cannabinol (CBN), and tetrahydrocannabivarin (THCV).

The *Cannabis* based therapeutic can be a pure compound or mix of compounds.

It can be in a liquid oil formulation, in an oil in water formulation, as a dry formulation, mixed with a liquid component, and any combination thereof. Some combinations would be storable in separate compartments in a capsule, as disclosed below.

In some embodiments, Naloxone can be delivered for emergency treatment of drug overdose. Typically, the Naloxone would be stored as a liquid formulation or a dry powder formulation.

In some embodiments, treatments for brain cancers such as Glioblastoma, secondary tumor, brain stem cancer and any combination thereof can be treated via delivery to the brain of medicaments such as, but not limited to, a chemotherapy drug, a biologic, an antibody and any combination thereof. Treatment of brain cancer can be:
a direct treatment of the brain cancer in order to reduce the tumor
a treatment for a patient with a non-brain cancer with the SipNose device, as a prevention of a possible metastasis of the cancer to the brain and
a combination thereof.

If metastasis is to be prevented, the treatment can be by delivery to the brain with the SipNose device of a drug or drugs already used systemically, the delivery to the brain can be of a drug or drugs not already used systemically, and any combination thereof.

Such brain cancer treatment comprises a chronic therapy, to increase the efficacy and reduce the side effects of a long-term treatment.

In some embodiments, vaccination can be provided via the nasal route. Non-limiting examples of vaccines include: an anthrax vaccine, a Hepatitis B vaccine, a Tetanus vaccine, an Influenza vaccine and any combination thereof.

In some embodiments, the treatment can be enhancement of the immune system as a method of treating CNS disorders such as, but not limited to, Alzheimer's disease, Parkinson's disease and any combination thereof, as there is evidence that immune system enhancement can enhance the body's ability to repair the damage caused by the disorder. One proposed mechanism for the means by which enhancement of the immune system works to treat CNS disorders such as Alzheimer's disease and Parkinson's disease is by enhancing the production of autoimmune cells which are targeted to destroy the pathology causing the disorder. Other drugs which can be applied include, but are not limited to, a pharmaceutical, a natural compound, a biologic, a hormone, a peptide, a protein, a virus, a cell, a stem cell and any combination thereof.

However, it should be emphasized that the device can be provided alone as well as in combination with a capsule.

In some cases the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucous membrane by means of a mucoadhesive agent, a permeability enhancer agent, a particulate formulation in the nano-particle or macro-particle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucous membrane to the active agent, for the enhancement of delivery of the active agent to and through the mucous membrane.

In contrast to prior-art nasal delivery devices and technologies, the devices of the present invention can produce a fine aerosol in the nasal cavity or other desired body orifice at the target area and at the location of the target tissue instead of producing the aerosol only immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time to activate.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose.

In contrast, in the present device, the pre-aerosolized mixture of gas and substance exits the device with a significant driving force as a mixture of aerosol and pre-aerosolized material (fluid or powder). When the pre-aerosolized material hits the walls of the nasal passages, it "explodes" into a fine aerosol that is capable of being driven by the pressure deep into the nasal passages to deposit in the desired region.

FIGS. 1A-D illustrate capsules of prior art intended to deliver medicaments to the nasal passages. FIG. 1A illustrates the LMA MAD nasal atomizer from Wolfe Tory, FIG. 1B illustrates a typical nasal pump, FIG. 1C illustrates a Simply Saline nasal spray, and FIG. 1D illustrates the Optinose™ breath powered delivery device.

Typical prior art devices release aerosolized medicament. However, ah have severe limitations.

The LMA MAD nasal atomizer (FIG. 1A) comprises a syringe, so the dose size can be quite accurate, if the user is careful. However, the delivery pressure is provided by the user depressing a plunger, so that control of delivery speed and delivery pressure (and the droplet size) depend on how hard the user depresses the plunger, making these parameters hard to control. Furthermore, syringe plungers are subject to stick-slip behavior, especially at the start of depression, making the delivery parameter harder to control accurately.

Devices such as nasal pumps (FIG. 1B) typically do not provide a fixed dose per activation, as the delivery energy is provided by pressure exerted by a user during activation. Typically, there is a wide dispersion in the size of the droplets produced following user activation, making it difficult to accurately target the medicament to a desired location.

The Simply Saline Nasal Mist (FIG. 1C) comprises a pressurized container. A button is pressed to release a portion of the contents. Each activation reduces the pressure inside the container, thereby reducing the velocity and pressure of delivery and altering the droplet size. The length of activation time depends on the time the button remains depressed, so that there is little control of the amount delivered.

The Optinose breath powered delivery device (FIG. 1D) is breath-powered. It uses a capsule containing a single dose of the medicament, so dose size is well-controlled. However, delivery speed and delivery pressure (and the particulates dispersion) depend on how hard the user exhales into the device and how long the user continues to exhale. Furthermore, exhalation pressures are typically higher at the start of exhalation than at the end, so the delivery parameters will vary during delivery.

Unlike the device of the present invention, none of the prior-art devices provide accurate control of all of the delivery parameters, which include dose volume, carrier volume, pressure, and delivery velocity.

A further advantage of the device of the present invention (the SipNose device) is that, unlike the prior art devices, it can be configured to accurately deliver large volumes (>100 ul) at high pressure, such that the high-velocity aerosol can be as reliably and reproducibly produced for large volumes as for small.

FIG. 2 illustrates locations for deposition of substances entering the nostrils. Typical locations are (a) deposition in the lungs after passage through the lower turbinates (240), thereby enabling transfer of the substance across the walls of the alveoli of the lungs; (b) deposition in the mucous membranes lining the nasal passages, especially the lower (240), and middle (230) turbinates, facilitating transfer of the substance to the blood; and (c) deposition in the olfactory epithelium mucous membranes of the upper turbinates (220) facilitating transfer, via the thin ethmoid bone (not shown) to the brain through the olfactory nerve endings (250) substance, typically as an aerosol, with the mixture of gas and substance entering the body orifice via the delivery end. Typically, discharge (delivery) time is less than about 500 ms.

The embodiments disclosed below disclose non-limiting examples of devices and methods for providing the predetermined volume of gas at the predetermined pressure.

Figure 3:
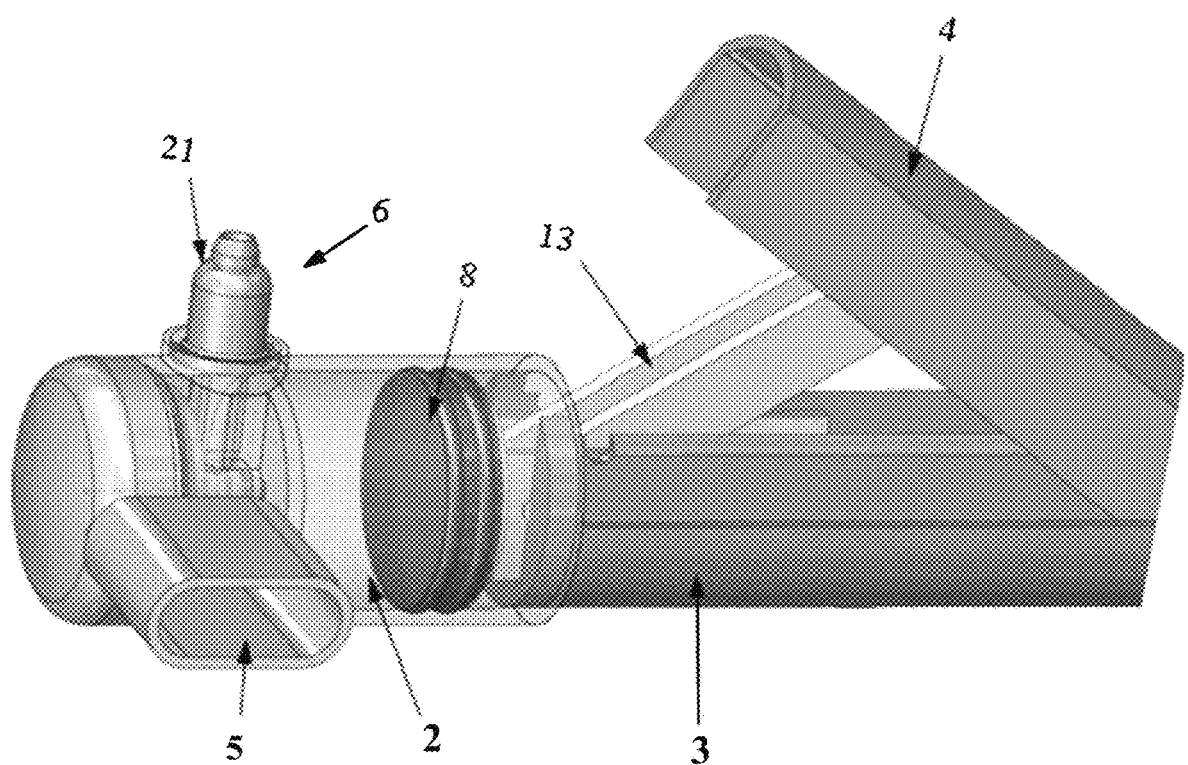
FIG. 3 illustrates an embodiment of a device of the present invention.

FIG. 3 shows an exemplary embodiment of the device. In the embodiment of FIG. 3, a piston (8) is used to compress the gas. The piston is moved by a lever (4) attached to the piston (8) by a rotatable connector (13). The piston (8) fits air-tightly and slideably in the air chamber (2). The lever (4) is rotatably attached to the handle (3) at its proximal end such that the distal end of the lever (4) can be pulled away from the handle (3) to retract the piston (8) toward the proximal end of the device and pull air into the air chamber (2) and the distal end of the lever (4) can be pushed toward from the handle (3) to extend the piston (8) toward the distal end of the device and compress the gas. In use, the mouthpiece (5) is placed in the mouth and the nosepiece (6) is placed in a nostril. Inhaling on the mouthpiece (5) activates the device (mechanism not shown), releasing the compressed gas from the air chamber (2), from whence it passes through the substance capsule (21) and exits the device through the distal end of the nosepiece (6).

The embodiments disclosed in FIG. 3 are typically configurable into four states: (a) a non-activated state where the valve is in its inactive configuration, the chamber contains non-pressurized gas, and the portion of the chamber in fluid connection with the valve is at a minimum, (b) a pre-activated state where the valve is in its inactive configuration, the chamber contains non-pressurized gas, and the portion of the chamber in fluid connection with the valve is at a maximum, in this stage the tip to be entered to the body orifice (the delivery end) can be under "vacuum" conditions or not, (c) a loaded configuration where the chamber contains a predetermined amount of pressurized gas and the valve is in its inactive configuration, and (d) an activated state where the valve is in its active configuration. Typically, the activated state discharges the device, with the mixture of gas and substance released from the device and thus able to enter a body cavity via the delivery end.

The characteristics of the aerosol, namely its size, shape and velocity, depend on the speed of exit of the gas from the chamber, the volume of air delivered, the characteristics of the delivery orifice and the activation time. The speed of exit of the gas from the chamber and the volume of air delivered depend on the pressure of the gas in the chamber in the loaded state, on the volume of the chamber in the loaded state, and on the characteristics of the fluid connection between the chamber and the delivery orifice. The less change there is in these characteristics during an activation and between activations, the more reliable and the more reproducible the device will be. Therefore, in controlling the characteristics of the fluid connection, the time taken to open the valve needs to be taken into consideration. In devices of the current invention, valve opening times are both reproducible and short and are not in any way dependent on the user, so that the delivery comprises a short, reproducible, high velocity pulse of the gas.

For some embodiments of the device with a mechanical valve, the non-activated state and the loaded state appear identical; they differ in that, in the loaded state the chamber contains pressurized gas whereas, in the non-activated state, the chamber does not contain pressurized gas.

In some embodiments, including embodiments intended for use in emergencies or daily home use, the device is a single-use device with only two states, a loaded state and an activated state. The device is provided in the loaded state; activation of a trigger mechanism discharges the gas and substance. In such single-use embodiments, typically the valve is not reconfigurable from an active configuration to an inactive configuration.

In some embodiments of the device, the valve comprises, instead of a mechanical valve, a frangible membrane. In such embodiments, activation comprises rupture of the membrane; in the inactive configuration, the membrane is whole, activation comprises rupturing the membrane and, in the active configuration, the membrane has ruptured. Preferably, substantially all of an orifice covered by the membrane is uncovered at the time of rupture.

Typically, embodiments comprising a frangible membrane are single use only.

The trigger mechanism can comprise any known method of rupturing a membrane. A trigger mechanism can comprise, for non-limiting example, a mechanism to pierce the membrane, application of pressure to the sides of the membrane either manually or mechanically until the membrane ruptures, application of pressure to a face of the membrane either manually or mechanically until the membrane ruptures, and any combination thereof. Another mechanism for single activation is by opening of a tight closure area by means of movement of the closing part from the gate area, thus allowing the pressurized air to flow through the open gate. The opening allows the release of all pressurized air, so the device can not be re-used.

In some embodiments, such as, but not limited to, embodiments where the valve comprises a frangible membrane or a single valve opening, the valve opening time (such as membrane rupture time) dt can be shorter, sometimes significantly shorter, than the time to deliver the medicament $dt_{deliver}$.

In other embodiments, the device is provided in the pre-activated state. The user transforms the device into the loaded state, pressurizing the gas, and activates the trigger mechanism to discharge the gas and substance.

Capsules can be single-compartment or multi-compartment. Single-compartment capsules can comprise a flexible silicone tube, preferably sealed at both ends.

Multi-compartment capsules can contain different components of a substance in the different compartments; at least one compartment can contain a carrier gas, and any combination thereof.

In some embodiments, there is a single capsule for the carrier gas and the substance. Some embodiments have separate capsules for substance and gas.

Some embodiments have the gas held in a gas holding chamber. The gas holding chamber can be filled at the time of manufacture or can be filled to the predetermined pressure by a charging mechanism.

Some embodiments have the substance held in a holding chamber. The holding chamber can be filled at the time of manufacture or can be filled by a filling mechanism such as, but not limited to, a syringe.

It should be emphasized that the present invention refers to both one compartment capsules as well as multi-compartment capsules.

FIG. 4A-E shows exemplary embodiments of multi-compartment capsules.

In multi-compartment capsules, walls divide the capsule into compartments. The compartments can have approximately the same volume or different volumes, and the same thickness or different thicknesses; if circular, they can have the same diameter or different diameters. They can have the same area at the end faces, or different areas.

The compartments, taken together, can form a large fraction of the volume of the capsule, or they can form a small fraction of the volume of the capsule.

Compartment walls can be equally spaced, either angularly or linearly, or they can be unequally spaced. Spacings can be arbitrary, they can be regular, they can follow a pattern, and any combination thereof.

Compartments can be near the edge of the capsule or at other positions within the capsule.

Before use, the compartments are preferably hermetically sealed to prevent mixing of the substances contained therein.

Compartment walls can be substantially similar in shape to the capsule walls (for non-limiting example, lenticular walls within a lenticular capsule) or at least one of the compartments' walls' shape differs from the shape of the cross-section of the capsule. (For non-limiting example, a lenticular wall within a circular capsule.)

Compartment walls can be non-frangible or frangible. Frangible walls permit mixing or reaction of the contents of adjacent compartments before the substances leave the compartments.

Compartments can, but need not, have a frangible membrane at least one end.

Any compartments can contain one substance or a mixture of substances; any two compartments can contain the same substance or mixture thereof, or different substances or mixtures thereof.

The material of any combination of capsule walls and compartment walls can be rigid, semi-flexible, flexible and any combination thereof. Flexible or semi-flexible compartment or capsule walls can reduce dead space—regions of low gas flow—in the air path during activation.

Figure 4A:
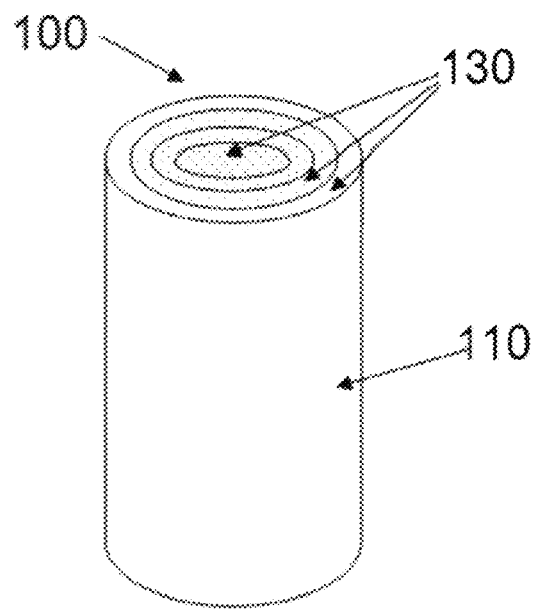
FIGS. 4A-E illustrate embodiments of multi-compartment capsules.

In the embodiment shown in FIG. 4A, the compartments (130) are coaxially disposed within the outer tegument (110), with the compartments nested within one another. The central compartment forms a cylinder and the remaining compartments, three in the exemplary embodiment of FIG. 4A, each forming an annulus of a cylinder. Nested compartments need not be coaxial.

Figure 4B:
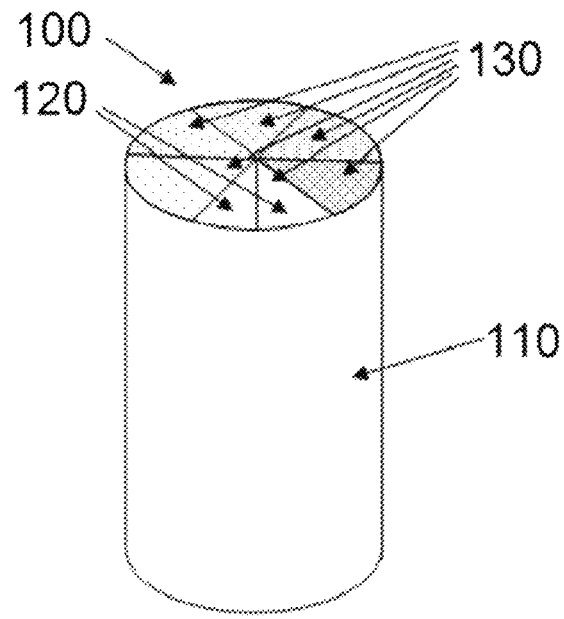

In the embodiment schematically illustrated in FIG. 4B, the capsule (100) comprises an outer tegument (110) enclosing n angularly disposed compartments (130) separated by walls (120), where n is less than about 10. In the embodiment shown in FIG. 4B, n is e.g., six.

Figure 4C:
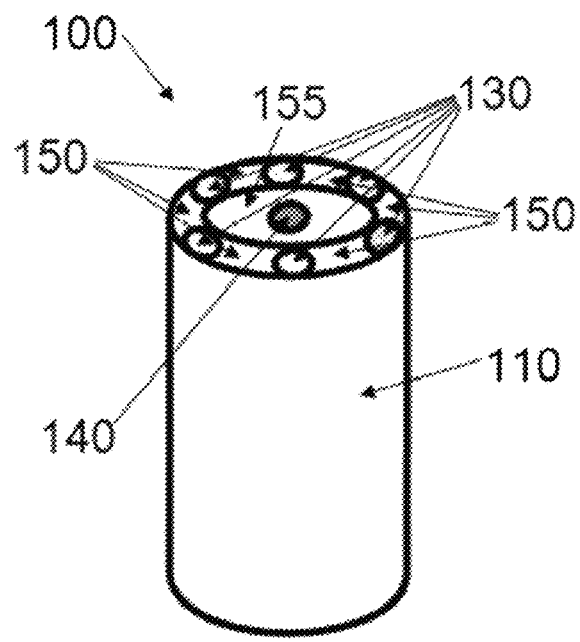

In the embodiment schematically illustrated in FIG. 4C, the capsule (100) comprises an outer tegument (110) enclosing six angularly disposed cylindrical compartments near the edge of the capsule (130), a central compartment (140), and auxiliary compartments (150, 155), for a total of 14 compartments.

In practice, the embodiment illustrated in FIG. 4C will have no more than about 20 compartments.

In some embodiments, there is no central compartment (140).

In the exemplary embodiment shown, the auxiliary compartments are hollow, containing a substance. In other embodiments, at least one of the auxiliary compartments (150, 155) is comprised of solid material, thereby forming part of the structure of the capsule.

In preferred embodiments, the central compartment (140) and the central auxiliary compartment (155) are solid, forming a solid central core for the structure. The remaining compartments (130, 150) comprise substance, where, in preferred embodiments, the compartments (130) contain a substance such as a medicament and the auxiliary compartments (150) contain a propellant, preferably compressed gas.

Figure 4D:
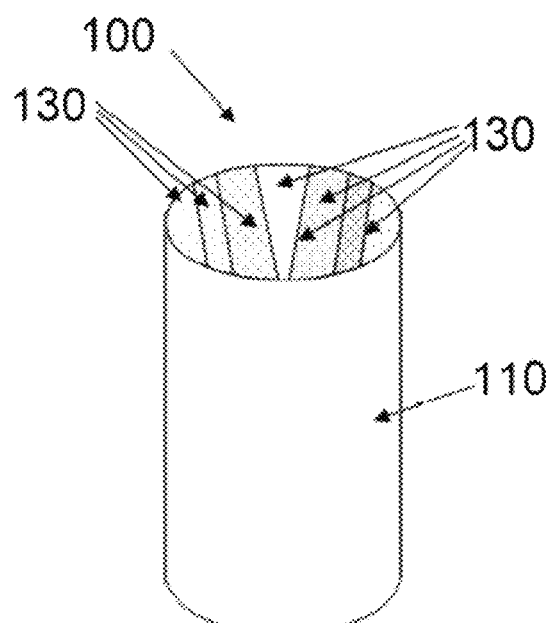

In the exemplary embodiment shown in FIG. 4D, the compartments (130) form slices within the outer tegument (110). In the exemplary embodiment of FIG. 4D, some of the slices have parallel sides, while the central slice is wedge-shaped; in other embodiments, all of slices have substantially parallel sides. In yet other embodiments, a plurality of slices are wedge-shaped. Slice-type capsules can have up to about 10 compartments.

Figure 4E:
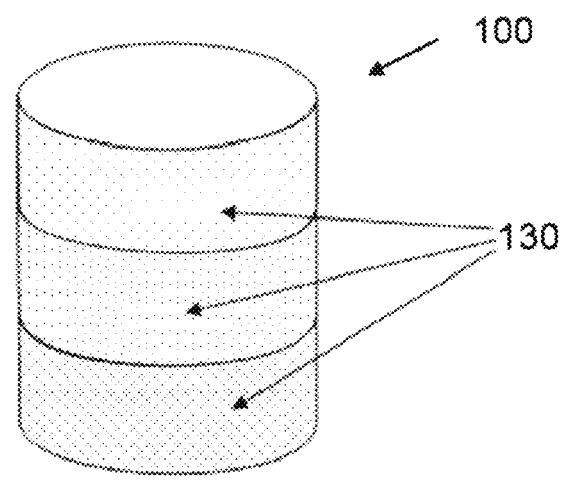

In the exemplary embodiment shown in FIG. 4E, the compartments (130) are arranged longitudinally, with the walls between the segments being frangible. Any number of such compartments can be used and the lengths of the compartments can differ.

These embodiments are merely exemplary; any combination of the above arrangements can be used.

In the exemplary embodiments shown, the walls separating the compartments are planar. In other embodiments, the walls can form a curve, either regular or irregularly shaped.

The main longitudinal axis of at least one of the compartments can be parallel to the main longitudinal axis of the capsule, it can be spirally disposed it can be at an angle to the main longitudinal axis of the capsule, and any combination thereof.

The main longitudinal axes of the compartments can be straight, they can form regular curve, they can form irregular curves, and any combination thereof. For any pair of compartments, the main longitudinal axes can be the same or they can be different.

In most embodiments, at least part of the upstream closure surface (not shown) and the downstream closure surface (not shown) of the capsule are frangible or otherwise removable, such that, when broken or otherwise removed, the medications can be delivered to the desired deposition site. In a variant of these embodiments, different portions at least one closure surface have different breaking strengths, such that the different portions can be broken at different times during delivery of the medication, enabling either differential mixing of medical formulations in different compartments or differential delivery of the medications in at least two of the compartments.

In some embodiments, at least part of the side surface of the capsule is frangible, enabling yet another mixing path or delivery path.

Capsules can be cylindrical with circular cross-section, as shown, cylindrical with oval, elliptical, lenticular, or polygonal cross-section, with the polygon having at least three sides and not more than about 20 sides. The polygon can be a regular or irregular.

Capsules can be spherical, elliptical, ovoid, pillow-shaped, football-shaped, stellate and any combination thereof. Capsules can form regular or irregular shapes.

Compartments can have substantially constant cross-section through the device or the cross-section can vary in area, in shape, or in any combination thereof.

Figure 5:
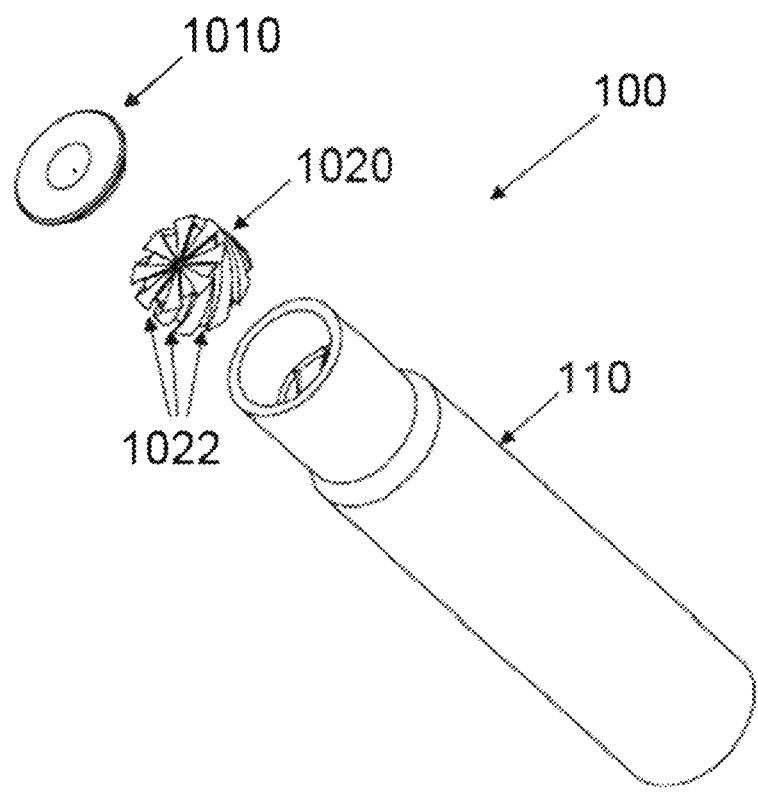
FIG. 5 shows a schematic of an exploded view of an exemplary embodiment of a mixing chamber in a capsule.

FIG. 5 shows a schematic of an exploded view of an exemplary embodiment of a mixing chamber in a capsule, the part of a capsule configured to mix components in a composition. In this exemplary embodiment, the tegument (110) of the capsule and the upstream closure surface (1010) of the capsule are shown. Also shown is a mixing mechanism (1020), in this case, a single-section mechanism. The substance compartments are not shown.

In this exemplary embodiment, the mixing mechanism (1020) comprises spirally-disposed air channels (1022) at the periphery of the mixing mechanism (1020). The central part of the mixing mechanism (1020) is solid, forcing the carrier gas and the substances to pass through the channels (1022). By narrowing the channel through which the gas passes and by changing the direction of the gas flow, mixing of the substances is enhanced. The mixing mechanism (1020) fits within the tegument (110) of the capsule (100) and mixing occurs within the capsule (100).

In some embodiments, a single channel is used. This can have a cross-section which is annular, circular, polygonal, lenticular, pie-shaped irregular, or any combination thereof. The channel main longitudinal axis can pass through any part of the capsule. Non-limiting examples include a circular cross-section with main longitudinal axis at the capsule center, and an annular cross-section at the periphery of the capsule, with main longitudinal axis at the capsule center.

In some embodiments, the capsule comprises two units, one comprising at least one substance and one comprising the mixing mechanism, such that the substances exit the compartments and are then mixed in the mixing mechanism.

In other embodiments, the mixing mechanism (1020) comprises channels disposed throughout its cross-section.

Channels can be arbitrarily arranged across a cross-section, regularly arranged across a cross-section, or irregularly arranged across a cross-section.

Channels can be linearly disposed, parallel to the main longitudinal axis of the capsule; or linear and disposed at an angle to the main longitudinal axis of the capsule.

The main longitudinal axis of at least one channel can be curved with respect to the main longitudinal axis of the mixing mechanism, with respect to an axis perpendicular to the main longitudinal axes, or any combination thereof.

Any combination of the above channel shapes can be used.

The shape of a channel cross-section can be substantially the same along the length of the channel, the shape can change along the length of the channel, the size of the cross-section can change along the length of the channel, and any combination thereof.

Shapes of the cross-sections of the channels can vary in the same manner along the length of the channel, or they can vary in different manners.

Shapes of the cross-sections of the channels can be the same for all the channels, or the shapes of the cross-sections of at least two channels can be different.

Sizes of the cross-sections of the channels can vary in the same manner along the length of the channel, or they can vary in different manners.

Sizes of the cross-sections of the channels can be the same for all the channels, or the sizes of the cross-sections of at least two channels can be different.

In some embodiments, the mixing mechanism (1020) comprises a plurality of longitudinal sections, with the sections having fluidly connected channels, but the channels are differently disposed longitudinally. For non-limiting example, a two-section device can have spirally disposed channels with left-handed spirals in the first section and right-banded spirals in the second section.

In some embodiments, there are different numbers of channels in the two sections. In other embodiments, there are the same number of channels in the two sections.

In other multi-section mixing mechanisms (1020), sections comprising channels are fluidly connected by substantially channel-free regions.

Mixing mechanisms can comprise between 1 and 10 regions. Individual regions can have any of the channel dispositions described hereinabove.

In some embodiments, mixing can be done by an integral mixing mechanism, either a single-section or a multi-section device. In other embodiments, mixing can be done by disposing a plurality of single-section mechanisms end-to-end, either abutting each other or with spacers to provide channel-free regions.

During the process of mixing, the first and second flowable substances can be mechanically mixed with each other and with the air or other gas, they can be reacted with each other, and any combination thereof.

In some embodiments, reaction of at least one flowable substance can be enhanced by a catalyst deposited on or part of the walls of the mixing region.

Criteria of the capsule, whether single-compartment or multi-compartment, can be optimized to include: ensuring that a single dose of the substance is delivered in its entirety, ensuring that the single dose contains the predetermined amount of the substance, ensuring that the dose is delivered to the desired region of the nose, and ensuring that delivery of the dose causes the minimum possible discomfort to the patient. Any combination of these criteria can be optimized for each particular combination giving rise to a different embodiment of the capsule.

The capsule can also be optimized for ease of insertion into a delivery device, for ease of removal from a delivery device, for stability of the contents during storage, for resistance of the capsule materials to environmental degradation, for resistance to undesired fracture, for reliability of use, for completeness of mixing, for completeness of reaction, and any combination thereof.

In some embodiments, the capsule comprises a filter configured to remove from the air at least one selected from a group consisting of particles, particulates, bacteria, viruses, moisture, and undesired gases before the air contacts the user. Such a filter, by preventing unpleasant odors or tastes from reaching the user and by preventing particles or particulates from reaching the user, can make the experience of using the device much more pleasant for the user and much safer. By removing bacteria and viruses, infection of the user can be prevented.

In some embodiments, the capsule contains only a single dose of the substance, the capsule being replaced after each use. In other embodiments, the capsule contains multiple doses of the substance, preferably packed separately, so that the dose is fresh for each use.

During dispensing of the substance, the gas passing through the capsule entrains the substances contained within the compartments such that the substances have a predetermined distribution within the dispensed mixture, where the predetermined distribution can be a homogeneous distribution or a heterogeneous distribution. Heterogeneous distributions can be: an arbitrary distribution, a distribution in which the dispersion of the at least one substance within the mixture follows a predetermined pattern, and any combination thereof.

According to another embodiment of the present invention, movement of air into the chamber during transformation of the device into said pre-activated state creates a vacuum in the region near or in the capsule.

FIGS. 6-7 show exemplary embodiments of the loading and triggering region of embodiments of devices with mechanical triggering mechanisms, all of which are configured to open fully, quickly and reproducibly, with the time over which the valve opens being reproducible, independent of how the user may operate the device. For example, in the suction devices described herein, a weak suction will induce the same full opening over the same time period as a strong suction, and, in the mechanical devices disclosed herein a slow activation of the triggering mechanism will induce the same full opening over the same time period as a rapid activation of the triggering mechanism.

In some embodiments, the loading region of the device comprises at least one filter to remove from the air (or other gas) at least one selected from a group consisting of particles, particulates, bacteria, viruses, moisture, and undesired gases before the air contacts the user.

Preferably, the air or gas is filtered on entrance to the air chamber from the outer environment (the room, the surrounding area). Alternatively or additionally, air can be filtered on exit from the air chamber, while within the loading air chamber, and any combination thereof.

FIG. 6A-D shows a preferred embodiment of the loading portion of the device (1000) with a pinch triggering mechanism. FIG. 6A shows a side view of the device, FIG. 6B shows a cross-section, taken along the line AA in FIG. 6A, FIG. 6C shows an exploded view, and FIG. 6D shows a perspective view.

The device comprises a hollow upstream portion (1881) fluid-tightly connected to a hollow downstream portion (1889). In this embodiment, the activation mechanism (1880) comprises a cup-shaped insert (1884) fitting snugly and fluid-tightly within the hollow interior of the device. The outer rim of the insert (1884) is preferably fixed to the outer wall of the activation mechanism (1880), with its inner rim (1885) able to slide on an inner wall (1886), preferably tubular, of the activation mechanism (1880). In the activation mechanism's (1880) closed position, a stop (1882) is firmly held by the inner rim (1885) of the insert.

The inner wall of the activation mechanism (1880) comprises a throughgoing bore (1883). In some variants of this embodiment, a flexible tube (1888) is fluid-tightly fixed to the wall (1886) such that there is flexible tubing in at least the portion of the wall abutting the stop (1882). In other variants of this embodiment, the flexible tube (1888) passes through the bore (1883).

In preferred variants of this embodiment of an activation mechanism, in the closed position, the stop (1882) fits into and sits in a hole in the inner wall (1886). In other variants, the stop (1882) fits into and sits in a depression in the inner wall (1886).

When the activation mechanism (1880) is in the closed position, the flexible tube (1888) is pinched between the stop (1882) and the inner side of the throughgoing bore (1883).

When the activation mechanism (1880) is activated, the insert (1884) slides up along the wall, releasing the stop (1882) so that the pinched region in the flexible tube (1888) is released, thereby releasing the pressurized gas and dispensing the substance.

In the embodiment shown in FIG. 6, the activation mechanism can be activated either by sucking on the suction mechanism (1810), creating a partial vacuum above the cup-shaped insert (1884) and pulling it upward, thereby releasing the stop (1882), or by pressing the pressable lever (1870). Pressing the pressable lever (1870) forces it inward so that the ramp portion (1782) of the pressable lever pushes the cup-shaped insert (1884) upward, thereby releasing the stop (1882), releasing the pressurized gas and dispensing the substance.

In some embodiments, flexible filling material such as, but not limited to, flexible tubing, can be placed within the region of the device (not shown) containing the substance to be delivered in order to reduce dead space within the device. Reducing dead space will not affect the characteristics of the aerosol formed after release, but it will decrease pressure loss and increase air speed within the device, thereby substantially reducing residual substance remaining within the device after completion of activation, either within the capsule or adhering to the interior walls of the device, e.g., within the nozzle. It is well known in the art that residual material within a delivery device can be released on subsequent uses of the device and that the amount of such residual material released during a given use of a device is extremely variable. Therefore, minimizing residual substance within the device will increase the accuracy and reproducibility of delivery, thereby increasing its repeatability and reliability, both by maximizing the fraction of the substance actually delivered from the current capsule and by minimizing the amount of residual substance on the walls of the device.

It should be noted that the capsules (disclosed hereinbelow) are designed so as to avoid residual volume within the capsule itself, since, even in the case of a single dose or disposable capsule there are safety issues involved in disposing of capsules containing residual amounts of hazardous drugs or other hazardous component in the composition.

Other trigger mechanisms include, but are not limited to, a releasable catch, a pressable button a detectable predetermined sound pattern, a detectable predetermined light pattern, a moveable lever, a slider moveable from a first position to a second position, a rotatable knob is rotated, a releasable latch configured and any combination thereof.

The predetermined sound pattern can be: a constant-pitch sound, a varying-pitch sound, a constant volume sound, a varying volume sound and any combination thereof.

The predetermined light pattern can be: a constant-color light, a varying-color light, a constant brightness light, a varying brightness light and any combination thereof.

In some embodiments, the device comprises a unidirectional valve such that gas can flow from the charging mechanism to the delivery end, but is unable to flow in the reverse direction.

In some embodiments, a substance to be dispensed (which can comprise any number of materials) can be stored within a capsule, either as the substance to be dispensed or as a precursor or precursors, with the capsule placeable within the device, as described hereinbelow. In such embodiments, the capsule is ruptured during activation, either all at once or in stages, thereby dispensing the substance.

In other embodiments, a substance, prepared in a conventional matter, is introducible into a holding chamber within the device and, on activation of the device, the substance is dispensed. Embodiments of this kind can be used as emergency dispensing devices, since any flowable substance can be introduced into the holding chamber and since the holding chamber, which has no facilities for separating precursors or for providing an inert atmosphere in the chamber, is not intended for long-term storage of substances.

In some embodiments, the capsule chamber in which the capsule can be placed can also function as a holding chamber, so that the substance can be dispensed either from the capsule or directly from the holding chamber.

In other embodiments, an insert can be placed within the capsule chamber, with the interior of the insert being a holding chamber.

Figure 7A:
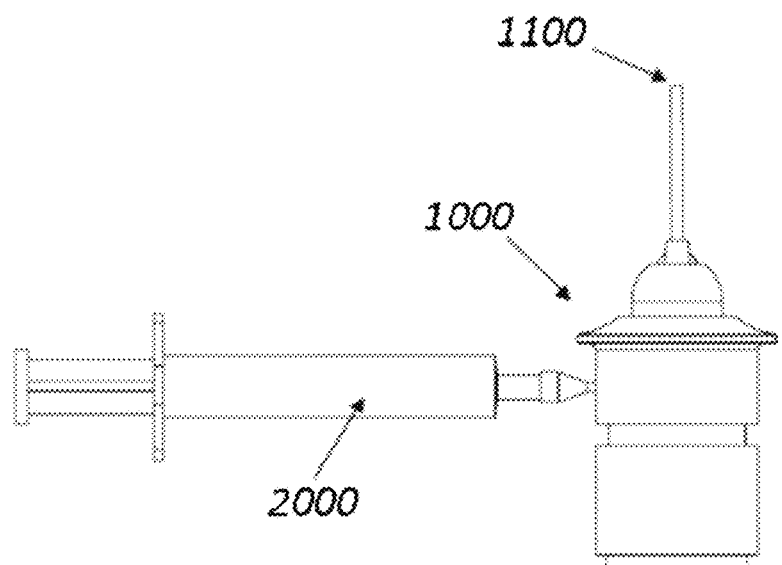
FIGS. 7A-C shows a preferred embodiment of the activation mechanism of the dispensing device into which any flowable substance is introducible.
Figure 7B:
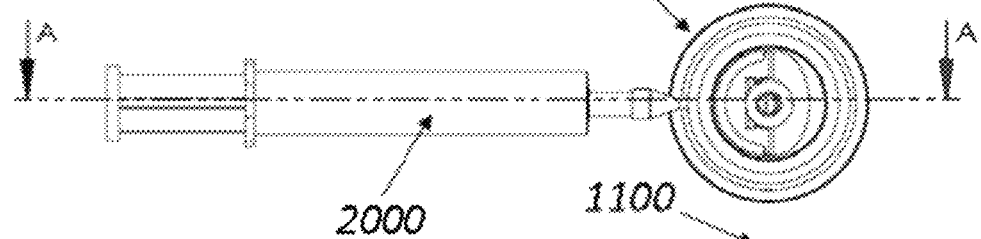
Figure 7C:
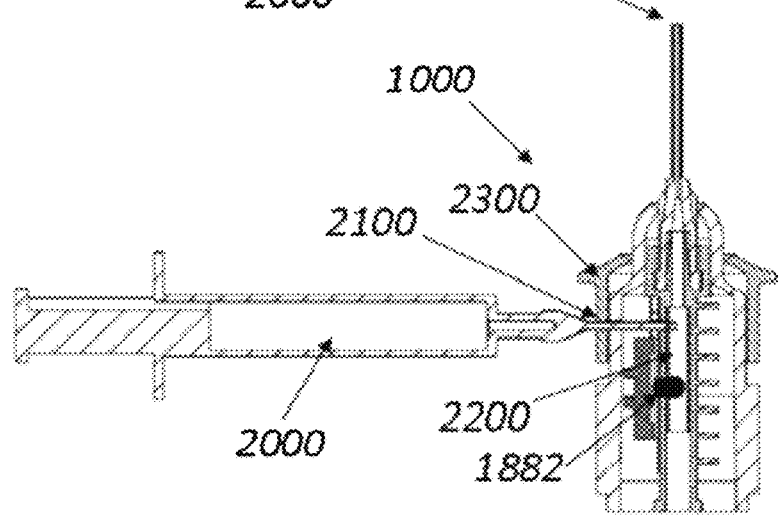

An embodiment of the activation mechanism a dispensing device (1000) into which any flowable substance is introducible is shown in FIG. 7A-C. The charging mechanism is not shown. FIG. 7A shows a side view of the embodiment, FIG. 7B shows a top view of the embodiment, and FIG. 7C shows a cross-section, taken along the line AA in FIG. 7B.

In this embodiment, the means of loading the substance into the device is a syringe (2000). The syringe (2000) can be placed in the injection port (2100, FIG. 7C) and the syringe plunger depressed so that the flowable substance enters a dispensing chamber (2200) within the device (1000). Before, during or after injection of the substance into the chamber, the device can be charged, in any manner described herein, using any activation mechanism described herein or known in the art.

In some embodiments, the syringe is left in the injection port. In other embodiments, a cover (2300) is provided for the injection port, so that, after loading the substance into the chamber, the injection port can be sealed by means of the cover. As shown in the embodiment of FIG. 7, the cover (2300) can slide longitudinally onto and off the injection port (2100), In other embodiments, it can rotate or spiral around the device to cover or uncover the injection port (2100), it can rotate around a hinge on the body of the device so that it flips onto and off the injection port (2100), or any other method of sealing the port can be used. In the embodiment as shown, in the open position, the syringe goes through a hole in the cover in order to reach the chamber. Any combination of the above embodiments can be used in a cover.

In some embodiments, the substance is stored in a capsule or in a sealed compartment in the device. Before or during activation, the capsule or sealed compartment is breached and pressure on the capsule (e.g., by pressing a button to move the piston of a built-in syringe) forces the contents into a dispensing chamber (2200). Dispensing gas passing through the dispensing chamber (2200) then entrains the substance and delivers it.

In some embodiments of a device with separate storage chamber and holding chamber, the capsule comprises a syringe or a syringe like compartment, a rubber piston and seals. The longitudinal axis of the syringe and piston are at right angles to the longitudinal axis of the device. Pressure on the piston moves the substance from the syringe into the holding chamber, in a manner similar to the syringe (2000) and holding chamber (2200) in FIG. 7.

In the embodiment shown, a pinch triggering mechanism is used, as shown hereinabove in FIG. 6, although any of the other activation mechanisms described herein or any conventional valve known in the art can be used.

In reference to FIGS. 7-9, three exemplary embodiments of nozzles (1100) are shown. In both FIG. 8 and FIG. 9, the nozzle (1100) has a tip extension (1110) with a larger diameter than the nozzle, the tip extension substantially surrounding the distal end of the nozzle (1100). In FIG. 7, the nozzle tip is substantially conical, lacking the optional tip extension (1110).

Figures 8A, 8B, 8C, 8D:
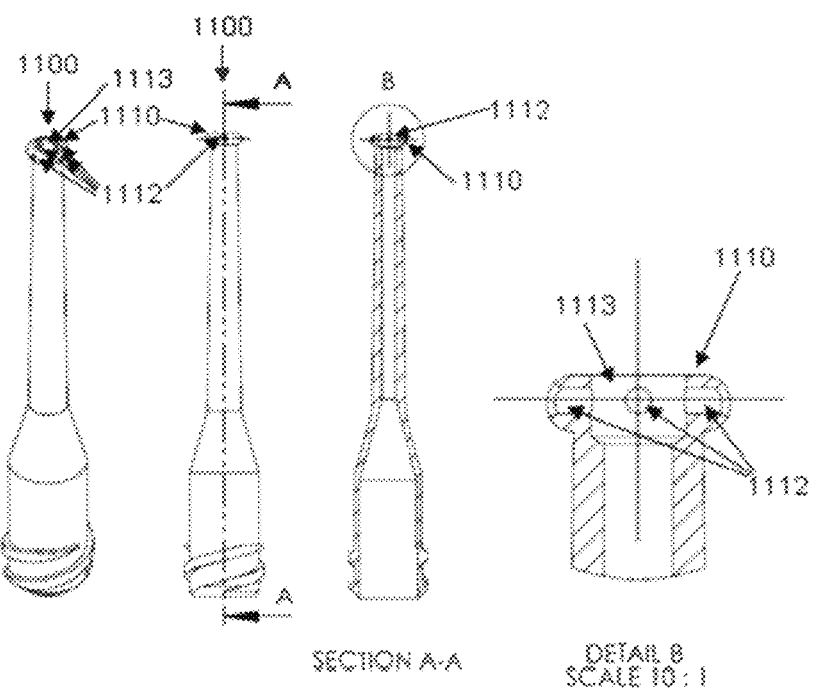
FIGS. 8A-D shows an embodiment of a nozzle with a tip extension.

In the exemplary embodiment of both FIG. 8 and FIG. 9, the tip extension (1110) has holes (1112) in it to allow substance to exit laterally from the extension, and the tip (1110) has at least one hole (1113) in its distal end to allow substance to exit longitudinally from the nozzle (1100). FIG. 8A-D shows an embodiment of a nozzle (1100) with a tip extension (1110). FIG. 8A shows a perspective view of the nozzle (1.100) from the distal end, while FIG. 8B shows a side view. FIG. 8C shows a cross-section of the nozzle along the line AA in FIG. 8A, while FIG. 8D shows an enlarged view of the circled region B at the tip of the nozzle in FIG. 8C, showing the tip of the nozzle and the tip extension in more detail. The holes (1112) in the tip extension (110) and the hole (1113) in the tip can be clearly seen. In some embodiments, the nozzle (1110) has only lateral holes (1112), so that no substance escapes from the distal end of the nozzle (1110). In some embodiments the tip has a plurality of holes.

In preferred embodiments, the distal end of the tip extension does not comprise any longitudinal protuberances, being substantially flat in the area around the opening (1113) and, where non-planar, extending proximally from the plane of the opening.

In order to prevent material from escaping from the nasal passages or entering undesired areas in the nasal cavity, in some embodiments, the nozzle comprises a medial extension, an expandable portion (1120). FIG. 9 shows an embodiment of a nozzle with a tip extension (1110) and an expandable portion (1120). FIGS. 9E and 9G show perspective views of the nozzle from the proximal end, while FIGS. 9A and 9C show side views of the nozzle (1100). FIGS. 9B and 9D show cross-sections of the nozzle (1100) along the lines AA in FIG. 9A and BB in FIG. 9C, respectively. FIG. 9F shows an enlarged view of the circled region C in the center of the nozzle in FIG. 98, while FIG. 9H shows an enlarged view of the circled region D in the center of the nozzle in FIG. 9D.

FIGS. 9A, 9B, 9E and 9F show the nozzle with unexpanded expandable portion, while FIGS. 9C, 9D, 9G and 9H show the nozzle with expanded expandable portion.

In the exemplary embodiments of FIGS. 8-9, the tip extension and the expanded medial extension are substantially toroidal; in other embodiments, they can be substantially spherical, substantially ovoid, substantially ellipsoidal, substantially the frustum of a cone (preferably with a rounded distal edge), substantially conic (preferably with a rounded distal edge) and any combination thereof.

The nozzle tip and the tip extension (1110) have a number of holes (1112, 1113) which fluidly connect the bore of the nozzle (1100) to the exterior of the device, allowing material to exit from the interior of the device. In the exemplary embodiments shown, there is a hole (1113) (FIGS. 8A and C; not shown in FIG. 9) in the distal end of the nozzle and four holes (1112) in the tip extension (1100). Both the extension and the distal end of the nozzle can have more or fewer holes and, in some embodiments, one or the other can have no holes. The holes (1112) can be regularly spaced around the periphery of the extension, the holes (1112) can be irregularly spaced around the periphery, the holes (1112) can be concentrated in a predetermined part of the periphery, and any combination thereof. Similarly, the holes in the distal end of the tip can be regularly or irregularly spaced in the tip.

In some embodiments, the extension (1110) can be padded, can comprise soft material, can comprise flexible material and any combination thereof.

Extensions, both tip extensions and medial extensions, can have a number of functions. A non-limiting list of such functions is (1) ensuring proper positioning of the nozzle (1100) in the nasal passages, where the proper position can be the nozzle (1100) centralized in the nasal passages, the nozzle (1100) touching a predetermined portion of the nasal passages, or the nozzle (1100) closer to a predetermined portion of the nasal passages, (2) sealing the nasal passages so that material can not escape therefrom, (3) sealing the nasal passage so that substance does not contact undesired portions thereof. (4) sealing the nasal passage so that substance remains in a predetermined region of the nasal passage, (5) reducing the discomfort of contact between the nozzle and the nasal passages, especially in embodiments where the extension is intended to seal against the walls of the nasal passages, by providing a soft and/or flexible contact region and any combination thereof. Proper positioning can be for the purpose of improving delivery of a substance to a predetermined area, preventing clogging of the holes by nasal secretions, preventing clogging of the holes by contact with the nasal passages, mucosa and any combination thereof.

Nozzle extensions, both those that are expanded during the activation procedure and those that have a predetermined shape and do not expand, can either (1) be attached to the nozzle in a way that they are removed from the nasal cavity with the nozzle tip itself, or (2) have the option of being releasable from the nozzle tip so that they stay in the nasal cavity until they are pulled out by the user or by a caregiver, or any combination thereof. In embodiments where at least one nozzle extension remains in a nasal cavity, preferably, the nozzle extension or extensions are removed after a predetermined time, preferably a short time.

In some embodiments, the holes (1112) in the nozzle (1100) do not lie substantially in a plane perpendicular to the main longitudinal axis of the nozzle (1100). In such embodiments, the holes (1112) can lie along a line parallel to the main longitudinal axis of the nozzle (1100), along a line forming a spiral around the nozzle (1100), irregularly in the distal portion of the nozzle (1100), regularly spaced in the distal portion of the nozzle (1100), and any combination thereof.

Therefore, dispersion of the drug can be substantially from a ring perpendicular to the main longitudinal axis of the nozzle (1100) (holes (1112) around the edge of the extension (1110), from a circle perpendicular to the main longitudinal axis of the nozzle (1100) (holes (1113) in the distal tip of the nozzle (1100), from a line (holes (1112) parallel to the main longitudinal axis of the nozzle (1100) or in a spiral around the main longitudinal axis of the nozzle (1100), or from at least part of the surface of a volume extending along the side of the nozzle (1100).

In some embodiments, the size of the tip extension (1110) is selected so that the extension (1110) is in contact with the nasal passages substantially along its entire circumference. In such embodiments, material exiting holes (1113) in the distal tip of the nozzle (1100) or holes (1112) on the distal face of the extension (1110) can not reach regions proximal to the extension (1110) and will reach only regions deeper in the nasal passages than the extension (1110). In such embodiments, the substance will reach the upper parts of the nasal passages.

Material exiting from holes (1112) in locations where the extension (1110) is in contact with the nasal passages will deposit directly on the walls of the nasal passages. In such embodiments, deposition is in a very narrow band; the location of the band can be tailored for the material of interest.

Material exiting holes (1112) proximal to the region of the extension (1110) in contact with the walls of the nasal passages will be unable to reach locations distal to the region of the extension (1110) in contact with the walls of the nasal passages and will therefore deposit in the lower parts of the nasal passages.

Returning to FIG. 9, in this embodiment, the expandable portion (1120) surrounds the nozzle (1100). In other embodiments, the expandable portion (1120) can partially surround the nozzle (1100). A single expandable portion (1120) or a plurality of expandable portions (1120) can be used. An expandable portion can be on the surface of the nozzle or it can be stored within the nozzle, popping out when it expands. An expandable portion can have a predetermined shape when expanded. The shape of the outward-facing part of an expandable portion can be part of the surface of a spheroid, can be part of a cylinder, a part of a cone, or can conform to the shape of a predetermined portion of a nasal passage. Such shaping can help ensure that, on inflation, the expandable portion or portions gently guide the nozzle so that it rests in the position with respect to the nasal passages or in the correct portion of the nasal passages. It can also reduce the user's discomfort when the device is in place or, if detachable from the device, it can seal the nasal passage for a time, before being removed by the user or a caretaker.

The expandable portion (1120) is preferably inflated after insertion of the device into the nasal passage. Inflation can be before or at the time of activation of the device.

FIG. 10-22 illustrate embodiments of devices with a dose-adjustable drug chamber, where it is possible for a user to adjust the amount of medicament delivered in each dose, either for a single-use device or for a multi-use device.

Figure 10:
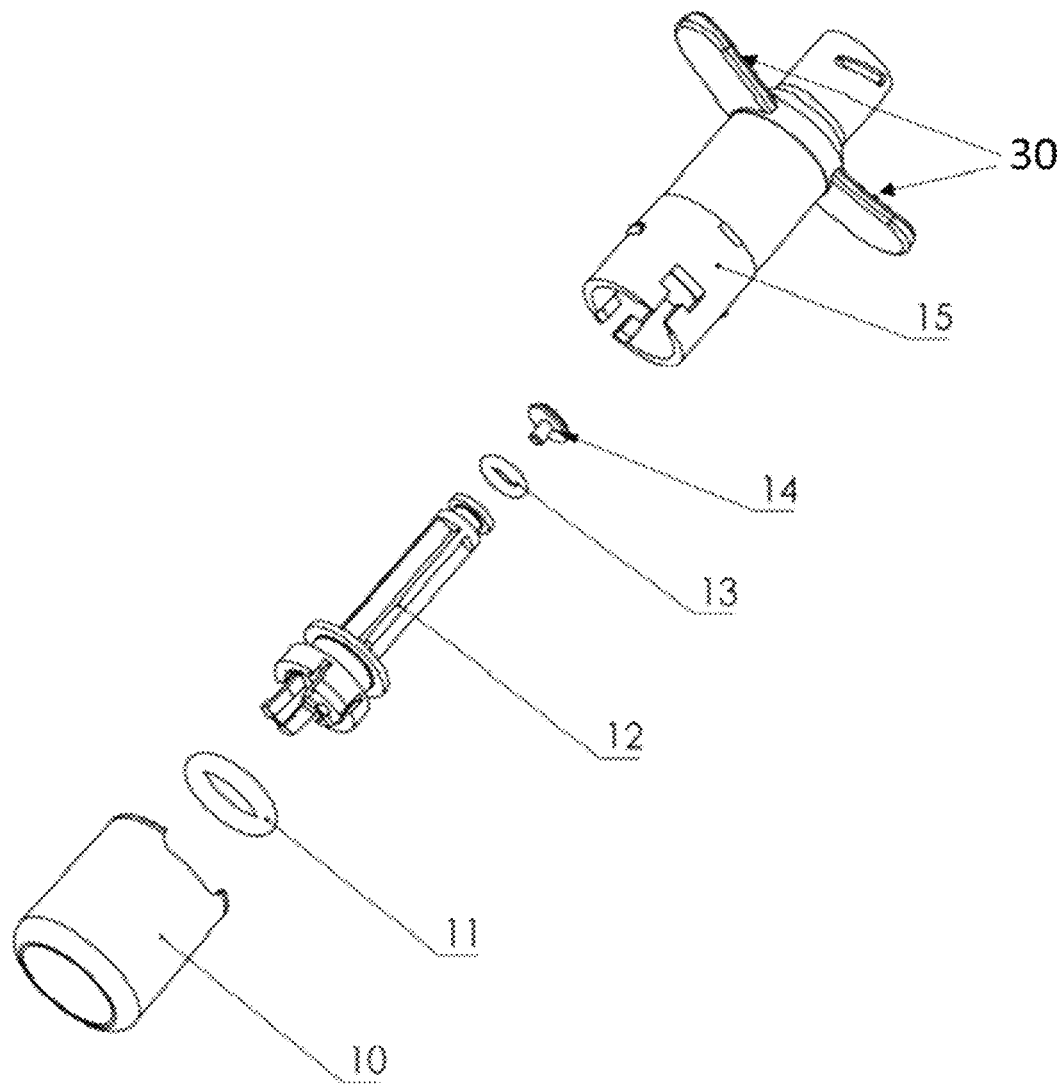
FIG. 10 shows an embodiment of the body of a nasal delivery device.

FIG. 10 shows an embodiment of the body of a nasal delivery device. The nosepiece is not shown. The body comprises a base (10), an air chamber gate (12) with a first gate O-ring (11) at its proximal end and a second gate O-ring (13) at its distal end. The first gate O-ring (11) corresponds to the gate O-ring of the embodiments of FIGS. 18-21 and the second gate O-ring corresponds to the septum of FIGS. 18-21. The distal end of the air chamber gate (12) is covered by a drug container base cover (14) which comprises a biocompatible material to ensure that substance that is to contact living tissue only contacts biocompatible material before the contact with living tissue. The compressed gas chamber (15) will fit over the air chamber gate (12), with the first gate O-ring (11) and the second gate O-ring (13) providing airtight seals before activation so that compressed gas is storable between the air chamber gate (12) and the compressed gas chamber (15). The compressed gas chamber (15) is connectable at its distal end with a nose piece (not shown). The distal portion of the compressed gas chamber (15) comprises activation holders (30) FIG. 11A-D shows an embodiment of the body of FIG. 10, as assembled, before activation.

Figure 11A:
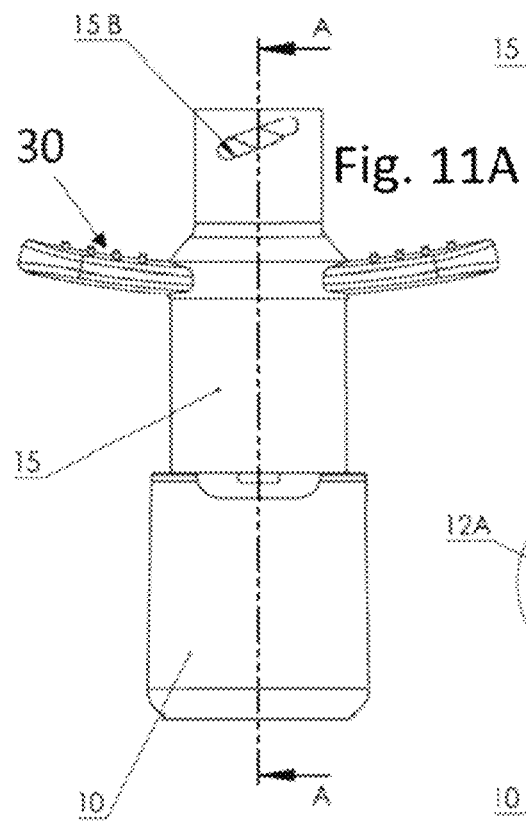
FIG. 11A-D shows an embodiment of the body of the nasal delivery device as assembled, before activation

FIG. 11A shows the exterior of the body, while. FIG. 23B shows a cross-section taken along the line A-A in FIG. 11A. FIG. 11C is an enlarged view of the circled section B in FIG. 11B, while FIG. 11D is a perspective view of the body of FIG. 11A. Activation is by compressing the upper end of the device toward its base, by holding the activation holders (30) with the fingers and the bottom of the base (10) with the thumb, and bringing the fingers toward the thumb.

As shown in FIGS. 11A and 11D, in the embodiment of FIGS. 10-11, the base of the device forms the activation button (10), to activate, the activation button (10) is pressed upward while the compressed gas chamber (gas chamber (15) is held stationary by fingers on the activation holders (30). The nosepiece is attachable to the compressed gas chamber (15) by means of the nose piece connector slot (15B); a protuberance on the nose piece engages with the nose piece connector slot (15B); permitting fast and easy replacement of the nose piece.

Figure 11B:
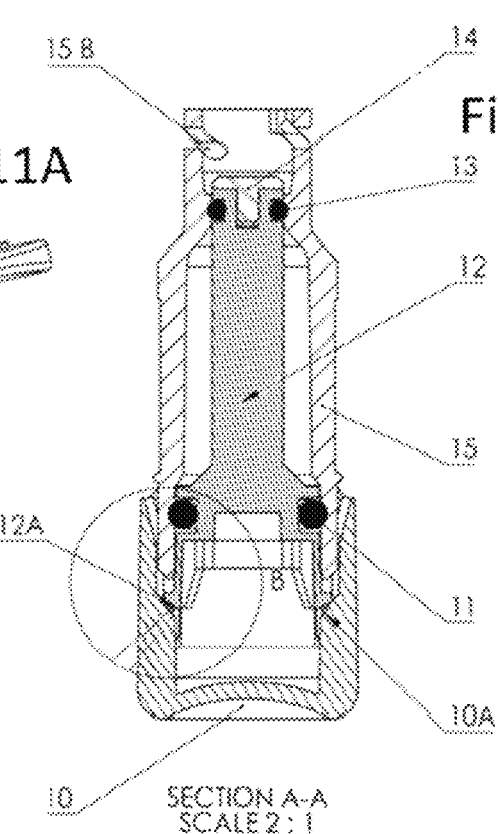
Figure 11C:
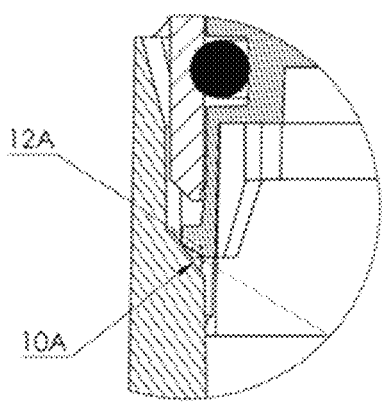
Figure 11D:
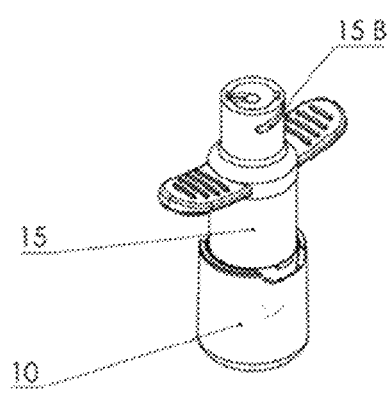
Figures 13A, 13B, 13C:
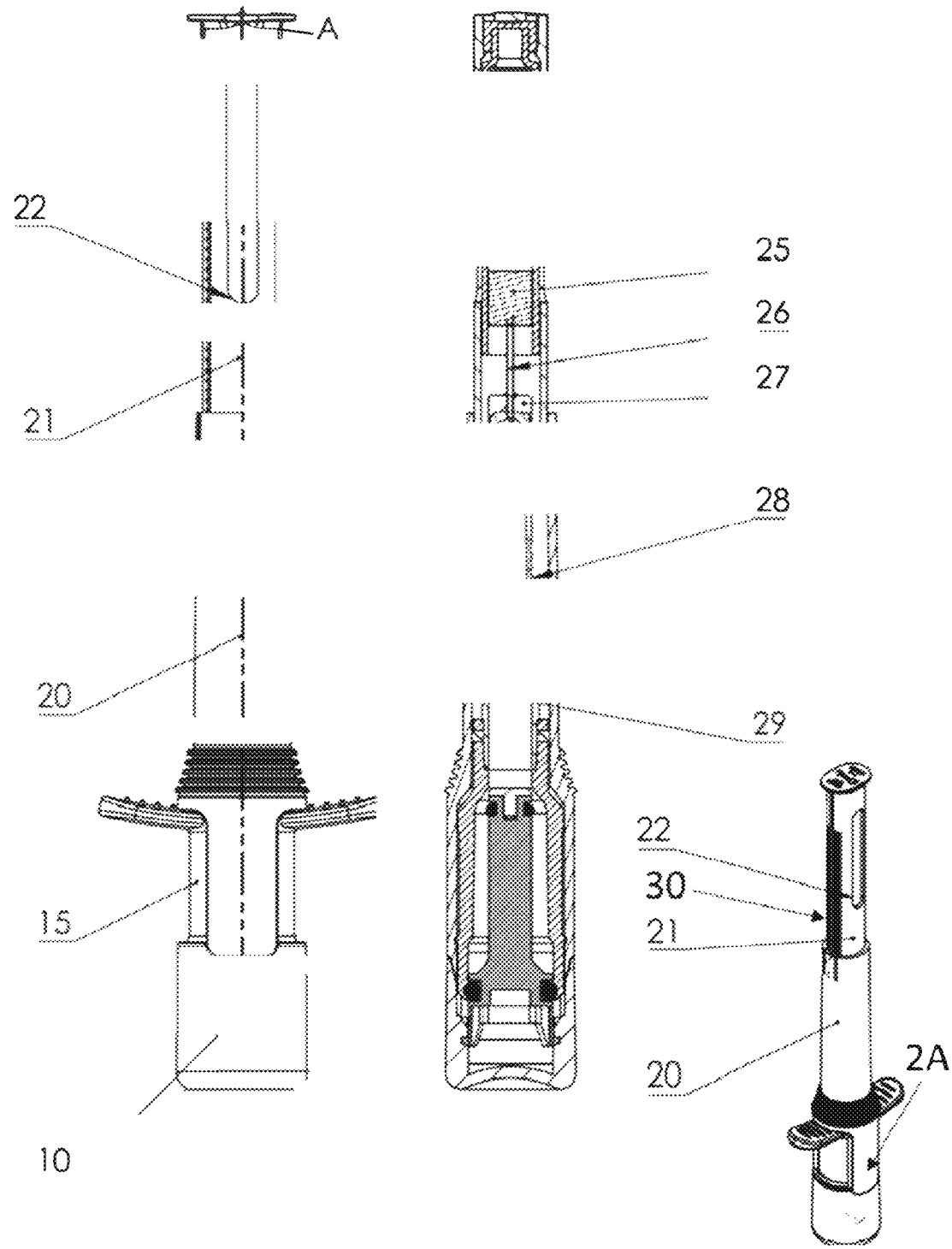
FIGS. 13A-C shows an embodiment of the device with the primary drug container in the nose piece cover.

As shown in FIG. 11B, the activation button (10) comprises a gate anchor (10A), a shoulder on which the air chamber gate stopper (12A) rests before activation. This to prevent movement of the air chamber gate (12) before activation. The first gate O-ring (11), at the proximal end of the gate anchor (10A) and the second gate O-ring (13), at its distal end, provide airtight seals before activation so that compressed gas is storable between the air chamber gate (12) and the compressed gas chamber (15). The distal end of the air chamber gate (12) is covered by a drug container base cover (14) which comprises a biocompatible material to ensure that substance that is to contact living tissue only contacts biocompatible material before the contact with living tissue. The compressed gas chamber (15) is connectable at its distal end with a nose piece (not shown) by means of the nose piece connector slot (15B).

FIG. 11C, the enlargement of the area within the circle B of FIG. 11B, clearly shows the gate anchor (10A), with the air chamber gate stopper (12A) resting on it.

FIG. 12A-D shows an embodiment of the body of FIG. 10, as assembled, after activation. FIG. 12A shows the exterior of the body, while. FIG. 12B shows a cross-section taken along the line A-A in FIG. 12A. FIG. 12C is an enlarged view of the circled section B in FIG. 12B, while FIG. 121) is an enlarged view of the circled section C in FIG. 12B. Activation is by compressing the upper end of the device toward its base, by holding the activation holders (30) with the fingers and the bottom of the base (10) with the thumb, and bringing the fingers toward the thumb.

As shown in FIGS. 12A and 12D, in the embodiment of FIGS. 10-11, the base of the device forms the activation button (10), to activate, the activation button (10) is pressed upward while the compressed gas chamber (gas chamber (15) is held stationary by fingers on the activation holders (30). The nosepiece is attachable to the compressed gas chamber (15) by means of the nose piece connector slot (15B); a protuberance on the nose piece engages with the nose piece connector slot (15B); permitting fast and easy replacement of the nose piece.

Figure 14A:
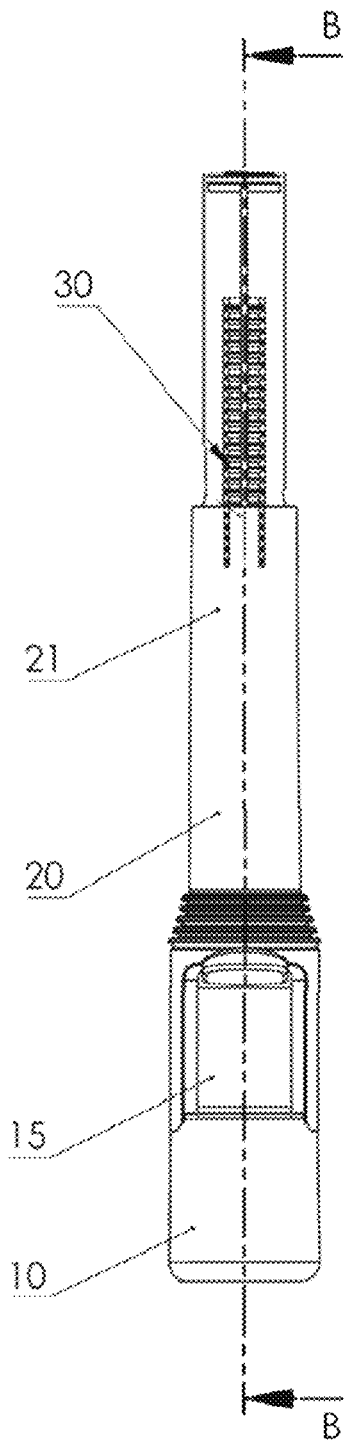
FIG. 14A-C shows the embodiment of the device with the primary drug container in the nose piece cover during loading of the drug into the integral drug volume from the primary drug container.
Figure 14B:
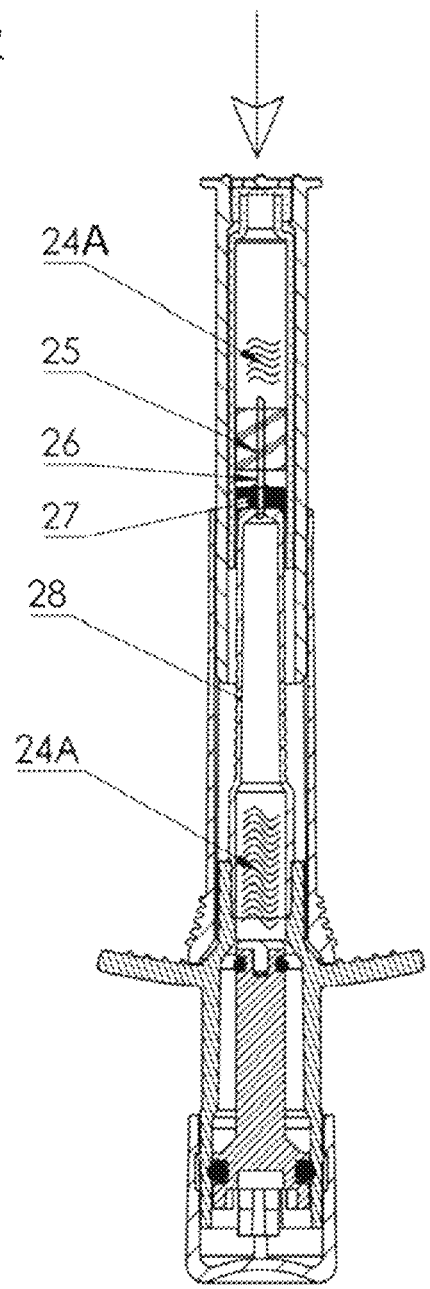

As shown in FIG. 11B, the activation button (10) comprises a gate anchor (10A), a shoulder on which the air chamber gate stopper (12A) rested before activation. During activation, the air chamber gate stopper (12A) is pressed inwards, so that the air chamber gate (12) moves proximally, opening up a gap (17) between the air chamber gate (12) and the distal end of the compressed gas chamber (15), allowing the gas (16) to exit the compressed gas chamber (15) through the gap, and to enter the nosepiece and forma an aerosol with the substance. The first gate O-ring (11), at the proximal end of the gate anchor (10A) still provide an airtight seal after activation, but the second gate O-ring (13), at its distal end, so that compressed gas is storable between the air chamber gate (12) and the compressed gas chamber (15) is no longer in contact with the compressed gas chamber (15). The distal end of the air chamber gate (12) is covered by a drug container base cover (14) which comprises a biocompatible material to ensure that substance that is to contact living tissue only contacts biocompatible material before the contact with living tissue. The compressed gas chamber (15) is connectable at its distal end with a nose piece (not shown) by means of the nose piece connector slot (15B).

FIG. 12C, the enlargement of the area within the circle B of FIG. 12B, clearly shows the gate anchor (10A), with the air chamber gate stopper (12A) no longer in contact with it, but is resting near the base of the activation button.

FIG. 12D, the enlargement of the area within the circle C of FIG. 12B, clearly shows the distal end of the air chamber gate (12), the drug container base cover (14), the second gate O-ring (13) and the gap (arrow) permitting air to escape from the compressed gas chamber into the intermediate space and then to the nose piece (not shown).

FIG. 13A-C shows an embodiment of the device with the primary drug container in the nose piece cover. The medicament or substance is delivered from the primary drug container to a secondary drug volume in the nose piece. The nose piece cover can then be removed and the device activated to aerosolize and deliver the drug.

FIG. 13A shows the exterior of the device. It comprises an activation button (10), a compressed gas chamber (15), and a nosepiece (not shown) protected by a nose piece cover (20). At the distal end of the nose piece cover (20) is a primary drug container (not shown) in a drug container housing (21). The embodiment also comprises an indicator window (22) to determine the quantity of drug remaining in the primary drug container.

FIG. 13B shows a cross-section of the device, taken along the line A-A in FIG. 13A. The base and aerosol generation and delivery mechanism are similar to those disclosed above in FIGS. 10-12. The device comprises a nose piece (28) with an integral drug volume (29) in its proximal portion. The deliverable substance is stored in a primary drug container (24) near the distal end of the nose piece cover (20). The primary drug container (24) is sealed at its proximal end by a plunger stopper (25). A loading needle (26) is fixed to the nose piece cover (20), with a needle adaptor (27) to guide the loading needle's (26) proximal end so that the proximal end of the needle adaptor (27) passes through the orifice at the tip of the nose piece (28). As shown in FIG. 13B, unless drug is being loaded into the integral drug volume (29), the needle does not pierce the plunger stopper (25) and the primary drug container (24) remains sealed.

FIG. 13C shows a perspective view of the device. The indicator window (22) and the drug container housing (21) can be seen, as well as the nose piece cover (20), which terminates at its proximal end in a safety lock ("safety latch") (2A) to prevent unwanted activation of the device.

FIG. 14 A-C shows the embodiment of the device of FIG. 13 during loading of the drug into the integral drug volume (29) from the primary drug container (24).

FIG. 14A shows the exterior of the device. It comprises an activation button (10), a compressed gas chamber (15), and a nosepiece (not shown) protected by a nose piece cover (20). At the distal end of the nose piece cover (20) is a primary drug container (not shown) in a drug container housing (21). The embodiment also comprises a volume scale (30), here a ratchet, to allow adjustment of the size of the dose.

FIG. 14B shows a cross-section of the device, taken along the line B-B in FIG. 14A. The base and aerosol generation and delivery mechanism are similar to those disclosed above in FIGS. 10-12. As shown in FIG. 14B, a drug or medicament (24A) is being loaded from the primary drug container into the integral drug volume (29). Loading is activated by pressing the primary drug container (24) proximally. It then slides along the nose piece (28). The loading needle (26) is steadied by the needle adaptor (27). Pressing the primary drug container (24) proximally forces the loading needle (26) through the plunger stopper (25) and into the primary drug container (24). Drug (24A) can then flow through the loading needle (26) into the integral drug volume (29). Releasing the primary drug container (24) will cause it to move distally and remove the loading needle (26) from the plunger stopper (25). The nose piece cover (20) can then be removed and a dose of the drug can be administered.

Figure 14C:
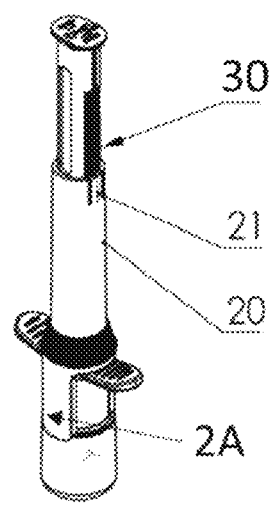

FIG. 14C shows a perspective view of the device. The volume scale (30) and the drug container housing (21) can be seen, as well as the nose piece cover (20), which terminates at its proximal end in a safety lock (2A) to prevent unwanted activation of the device.

Figure 15:
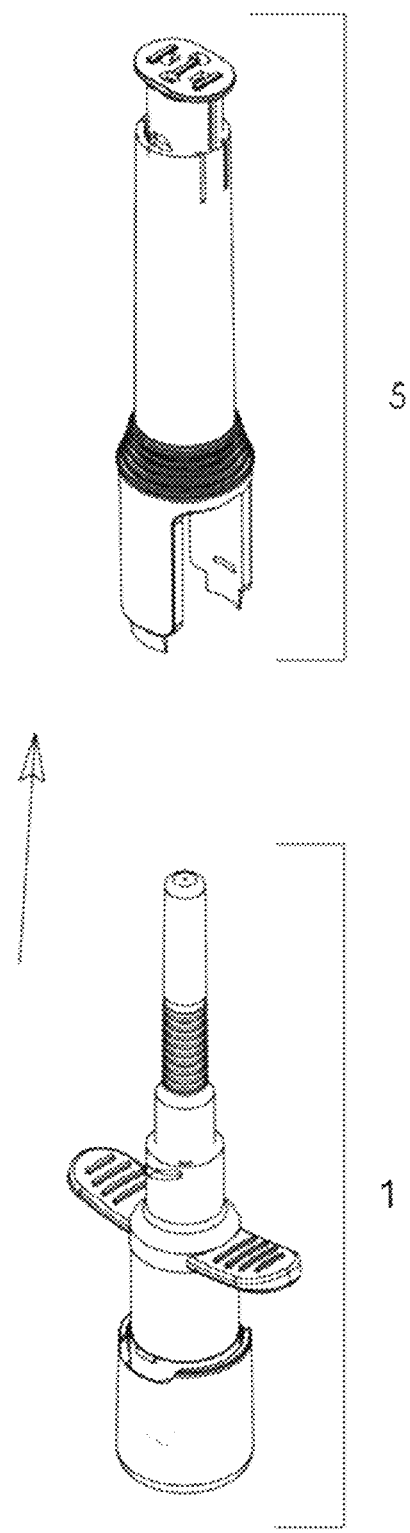
FIG. 15 illustrates removal of the nose piece cover or medicine chamber (5) from an aerosol delivery device.

FIG. 15 illustrates removal of the nose piece cover or medicine chamber (5) from an aerosol delivery device (1) by pulling (arrow) the medicine chamber (5) away from the aerosol delivery device (1), FIG. 16A-D illustrates a device with a replaceable nose piece preloaded with a single dose of a medicament. The medicament can comprise one or more substances, as disclosed above. The device further comprises a nose piece cover with a removable top. FIGS. 16A and 16D show the exterior of the device with the nose piece cover in place, with FIG. 16A showing it from the side and FIG. 16C showing a perspective view. FIG. 16I shows a cross section taken along the line A-A in FIG. 16A and FIG. 16C provides a partially exploded view.

FIG. 16A shows an activation button (10) and compressed gas chamber (15), as disclosed above. The nose piece cover (40) has a removable orifice closure (41) at its distal end.

FIG. 16B shows a cross-section of the device. The nose piece cover (40) has a reversibly removable nose piece orifice cover (41). The nose piece (28), which comprises an integral drug volume (29), has, at its distal end, a nose piece cover pin (41A) to protect the distal end of the nose piece.

FIG. 16C shows a partially-exploded view of the device. The nose piece (28) is reversibly connectable to the activation button (10) and compressed gas chamber (15) by means of a nose piece connecting pin (42A) which slots into a connector slot (42B) at the distal end of the compressed gas chamber (1). The removable orifice closure (41) is shown separated from the nose piece cover (40). By this means, only the removable orifice closure (41) needs to be removed to replace a nose piece (28); there is no need to remove the entire nose piece cover (40). The safety lock (2A) to prevent accidental activation of the device is also shown.

FIG. 17A-D illustrates a device which can be loaded with a medicament, drug or substance via a syringe. FIGS. 17A and 17D show the exterior of the device, FIG. 17A from the side and FIG. 17D from an angle. FIG. 17B shows a cross section taken along the line A-A in FIG. 17A and FIG. 17C shows the loading needle.

As shown in FIG. 17A, the device comprises an activation button (10) and compressed gas chamber, as disclosed above. The nose piece cover (40) comprises a drug loading adaptor (45) and a reversibly removable drug loading adaptor cap (46) at its distal end. In the embodiment shown, the drug loading adaptor cap (46) is attached to the nose piece cover (40) by an integral flexible strip (46A), to prevent the drug loading adaptor cap (46) from getting lost.

As shown in FIG. 17A, a drug loading needle ("nosepiece puncturing member")(47) is held firmly within the drug loading adaptor (45). The drug loading needle (47) extends from the top of the nose piece cover (40) through the distal end of the nose piece (42) to a drug storage volume near the proximal end of the nose piece (42). The distal portion of the drug loading needle (47) is configured by means of shape and size to accept the delivery end of a syringe (not shown). During storage and transport, the drug loading needle (47) is retained firmly in place with its distal portion help firmly between the closed drug loading adaptor cap (46) and the distal tip of the nose piece (42).

FIG. 17C shows the drug loading adaptor (45) with the drug loading needle (47) extending proximally therefrom.

FIG. 17D shows the nose piece cover (40), the drug loading adaptor cap (46) and the drug delivery device with activation button (10).

FIG. 18A-D shows the device of FIG. 17A-D with a syringe in place. The syringe can be a proprietary syringe, with a tip matched in shape and size to the opening in the distal portion of the drug loading needle (47) or it can be a commercial syringe with a tip that fits into the opening in the distal portion of the drug loading needle (47).

Figure 18A:
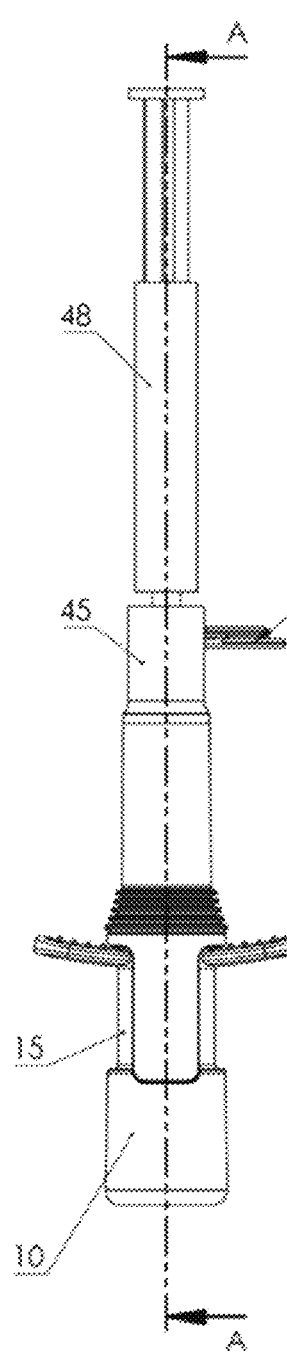

FIG. 18A shows a side view of the device with a labeled (49) loading syringe (48) in place. The drug loading adaptor cap (46) is open and the tip (not shown) of the loading syringe (48) is resting in the distal portion of the drug loading adaptor (45) and nose piece cover (40), with the nose piece cover in communication with the activation button (10) and compressed gas chamber (15) of the delivery device.

Figure 18B:
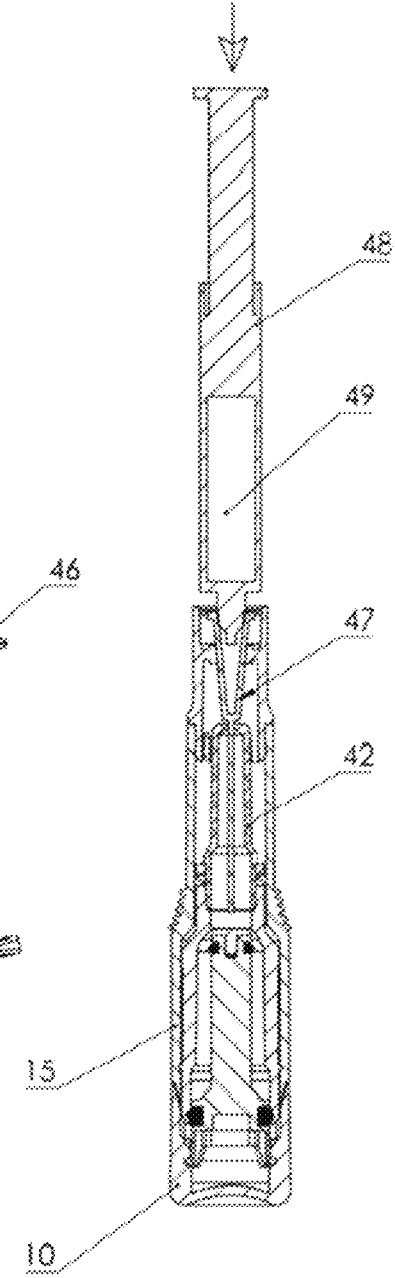

FIG. 18B shows a cross-section of the set-up of FIG. 30A, taken along the line A-A of FIG. 30A. The loading syringe (48) is resting in the distal portion of the drug loading needle (47). The prosimal portion of the drug loading needle (47) passes through the nose piece (42). The nose piece (42) is attached, either reversibly or fixedly, to the activation button (10) and compressed gas chamber (15) of the delivery device.

Figure 18D:
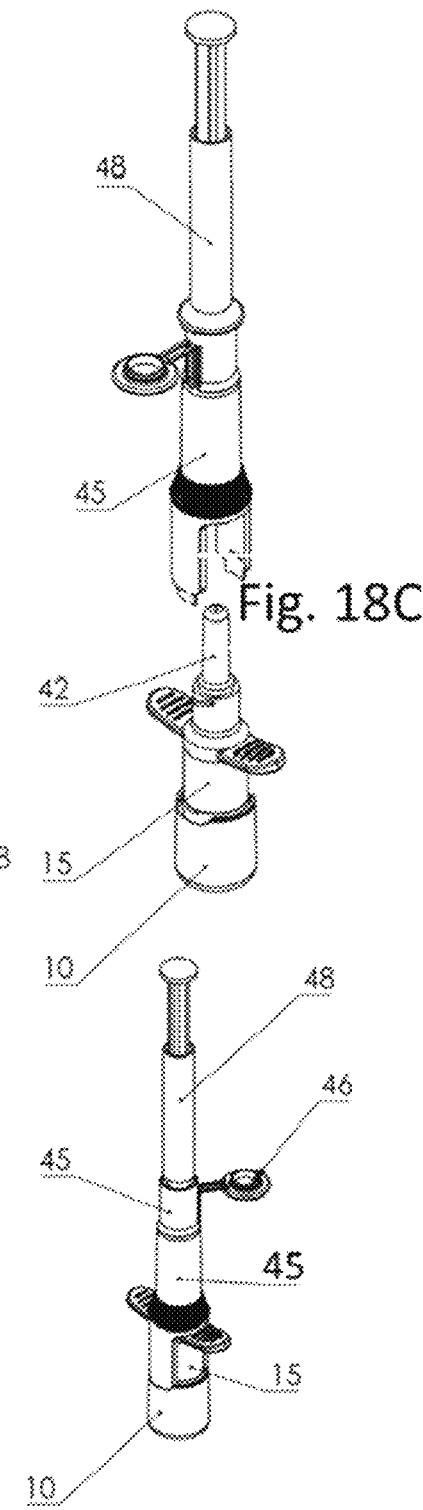

FIG. 180C-D shows how a loading syringe (48) in place in a drug loading adaptor (45), is connectable to a drug delivery device, comprising nose piece (42), compressed gas chamber (15) and activation button (10). FIG. 18C shows the loading syringe (48) in place in a drug loading adaptor (45), with the drug loading adaptor (45) in position to be attached to the delivery device. FIG. 18D shows the loading syringe (48) and drug loading adaptor (45), with the drug loading adaptor cap (46) open, attached to the compressed gas chamber (15) and activation button (10) of the delivery device.

Figure 19:
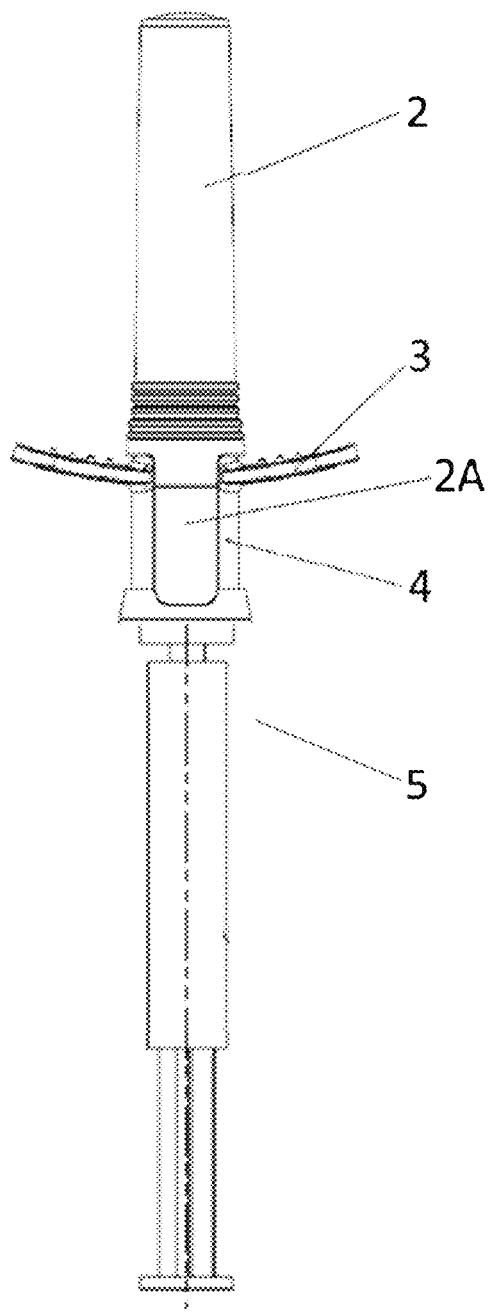
FIG. 19 show an embodiment of delivery device where adjustment of the sire of the dose is made from the proximal end of the device from the adjustment mechanisms.

FIG. 19 shows an embodiment of delivery device where adjustment of the size of the dose is made from the proximal end—the opposite end of the device from the adjustment mechanisms disclosed above. The nose piece is covered by a nose piece cover (2) with a safety lock (2A) to prevent accidental activation of the device. The safety lock (2A) is latched to the compressed gas chamber (4) of the delivery device. Proximal to the compressed gas chamber (4) is an activation mechanism base (5). The activation holders (3) are also shown.

For many medicines, one dose is supplied to each nostril, with the patient receiving two doses altogether. In the prior art, for a single-dose delivery device, this required two delivery devices, with the consequent waste of packaging material, waste of time spent unpacking two devices, both of which tend to reduce patient compliance.

Figure 20A:
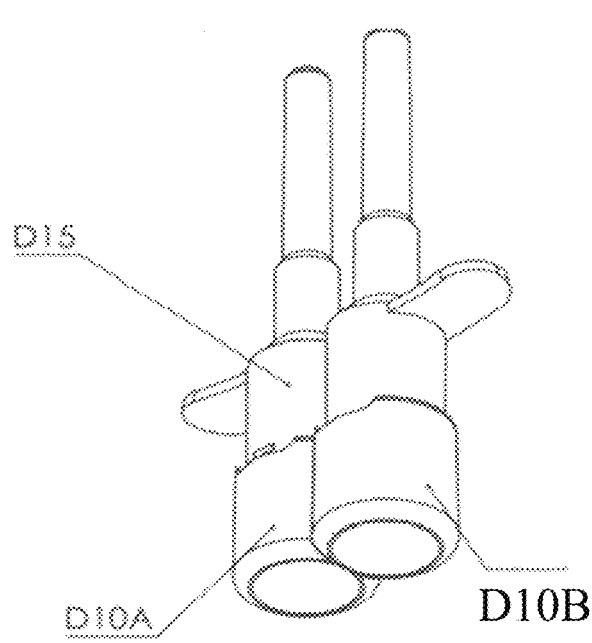
FIGS. 20A-C show embodiments of a devices configured to supply a single dose of a medicament to each of two nostrils.
Figure 20B:
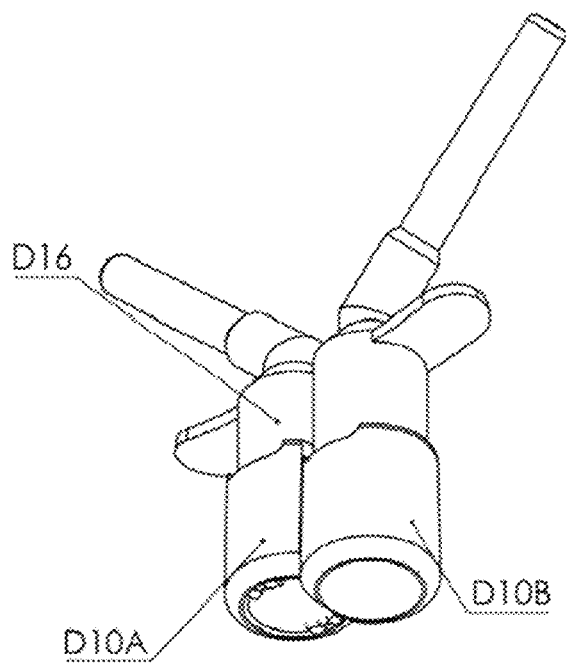
Figure 20C:
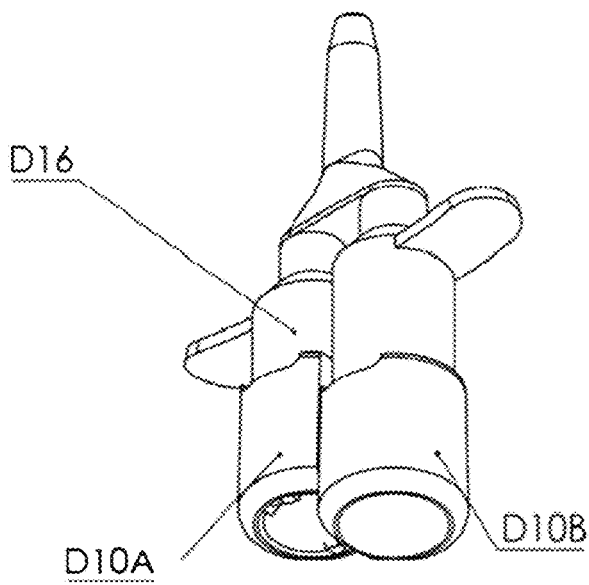

FIG. 20A-C shows embodiments of a devices configured to supply a single dose of a medicament to each of two nostrils. The devices (D15 and D16) of FIGS. 20A and 20B have two independent aerosolization and delivery devices (D10A and D10B), each containing a single dose of a drug, and each of which is in independent fluid communication with a nosepiece. In FIG. 20A, the nosepieces are parallel to each other, whereas in FIG. 20B, the nosepieces are at approximately right angles to each other.

The device (D16) of FIG. 20C also comprises two independent single-dose aerosolization and delivery devices (D10A and D10B), but both of these are in communication with a single nosepiece.

FIG. 21A-E shows a front view (FIG. 21A), a side view (FIG. 21B), a cross-section view (FIG. 21C) a top view (FIG. 21D), and a perspective view (FIG. 21E) of an embodiment with nose pieces at approximately right angles to each other (FIG. 20B).

The device (D16) comprises two independent aerosolization and delivery devices (D10A and D10B), each in fluid connection with a single nosepiece. Each aerosolization and delivery device (D10A and D10B) comprises a single dose of a drug, which can comprise a single substance or a plurality of substance, stored as a mixture or stored in independent compartments, as disclosed above. The device also comprises activation holders; the aerosolization and delivery devices (D10A and D10B) will be activated one at a time, as disclosed above, with fingers on the activation holders; and a thumb on the activation button at the base of an aerosolization and delivery device (D10A or D10B). It can be seen from FIGS. 21B and 21D that the nose pieces of the device (D16) lie substantially in the same plane in this embodiment; in other embodiments, they could lie in different planes.

Figures 21A, 21B, 21C:
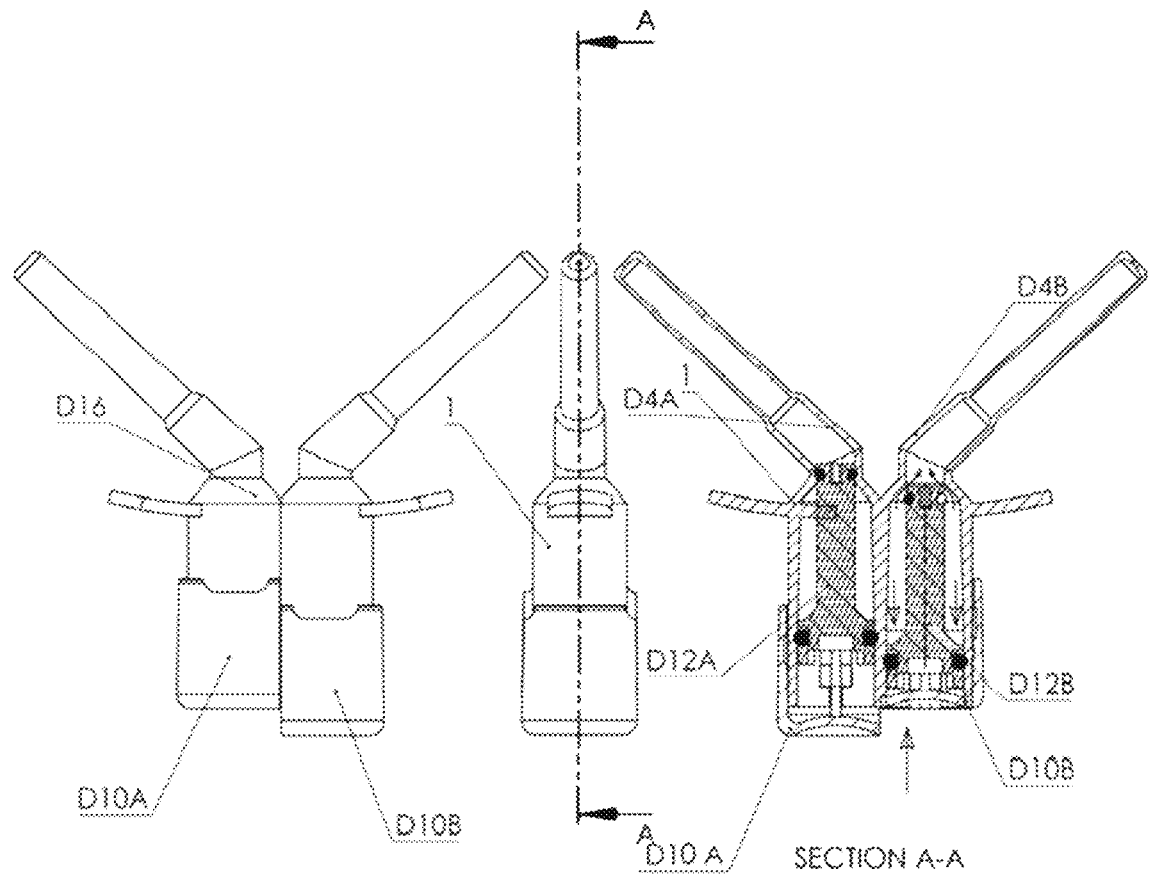
FIGS. 21A-E show an embodiment of the device with nose pieces at approximately right angles to each other
Figures 21D, 21E:
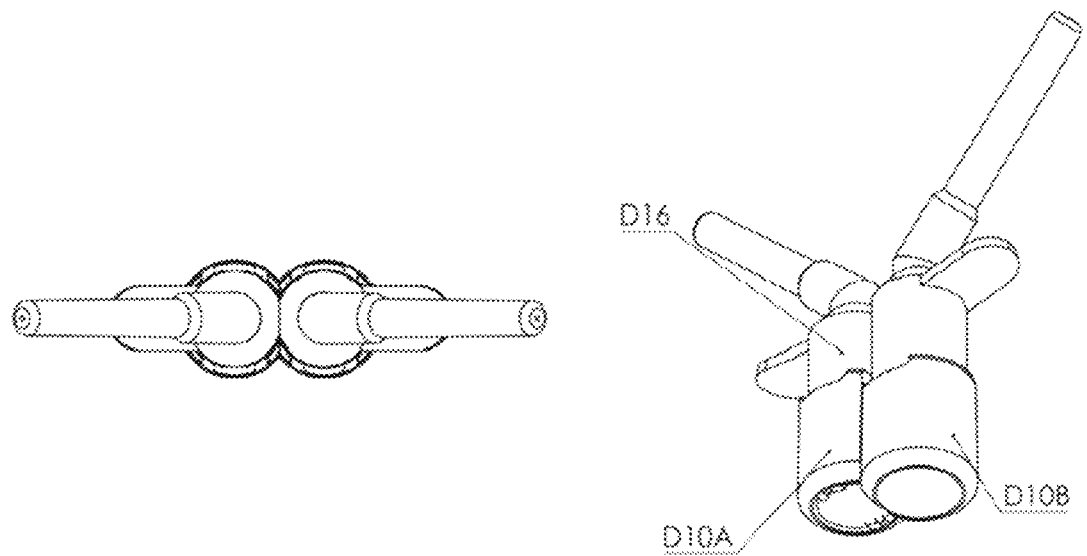

FIG. 21C is a cross-section through the device, along the line of A-A in FIG. 21B. In FIG. 21C, one aerosolization and delivery device (D10A) has not yet been activated, while the other (D10B) has been activated (large upward arrow). In the non-activated delivery device (D10A), the air chamber gate (D12A) is in the distal position, with the distal end of the air chamber gate (D12A) blocking passage of gas into the mixing chamber (D4A). In the activated delivery device (D10B), the air chamber gate (D12B) has moved proximally (large downward arrows), leaving a gap between the distal end of the air chamber gate (D12B) and the mixing chamber (D4B) which allows passage of gas (small upward arrows) into the mixing chamber (D4B) from whence gas can pass through the nose piece and exit the device.

FIG. 22A-E shows a front view (FIG. 22A), a side view (FIG. 22B), a cross-section view (FIG. 22C), a top view (FIG. 22D), an enlarged top view (22F) and a perspective view (FIG. 22E) of an embodiment with a single nose piece (FIG. 20C).

The device (D16) comprises two independent aerosolization and delivery devices (D10A and D10B), and a single nosepiece, with both aerosolization and delivery devices (D10A and D10B) in fluid communication with the single nosepiece. Each aerosolization and delivery device (D10A and D10B) comprises a single dose of a drug, which can comprise a single substance or a plurality of substance, stored as a mixture or stored in independent compartments, as disclosed above. The device also comprises activation holders; the aerosolization and delivery devices (D10A and D10B) will be activated one at a time, as disclosed above, with fingers on the activation holders; and a thumb on the activation button at the base of an aerosolization and delivery device (D10A or D10B).

FIG. 22C is a cross-section through the device, along the line of A-A in FIG. 22B. As shown in FIG. 22C, the single nosepiece comprises two mixing chambers (D4A and D4B), two sets of air passages (D6A and D6B) and two aerosol exits (D7A and D7B) allowing the aerosol to exit from the device. Therefore, although there is only one nose piece, substance from one of the delivery devices (D10A or D410B) will not come into contact, within the device, with substance from the other delivery device.

In FIG. 22C, one aerosolization and delivery device (D10A) has not yet been activated, while the other (D10B) has been activated (large upward arrow). In the non-activated delivery device (D10A), the air chamber gate (D12A) is in the distal position, with the distal end of the air chamber gate (D12A) blocking passage of gas into the mixing chamber (D4A). In the activated delivery device (D10B), the air chamber gate (D12B) has moved proximally (large downward arrows), leaving a gap between the distal end of the air chamber gate (D12B) and the mixing chamber (D4B) which allows passage of gas (small upward arrows) into the mixing chamber (D4B) from whence gas can pass through the nose piece and exit the device.

FIG. 22D shows a top view of the device. In the enlarged view (FIG. 22F), the two independent exits (D7A and D7B) can be clearly seen.

It should be noted that the embodiments of the device are not limited to the exemplary embodiments shown above.

In embodiments where delivery is to a nostril, delivery of the substance can be improved by inducing sniffing in the user.

Sniffing (short, sharp breaths through the nose, for example, when smelling something) is highly correlated with soft palate (Velum) position. Sniffs are rapidly modulated in an odorant-dependent fashion by a dedicated olfactomotor system, and affect the position of the soft palate at the posterior end of the nasal cavity. When sniffing through the nose, the palate is in its upper position to cause separation between the nasal cavity and the oral cavity.

In addition to conscious control, sniffing may be reflexively elicited by chemicals, functioning as either irritants or odors in the nose. Overall sniff duration and pattern can be modulated in real time to optimize olfactory perception. When the olfactory system encounters a concentrated odorant, sniff vigor is reduced and sniff time is reduced; when it encounters a diluted odorant, sniff vigor is increased and duration lengthened. Odorant pleasantness also affects sniffing; sniff vigor and duration increase when smelling a pleasant odor and decrease when smelling an unpleasant odor.

In preferred embodiments, the device disclosed herein can release odorant into the nasal cavity of the user in order to reflexively elicit sniffing. The odorant can be a single odorant or a mixture of odorants and can comprise compounds from different chemical families, for non-limiting example:

Esters: Geranyl Acetate, Ethyl Acetate, Benzyl Acetate, Octyl Acetate.
Linear Terpens: Geraniol, Citral, Citronella, Nerolidol.
Cyclic Terpens: Terpineol, Thujone.
Aromatic: Eugenol, Vanillin, Anisole, Thymol.
Amines: Indole.
Also aromatic compounds of alcohols, aldehydes, esters, ketones, lactones, and thiols.

In preferred embodiments, the substance is contained within a capsule. The capsule can have a single compartment or it can be multi-compartment. The capsule can contain a broad range of drugs and materials. The aromatic compound can be stored in the nozzle, or the nozzle or a portion thereof can be impregnated with aromatic compound, so as to trigger the closing of the velum when the nozzle tip is being placed in the nasal cavity. The delivery can be for local effect, to the systemic circulation, to the central nervous system, preferably via the olfactory epithelium, and any combination thereof.

As described hereinabove, a drug or material to be delivered can be, but is not limited to, a pharmaceutical, a natural compound, a biologic, a hormone, a peptide, a protein, a virus, a cell, a stem cell and any combination thereof.

The stored substance or substances can be stored as a liquid, an aerosol, a powder, a slurry, a suspension, or a gel, if thin enough. The substance or substances can be stored either with or without a carrier; the carrier can be a liquid, a gas or a powder.

The substance as delivered can comprise a powder, a mixture of liquid and powder, a mixture of gas and powder, a mixture of powders, a liquid, a mixture of liquid and gas, a mixture of liquids, a gas, or a mixture of gases.

The stored substance or substances can be packaged to minimize degradation, for example, by packaging it in vacuum or under an inert atmosphere. Preferably, capsules are single-use so that a single, controllable dose can be delivered with each use of the device. Capsules can be placed in the container of the device, or the container can comprise the capsule.

Use of an inert gas for the carrier for delivery of the medication obviates the possibility of interactions between the user and the delivery carrier; allergies to carriers, especially in medications used for chronic illnesses, are a growing problem. Furthermore, the delivery carrier is in contact with the medicament for no more than a few seconds and more commonly for no more than a few milliseconds, thereby minimizing degradation of the medicament due to interactions with the delivery carrier.

Examples of drugs and materials deliverable using the device are given hereinbelow. All examples listed below are exemplary and are not limiting.

Deliverable drugs and materials include: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease; treatment for pain and anti-migraine treatment.

Medicaments for treatment of allergic rhinitis include: steroids, including corticosteroids, Flonase, Patanase, Beconase, antihistamine, Astelin, Otrivin™, Livostin, Theramax, Avamys, Lufeel, Sinofresh, Nasonex, Nasocort and Veramyst.

Medicaments for treatment of osteoporosis include: Miacalcin, Fortical and Stadol.

Medicaments for vaccinations and immunizations include: LAVIN, and influenza vaccines including FluMist.

Medicaments for smoking cessation include: NasalFent.

Other medicaments which can be delivered include: calcitonin and parathyroid hormone.

Neurotransmitters and neuromodulators that can be delivered include: acetylcholine (ACH), Anticholinergic drugs, adenosine triphosphate (ATP), aspartate (Asp), beta-amyloid, beta-endorphin, bradykinin, dopamine (DA), L-DOPA, Carbio-Dopa, epinephrine, dynorphins, endomorphins, enkephalins, 5-hydroxytryptamine (5-HT), Sumatriptan, Imitrex, Migranal, Zolmitriptan, Zomig, Gamma-aminobutyric acid (GABA), glutamate (glu), glycine, histamine, leptin, nerve growth factor and other growth factors), norepinephrine, nitric oxide, and Substance P.

General anesthetics which can be delivered include: alfentanil, desflurane, enflurane, etomidate, fentanyl, halothane, isoflurane, ketamine, methohexital, methoxyflurane, midazolam, lorazepam, diazepam morphine, nitrous oxide (NzO), propofol, sevoflurane, Sufentanil, Sublimase, and thiopental.

Local anesthetics which can be delivered include: benzocaine, bupivacaine, cocaine, lidocaine, prilocaine, procaine, ropivacaine, and tetracaine.

Opioid analgesics, agonist-antagonists, and antitussives which can be delivered include: agonists, codeine, diphenoxylate, fentanyl, heroin and other opioids, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include: amantadine, apomorphin, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (deprenyl), trihexyphenidyl, rasagiline, azilect, selegiline, ladostigil, rotigotine, neupro, mono amine oxidase inhibitor, and COMT inhibitor.

Antiepileptics which can be delivered include: acetazolamide, carbamazepine, clonazepam, diazepam, ethosuximide, felbamate, gabapentin, Lamotrigine, lorazepam, phenobarbital, phenytoin, primidone, tiagabine, topiramate, valproic acid, Vigabatrin and Midazolam.

Drugs used in affective disorders which can be delivered include: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include: alprazolam, chlorazepate, chlordiazepoxide, diazepam, flumazenil (antagonist), lorazepam, and oxazepam.

Treatments for Alzheimer's disease which can be delivered include: donepezil, galantamine, rivastigmine, Tacrine, Detemir, Novolin, Humulin, Insulin, insulin like hormone, an insulin analog such as NPH Insulin, Lispro, Aspart, Detemir Insulin, Glulisin, Glargin Insulin, Insulin degludec, BDNF, GDNF, MIBG, anti-cancer agents, anti-cancer drugs, dopamine agonist and dopamine antagonist.

Other drugs which can be delivered include: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, Pentobarbital, neuroprotective compounds, neuroprotective peptides, neuroprotective factors, davunetide, anti-schizophrenic drugs, anti-depression drugs, comtan, Entacopone, anti-ADHD agents, anti-ADHD drugs such as Methylphenidrate (Ritalin), and anti-autism and anti-autism symptoms drugs.

Other materials that can be delivered include nanoparticles and microparticles. The nanoparticles and microparticles can comprise drugs; they can be carriers for drugs, cells or parts of cells; and any combination thereof.

In preferred embodiments, the substance comprises permeation enhancers to improve penetration of the active components of the substance through the mucosal membranes.

In some formulations, the formulation can comprise polymeric microparticles comprising at least one active agent and a permeation enhancer, where the active agent is selected from a group consisting of a peptide, a protein, an antibody, nucleic acid, small molecules, cells and any combination thereof.

A great number of penetration enhancers are known in the literature.

One such penetration enhancer is Hyaluronic acid (also referred to as HA or hyaluronan), which is a polysaccharide that occurs naturally in the body. Due to its exceptional water-binding, viscoelastic and biological properties, HA can improve the attributes, such as, but not limited to, the absorption characteristics, of existing formulations and can also add new attributes to existing formulations. Inclusion of HA can be advantageous when developing new formulations.

When used for drug delivery and targeting, HA can provide clear advantages over traditional polymeric substances such as synthetic polymers such as, but not limited to, poly(ethylene glycol), poly(lactic acid), poly(glycolic acid), poly Acrylic Acid and Poly-(N-isopropylacrylamide), or other biopolymers such as chitosan and alginate.

HA's benefits in the drug delivery area include, but are not limited to:
Flexibility when designing controlled drug release profiles;
More stable drug formulations;
Effective drug targeting via accumulation at the targeted site and receptor-mediated uptake;
Enhancement of bioavailability and biocompatibility of drugs; and
Reduction of drug cytotoxicity in healthy tissues polymeric microspheres polymeric controlled release preparation a mucoadhesive agent.

Other penetration enhancers include, but are not limited to the following:

A group containing: a fatty acid, a medium chain glyceride, surfactant, steroidal detergent, an acyl carnitine, Lauroyl-DL-carnitine, an alkanoyl choline, an N-acetylated amino acid, esters, salts, bile salts, sodium salts, nitrogen-containing rings, and derivatives. The enhancer can be an anionic, cationic, zwitterionic, nonionic or combination of both. Anionic can be but not limit to: sodium lauryl sulfate, sodium decyl sulfate, sodium octyl sulfate, N-lauryl sarcosinate, sodium carparate. Cationic can be but not limit to: Cetyltrimethyl ammonium bromide, decyltrimethyl ammonium bromide, benzyldimethyl dodecyl ammonium chloride, myristyltimethyl ammonio chloride, deodecyl pridinium chloride. Zwitterionic can be but is not limited to: decyldimethyl ammonio propane sulfonate, palmityldimethyl ammonio propane sulfonate. Fatty acid including but not limit to: butyric, caproic, caprylic, pelargonic, capric, lauric, myristic, palmitic, stearic, arachidic, oleic, linoleic, linolinic acid, their salts, derivatives and any combinations or glyceride, monoglyceride, diglyceride, or triglyceride of those fatty acids. Bile acids or salts, including conjugated or unconjugated bile acids, such as but not limited to: cholate, deoxycholate, taurocholate, glycocholate, taurodexycholate, ursodeoxycholate, tauroursodeoxycholate, chenodeoxycholate and their derivatives and salts and combinations. Permeation enhancer as comprises a metal chelator, such as EDTA, EGTA, a surfactant, such as sodium dodecyl sulfate, polyethylene ethers or esters, polyethylene glycol-12 lauryl ether, salicylate polysorbate 80, nonylphenoxypolyoxyethylene, dioctyl sodium sulfosuccinate, saponin, palmitoyl carnitine, lauroyl-1-carnitine, dodecyl maltoside, acyl carnitines, alkanoyl cjolline and combinations. Other include but not limited, 3-nitrobenzoate, zoonula occulden toxin, fatty acid ester of lactic acid salts, glycyrrhizic acid salt, hydroxyl beta-cyclodextrin, N-acetylated amino acids such as sodium N-[8-(2-hydroxybenzoyl)amino]caprylate and chitosan, salts and derivatives and any combinations.

Other enhancers include: formulations of water in oil, formulations of oil in water, emulsions, double emulsions, micro-emulsions, nano-emulsions, water in oil emulsions, oil in water emulsions; steroidal detergent, and an acylase; to allow better absorption in the mucosal tissue, better permeation and absorption in the target cells, better stability of the encapsulated drug/active ingredient.

Some embodiments comprise, either alone or in combination with a penetration enhancer, a mucoadhesive agent such as, but not limited to, bioadhesive proteins, carbohydrates and mucoadhesive polymers In the capsule of the present invention, the device comprises at least one compartment, and preferably a plurality of compartments, each containing a flowable substance. The delivery device is designed to rupture the compartments such that the flowable substances are mixed with a carrier, preferably air, and delivered to a predetermined deposition site, typically, but not exclusively, in the nasal passages.

Medicaments may be supplied as liquids, as powders, or as aerosols. In the preferred embodiment, the medicament is supplied in a single-dose capsule. In other embodiments, the medicament is supplied in a multi-dose capsule means, the multi-dose capsule configured to provide a single dose per activation.

In preferred embodiments, the flowable-substance capsule has a plurality of compartments. A compartment can contain at least one medicament, at least one medicament precursor, carrier gas, compressed gas, and any combination thereof.

The different compartments can contain different medicaments, with the plurality of medicaments delivered to the nostril or other delivery site in a single dose. In this manner, a plurality of medicaments may be supplied to the nostril in a single injection, with interactions occurring between the medicaments at most during the short time between activation of the device and the delivery of the substances and their deposition at the target site.

In some embodiments, interactions between components are unwanted. In such embodiments, a sequential release will utilize the short time period between release of the components and their absorption in the body to prevent such unwanted interactions and/or reactions.

In other embodiments, mixing and/or reactions are desired. In such embodiments, the reactions can occur all at once, by rupturing all of the compartments at the same time and mixing/interacting the components, either in the aerosol or in at least one mixing chamber. In other embodiments, a component can be added by needle insertion at a desired time before use, either into an empty compartment or into an occupied compartment (so that a desired reaction can occur). In other embodiments, the compartment walls rupture in a predetermined order, so that mixing/interaction occurs in stages, in a predetermined order. Mixing/interaction can occur in a compartment or compartments, in a mixing chamber, in the air passages of the device, in the aerosol, in the nasal (or other) passages of the body, and any combination thereof.

As a non-limiting example, a medicament can comprise four components, stored in four compartments of a capsule. Prior to activation, a fifth component is injected into compartment 1. After a predetermined time, the device is activated and the walls between compartment 1 and compartment 2 are broken, allowing mixing of 5/1 and 2. This followed by rupture of the walls surrounding component 3, which then mixes with 5/1/2 and reacts with 2. The last walls to rupture are those surrounding compartment 4; material 4 remains in a separate part of the aerosol and deposits on the nasal passages after deposition of 5/1/2/3.

In another example, precursor A mixes with precursor B to form intermediate C, and, subsequently, intermediate C mixes with precursor D to form final product E.

Mixing or reactions or release of components from different compartments can occur simultaneously, in different linked compartments, or they can occur sequentially, as in the example above. Any combination of sequential and simultaneous reactions and/or mixing and/or release can be used. Components can arrive at the deposition site simultaneously, either mixed or unmixed, sequentially, and any combination thereof.

It should be noted that there can be a predetermined delay of some fractions of a second between rupturing of walls of different compartments, in order to, for non-limiting example, allow complete mixing of one set of components or allow a reaction between one set of components to go to completion before the next mixing/reaction starts or the delivery starts.

In some embodiments, the device or, preferably, the capsule, comprises a mixing mechanism or mixing chamber, so that, as described above, components of the composition can mix and/or react during the activation process, enabling components to be stored separately and/or to be stored as stable precursors, but to deliver a predetermined treatment comprising at least one medicament to a predetermined delivery site.

In preferred embodiments of the device, the mixture of aerosol and pre-aerosolized mist is formed within the nozzle, with the hole at the lateral end of the nozzle having little effect on either the shape of the dispersion plume or the velocity of the aerosol.

Figures 23, 24:
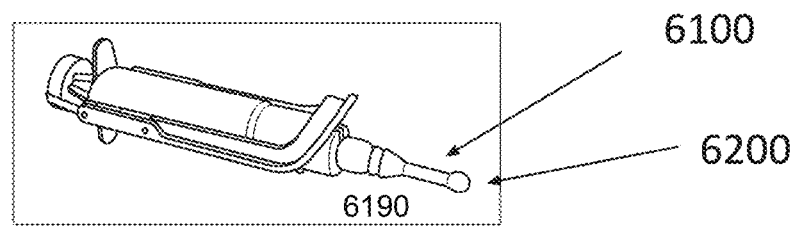
FIG. 23 illustrates an experimental setup to demonstrate the location of formation of the mist.
FIG. 24 illustrates the location of formation of the mist.

An experimental setup to demonstrate the location of formation of the mist is shown in FIG. 23, and the results of tests for three different operating conditions (1, 2 and 3) are shown in Table 1 and FIG. 24.

TABLE 1

| | Location of Aerosol Formation | | | |
|---|---|---|---|---|
| Test | Air Volume (ml) | Pressure (bar) | Orifice Diameter (mm) | Aerosol produced Before Exit from Device? |
| 1 | 19 | 6 | 0.8 | Yes |
| 2 | 8 | 4 | 0.8 | Yes |
| 3 | 8 | 6 | 0.8 | Yes |

FIG. 23 shows an embodiment of the device, with the nozzle (6100) and the nozzle tip (6200) on the right, with the bracket indicating the region shown enlarged (6190) in FIG. 24.

Representation before activation is shown in the center of FIG. 24, and representation during activation is shown on the right. Before activation, the nozzle is clear, there is no aerosol therein. After activation, the nozzle appears opaque due to the aerosol and/or pre-aerosolized mist therein. If no aerosol or pre-aerosolized mist had been formed, the liquid would exit as a thin stream, which would appear in the image as a streak down the center of the nozzle.

Tests were made for exemplary embodiments of a pressurized air carrier for providing controlled drug delivery to the nasal cavity. Other embodiments can be used for delivery to the ear, mouth, throat and rectum.

In these embodiments of the device, the following parameters were variable, over the ranges given:
Pressure $P_{gas}$, between about 1 barg and about 20 barg
Air volume $V_{gas}$, between about 1 cc and about 50 cc
Time of activation dt, less than 0.5 s.
Typical ranges for the operating parameters are:
(a) $P_{gas}$ is in a range of about 1-10 barg;
(b) $V_{gas}$ is in a range of about 1-21 ml;
(c) $V_{sub}$ is in a range of about 0.01-7 ml;
(d) D is in a range of 0.2-6 mm;
(e) said pressure rate $$\frac{dP_{gas}}{dt_{deliver}} \to \infty_{\frac{dP}{dT} \to \infty};$$

(f) said pressure velocity $dP_{gas}/dt_{deliver}$ is greater than about 0.001 barg/ms;
(g) said amount rate $dV_{sub}/dt_{deliver}$ is greater than about 0.0001 ml/ms;
(h) said volume rate $dV_{gas}/dt_{deliver}$ is greater than about 0.001 ml/ms;
(i) said predetermined period of time, dt→0;
(j) dt is in a range of about 0 to 500 ms; and
(k) any combination thereof.

Another important consideration, not investigated in these tests, is the location of the nozzle in the body orifice, for non-limiting example, the depth of insertion of the nozzle in the nasal cavity.

In practice, at least one of: the pressure, air volume and time between charging and activation can be optimized based on the characteristics of the compound, drug or medicament such as, but not limited to, the volume, density, viscosity, state of matter, drug formulation, and any combination thereof. The compound can be a liquid, a powder or any combination thereof.

Pressure, air volume, time between charging and activation, and location of the orifice together with the characteristics of the delivered substance; all of the above contribute to the final distribution of aerosolized matter in the nasal cavity, or, in other words, the pattern of deposition of the aerosolized matter in the nasal cavity following discharge of the matter from a device with given predetermined parameters.

Other criteria which can be optimized include, but are not limited to, droplet size, droplet size distribution, droplet size as a function of time, and droplet size distribution as a function of time, plume geometry, pattern characteristics and particles' velocities.

The material as delivered is then a predetermined volume of the selected medicament in a predetermined form within a carrier comprising a predetermined volume of air/gas, with the volume of air/gas condensed at a predetermined pressure.

Tests showing the effect of changing pressure, air volume and time between charging and activation are given below. Deposition was measured in models that mimicked at least one aspect of the human nasal cavity (structure, friction, air flow, surface area or surface mucosa).

Model 1

A 36 cm long plastic tube with an inner diameter of 0.6 cm was used as a model for nasal friction and air resistance in the nasal cavity. The length of the aerosol distribution was measured, as well as the characteristics of the aerosol distribution.

2 mg/ml Methylene Blue in saline was used. The dye distribution pattern in the tube and the amount of dye that reached the end of the tube were observed.

Figure 25:
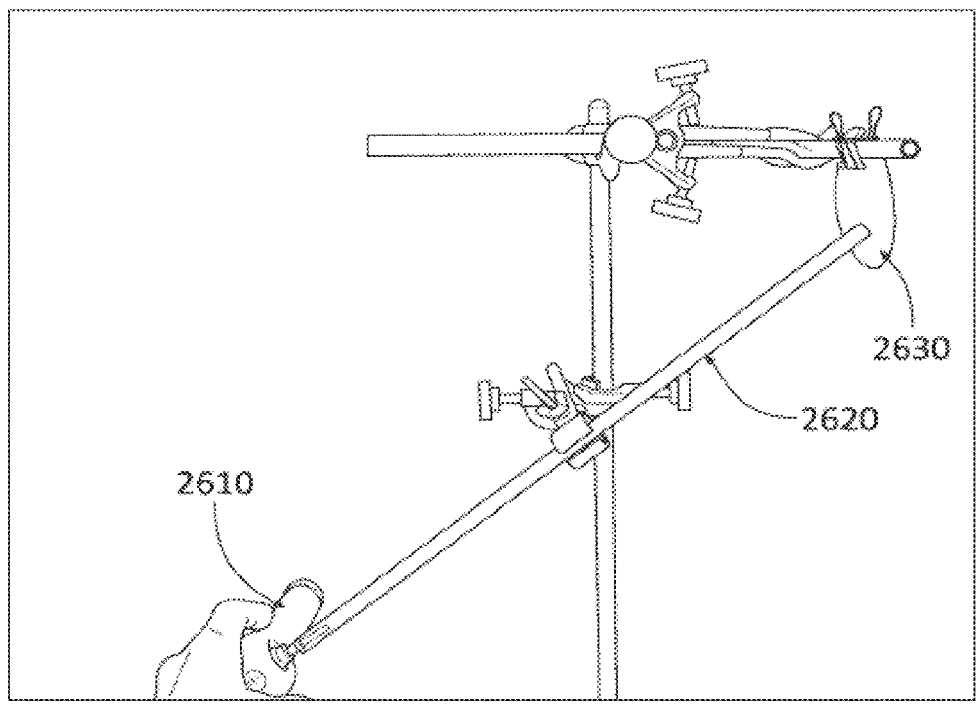
FIG. 25 illustrates an experimental setup of the delivery device.

In reference to FIG. 25, a test setup is shown, showing a delivery device (2610), the plastic tube (2620), and an absorbent pad (2630) to capture material that has passed entirely through the tube.

Figures 26A, 26B:
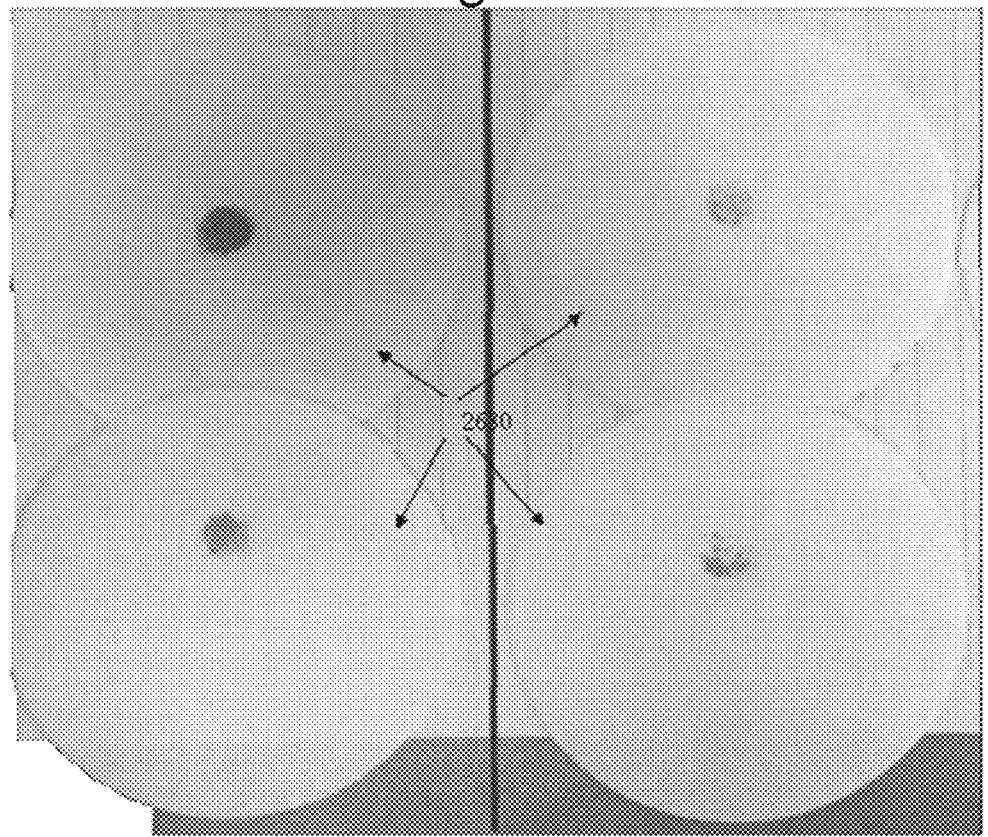
FIGS. 26A-B shows the results of droplet penetration through a tube with a pressure of 4 barg on the absorbent.
Figures 29A, 29B, 29C, 29D:
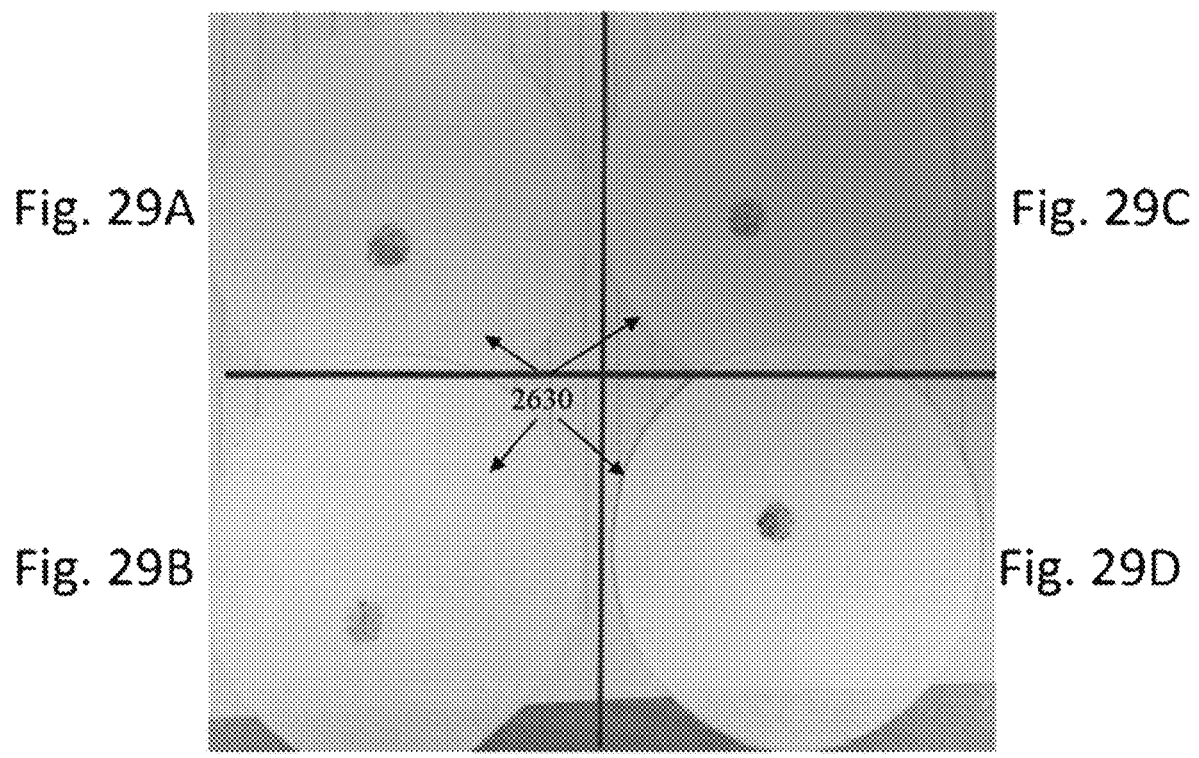
FIGS. 29A-D shows the results of droplet penetration through a tube with a pressure of 7 barg on the absorbent.

In reference to FIG. 26A-B, a pressure of 4 barg and a liquid volume of 100 microliters were used for the tests. An air volume of 18 cc was used for the two results shown in FIG. 26A, while an air volume of 10 cc was used for the two results shown in FIG. 26B.

Delivery of the liquid dye through the end of the tube (2620), as determined by its deposition on the absorbent (2630), was more efficient for the air volume of 18 cc, as shown by the stronger color (showing more deposited material) and more-even distribution in FIG. 26A as compared to FIG. 26B.

In reference to FIG. 27A-B, the deposition characteristics on the inner tube surface were much better for the 18 cc air volume (FIG. 27A) than for the 10 cc volume (FIG. 27B), with deposition of aerosol on the inner tube surface being much more homogeneous, being delivered over a longer distance and having much smaller droplets with the 18 cc air volume (FIG. 27A) than with the 10 cc air volume (FIG. 27B).

In reference to FIG. 28A-B, a pressure of 2 barg and a liquid volume of 100 microliters were used for the tests. An air volume of 14 cc was used for the two results shown in FIG. 28A, while an air volume of 5 cc was used for the two results shown in FIG. 28B. Similarly to the results for FIG. 26, delivery of the liquid dye through the tube to the end of the tube (2620), as determined by its deposition on the absorbent (2630), was more efficient for the air volume of 14 cc, as shown by the stronger color (showing more deposited material) and more-even distribution in FIG. 28A as compared to FIG. 28B.

In reference to FIG. 29A-D, an air volume of 20 cc, a pressure of 7 barg and a liquid dye volume of 100 µl was used for the tests. In these tests, the device was charged, a time of 0.5 min (FIG. 29A), 5 min (FIG. 29B), 50 min (FIG. 29C), and 150 min (FIG. 29D) was allowed to elapse; and the device was activated. As can be seen from FIG. 29A-D, the elapsed time between charging the device and its activation has virtually no influence on the results, indicating that the device can remain in the charged state for a prolonged period prior to activation and drug release.

Model 2

Material dispersion and penetration into the nasal cavity layers in a nasal cast model was found to be dependent on the pressure and air volume and the form and characteristics of the material deposited.

Figure 30:
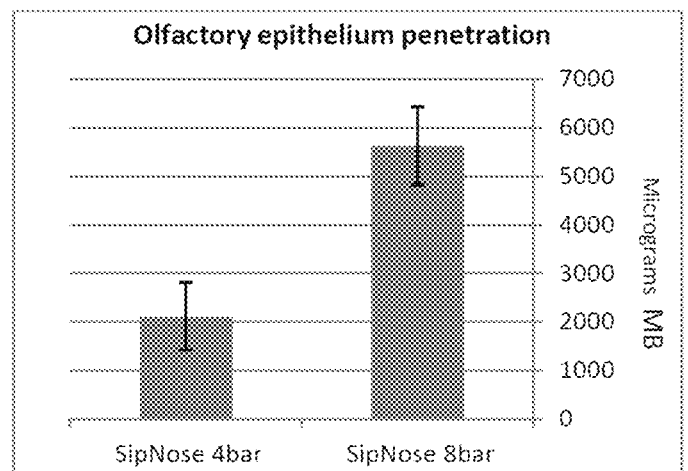
FIG. 30 illustrates the effect of pressure on deposition of a powder.

FIG. 30 shows the effect of pressure (with other parameters held constant) on deposition of a powder. More than 2½ times as much powder reached the olfactory epithelium with the 8 barg pressure, compared to the 4 barg pressure.

Model 3

The effects of air volume and air pressure on the distribution of 99mTC-DTPA aerosol in the nasal cavity and nasopharynx were examined using SPECT-CT for two human volunteers.

In both cases, the deposited material comprised 300 microliters of DTPA; 1.75 mc (milli Ciri) and the air volume was 20 ml. A pressure of 6 barg was used for the results shown in FIG. 31A, while a pressure of 4 barg was used for the results shown in FIG. 31B.

Figure 31A:
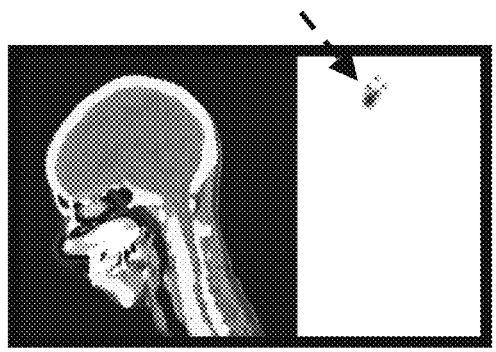
FIG. 31A-B illustrates the effects of air volume and air pressure on the distribution of aerosol in the nasal cavity and nasopharynx.

In FIG. 31A, the aerosol is localized in the nasal cavity at the respiratory and olfactory epitheliums (dashed arrow) and did not reach the Nasopharynx and did not enter the GI tract.

Figure 31B:
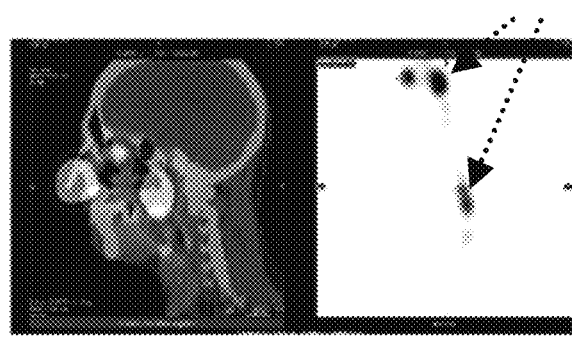

In FIG. 31B, with a lower pressure, the aerosol is localized in the nasal cavity at the respiratory and olfactory epitheliums and also moved down into the Nasopharynx (upper dotted arrow) and into the GI tract (lower dotted arrow).

The pressure affected the distribution and thus the absorption of the aerosolized drug in the human body.

As shown hereinabove, the location and distribution of deposition of a desired substance and the characteristics of the substance on deposition are controllable by controlling parameters such as pressure, air volume, substance volume and nozzle shape.

Location of Formation of Aerosol

In all known other mechanisms of creating aerosols, an orifice is placed at the end of a nozzle and the inner diameter of the device's nozzle and, especially, its orifice, is the main parameter that influences aerosol formation and the aerosol's characteristics. In contrast, in the present invention, no orifice is needed. More than that, putting a conventional orifice at the end of the nozzle will actually limit the forces reaching the liquid or powder being dispensed, and thus will reduce the ability to create the desired fine aerosol at the target site. Thus, the large diameter tubing that can be used in the present invention, about an order of magnitude larger than the diameter of commonly-used tubes and orifices, results in the desired fine aerosol, carried efficiently into the nasal cavity with droplet median diameters (DV50) on the order of 1-100 micrometer.

In the present invention, the aerosol is created as a result of the air volume-pressure parameters of the device and is influenced by the nasal cavity resistance rather than primarily by the orifice diameter.

In order to model nasal friction and air resistance and as a model for aerosol formation in the nasal cavity, a 36 cm long glass tube with an inner diameter of 2 cm, filled with oil up to 22 cm of its length, was used.

Theoretical analysis has indicated that 5 cm of tube is equivalent to about 0.1-0.5 cm of the nasal passages; therefore the 22 cm, tube would approximately simulate the full depth of a nasal passage.

The test material was 200 microliter of Methylene Blue liquid solution.

The liquid solution was discharged from a device into the base of the tube and pictures and videos were taken in order to be able to follow the process of aerosol formation. The length of the deposition region, the aerosol distribution and the diameter of the aerosol droplets were determined as a function of time.

FIGS. 32A-D show the effect of orifice size on droplet size (FIGS. 32B, D) and droplet distribution (FIGS. 32A, C) in a conventional device.

Figure 32A:
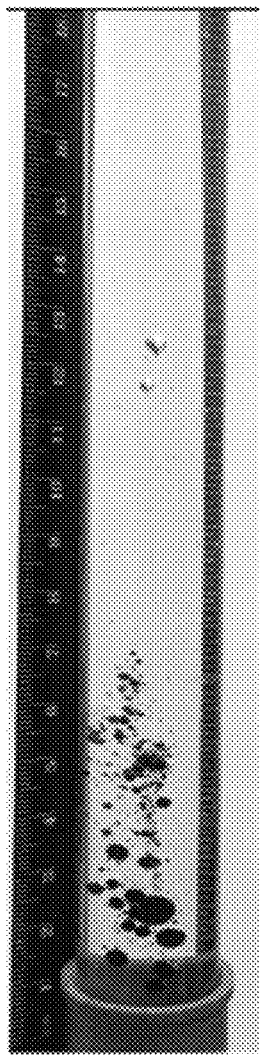
FIGS. 32A-D show the effect of orifice size on droplet size and droplet distribution in a conventional device after droplet penetration through a liquid filled tube.
Figure 32B:
Figure 32C:
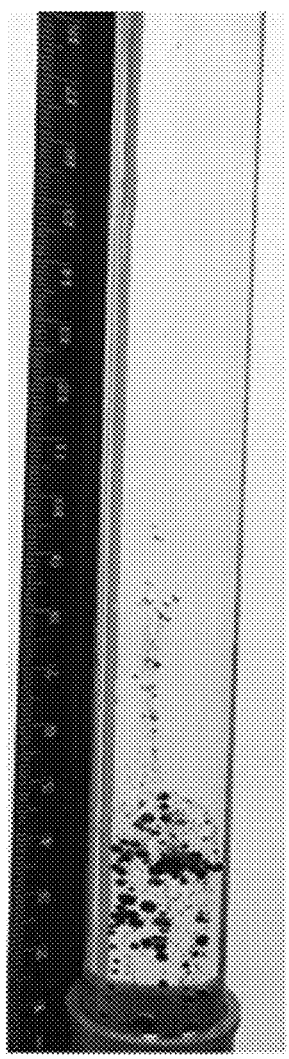
Figure 32D:
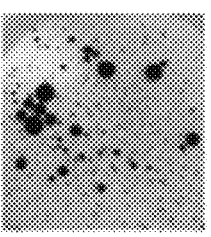

The Methylene blue solution was injected into the tube using a syringe. FIGS. 32A-B show droplet distribution and size for a larger needle (21G; approx. 0.5 mm) and FIGS. 32C-D show droplet distribution and size for a smaller needle (25G; approx. 0.2 mm). The larger diameter needle (FIGS. 32A-B) creates larger droplets than the smaller diameter needle (FIGS. 32C-D).

In contrast, FIGS. 33A-E and 34A-D show that the opposite is true if the technique of the present invention is used, where the aerosol is created by means of a pressurized gas.

Figure 33A:
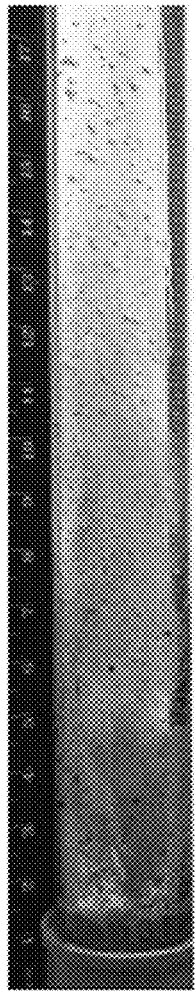

In reference to FIG. 33, FIGS. 33A-E show the effect of orifice size on droplet size (FIGS. 33B, D) and droplet distribution (FIGS. 33A, E, C) in a device of the present invention. FIG. 33A shows the distribution in the lower part of the tube, while FIG. 33E shows the distribution in the upper part of the tube.

Figure 33B:
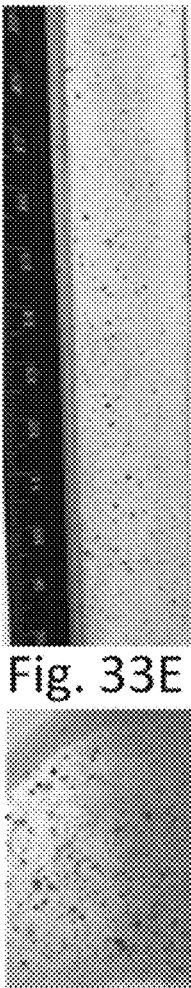
Figure 33C:
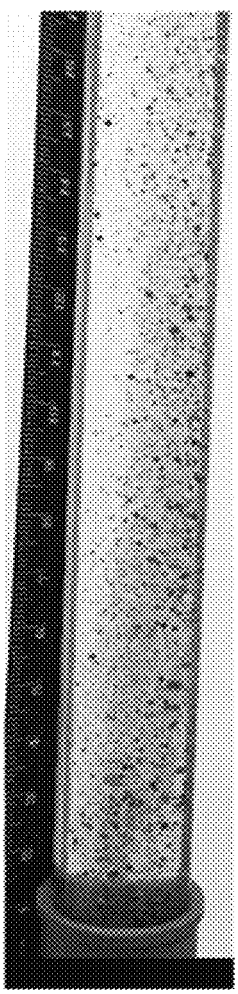
Figure 33D:

In FIGS. 33A-E, the device of the present invention is charged to 7 barg pressure and 20 ml of Methylene Blue solution is discharged through an orifice into the base of the tube. FIGS. 33A-B,E show droplet distribution and size for a larger needle (21G; approx. 0.5 mm) and FIGS. 33C-D show droplet distribution and size for a smaller needle (25G; approx. 0.2 mm). In this case, the larger nozzle (FIGS. 33A, B) has smaller diameter droplets, a more homogeneous aerosol and a distribution that extends much further up the tube than the smaller diameter nozzle (FIGS. 33C, D).

In reference to FIG. 34, FIGS. 34A-D show the effect of orifice size on droplet size (FIGS. 34B, D) and droplet distribution (FIGS. 34A, C) in a device of the present invention.

In FIGS. 34A-D, the device of the present invention is charged to 4 barg pressure and 18 ml of Methylene Blue solution is discharged through an orifice "fluid discharging outlet port") into the base of the tube. FIGS. 34A-B show droplet distribution and size for a larger needle (21G; approx. 0.5 mm) and FIGS. 34C-D show droplet distribution and size for a smaller needle (25G; approx. 0.2 mm). In this case, the larger nozzle (FIGS. 34A, B) has smaller diameter droplets and a more homogeneous aerosol than the smaller diameter nozzle (FIGS. 34C, D).

A comparison of FIGS. 33 and 34 shows that the higher volume-higher pressure combination (20 ml, 7 barg) has smaller diameter droplets with a greater homogeneity and a distribution that extends much further up the tube than the lower volume-lower pressure combination (18 cc, 4 barg).

Figure 35A:
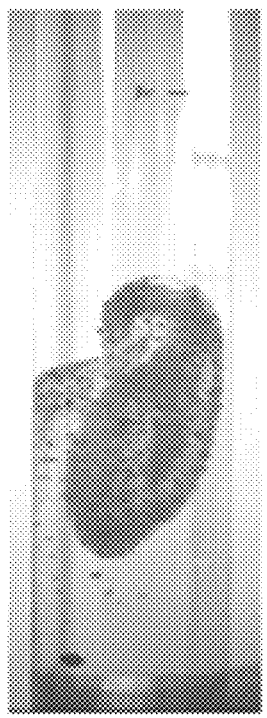
FIGS. 35A-C show a comparison between Otrivin™, Otrimer™, and the present invention.
Figure 35B:
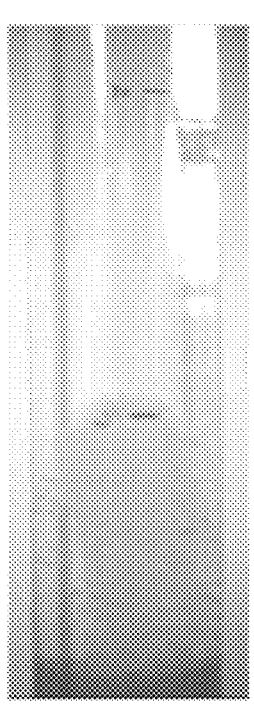
Figure 35C:
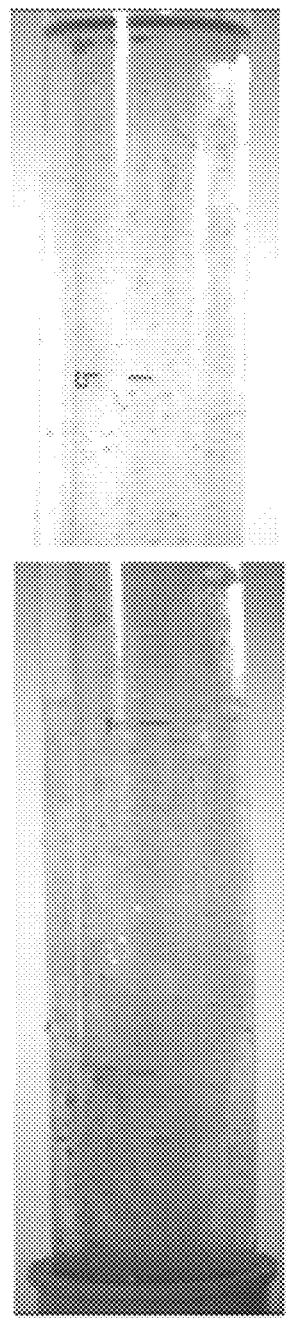
Figures 36A, 36B, 36C:
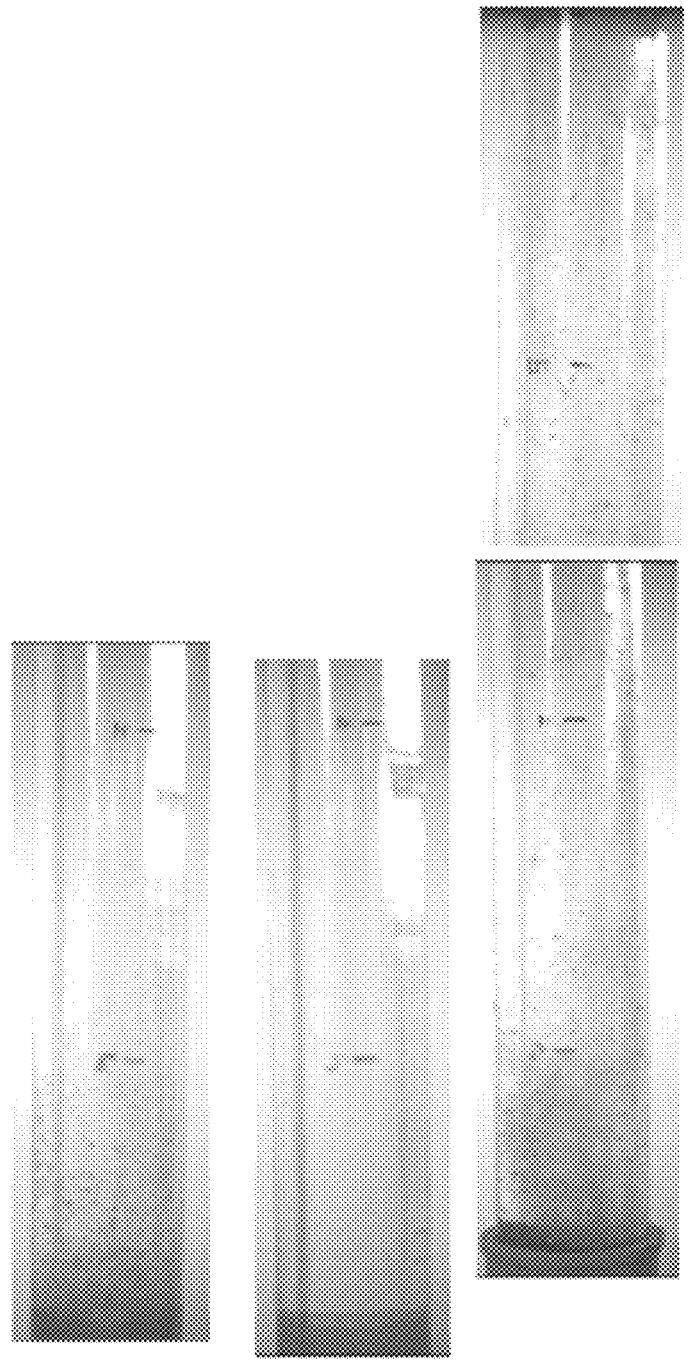
FIGS. 36A-C show a comparison between Otrivin™, Otrimer™, and the present invention after 2 minutes.

In FIGS. 35 and 36 a comparison is made between two commercial, prior art devices and the present invention device. In all cases, 0.1 ml of aqueous solution was tested. In FIGS. 35A and C and 36A and 36C, the liquid was Methylene Blue in aqueous solution; in FIGS. 35B and 36B, saline solution alone was used. The liquid was discharged from the device into the base of a tube filled with oil. In FIGS. 35A and 36A, the Otrivin™ device was use, in FIGS. 35B and 36B, the Otrimer™ device was used, and in FIGS. 35C and 36C, the present invention technology was used. For both the Otrivin™ (FIG. 35A) and the Otrimer™ (FIG. 35B) devices, the height reached by the solution at the time of application is less than 10 cm and the liquid forms a distinct bolus near the bottom of the tube. In contrast, with the device demonstrates the present invention (FIG. 35C), the liquid appears in the tube as small droplets, with some of the droplets reaching a height in the tube of 20 cm.

Two minutes later, (FIGS. 36A-C), the liquid from the Otrivin™ device has reached a height of about 5 cm (FIG. 36A), while the liquid in from the Otrimer™ device has fallen to the base of the tube; it is barely visible at the bottom of the tube in FIG. 36B. In contrast, the droplets are fairly stable in the tube in the present invention technique (FIG. 36C); there is a fairly even distribution of droplets until a height of about 12 cm is reached, and some of the droplets have reached a height of nearly 20 cm.

Figure 37:
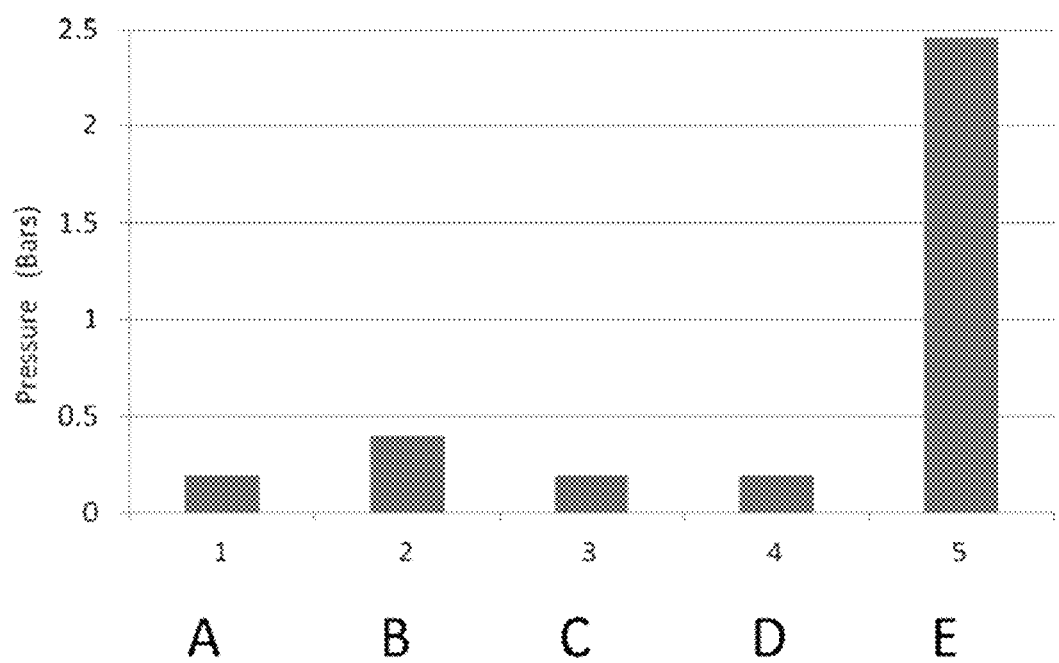
FIG. 37 illustrates the pressure generable in a tube by various devices.

In reference to FIG. 37, nasal applicators were connected to a ~7 ml volume closed tubing, with a connection to a pressure sensor. The ~7 ml volume represents the approximate volume of the nasal cavity. The devices were discharged into the closed tubing and the maximum pressure developed in the tubing was measures. The pressure in the tubing for the four commercial devices, the Otrivin™ device (FIG. 37A), the Marimer device (FIG. 37B), the Rhinox device (FIG. 37C), and the Alrin™ device (FIG. 37D) were less than 1 barg. In contrast, the pressure in the tubing from the present invention technology (FIG. 37E), was almost 2.5 barg, more than 2½ times as much as the closest commercial device, the Marimer device (FIG. 37B).

Figure 38A:
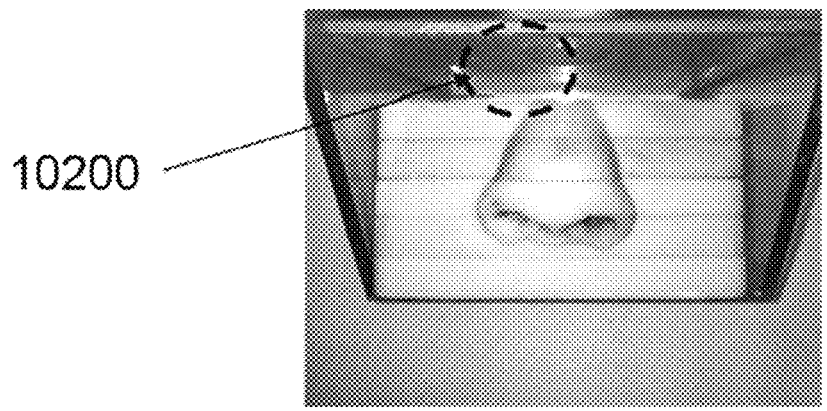
FIG. 38A-C illustrates spray penetration in a nasal cast model.
Figure 38B:
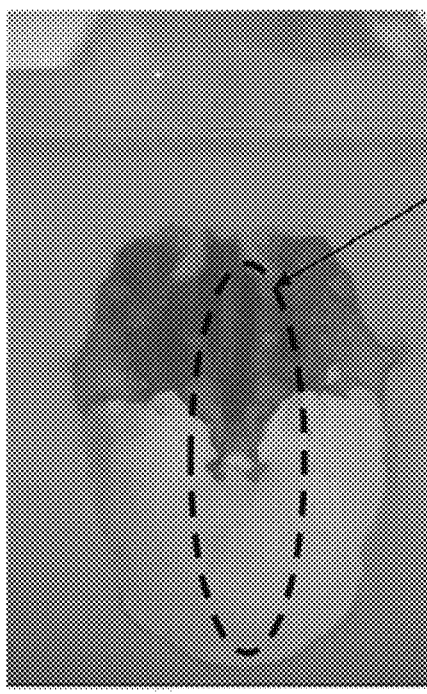
Figure 38C:
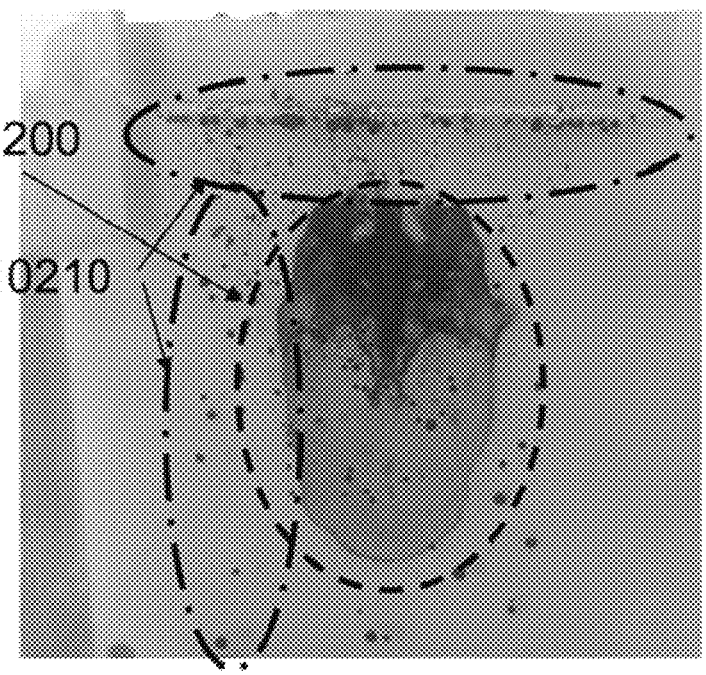

In reference to FIG. 38A-C, Methylene Blue in aqueous solution was delivered through a nostril of a human nasal cast model (FIG. 38A) filled with oil to mimic the nasal cavity's inner pressure and conditions. The dashed circles (10200) show the exit from the top of the nasal cast; material that reaches the exit would reach the olfactory epithelium in the nose. FIGS. 38B and 38C show nasal cast models after application of the Otrivin™ device (FIG. 38B) and the present invention technology based device (FIG. 38C) to a nostril of the nasal cast. As can be seen from FIG. 38B, no material would reach the olfactory epithelium with the Otrivin™ device—no material has reached the exit from the nasal cast. In contrast, droplets of material (dotted circle, 10210) have exited the nasal cast, showing that, unlike the commercial devices, the material discharged from the present invention technology based device is capable of reaching the olfactory epithelium.

In the following tests, results were obtained in a set of experiments made using the device, where, in each example, one parameter is changed and all others are fixed.

In Tests 1-8 below, the distance the aerosol migrated was measured in a plastic tube with an inner diameter of 0.5 cm and 345 cm long. Measurements were done at room temperature.

In Tests 1-6, the substance was a liquid and 100 microliters of saline were used for each activation of the device unless otherwise stated, and in Tests 7-8, the substance was a powder.

A. Liquid Aerosol Experiments

1. Effect of Pressure

Figure 39A:
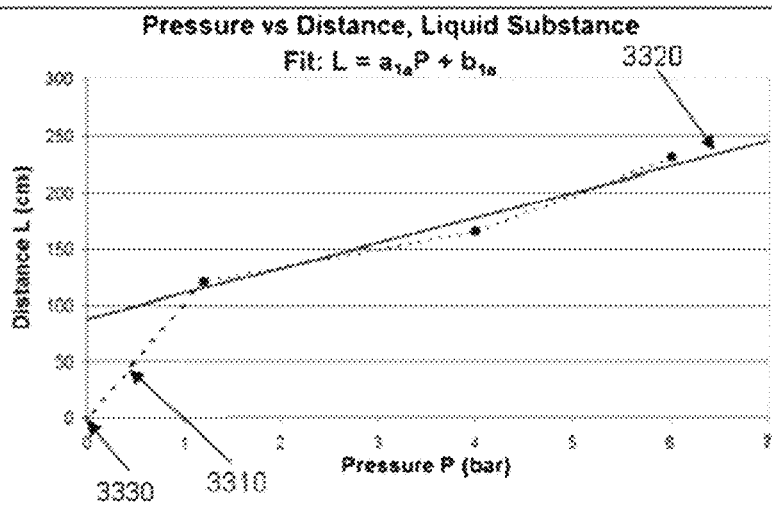
FIGS. 39A-C illustrate the effect of changing pressure on distance traveled by an aerosol through a tube.
Figure 39B:
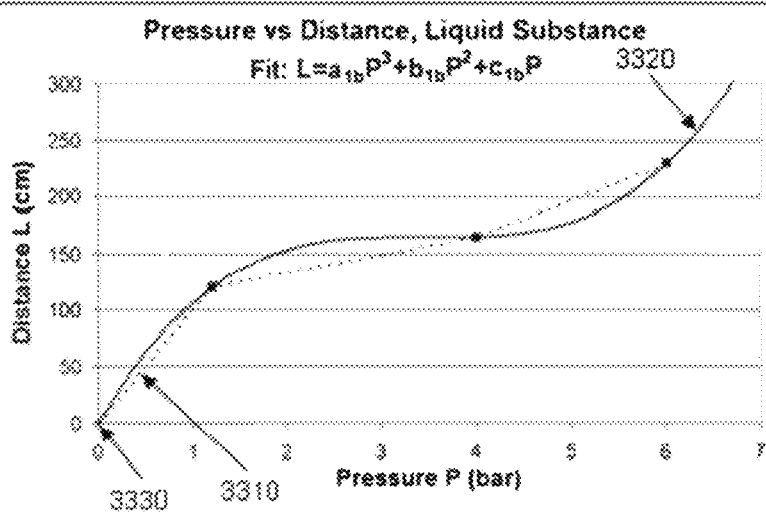
Figure 39C:
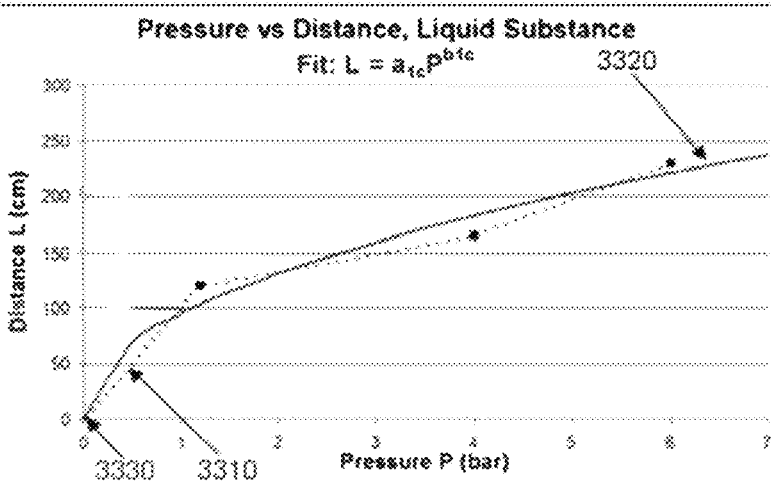

For a SipNose device, for an orifice diameter of 0.8 mm and an air volume of 3 ml, the effect of pressure on the distance the aerosol migrates is shown in Table 2 and FIG. 39A-C.

TABLE 2

Effect of pressure on distance aerosol migrates

| Pressure (Barg) | Distance Aerosol Migrates (cm) |
|---|---|
| 1.2 | 120 |
| 4.0 | 165 |
| 6.0 | 230 |

The point at (0,0) (3330) was not a measured point, but could be included to improve the quality of the fits. The dotted line (3310) connects the data points, including the additional point at (0,0). The solid line (3320) shows fits to the data.

FIG. 39A shows a best-fit straight-line to the data, excluding the point at zero, where the distance L is $L=a_{1a}P+b_{1a}$ for distance L is in cm and pressure P is in barg. The parameter $a_{1a}$ is in a range of about 0 to about 70 and $b_{1a}$ is in a range of about 0 to about 130 for distance L is in cm and pressure P is in barg. The data fit well to the straight line, although the line does not pass near the point at (0,0).

FIG. 39B shows a best-fit cubic to the data, including the point at zero, where the distance L is $L=a_{1b}P^3-b_{1b}P^2+c_{1b}P$ for distance L is in cm and pressure P is in barg. The parameter $a_{1b}$ is in a range of about 2 to about 6, and $b_{1b}$ is in a range of about −20 to about −60 and $c_{1b}$ is in a range of about 70 to about 230 for distance L is in cm and pressure P is in barg. The data fit well to the cubic line.

FIG. 39C shows a best-fit power fit to the data including the point at zero, where the distance L is $L=a_{1c}P^{b_{1c}}$. The parameter $a_{1c}$ is in a range of about 71 to about 120 and $b_{1c}$ is in a range of about 0.30 to 0.63 for distance L is in cm and pressure P is in barg. The data fit well to the power-law curve.

2. Effect of Orifice Diameter

Figure 40A:
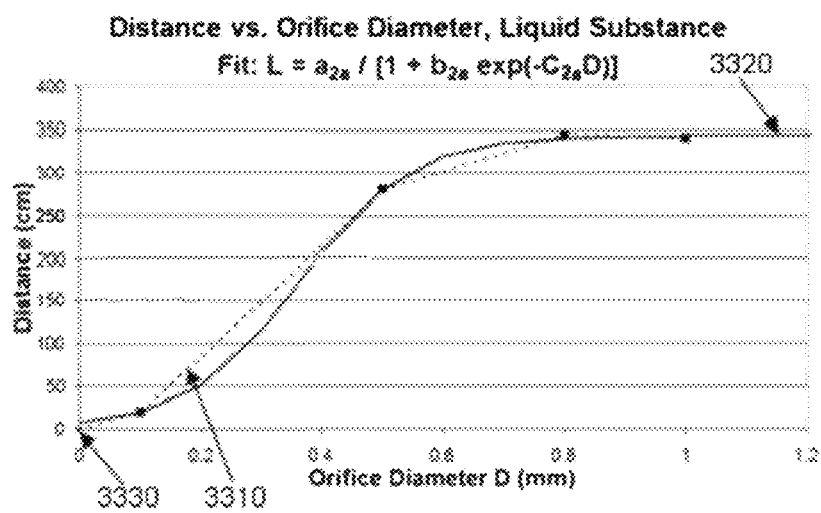
FIGS. 40A-B illustrate the effect of changing orifice diameter on distance traveled by an aerosol through a tube.
Figure 40B:
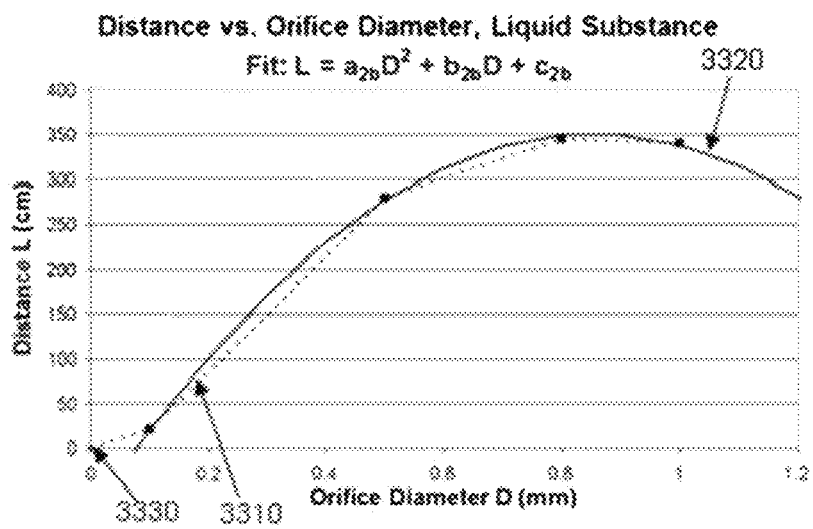

For a SipNose device, the effect of orifice diameter on the distance the aerosol migrates is shown in Table 3 and FIG. 40A-B.

TABLE 3

Effect of orifice diameter on distance aerosol migrates

| Pressure (barg) | Air Volume (ml) | Orifice Diameter (mm) | Distance Aerosol Migrates (cm) |
|---|---|---|---|
| 6 | 19 | 0.26 | 20 |
| 6 | 19 | 0.49 | 280 |
| 6 | 19 | 0.8 | ≥345 |
| 6 | 19 | 1 | 340 |

For constant pressure and air volume, the larger the orifice diameter, up to about 0.8 mm, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

FIG. 40A shows a best-fit line, including the point at zero, to the equation $L=a_{2a}/(1+b_{2a}\exp(-c_{2a}D))$ where the distance L in cm and pressure P is in barg. The parameter $a_{2a}$ is in a range of about 325 to about 363, $b_{2a}$ is in a range of about −47 to about 163 and $c_{2a}$ is in a range of about 7 to about 15. The data fit well to the equation.

FIG. 27B shows a best-fit line, including the point at zero, to the equation $L=a_{2d}/(1+b_{2b}\exp(-c_{2a}D))$ where the distance L in cm and pressure P is in barg The parameter $a_{2b}$ is in a range of about −928 to about −229, $b_{2b}$ is in a range of about 600 to about 1378 and $c_{2b}$ is in a range of about −160 to about 15. The data fit well to the equation.

3. Effect of Drug Volume

Figure 41A:
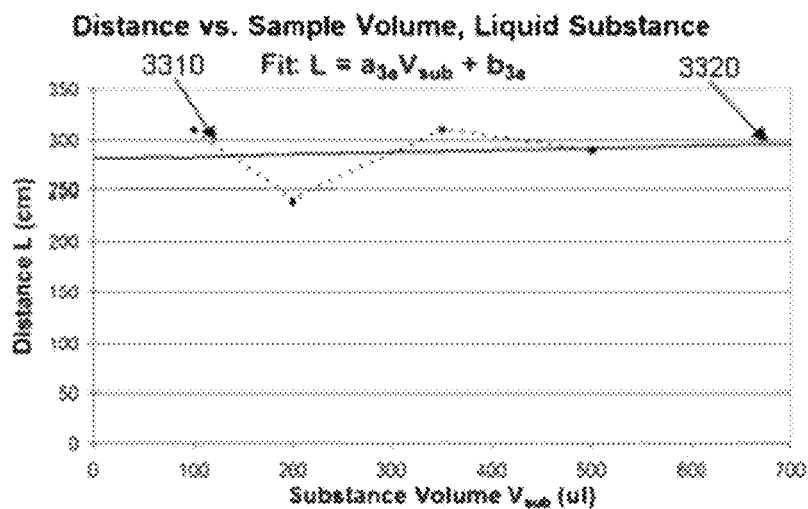
FIGS. 41A-B illustrate the effect of changing drug volume on distance traveled by an aerosol through a tube.
Figure 41B:
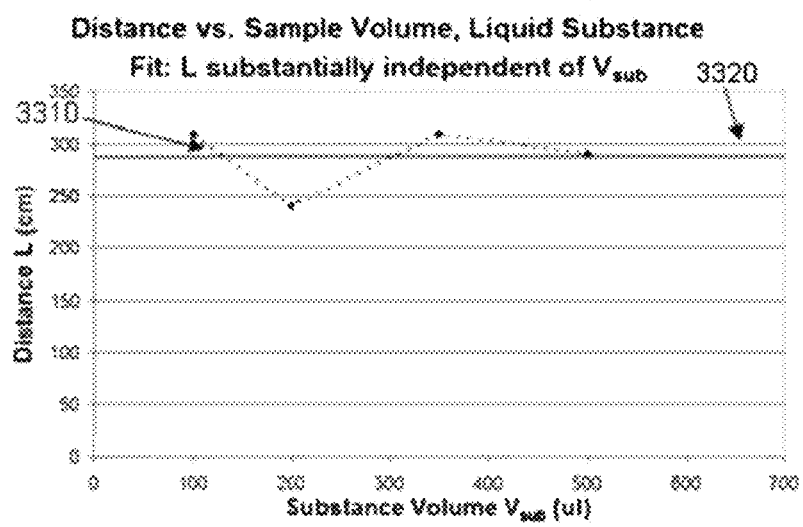

The effect of the amount of drug on the distance the aerosol migrates is shown in Table 4 and fits to the SipNose data are shown FIG. 41A-B.

TABLE 4

Effect of drug volume on distance aerosol migrates

| Device Type | Substance Type | Pressure (barg) | Air Volume (ml) | Orifice Diameter (mm) | Amount of Drug | Distance Aerosol Migrates (cm) |
|---|---|---|---|---|---|---|
| SipNose | Liquid | 6 | 19 | 1 | 100 μl | 310 |
| SipNose | Liquid | 6 | 19 | 1 | 200 μl | 240 |
| SipNose | Liquid | 6 | 19 | 1 | 350 μl | 310 |
| SipNose | Liquid | 6 | 19 | 1 | 500 μl | 290 |
| Nasal Pump from Alrin | Liquid | — | — | — | 100 μl | 45 |
| MAD, Wolfe Tory | Liquid | — | — | — | 100 μl | 30 |
| MAD, Wolfe Tory | Liquid | — | — | — | 200 μl | 40 |
| MAD, Wolfe Tory | Liquid | — | — | — | 600 μl | 45 |
| Simply Saline Nasal Mist | Liquid | — | — | — | ~200 μl | 40 |
| Optinose/Direct Haler technology, release time >1 sec) | Straw with dry powder | — | — | — | ~100 mg | 180 |

In all cases, the aerosol migrates significantly further down the tube for the SipNose device than for the commercial devices.

For the SipNose device, the point at (0,0) (3330) was not a measured point, but could be included to improve the quality of the fits. The dotted line (3310) connects the data points, including the additional point at (0,0). The solid line (3320) shows fits to the data.

FIG. 41A shows a best-fit line for the SipNose data, including the point at zero, to the equation $L=a_{3a} V_{sub}+b_{3a}$ where the distance L in cm and pressure P is in barg. The parameter $a_{3a}$ is in a range of about −0.55 to about 0.59 and $b_{3a}$ is in a range of about 96 to about 467. The data fit well to the equation although it is clear that the primary effect on the migration distance L is the carrier gas volume rather than the drug volume, since the line clearly does not pass through zero.

FIG. 41B shows that, for the SipNose data, for drug volumes in the range of interest, a good fit can be had by assuming that the drug volume has no effect on the migration distance.

4. Effect of Sample Viscosity

Figure 42:
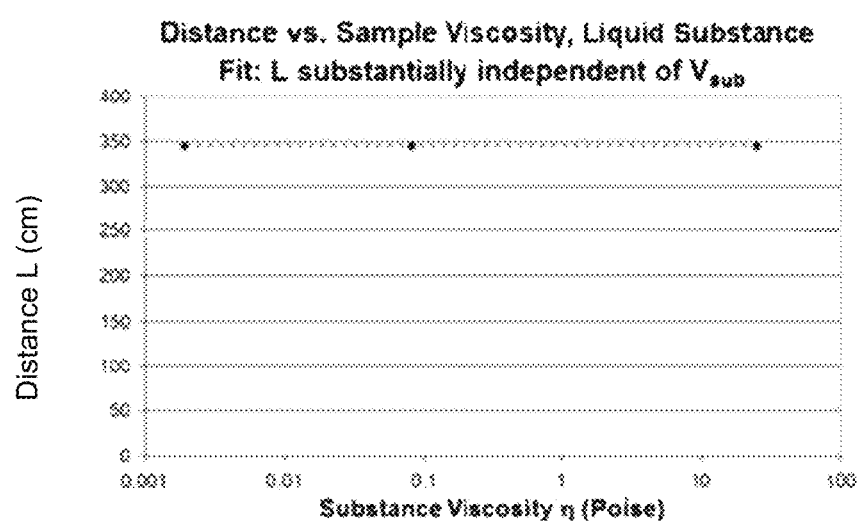
FIG. 42 illustrates the effect of viscosity on distance traveled by an aerosol through a tube.

The effect of the viscosity of the sample on the distance the aerosol migrates is shown in Table 5 and FIG. 42.

It is clear that, over the range of viscosities investigated, the viscosity has no more than a negligible effect on the migration distance.

TABLE 5

Effect of sample viscosity on distance aerosol migrates

| Sample | Sample Viscosity (cP) | Orifice Diameter (mm) | Air Volume (ml) | Pressure (barg) | Distance Aerosol Migrates (cm) |
|---|---|---|---|---|---|
| Saline | 0.94 | 0.8 | 19 | 6 | ≥345 |
| Oil | 10 | 0.8 | 19 | 6 | ≥345 |
| Otrivin ™ | 23 | 0.8 | 19 | 6 | ≥345 |

For viscosity in the range tested, from about 0.9 to about 23 cP, viscosity had no effect on the distance the aerosol migrates.

5. Effect of Gas Volume

Figure 43A:
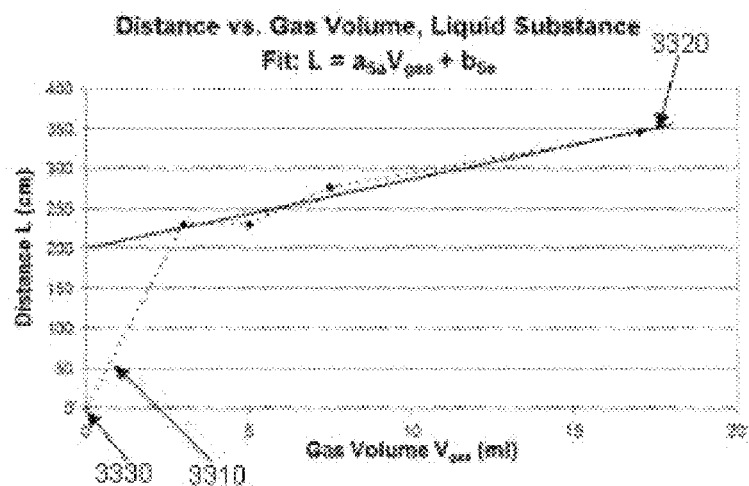
FIGS. 43A-C illustrate the effect of changing air volume on distance traveled by an aerosol through a tube.
Figure 43B:
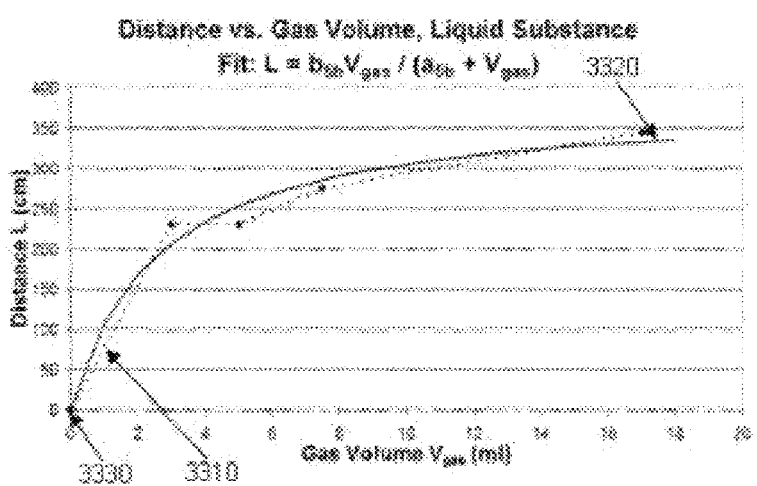
Figure 43C:
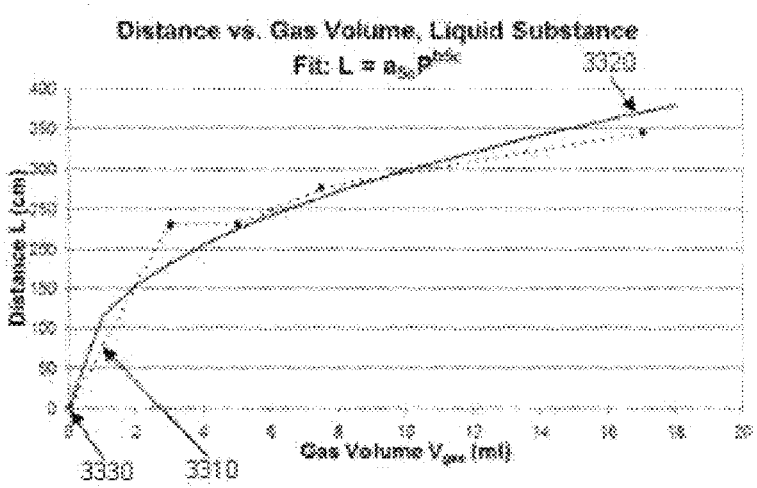

The effect of the volume of air in the sample on the distance the aerosol migrates is shown in Table 6 and FIG. 43A-C.

TABLE 6

Effect of gas volume on distance aerosol migrates

| Orifice Diameter (mm) | Gas Volume (ml) | Pressure (barg) | Distance Aerosol Migrates (cm) |
|---|---|---|---|
| 0.8 | 5 | 6 | 230 |
| 0.8 | 7.5 | 6 | 275 |
| 0.8 | 17 | 6 | ≥345 |

For constant orifice diameter and pressure, the larger the gas volume, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

FIG. 43A shows a best-fit line, excluding the point at zero, to the equation $L=a_{5a} V_{gas}+b_{5a}$ where the distance L in cm and pressure P is in barg. The parameter $a_{5a}$ is in a range of about 3.7 to about 13.5 and $b_{5a}$ is in a range of about 152 to about 248. The data fit well to the straight line, although the line does not pass near the point at (0,0).

FIG. 43B shows a best-fit line, including the point at zero, to the equation $L=b_{5b} V_{gas}/(a_{5b}+V_{gas})$ where the distance L is in cm and pressure P is in barg. The parameter $a_{5b}$ is in a range of about −0.18 to about 5.3 and $b_{5b}$ is in a range of about 268 to about 498. The data fit well to the cubic line.

FIG. 43C shows a best-fit power fit to the data including the point at zero, where the distance L is $L=a_{5c} V_{gas}^{b5c}$. The parameter $a_{5c}$ is in a range of about −19 to about 250 and $b_{5c}$ is in a range of about −0.09 to about 0.9 for distance L is in cm and pressure P is in barg. The data fit well to the power-law curve.

6. Effect of Activation Duration

Figure 44:
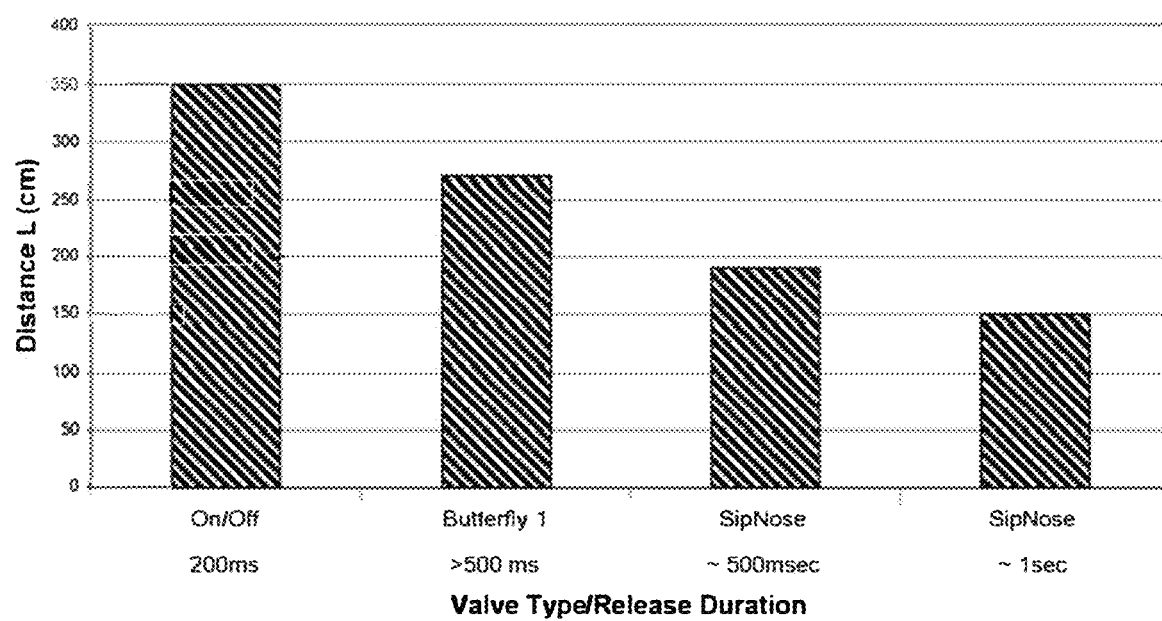
FIG. 44 illustrate the effect of valve type on distance traveled by an aerosol through a tube.

The effect of the valve type (and therefore the duration of activation) on the distance the aerosol migrates is shown in Table 7 and FIG. 44.

TABLE 7

Effect of valve type and release duration on distance aerosol migrates. Release duration reflects release time of the device

| Pressure (Barg) | Air Volume (ml) | Substance Volume (µl) | Tap Type | Release Duration (sec) | Orifice Diameter (mm) | Distance Aerosol Migrates (cm) |
|---|---|---|---|---|---|---|
| 6 | 19 | — | SipNose On/Off | 0.2 | 0.8 | 350 |
| 6 | 19 | — | SipNose Butterfly 1 | ~500 ms | 0.8 | 270 |
| 6 | 19 | 100 | SipNose | >500 msec | | 190 |
| 6 | 19 | 100 | SipNose | ~1 sec | | 150 |

Table 7 and FIG. 44 show that, typically, the shorter the time over which the gas is released, the further the aerosol migrates down the tube. Although not shown in Table 2, the on/off valve also had the largest diameter valve opening.

B. Powder Release Experiments

7. The Effect of Pressure

Figure 45:
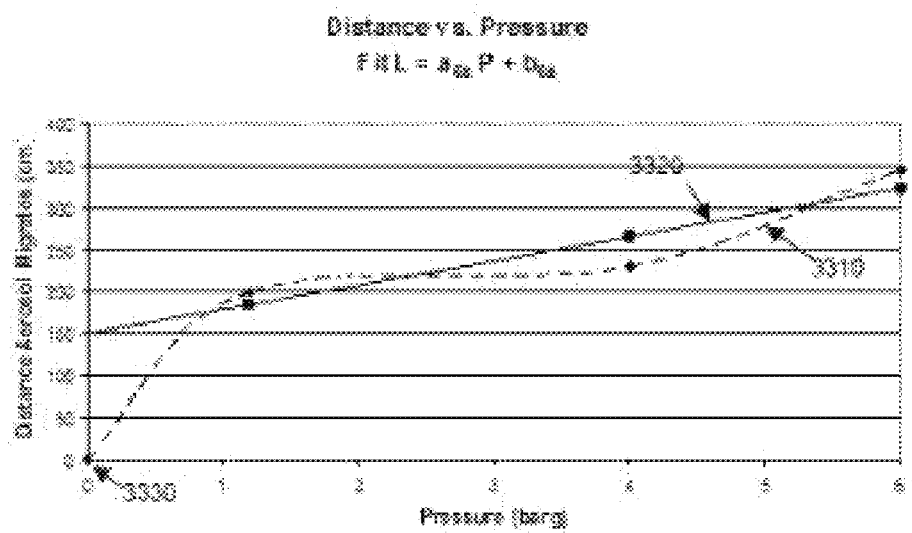
FIG. 45 illustrates the effect of changing pressure on distance traveled by a powder through a tube.

The effect of pressure on the distance the powder migrates is shown in Table 8 and FIG. 45.

TABLE 8

Effect of pressure on distance powder migrates

| Air Volume (ml) | Pressure (barg) | Orifice Diameter (mm) | Distance Aerosol Migrates (cm) |
|---|---|---|---|
| 5 | 1.2 | 2 | 200 |
| 5 | 4 | 2 | 230 |
| 5 | 6 | 2 | ≥345 |

The point at (0,0) (3330) was not a measured point, but could be included to improve the quality of the fits. The dotted line (3310) connects the data points, including the additional point at (0,0). The solid line (3320) shows fits to the data.

FIG. 45 shows a best-fit straight-line to the data, excluding the point at zero, where the distance L is L=$a_{6a}$ P+$b_{6a}$, for distance L in cm and pressure P in barg. The parameter $a_{6a}$ is in a range of about 0 to about 116 and $b_{6a}$ is in a range of about 0 to about 306 for distance L is in cm and pressure P is in barg. The data fit well to the straight line, although the line does not pass near the point at (0,0).

Similarly to the liquid substance example (Example 3, FIG. 45), a good fit is found (not shown) to the cubic L=$a_{6b}$ $P^3$−$b_{6b}$ $P^2$+$c_{6b}$ P, for distance L in cm and pressure P in barg, where the parameters are: $a_{6b}$ is in a range of about 6.5 to about 9.75, $b_{6b}$ is in a range of about −65 to about −97.5 and $c_{6b}$ is in a range of about 202 to about 303.

Similarly to the liquid substance example (Example 3, FIG. 45), a good fit is found (not shown) to the power-law equation L=$a_{6c}$ $P^{b6c}$, for distance L in cm and pressure P in barg, where the parameters are: $a_{6c}$ is in a range of about 0 to about 902 and $b_{6c}$ is in a range of about 0 to about 3.72.

8. Effect of Air Volume

Figure 46:
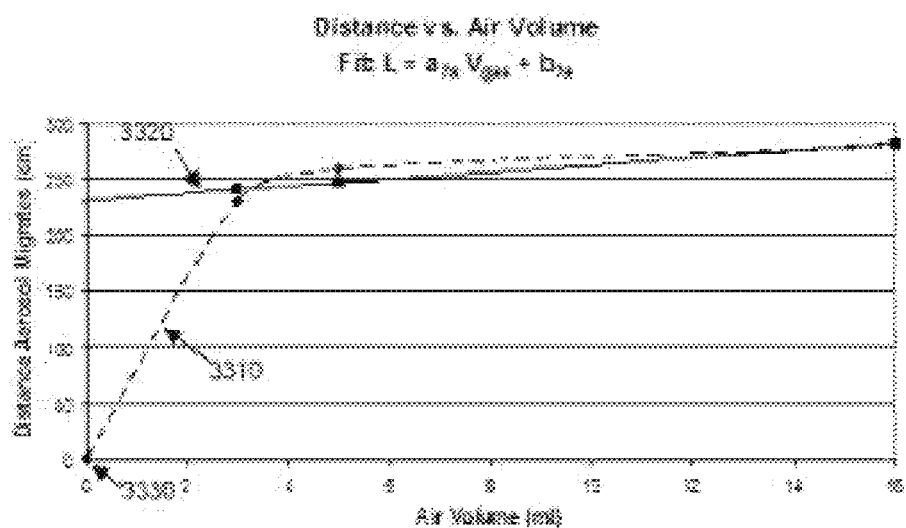
FIG. 46 illustrates the effect of air volume on distance traveled by a powder through a tube.

The effect of air volume on the distance the powder migrates is shown in Table 9 and FIG. 46.

TABLE 9

Effect of air volume on distance powder migrates

| Pressure (barg) | Air Volume (ml) | Orifice Diameter (mm) | Distance Aersol Migrates (cm) |
|---|---|---|---|
| 4 | 3 | 2 | 230 |
| 4 | 5 | 2 | 260 |
| 4 | 16 | 2 | 280 |

For constant pressure and orifice diameter, the larger the air volume, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

FIG. 46 shows a best-fit straight-line to the data, excluding the point at zero, where the distance L is L=$a_{6a}$ P+$b_{6a}$, for distance L in cm and pressure P in barg. The parameter $a_{6a}$ is in a range of about 0 to about 116 and $b_{6a}$ is in a range of about 0 to about 306 for distance L is in cm and pressure P is in barg. The data fit well to the straight line, although the line does not pass near the point at (0,0).

Similarly to the liquid substance example (Example 3, FIG. 46), a good fit is found (not shown) to the cubic L=$a_{6b}$ $P^3$−$b_{6b}$ $P^2$+$c_{6b}$ P, for distance L in cm and pressure P in barg, where the parameters are: $a_{6b}$ is in a range of about 6.5 to about 9.75, $b_{6b}$ is in a range of about −65 to about −97.5 and $c_{6b}$ is in a range of about 202 to about 303.

Similarly to the liquid substance example (Example 3, FIG. 46), a good fit is found (not shown) to the power-law equation L=$a_{6c}$ $P^{b6c}$ for distance L in cm and pressure P in barg, where the parameters are: $a_{6c}$ is in a range of about 0 to about 902 and $b_{6c}$ is in a range of about 0 to about 3.72.

Effect of Air Volume on Depth of Penetration into a Nasal Cast

In the nasal cast experiments, a model of the human nose was used, with slices of 1 cm each. In the following experiments, the distribution of the material (liquid aerosol or powder) was measured for a nasal cast model.

Figure 47:
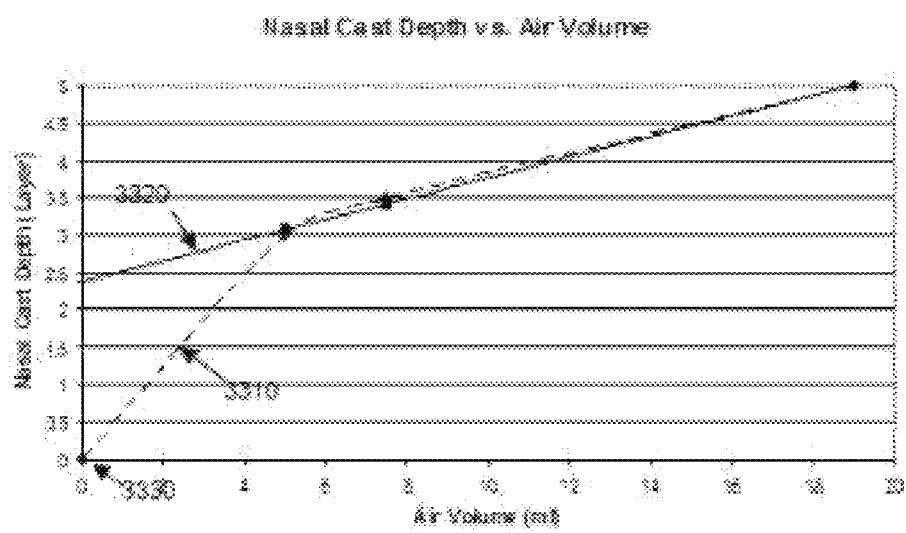
FIG. 47 illustrates the effect of air volume on depth of penetration into a nasal cast.

The effect of air volume on the depth the sample reaches in the nasal cast model is shown in Table 10 and FIG. 47.

TABLE 10

Effect of air volume on depth in nasal cast

| Pressure (barg) | Air Volume (ml) | Orifice Diameter (mm) | Deposition Layer (cm) |
|---|---|---|---|
| 6 | 5 | 2 | 3 |
| 6 | 7.5 | 2 | 3.5 |
| 6 | 19 | 2 | 5 |

The point at (0,0) (3330) was not a measured point, but is shown for reference, as a penetration of 0 layers would be expected for an air volume of zero (no delivery gas). The dotted line (3310) connects the data points, including the additional point at (0,0). The solid line (3320) shows a linear fit to the measured data. Over the range of air volumes of interest, between about 5 ml and about 19 ml, the depth of penetration into the nasal cast increases substantially linearly with air volume, although the irregularities of the nasal passages, as reflected in the nasal cast, might have suggested a sublinear relationship.

According to another embodiment, the fit can be selected from a group consisting of logarithmic, parabolic, exponential, sigmoid, power-low, and any combination thereof.

Plume Angle

In contrast to prior-art nasal delivery devices and technologies, the devices of the present invention can produce a fine aerosol in the nasal cavity or other desired body orifice at the target area and at the location of the target tissue instead of immediately after exit from the device. Utilizing the pressure as a driving force and the air as a carrier allows the material to be released from the nozzle as a combination of material in a pre-aerosolized state and an aerosol. The properties of the resultant aerosol are typically dependent on the properties of the device and of the medium into which the aerosol is discharged. The properties of the device which affect the aerosol characteristics are the delivery speed, the volume of the delivery gas, and the characteristics of the delivery orifice.

In some embodiments, the aerosol properties are fairly independent of the delivered substance, in other embodiments, the pressure, volume, orifice characteristics and delivered substance properties can be co-optimized.

In prior-art devices the aerosol is produced at the exit to the device. Typically, the aerosol comprises a wide dispersion of particle sizes, a wide "fan" of aerosol and a low driving force. Therefore, the large droplets typically deposit very close to the exit from the device; smaller droplets tend to quickly contact the walls of the passage, so that deposition is typically predominantly close to the exit from the device, with little of the substance reaching desired sites deeper in the orifice, such as the turbinates of the nose.

In contrast, in the present device, the aerosol and pre-aerosolized mixture of gas and substance exits the device with a significant driving force, when the pre-aerosolized fluid hits the walls of the nasal passages, it "explodes" into a fine aerosol that is capable of being driven by the pressure deep into the nasal passages to deposit in the desired region.

In reference to FIG. 48, a schematic is shown of a nozzle and the aerosol it releases. The orifice emits an aerosol which forms a conical plume (1) with a distribution of particles (2) in it.

The plume angle is the total angle subtended by the plume, as shown by the angle α in FIG. 48 and by the angle θ subtended between the lines, as shown in FIG. 49A.

In FIG. 49, the plume angle θ is compared for 2 commercial nasal delivery devices (FIG. 49A-B) and the SipNose device (FIG. 49C). Aerosol was measured at room temperature. The widths of the plumes were measured at the same distance (3 cm) from the discharge site in each device.

The SipNose device has a much narrower plume than the two commercial devices. The plume angles for the commercial devices, the Alrin™ from Teva (FIG. 49A) had a plume angle of 35°, the LMA MAD Nasal™ (FIG. 49B) had a plume angle of 27°, while the plume angle for the SipNose device (FIG. 49C) had a plume angle of only 8.7°.

All the above parameters allow the aerosol to better deposit in the area of interest—such as the area of the olfactory epithelium in the nasal cavity; and to be better absorbed by the target tissue such as the brain.

Plume Intensity

Figure 50A:
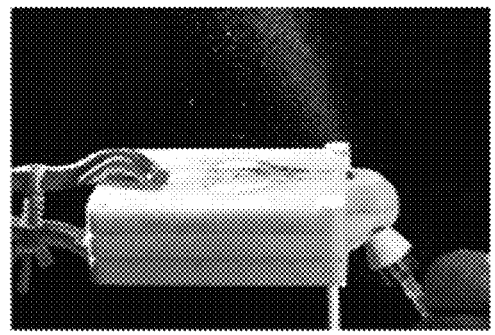
FIG. 50A-B illustrates plume intensity for various devices.
Figure 50B:
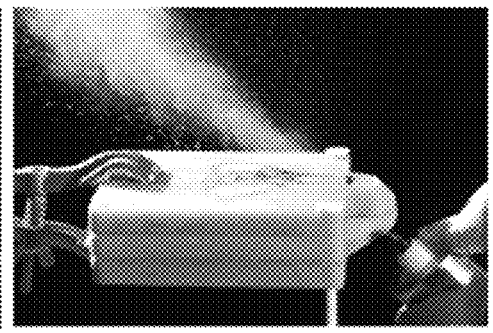

FIG. 50 compares the amount of material reaching the upper layers of the nasal model for one of the prior-art devices (commercial 2—LMA MAD Nasal™) and the device of the present invention (SipNose). In each case, 100 μl of liquid aerosol was discharged into a human nasal model (a nasal cast). The upper layer of the nasal cast was removed in order to observe the amount and characteristics of the aerosol that reaches the area of the upper portion of the nasal cavity. It is clear that there is a better distribution of the substance in the area of interest, the uppermost portions of the nasal cavities when the present invention technology is in use (FIG. 50B).

Figure 51:
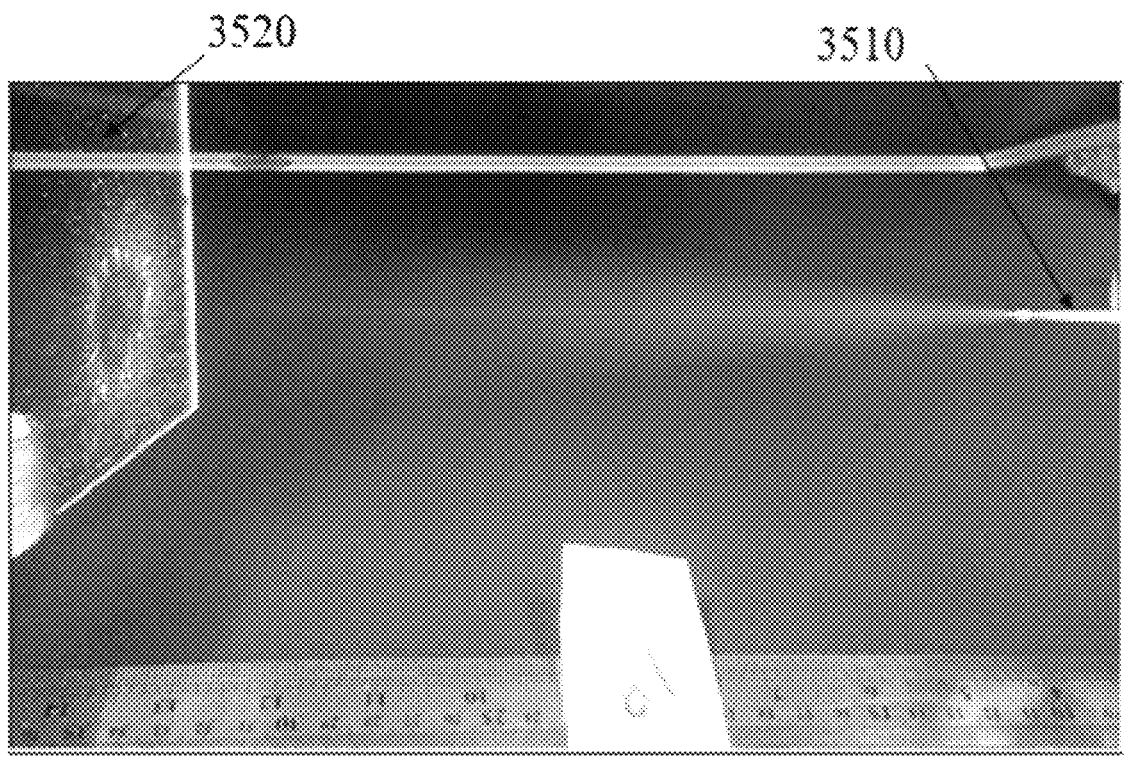
FIG. 51 shows an experimental setup for determining coverage of a spray plume.
Figure 53A:
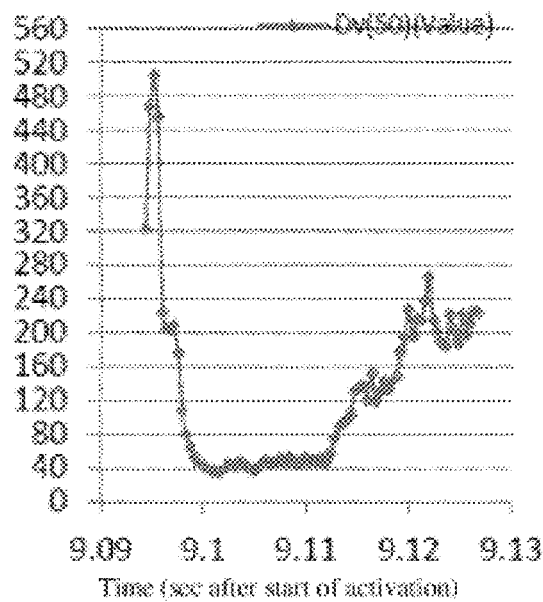
FIGS. 53A-D show the particle size as a function of time for an orifice diameter of 1.5 mm and a Saline volume of 100 ul.
Figure 53B:
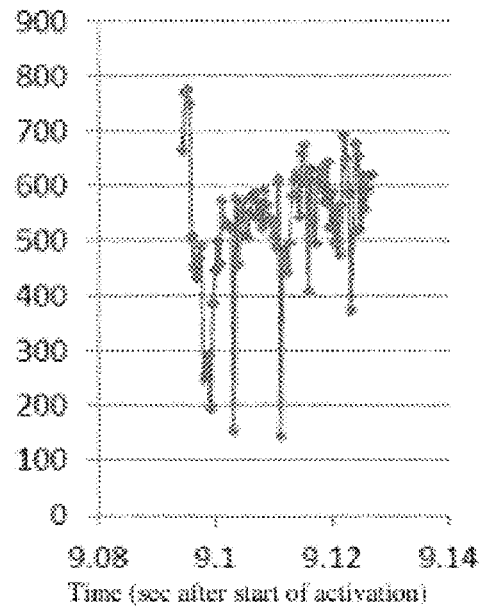
Figure 53C:
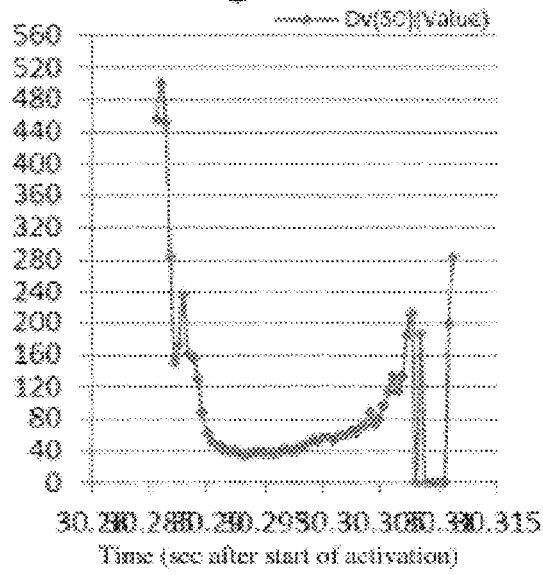
Figure 53D:
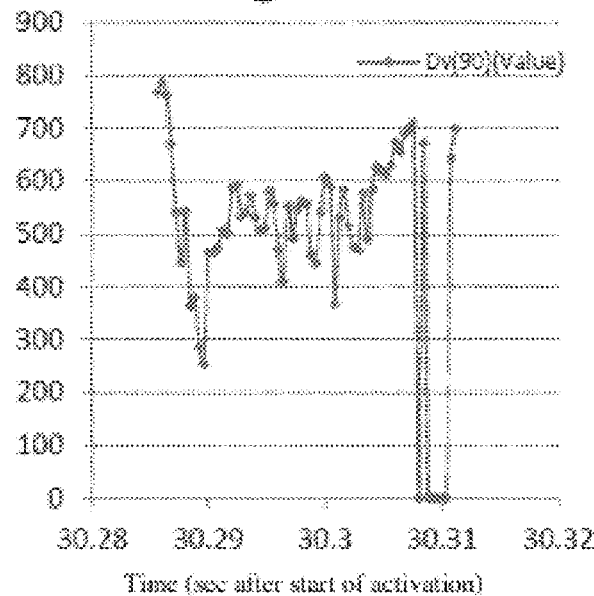

FIG. 51 shows an experimental setup for determining coverage of a spray plume. A device (3510) is at the left, and a screen for measuring coverage is at the right (3520). The distance between device and screen is about 25 cm.

FIGS. 52A-J show examples of spray coverage for different devices. FIGS. 52A-D show coverage and droplet distribution for the SipNose device for different device parameters, while FIGS. 52E-J show coverage and droplet distribution for a number of different commercial devices.

In all cases, the SipNose device produces a spray pattern covering a well-defined area of the screen. A large number of particles reach the screen and, in the coverage area, this is significantly more than for any of the commercial devices.

Commercial devices F and J are the best of the prior-art devices, with a reasonable amount of the aerosol reaching the screen, but the distribution is very much wider than for the SipNose device, covering virtually the entire screen. Commercial devices H and I are the worst of the prior-art devices, with very little of the aerosol even reaching as far as the screen.

Tables 11 and 12 show plume characteristics for the SipNose device for different operating parameters and an orifice size of 0.8 mm (Table 11) and for four commercial devices (Table 12).

TABLE 11

Plume Characteristics for the SipNose device

| Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|
| 2 | 8 | 500 | 15 | 10 | 16 | 23 |
| 6 | 8 | 500 | 20 | 12 | 18 | 15.8 |
| 6 | 19 | 100 | 15 | 10 | 21 | |
| 6 | 19 | 500 | 20 | 11 | 18 | |
| 2 | 5 | 100 | 9 | 10 | 12 | |
| 2 | 10 | 100 | 15 | 8 | 15 | |
| 2 | 5 | 500 | 17 | 18 | 20 | |
| 2 | 10 | 500 | 16 | 11 | 17 | 11.9 |
| 6 | 12 | 100 | 12 | 9 | 18 | |
| 6 | 6 | 500 | 12 | 5 | 6 | |
| 6 | 12 | 500 | 16 | 8 | 13 | |

TABLE 12

Plume Characteristics for the commercial devices

| Device | Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|---|
| MAD Nasal ™; Wolfe Tory | — | 6 | 100 | 35 | 18 | 30 | 2.3 |
| | — | 18 | 100 | 55 | 30 | 40 | |
| | — | 0 | 500 | 55 | 38 | 55 | |
| | — | 3 | 500 | 35 | 25 | 30 | |
| | — | 6 | 500 | 35 | 21 | 35 | 2.3 |
| | — | 18 | 500 | 33 | 20 | 29 | |
| Simply Saline Nasal Mist; Church & Dwight Co., Inc. | 7 | — | 500 | 45 | 37 | 53 | |
| Otrimer; Novartis | 7 | — | 500 | 35 | 20 | 33 | |
| Alrin, Teva | — | 0 | 100 | 35 | 26 | 33 | 3.3 |

Significant differences were seen between the properties of the plumes between the SipNose device and the commercial devices; small, if any, overlap was seen between the plume angles, the plume heights or the plume velocities. For the SipNose devices, the range of plume angles was 5° to 25°, the range of plume heights 3 cm from the device was 1 to 20 mm, the range of plume heights 6 cm from the device was 5 mm to 25 mm and the range of plume velocities was 5 m/s to 50 m/s. For the commercial devices, the plume angles were over 33°, the plume heights 3 cm from the device were over 18 mm, the plume heights 6 cm from the device were over 29 mm and the plume velocities were less than 5 m/s.

Droplet Size Distribution

FIG. 53-D shows the particle size as a function of time for an orifice diameter of 1.5 mm and a Saline volume of 100 ul. Two runs were made, the first shown in FIG. 53A-B, the second in FIG. 53C-D. The median particle size by volume (DV50 value) is shown in FIG. 53A and FIG. 53C, while the DV90 value, the particle volume larger than 90% of the particles, is shown in FIG. 53B and FIG. 53D. After a burst of large particles (LD 50 about 480-550 μm), the median particle size is 40-45 μm. The LD90 value is less consistent, but is in the range of about 500-600 μm.

Figure 54A:
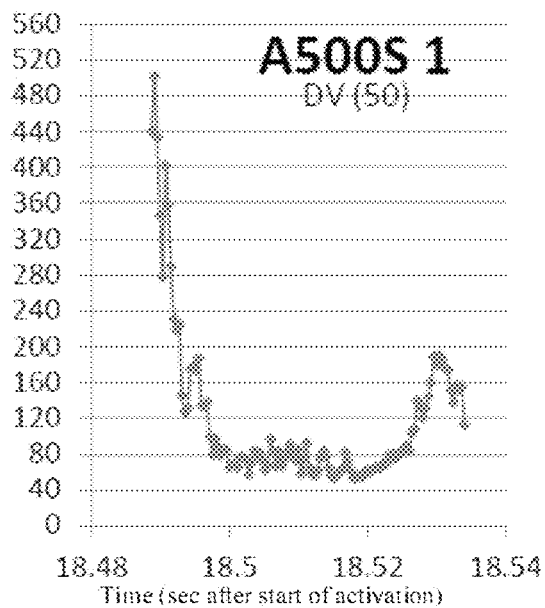
FIGS. 54A-D show the effect of time after activation on the particle size for an orifice diameter of 1.5 mm and a saline volume of 500 ul.
Figure 54B:
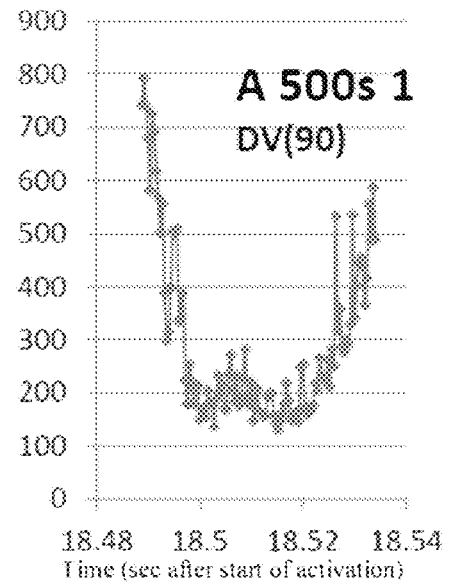
Figure 54C:
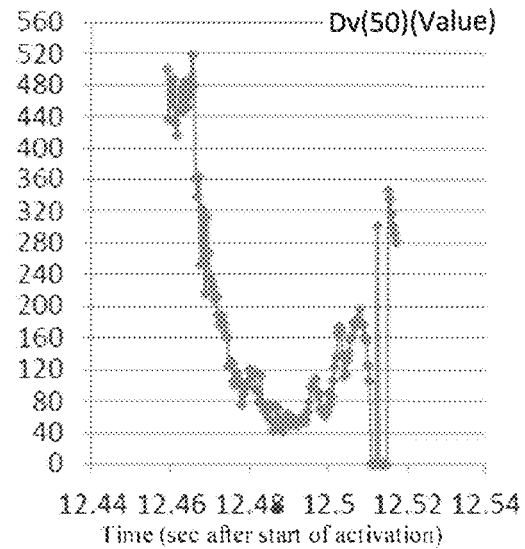
Figure 54D:
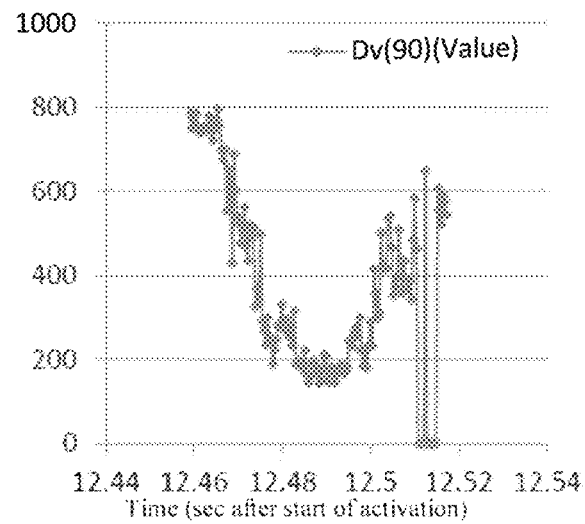

FIG. 54A-D shows the effect of time after activation on the particle size for an orifice diameter of 1.5 mm and a saline volume of 500 ul. Two runs were made, the first shown in FIG. 54A-B, the second in FIG. 54C-D. The median particle size by volume (DV50 value) is shown in FIG. 54A and FIG. 54C, while the DV90 value, the particle volume larger than 90% of the particles, is shown in FIG. 54B and FIG. 54D. After a burst of large particles (LD50 about 480-550 μm), the median particle size is about 50-65 μm. The LD90 value is less consistent, but is on the order of about 170 μm.

Figure 55A:
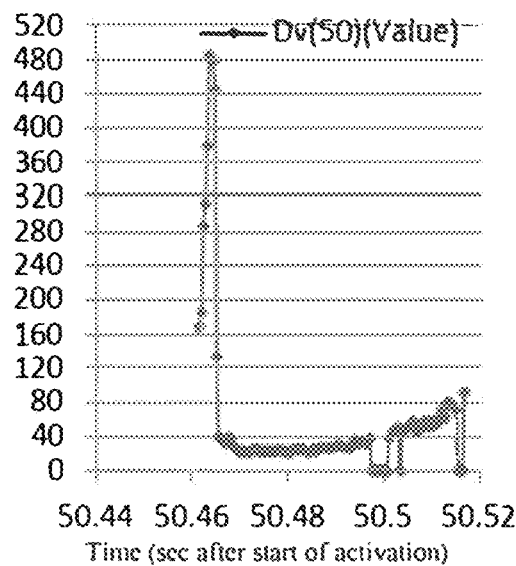
FIGS. 55A-D show the effect of time after activation on the particle size for an orifice diameter of 1.0 mm and a saline volume of 100 ul.
Figure 55B:
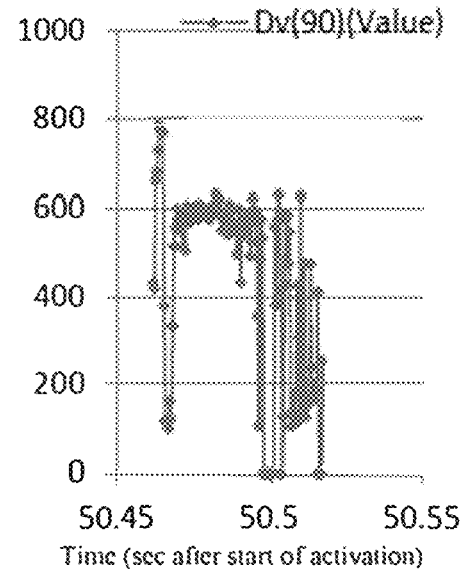
Figure 55C:
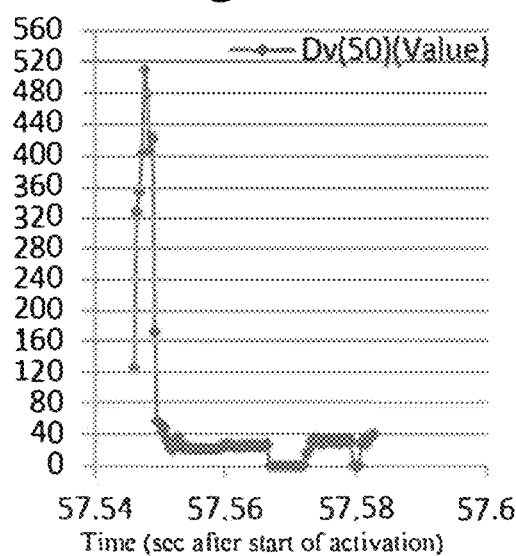
Figure 55D:
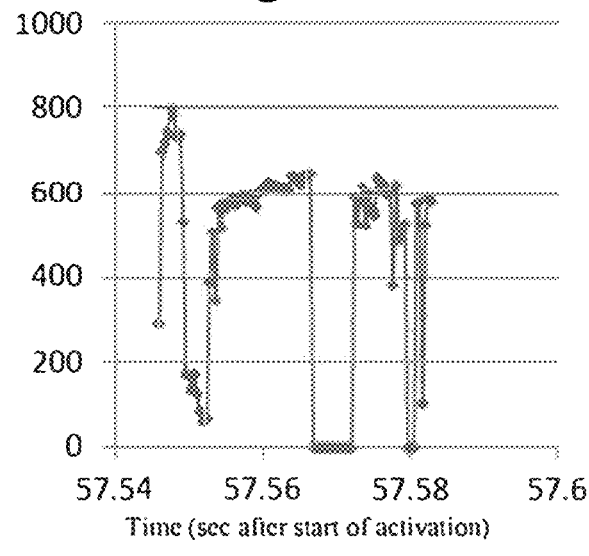

FIG. 55A-D shows the effect of time after activation on the particle size for an orifice diameter of 1.0 mm and a saline volume of 100 ul. Two runs were made, the first shown in FIG. 55A-B, the second in FIG. 55-D. The median particle size by volume (DV50 value) is shown in FIG. 55A and FIG. 55C, while the DV90 value, the particle volume larger than 90% of the particles, is shown in FIG. 55B and FIG. 55D. After a burst of large particles (LD50 about 480-520 μm), the median particle size is about 25 μm. The LD90 value is less consistent, but is on the order of about 600 μm.

Figure 56A:
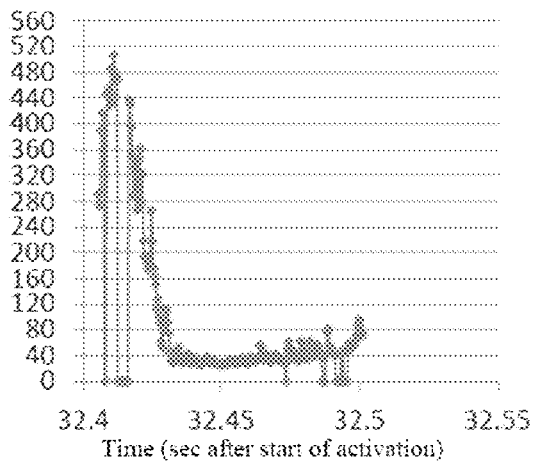
FIGS. 56A-D show the effect of time after activation on the particle size for an orifice diameter of 1.0 mm and a saline volume of 500 ul.
Figure 56B:
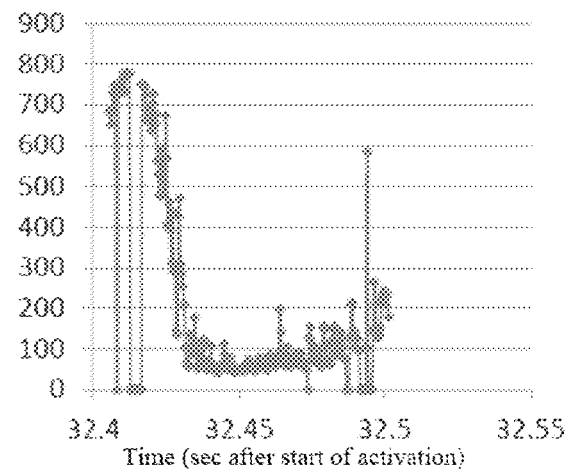
Figure 56C:
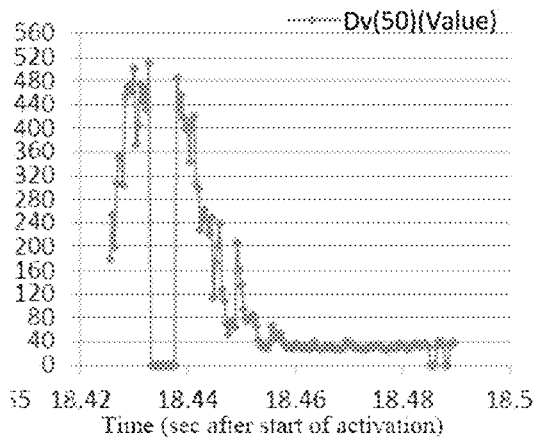
Figure 56D:
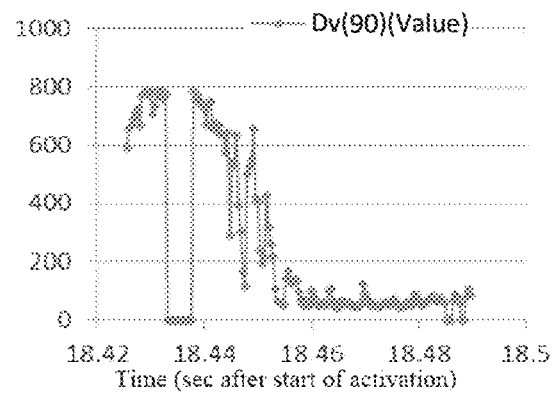

FIG. 56A-D shows the effect of time after activation on the particle size for an orifice diameter of 1.0 mm and a saline volume of 500 ul. Two runs were made, the first shown in FIG. 43A-B, the second in FIG. 56C-D. The median particle size by volume (DV50 value) is shown in FIG. 56A and FIG. 56C, while the DV90 value, the particle volume larger than 90% of the particles, is shown in FIG. 56B and FIG. 56D. After a burst of large particles (LD50 about 480-550 μm), the median particle size is about 28-30 μm. The LD90 value is less consistent, but, after a burst of large particle of volumes of 700-800 μm, is on the order of about 50 μm.

Figure 57A:
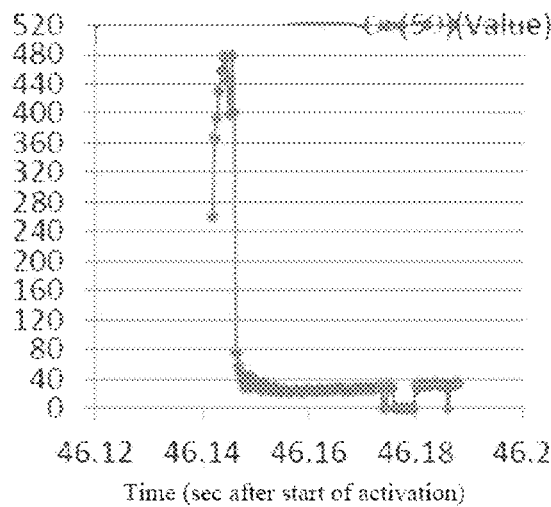
FIGS. 57A-D show the effect of time after activation on the particle size for an orifice diameter of 0.8 mm and a saline volume of 100 ul.
Figure 57B:
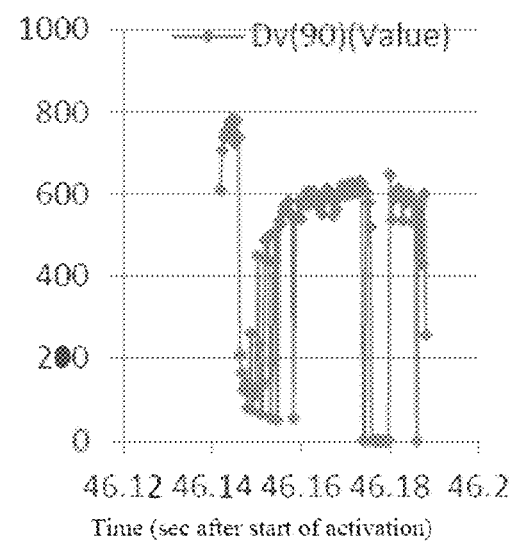
Figure 57C:
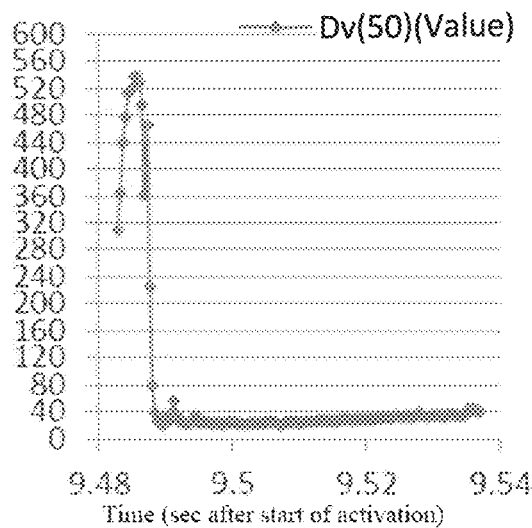
Figure 57D:
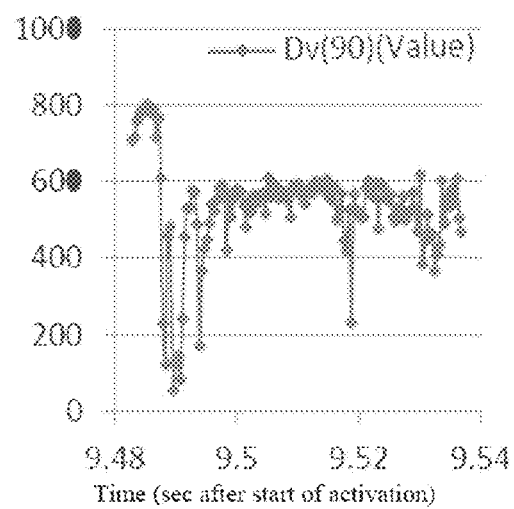

FIG. 57A-D shows the effect of time after activation on the particle size for an orifice diameter of 0.8 mm and a saline volume of 100 ul. Two runs were made, the first shown in FIG. 57A-B, the second in FIG. 57C-D. The median particle size by volume (DV50 value) is shown in FIG. 57A and FIG. 57C, while the DV90 value, the particle volume larger than 90% of the particles, is shown in FIG. 57B and FIG. 57D. After a burst of large particles (LD50 about 480-520 μm), the median particle size is about 23-24 μm. The LD90 value is less consistent, but is on the order of about 600 μm.

Figure 58A:
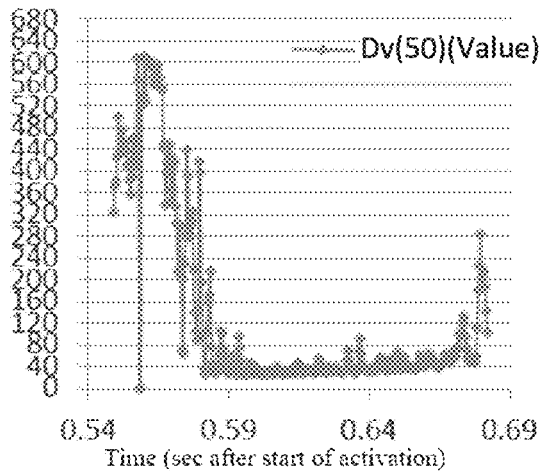
FIGS. 58A-D show the effect of time after activation on the particle size for an orifice diameter of 0.8 mm and a saline volume of 500 ul.
Figure 58B:
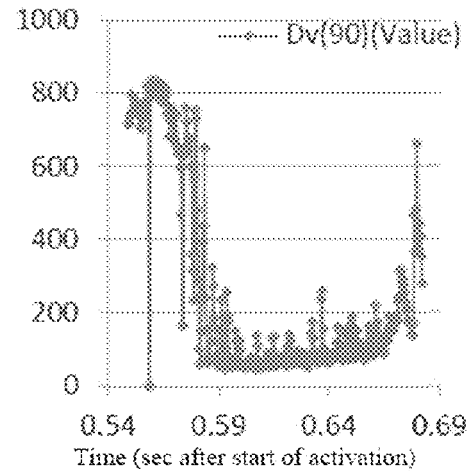
Figure 58C:
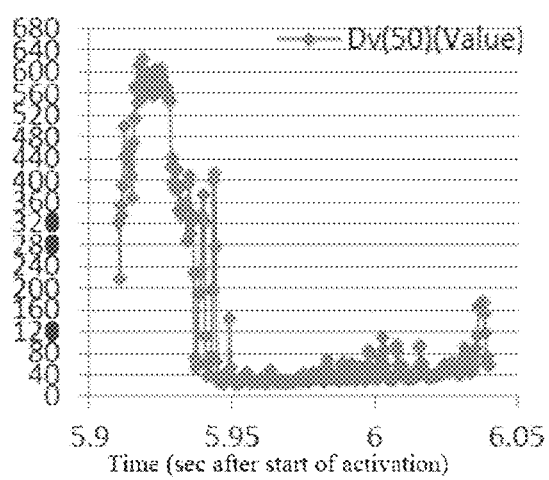
Figure 58D:
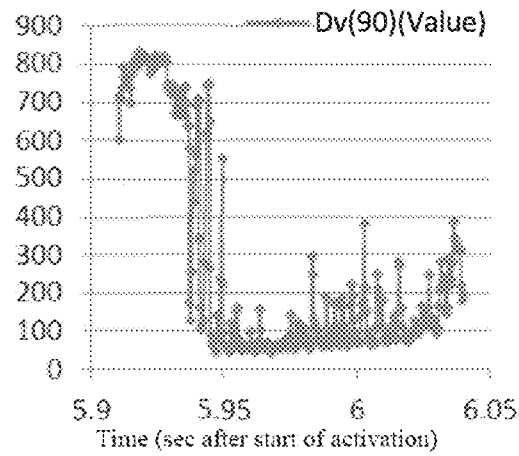

FIG. 58A-D shows the effect of time after activation on the particle size for an orifice diameter of 0.8 mm and a saline volume of 500 ul. Two runs were made, the first shown in FIG. 58A-B, the second in FIG. 58C-D. The median particle size by volume (DV50 value) is shown in FIG. 58A and FIG. 58C, while the DV90 value, the particle volume larger than 90% of the particles, is shown in FIG. 58B and FIG. 58D. After a burst of large particles (LD50 about 550-650 μm), the median particle size is about 32-35 μm. The LD90 value is less consistent, but, after a burst of large particle of volumes of 700-800 μm, is on the order of about 60-65 μm.

Figure 59A:
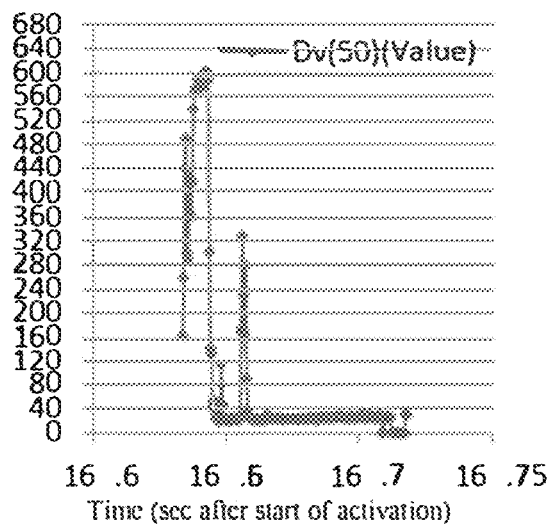
FIGS. 59A-D show the effect of time after activation on the particle size for an orifice diameter of 0.5 mm and a saline volume of 100 ul.
Figure 59B:
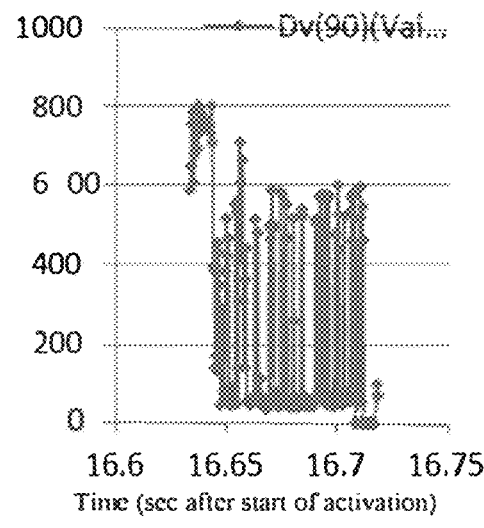
Figure 59C:
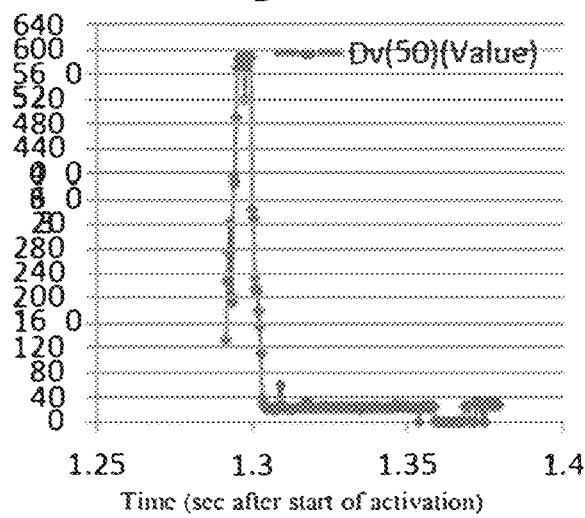
Figure 59D:
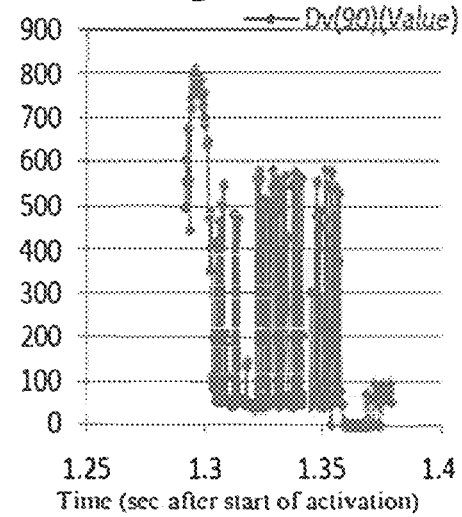

FIG. 59A-D shows the effect of time after activation on the particle size for an orifice diameter of 0.5 mm and a saline volume of 100 ul. Two runs were made, the first shown in FIG. 59A-B, the second in FIG. 59C-D. The median particle size by volume (DV50 value) is shown in FIG. 59A and FIG. 59C, while the DV90 value, the particle volume larger than 90% of the particles, is shown in FIG. 59B and FIG. 59D. After a burst of large particles (LD50 about 550-600 μm), the median particle size is about 23 μm. The LD90 value is less consistent, but, after a burst of large particle of volumes of 700-800 m, is on the order of about 55 μm.

Figure 60A:
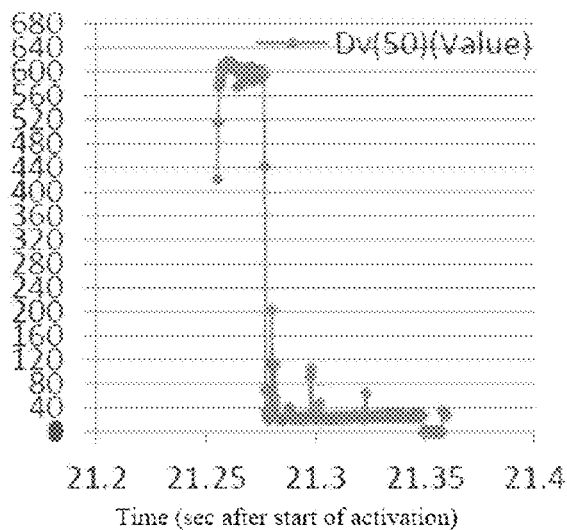
FIGS. 60A-D show the effect of time after activation on the particle size for an orifice diameter of 0.5 mm and a saline volume of 200 ul.
Figure 60B:
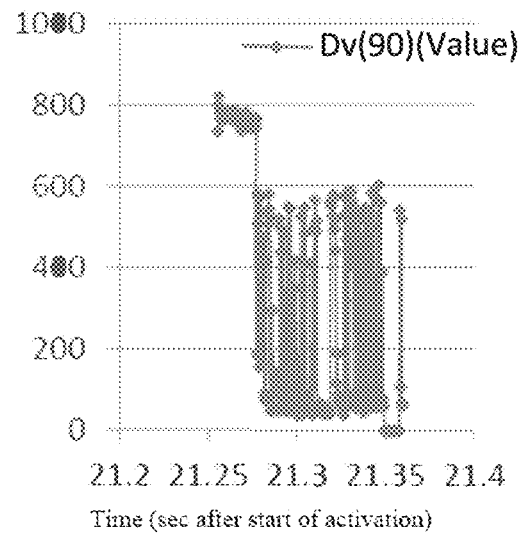
Figure 60C:
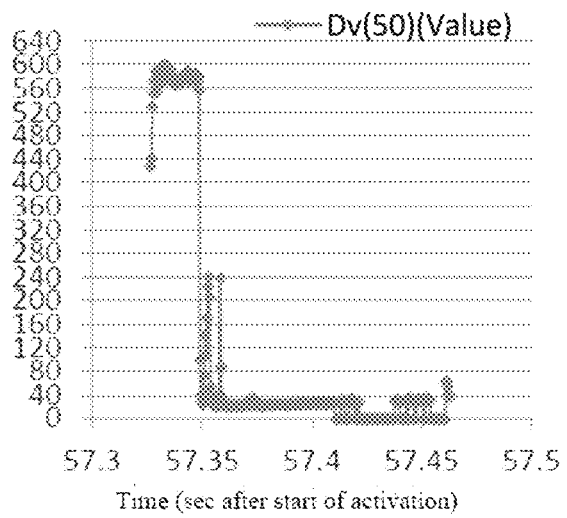
Figure 60D:
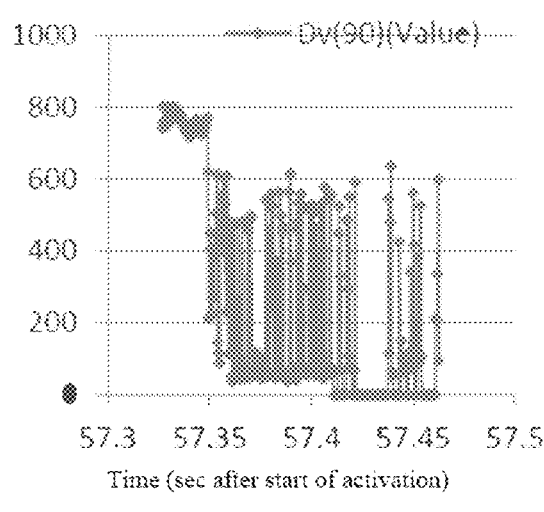

FIG. 60A-D shows the effect of time after activation on the particle size for an orifice diameter of 0.5 mm and a saline volume of 200 ul. Two runs were made, the first shown in FIG. 60A-B, the second in FIG. 60C-D. The median particle size by volume (DV50 value) is shown in FIG. 60A and FIG. 60C, while the DV90 value, the particle volume larger than 90% of the particles, is shown in FIG. 60B and FIG. 60D. After a burst of large particles (LD50 about 550-650 μm), the median particle size is about 25 pun. The LD90 value is less consistent, but, after a burst of large particles of volumes of 700-800 μm, is on the order of about 55-60 μm.

Figure 61A:
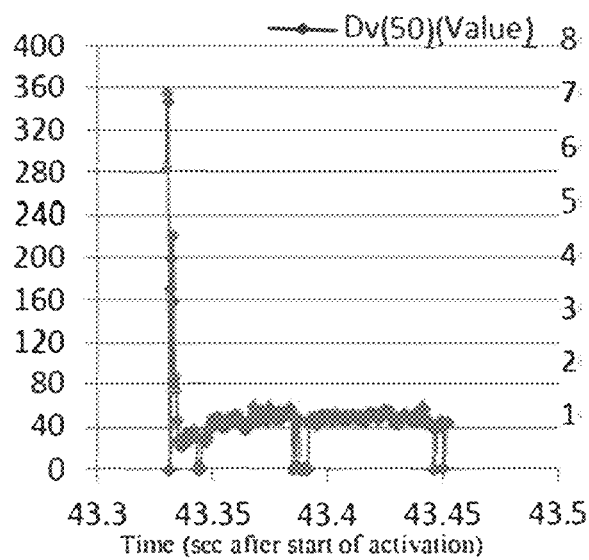
FIGS. 61A-D show the effect of time after activation on the particle size for a SipNose device with no orifice and a saline volume of 300 ul.
Figure 61B:
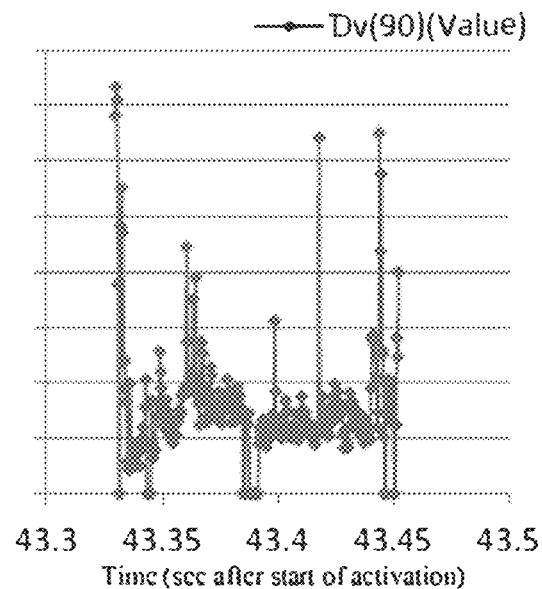
Figure 61C:
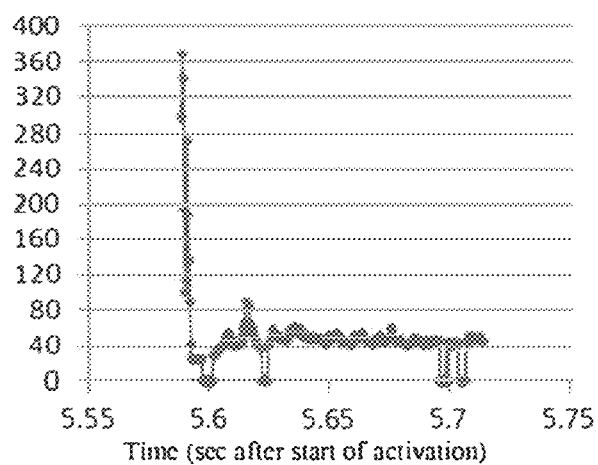
Figure 61D:
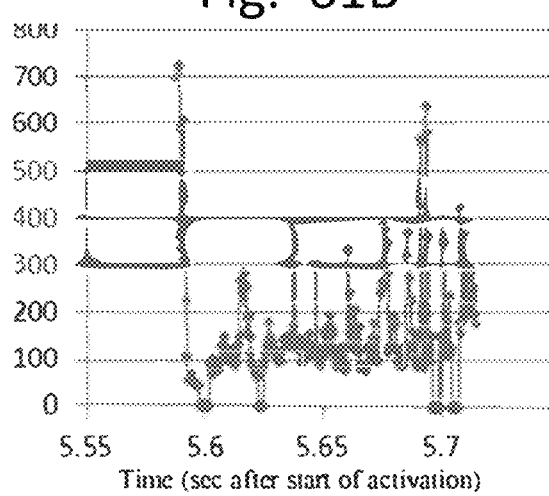

FIG. 61A-D shows the effect of time after activation on the particle size for a SipNose device with no orifice and a saline volume of 300 ul. Two runs were made, the first shown in FIG. 61A-B, the second in FIG. 61C-D. The median particle size by volume (DV50 value) is shown in FIG. 61A and FIG. 61C, while the DV90 value, the particle volume larger than 90% of the particles, is shown in FIG. 61B and FIG. 61D. After a small burst of large particles (LD 50 about 360-400 μm), the median particle size is about 45-48 μm. The LD90 value is less consistent, but, after a burst of large particle of volumes of 700-800 μm, is on the order of about 100-140 μm.

Figure 62A:
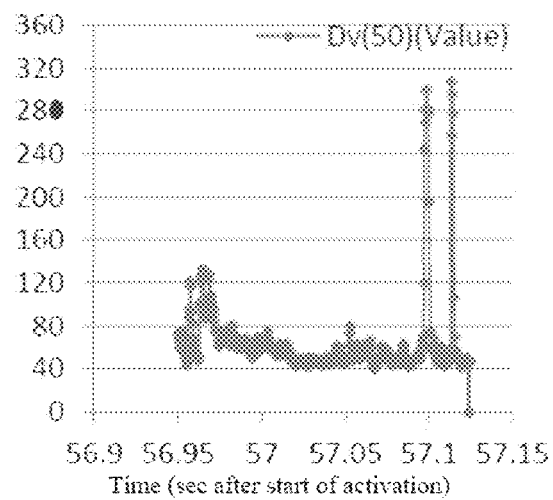
FIGS. 62A-D show the effect of time after activation on the particle size for a SipNose device with no orifice and a saline volume of 1000 ul.
Figure 62B:
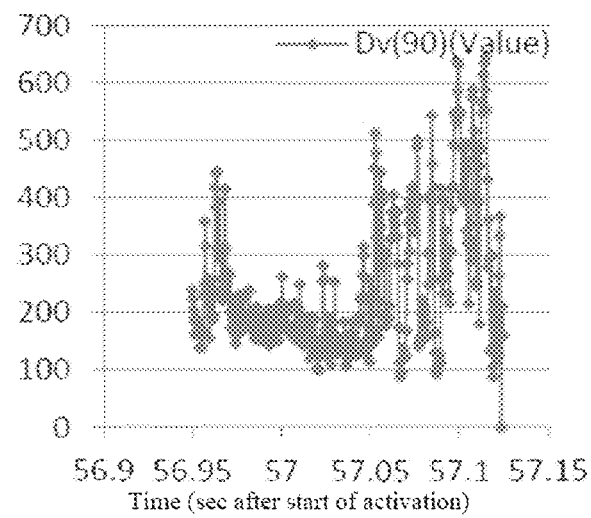
Figure 62C:
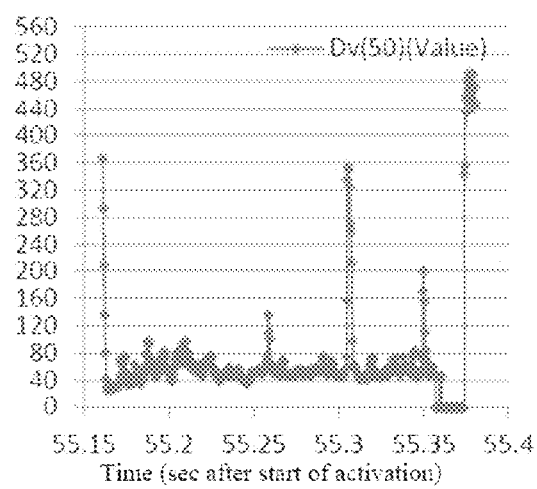
Figure 62D:
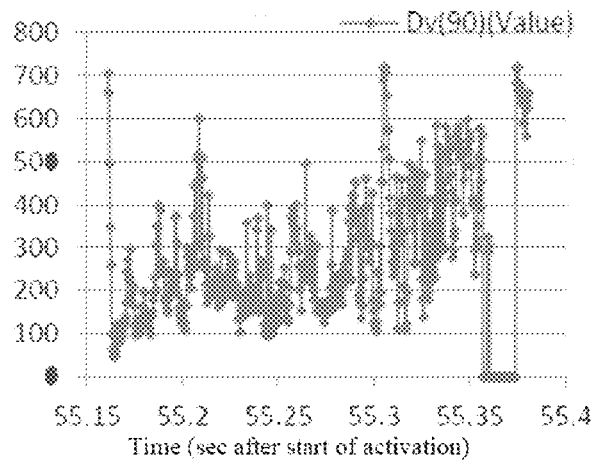

FIG. 62A-D shows the effect of time after activation on the particle size for a SipNose device with no orifice and a saline volume of 1000 ul. Two runs were made, the first shown in FIG. 62A-B, the second in FIG. 62C-D. The median particle size by volume (DV50 value) is shown in FIG. 62A and FIG. 62C, while the DV90 value, the particle volume larger than 90% of the particles, is shown in FIG. 62B and FIG. 62D. The median particle size is about 45-50 μm. The LD90 value is very inconsistent but is on the order of about 180 μm.

Figure 63A:
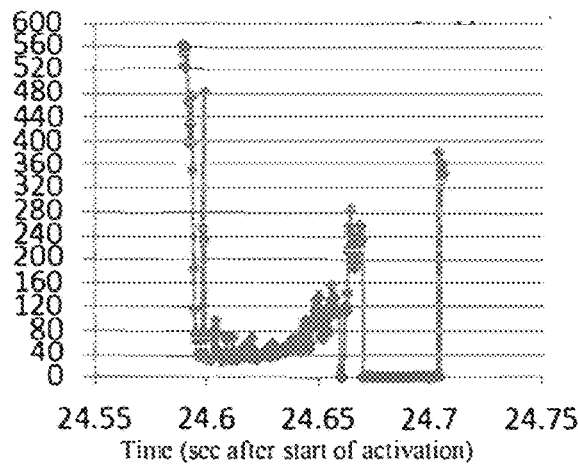
FIGS. 63A-D shows the effect of time after activation on the particle size at a gas pressure of 3 barg, for an orifice diameter of 0.8 mm and a saline volume of 100 ul.
Figure 63B:
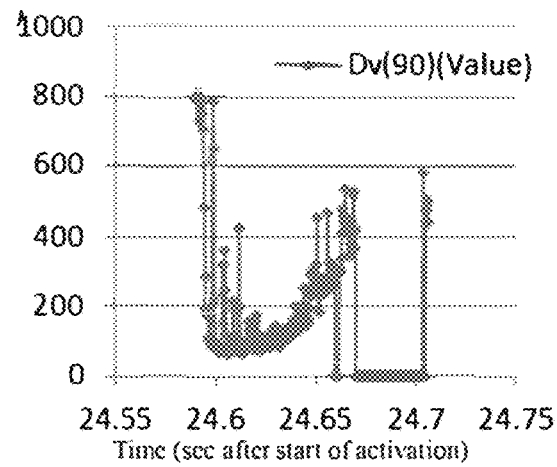
Figure 63C:
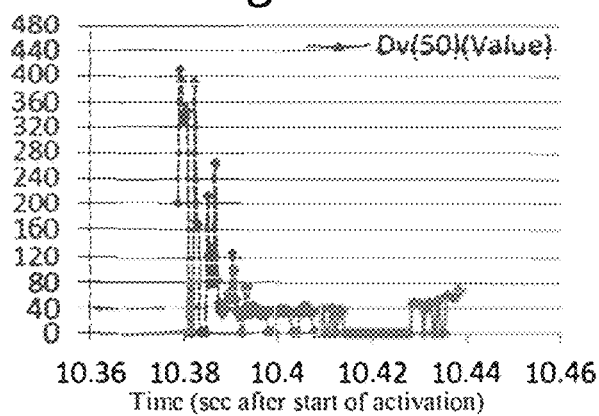
Figure 63D:
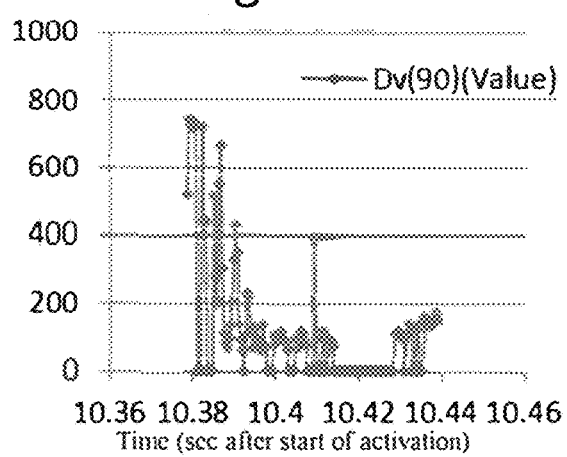

FIG. 63A-D shows the effect of time after activation on the particle size at a gas pressure of 3 barg, for an orifice diameter of 0.8 mm and a saline volume of 100 ul. Two runs were made, the first shown in FIG. 63A-B, the second in FIG. 63C-D. The median particle size by volume (DV50 value) is shown in FIG. 63A and FIG. 63C, while the DV90 value, the particle volume larger than 90% of the particles, is shown in FIG. 63B and FIG. 63D. After a small number of large particles (LD 50 about 400-560 μm), the median particle size is about 35-40 μm. The LD90 value is less consistent, but is on the order of about 90-100 μm.

Figure 64A:
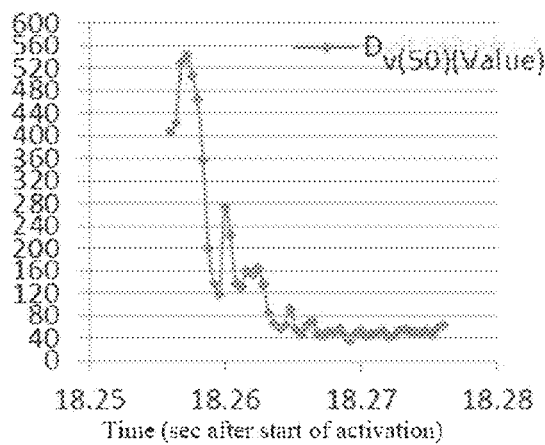
FIGS. 64A-D show the effect of time after activation on the particle size for a high viscosity substance, Otrivine™ with a viscosity of 23 cP, using the SipNose device with an orifice of 1 mm.
Figure 64B:
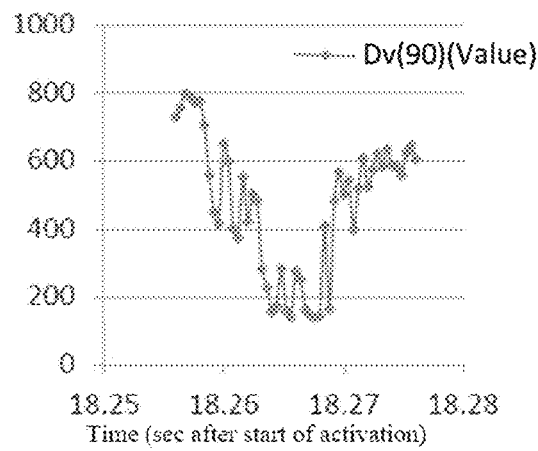
Figure 64C:
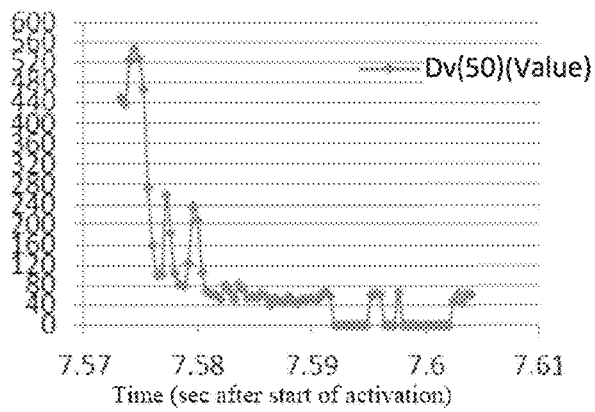
Figure 64D:
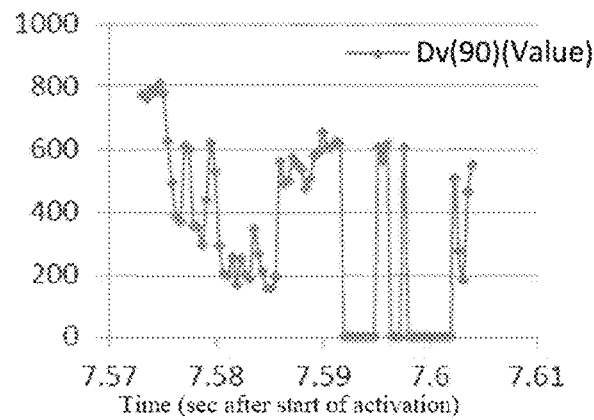
Figure 65A:
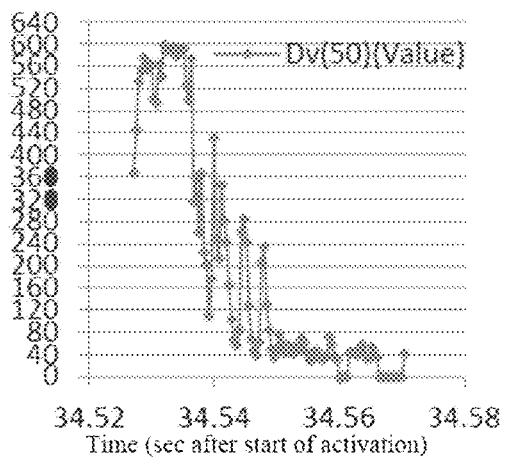
FIGS. 65A-D show the effect of time after activation on the particle size for a high viscosity substance, Otrivine™ with a viscosity of 23 cP, using the SipNose device with an orifice of 0.5 mm.
Figure 65B:
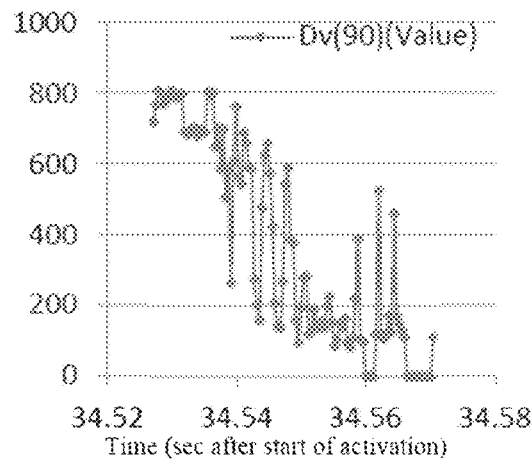
Figure 65C:
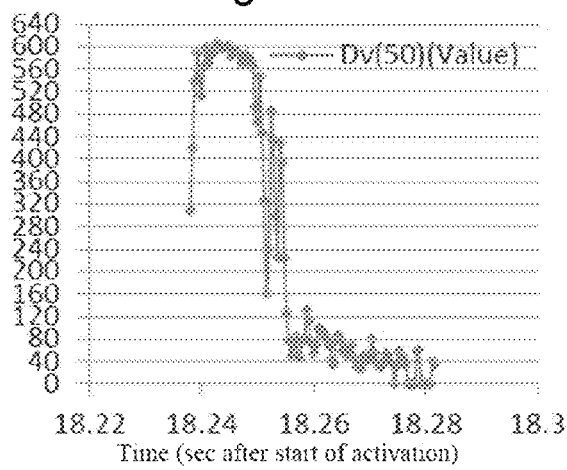
Figure 65D:
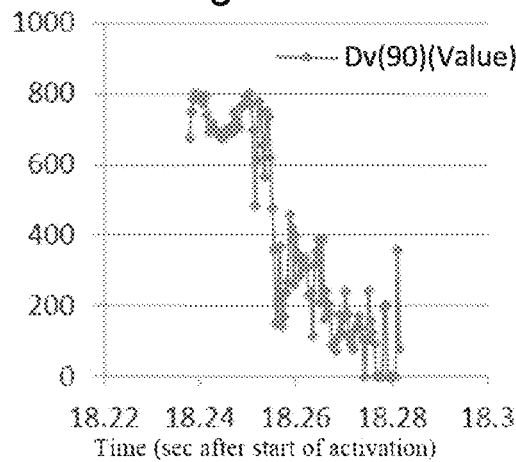
Figure 66A:
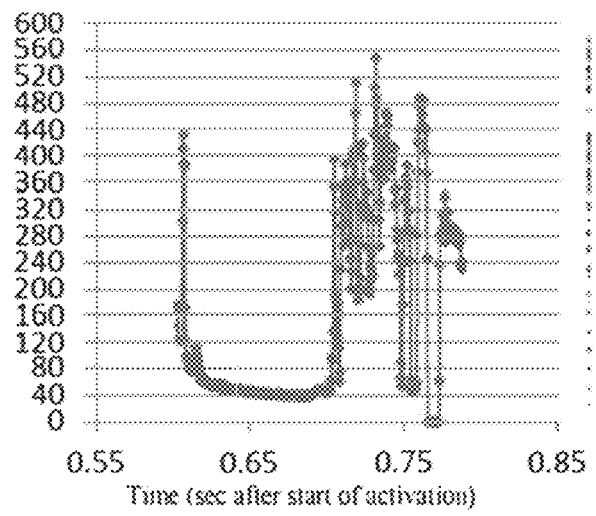
FIGS. 66A-D show the effect of time after activation on the particle size for the Alrin™ prior-art device.
Figure 66B:
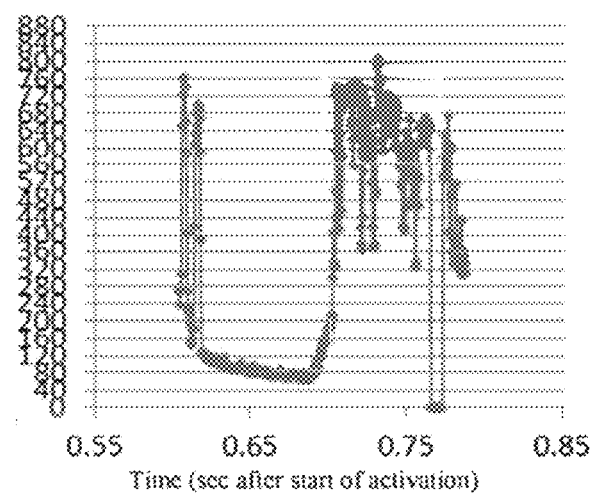
Figure 66C:
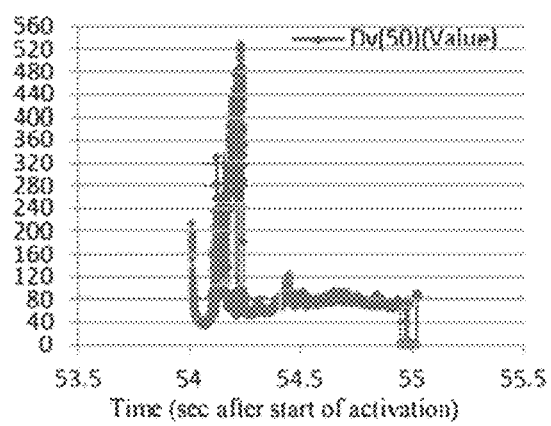
Figure 66D:
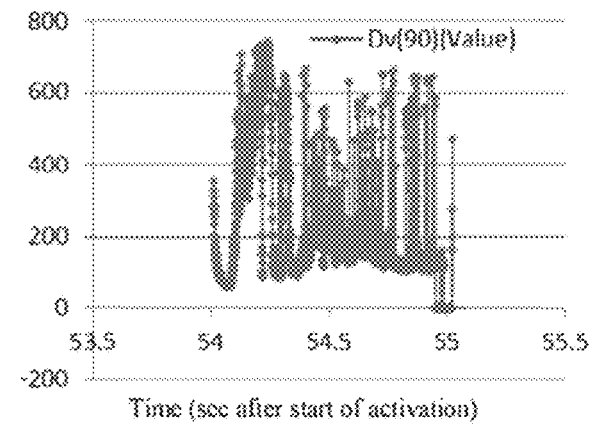

FIG. 64A-D shows the effect of time after activation on the particle size for a high viscosity substance, Otrivine™ with a viscosity of 23 cP, using the SipNose device with an orifice of 1 mm. Two runs were made, the first shown in FIG. 64A-B, the second in FIG. 64C-D. The median particle size by volume (DV50 value) is shown in FIG. 64A and FIG. 64C, while the DV90 value, the particle volume larger than 90% of the particles, is shown in FIG. 64B and FIG. 64D. After a small burst of large particles (LD 50 about 520-560 μm), the median particle size is about 45-48 μm. The LD90 value is very inconsistent, but is on the order of about 300 μm, FIG. 65A-D shows the effect of time after activation on the particle size for a high viscosity substance, Otrivine™ with a viscosity of 23 cP, using the SipNose device with an orifice of 0.5 mm. Two runs were made, the first shown in FIG. 65A-B, the second in FIG. 65C-D. The median particle size by volume (DV50 value) is shown in FIG. 65A and FIG. 65C, while the DV90 value, the particle volume larger than 90% of the particles, is shown in FIG. 65B and FIG. 65D. The particle sizes are less consistent than they were with the 1 mm diameter orifice. After a small burst of large particles (LD 50 about 560-600 μm), the median particle size is about 40-55 μm. The LD90 value is very inconsistent.

FIG. 66A-D shows the effect of time after activation on the particle size for the Alrin™ prior-art device. The Alrin™ device, like the SipNose device, was hand activated. The particle sizes for the Alrin™ device have less run-to-run consistency than was seen for the SipNose device. The median particle size for the Alrin™ device is about 40-70 μm, while the DV90 particle size is about 65-120 μm.

These results are summarized in Table 13.

TABLE 13

Effect of various Parameters on Particle Size

| Device | Pressure (barg) | Orifice Size (mm) | Medicament | Medicament Volume (μl) | DV50 (μm) | DV90 (μm) |
|---|---|---|---|---|---|---|
| SipNose | 6 | 1.5 | Saline | 100 | 40-45 | — |
| SipNose | 6 | 1.5 | Saline | 500 | 50-65 | — |
| SipNose | 6 | 1.0 | Saline | 100 | 25 | — |
| SipNose | 6 | 1.0 | Saline | 500 | 28-30 | 50 |
| SipNose | 6 | 0.8 | Saline | 100 | 23-24 | — |
| SipNose | 6 | 0.8 | Saline | 500 | 32-35 | 60-65 |
| SipNose | 6 | 0.5 | Saline | 100 | 23 | 55 |
| SipNose | 6 | 0.5 | Saline | 200 | 25 | 55-60 |
| SipNose | 6 | 0.5 | Saline | 500 | 27, 30, 35 | 55, 55, 65 |
| SipNose | 6 | No orifice | Saline | 300 | 45-48 | 100-140 |
| SipNose | 6 | No orifice | Saline | 1000 | 50 | 180 |
| SipNose | 3 | 0.8 | Saline | 100 | 35-40 | 90-100 |
| SipNose | 6 | 1 | Otrivine ™ (25 cP viscosity) | 100 | 45-48 | — |
| SipNose | 6 | 0.5 | Otrivine ™ (23 cP viscosity) | 100 | 40-55 | — |
| Alrin ™ | — | — | Saline | 100 | 45, 40, 70 | 70, 65, 120 |

SipNose aerosol droplets have a mean diameter in the typical range of other nasal delivery devices, and even smaller. Replacement of the saline with a high viscosity solution of 23 cP appears to have made little difference to the particle size distribution.

For the range of parameters used, the delivery parameters appear to have little effect on the particle size.

Figure 67:
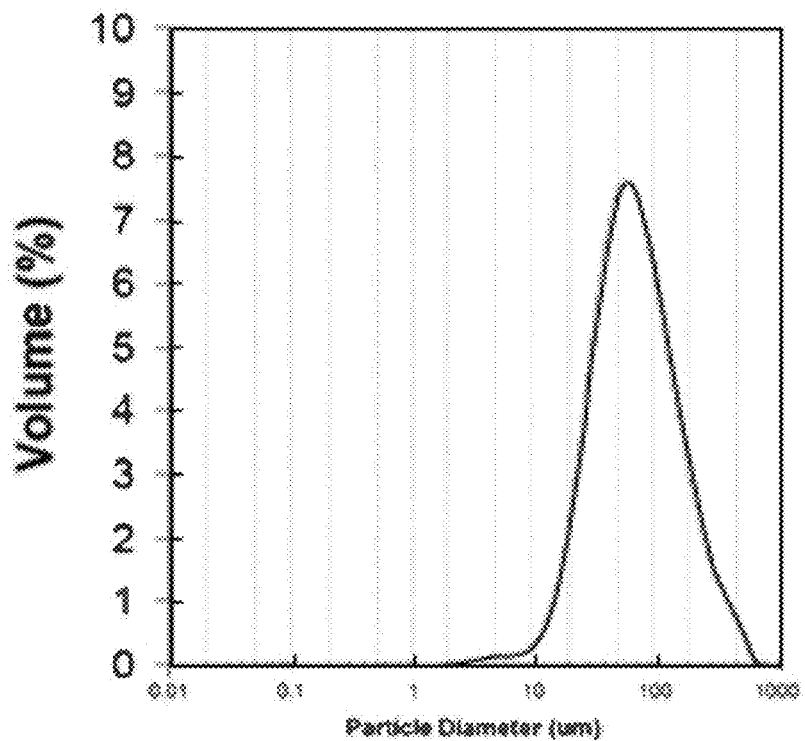
FIG. 67 shows a typical SipNose particle size distribution.

An exemplary droplet size distribution is given in FIG. 67, which shows a plot of the number of particles vs. partic TABLE 15-continued Device 23-12

| Device Version | D v (0, 0.5) (μm) | Obscuration (%) |
|---|---|---|
| 23-12 | 92.3 | 6.4 |
| 23-12 | 108.6 | 3.4 |
| Mean | 88.3 ± 12.9 | |

*anomalous value

Table 16 shows reproducibility for the SipNose device. The measurements were done by weighing, and part of the variability shown probably depends on the measurement technique.

TABLE 16

Reproducibility for a SipNose device

| | Amount loaded (gm) | Residual amount (gm) | Released (%) | Residual volume (%) |
|---|---|---|---|---|
| 1 | 0.3996 | 0.0584 | 85.4 | 14.6 |
| 2 | 0.4058 | 0.0414 | 89.8 | 10.2 |
| 3 | 0.3915 | 0.0054 | 98.6 | 1.4 |
| 4 | 0.4143 | 0.0063 | 98.5 | 1.5 |
| 5 | 0.3772 | 0.0069 | 98.2 | 1.8 |
| 6 | 0.3902 | 0.0509 | 87.0 | 13.0 |
| 7 | 0.4010 | 0.0626 | 84.4 | 15.6 |
| 8 | 0.3853 | 0.0490 | 87.3 | 12.7 |
| 9 | 0.4302 | 0.0511 | 88.1 | 11.9 |
| 10 | 0.4052 | 0.0482 | 88.1 | 11.9 |
| Average | 0.4000 | 0.0380 | 90.5 | 9.5 |
| Std. Dev. | 0.0152 | 0.0227 | 5.6 | 5.6 |

SipNose aerosol droplets have a mean diameter in the typical range of other nasal delivery devices, and even smaller.

Although the droplets have a small diameter, the width of the aerosol plume is very narrow, and this allows the aerosol to be better distributed in the inner part of the nasal cavity, without depositing at the from of a cavity such as the nasal cavity.

The SipNose device shows high consistency.

Effect of Pressure on Release Time

Figure 68:
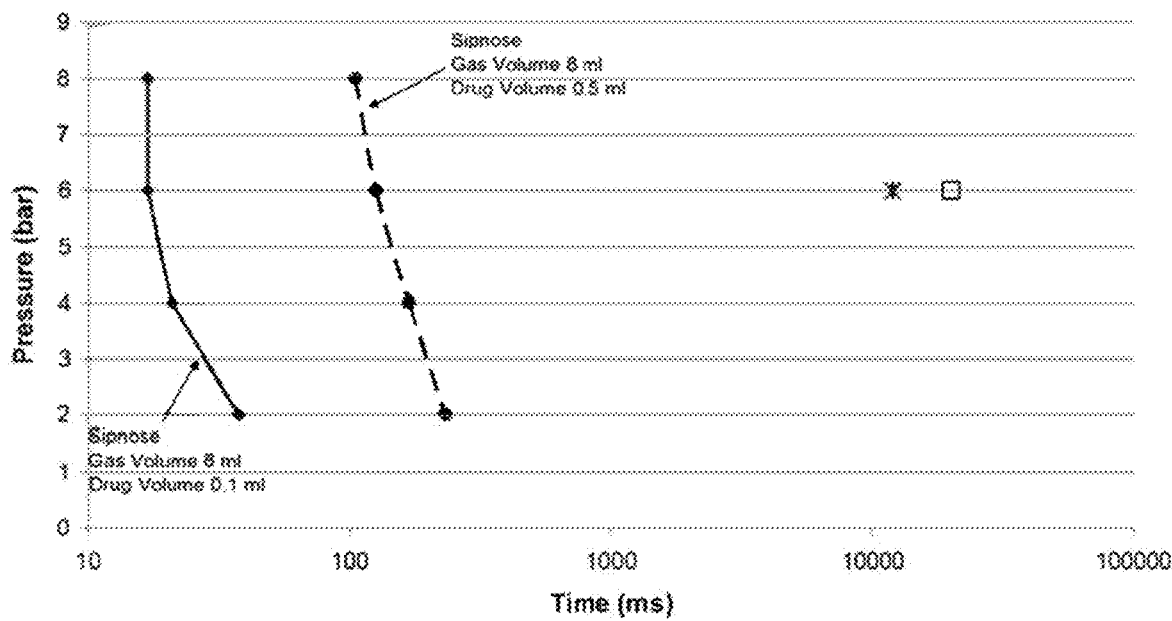
FIG. 68 shows the effect of gas pressure on emptying/release time for 8.1 ml or 8.5 ml of gas.

In reference to FIG. 68, the effect of gas pressure on emptying/release time for 8.1 ml or 8.5 ml (of gas+substance) was tested in a SipNose device (solid line and dashed line) and two commercial devices (star and open square) were examined. For the first SipNose experiment (solid line), the drug volume was 100 μl (total volume of 8.1 ml) and for the second SipNose experiment, (dashed line), the drug volume was 500 μl (total volume of 8.5). The first commercial device (star) was the Otrimer™ from Novartis; the second was the Simply Saline Nasal Mist from Church & Dwight Co., Inc. (http://www.armandhammer.com/SimplySaline.aspx). It can be seen that the time needed for the release of 8.1 and 8.5 ml of gas+substance was less than 300 ms even for the larger volume, and that the time was very much less than the 12 s (Otrimer™, star) and 20 s (Simply saline, square) needed for the commercial devices to release the volume of 8 ml.

Figure 69:
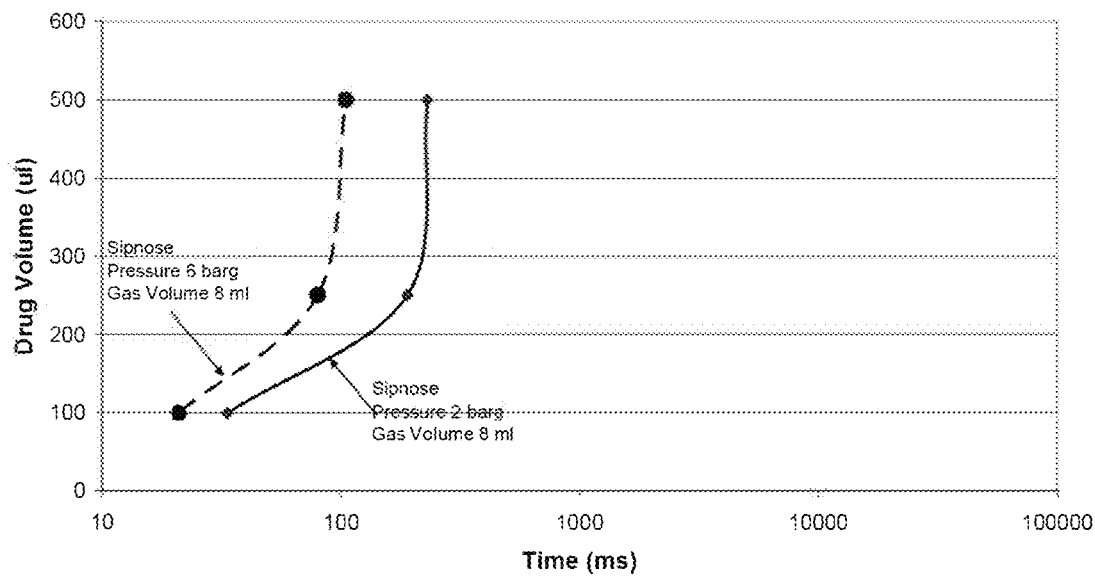
FIG. 69 shows the effect of drug volume on the release time.

In reference to FIG. 69, the effect of drug volume on the release time, the time for the drug and carrier gas to substantially completely exit the device is shown. Typically, for the SipNose device (solid line and dashed line), the release time is affected by the activation time and reflects the time for the device to reconfigure from the active configuration to the inactive configuration or vice versa For the SipNose device, 8 ml of gas was used. For pressures of 2 barg and 6 barg, the release time was less than 300 ms.

Figure 70:
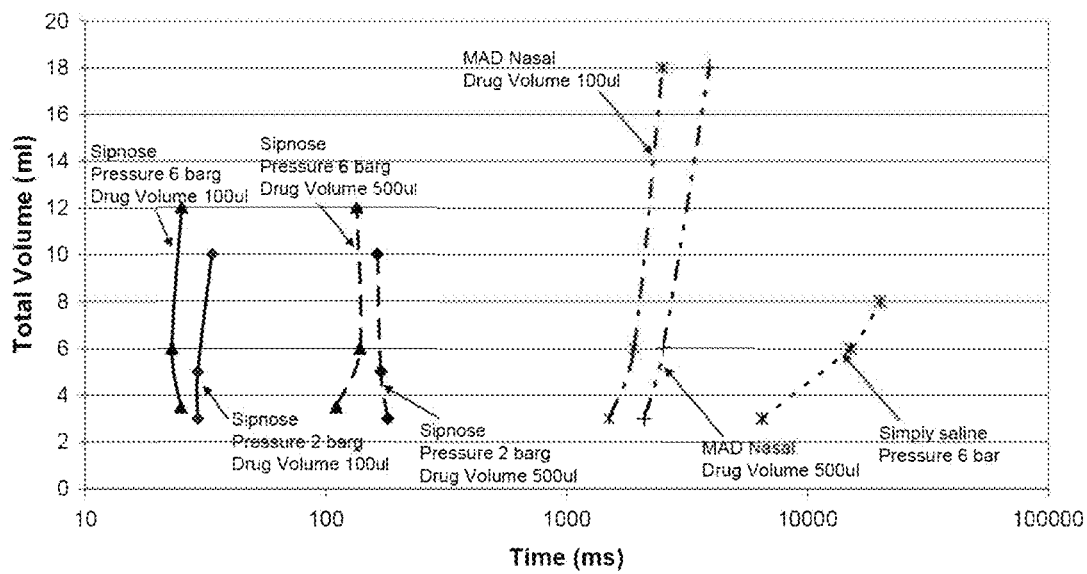
FIG. 70 shows the effect of gas volume on the release time.

In reference to FIG. 70, the effect of gas volume on the release time was examined for the SipNose device (solid line and dashed line) and for two commercial devices, the MAD Nasal from LMA (dot-dash line and dash-double dot line) and the Simply Saline Nasal Mist from Church & Dwight Co., Inc. (http://www.armandhammer.com/SimplySaline.aspx) (dotted line). For the SipNose device, pressures of 2 barg (diamonds) and 5 barg (triangles), and drug volumes of 100 μl (solid line) and 500 μl (dashed line) were used. For the MAD Nasal device, drug volumes of 100 μl (dot-dash line) and 500 μl (dash-double dot line) were used and pressure was generated by manually compressing the devices. For the Simply Saline device, a pressure of 6 barg was used.

The release times were less than 300 ms for the SipNose device, even for the lower pressure and higher volume, significantly less than the 1.5 s to 20 s needed with the commercial devices.

In all of the SipNose experiments, over a range of pressures from 2 barg to 10 barg, a range of gas volumes from 2 ml to 12 ml and a range of drug volumes from 100 μl to 500 μl, significantly less than 0.5 s was needed to empty the SipNose device of drug plus gas. This is significantly less than the more than 1.5 s needed by even the fastest of the commercial devices.

In some embodiments, the release time is less than 1 s.

In some embodiments, it is less than 0.5 s.

In preferred embodiments, the release time is between 100 ms and 500 ms.

It should be emphasized that any embodiment of the present invention and any variant thereof can be used for both for humans (medical use) and animals. Thus, any of the devices as disclosed above and any variant thereof can be used for veterinary applications as well as (human) medical applications.

The pressure rate $\Delta P/\Delta t$ for a SipNose device with 0.8 mm orifice and a gas volume of 8 ml and for saline delivered by the Alrin™ nasal pump and the Simply Saline™ nasal pump is shown in Table 17. For the simply Saline™ nasal pump, there is no pre-defined release time. Release begins when an activation button is pressed and continues as long as the button remains depressed.

TABLE 17

Pressure Rate $\Delta P/\Delta t$

| | Drug Volume (ml) | Total Volume (ml) | Pressure Rate (barg/ms) |
|---|---|---|---|
| SipNose | 0.1 | 8.1 | −0.22 |
| SipNose | 0.5 | 8.5 | −0.045 |
| Saline, via Alrin ™ nasal pump | 0.1 | 0.1 | −5 × 10−4 |
| Simply Saline | same as total volume | dependent on release duration | −3 × 10−4 |

It is clear that the pressure rate for the SipNose device is on the order of 2 orders of magnitude greater than for the commercial devices.

The pressure as a function of time for pressures above 2 barg for a gas volume of 8 ml, a drug volume of 0.1 ml and an orifice diameter of 0.8 mm can be calculated from $$P = 471 V_{sub}^{-1.5}$$

The pressure as a function of time for pressures above 2 barg for a gas volume of 8 ml, a drug volume of 0.5 ml and an orifice diameter of 0.8 mm can be calculated from $$P=8510 V_{sub}^{-1.5}$$

In general, for an orifice diameter of 0.8 mm and pressures above 2 barg, the pressure can be calculated from $$P=a_{p1} V_{sub}^{-bp1}$$

where $a_{p1}$ is in a range from 1 to 20,000 and $b_{p1}$ is in a range from 1 to 2.

The drug volume rate $\Delta V_{sub}/\Delta t$ is shown in Table 18. For the SipNose device, the orifice diameter was 0.8 mm orifice and the gas volume was 8 ml.

TABLE 18

Drug Volume Rate $\Delta V_{sub}/\Delta T$

| Pressure (barg) | Drug Volume Rate (ml/ms) |
|---|---|
| Drug volume less than 250 µl | |
| 2 | 0.97 |
| 6 | 2.54 |
| Drug volume more than 250 µl | |
| 2 | 5.95 |
| 6 | 10 |

The release time for a pressure of 2 barg, a gas volume of 8 ml and an orifice diameter of 0.8 mm can be calculated from $$T=37+\exp(2+0.018 V_{sub})$$

The release time for a pressure of 6 barg, a gas volume of 8 ml and an orifice diameter of 0.8 mm can be calculated from $$T=-2.9+2\exp(2.86+0.025 V_{sub})$$

In general, for an orifice diameter of 0.8 mm, the release time if the drug volume only is varied can be calculated from $$T=a_{v1}+b_{v1}\exp(c_{v1}+d_{v1} V_{sub})$$

where $a_{v1}$ is in a range from −50 to 50, $b_{v1}$ is in a range from 0.1 to 5, $c_{v1}$ is in a range from 1 to 5 and $d_{v1}$ is in a range from 0.01 to 0.05.

The gas volume rate $\Delta V_{gas}/\Delta t$ is shown in Table 19. For the SipNose device, the orifice diameter was 0.8 mm. For the SipNose device, the pressure was 2 barg, while, for the MAD Nasal device, the device was pressed by hand; the delivery pressure was not measured.

TABLE 19

Gas Volume Rate $\Delta V_{gas}/\Delta T$

| Device | Pressure (barg) | Drug volume (µl) | Gas Volume Rate (ml/ms) |
|---|---|---|---|
| SipNose | 2 | 100 | 1.43 |
| SipNose | 2 | 500 | 0.367 |
| SipNose | 6 | 100 | 1.11 |
| SipNose | 6 | 500 | 0.182 |
| MAD Nasal | | 100 | 0.015 |
| MAD Nasal | | 500 | 0.0084 |
| Simply Saline | 6 | | 0.0004 |

The release time for the SipNose device, for a pressure P of 2 barg and a drug volume $V_{sub}$ of 100 µl can be calculated from $$T=-38+1.43 V_{gas}$$

The release time for the SipNose device for a pressure P of 2 barg and a drug volume $V_{sub}$ of 500 µl can be calculated from $$T=68.5-0.367 V_{gas}$$

The release time for the SipNose device, for a pressure P of 6 barg and a drug volume $V_{sub}$ of 100 µl can be calculated from $$T=-20+1.11 V_{gas}$$

The release time for the SipNose device, for a pressure P of 6 barg and a drug volume $V_{sub}$ of 500 µl can be calculated from $$T=-16+0.182 V_{gas}$$

In general, for an orifice diameter of 0.8 mm, the release time can be calculated from $$T=a_{v2}+b_{v2} V_{gas}$$

where $a_{v2}$ is in a range of −100 to 100 and $b_{v2}$ is in a range of −5 to 5.

Carrying Distance and Spread Width Area

Carrying distance and spread width area were compared for the SipNose device and two commercial devices, the Alrin and the Otrivin devices, by firing them at a target (9200) 50 cm from the tip of the nozzle (9100) of the device being fired. FIG. 71A-C shows the devices during firing.

For the SipNose device (FIG. 71A), the aerosol (9150) is visible for the majority of the distance between the nozzle (9100) and the target (9200) and the material deposited forms a distinct patch (9300) on the target (9200).

For the Alrin device (FIG. 71B) and the Otrivin device (FIG. 71C), the aerosol is virtually invisible, even near the tip or the nozzle (9100) and no evidence that any of the material has reached the target (9200).

Penetration of Aerosol Through Fabric

For a distance between nozzle and target of 30 cm, dispensing 100 µl a liquid in a carrier volume, the penetration of the aerosol through 4 mm of a fabric medium was compared for different operating conditions for the SipNose device and three commercial devices, the Akin, the MAD Nasal from Wolfe Tory and the Otrivin devices. In all cases, the aerosol from the SipNose device penetrated the 4 mm of fabric (FIG. 72A-E and Table 20).

TABLE 20

Spread on absorbing surface

| | | Spread | | | | |
| | | Diameter | | Area | | |
| | Carrier | | | | | |
| | Pressure (barg) | Volume (ml) | Inner (cm) | Outer (cm) | Inner (cm²) | Outer (cm²) | Penetration? |
|---|---|---|---|---|---|---|---|
| SipNose | | | | | | | |
| 1 | 5.6 | 18 | 2.5 | 6 | 4.9 | 28.3 | YES |
| 2 | 4 | 8 | 2 | 6.5 | 3.1 | 33.2 | YES |
| 3 | 6 | 8 | 3 | 5 | 7.1 | 19.6 | YES |
| Commercial | | | | | | | |
| Alrin ™ nasal pump | — | — | — | 15 | — | 177 | NO |
| MAD Nasal | — | — | 8 | 12 | 50.2 | 113 | NO |
| Otrivin ™ nasal pump | — | — | — | 23 | — | 415 | NO |

Figure 72A:
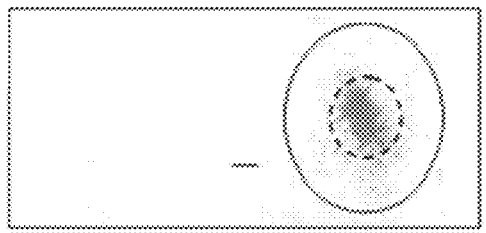
FIGS. 72A-E show the penetration of aerosol through fabric using different devices.
Figure 72B:
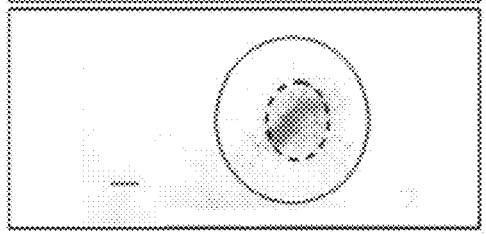
Figure 72C:
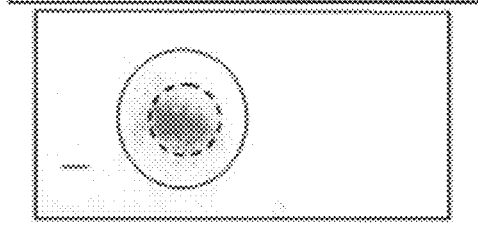
Figure 72D:
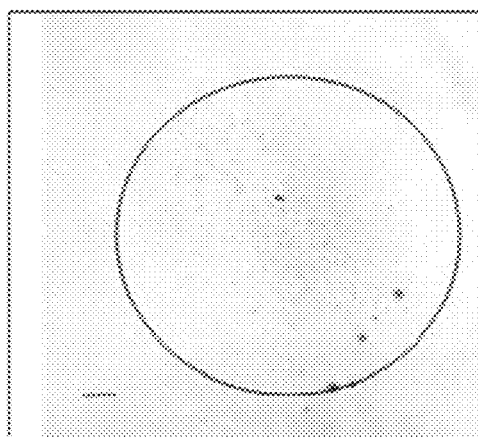
Figure 72E:
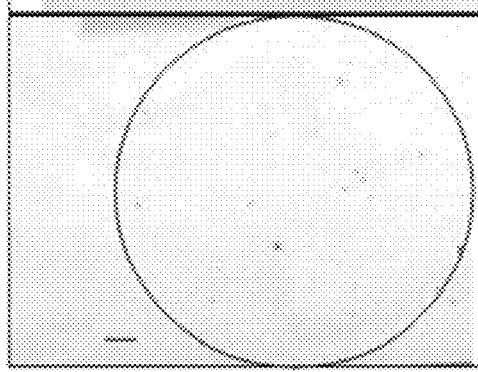

FIG. 72A-C shows that, for the three typical operating conditions, significant amounts of the material penetrate through the 4 mm of fabric, consistent with what was seen for the nasal cast example (Example 14, FIG. 37).

FIG. 72A-C also shows the inner area (dashed circle) delineating the area of heavier deposition and the outer area (solid circle) delineating the area of lighter deposition. For the two commercial devices, the MAD Nasal from Wolfe Tory (FIG. 72D) and the Alrin (FIG. 72E), deposition is light across the entire area, and the edges of the deposition region are not well defined.

Spot Diameter

Figure 73:
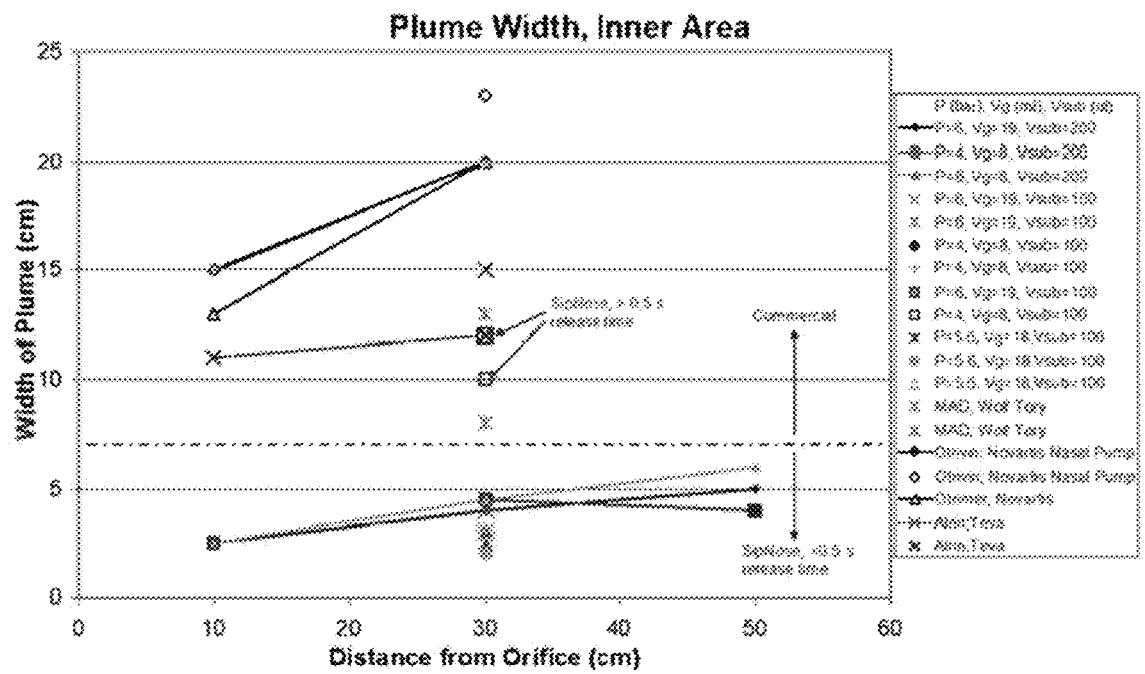
FIG. 73 illustrates spot diameter for various devices.

In reference to FIG. 73, the diameter of the inner (more dense) area (see the dashed circles in FIGS. 72A-C) is shown for different operating conditions for the SipNose device and the total diameter is shown for four commercial devices, the Otrivin device from Novartis, the Otrimer device from Novartis, the Alrin device from Teva and the MAD device from Wolfe Tory.

The SipNose results differed depending on valve opening time. For valve opening times less that about 500 ms, the plume width is significantly smaller for the SipNose device for all operating conditions. For valve opening times greater than about 500 ms, the results depended on the diameter of the open valve. Where the diameter of the open valve was small (0.22 mm), no aerosol was formed. Where the valve diameter was large (0.8 mm), an aerosol was formed but the plume was wide (12 and 10 cm). This indicates that, for a narrow plume width, the valve opening time should be less than 500 ms and that, as long as the opening time is in this range, the plume is both much narrower than that for the commercial devices and is better defined.

Repeatability

Figure 74:
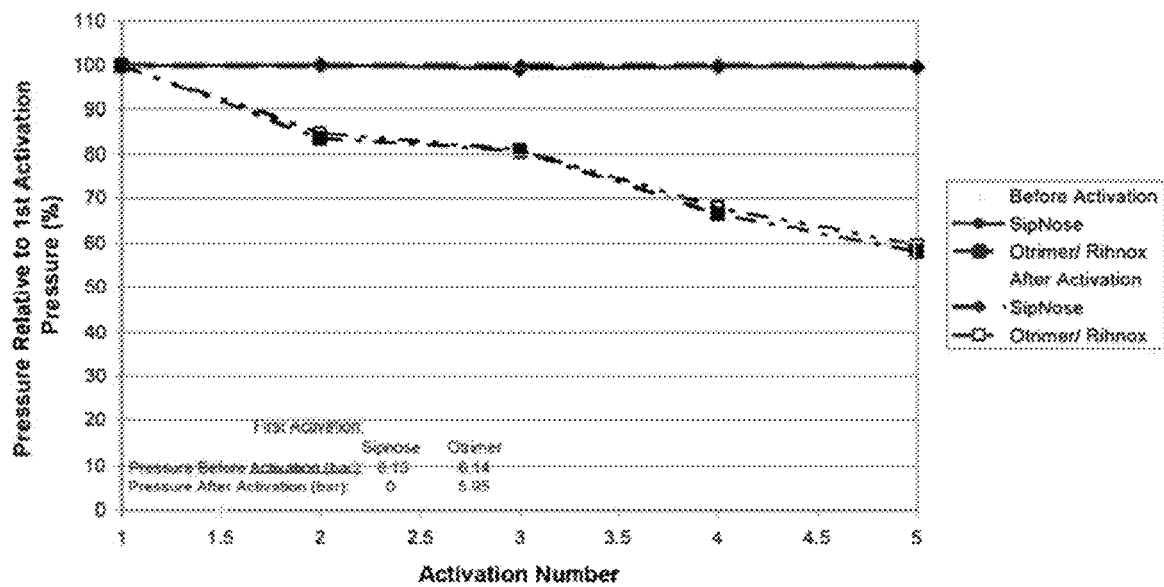
FIG. 74 illustrates repeatability for various devices.
Figure 75:
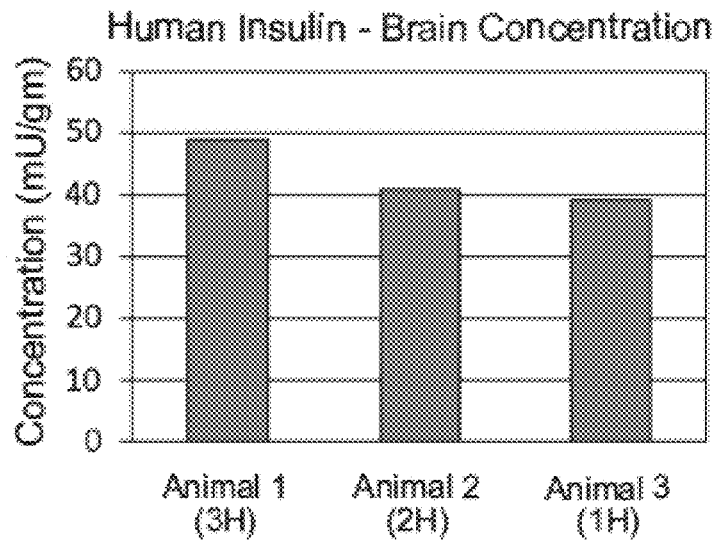
FIG. 75 demonstrates absorption of the desired substance into the brain as a function of time after administration.
Figure 76A:
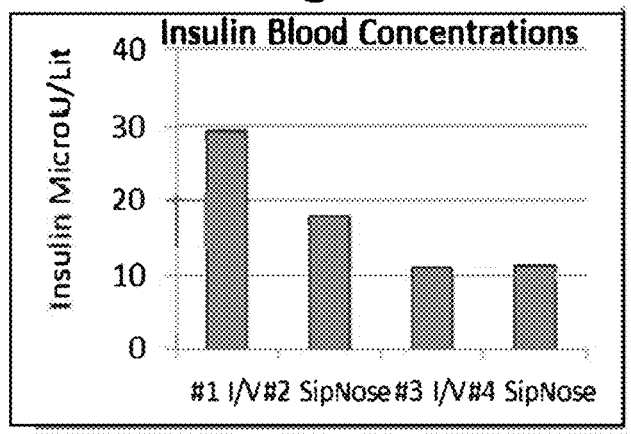
FIG. 76A-C shows the concentration of insulin in the blood and brain.
Figure 76B:
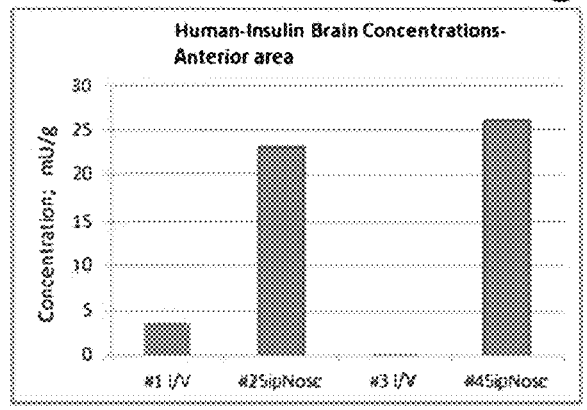
Figure 76C:
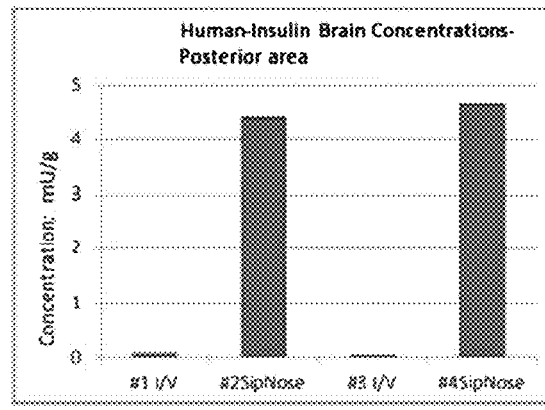

As shown in FIG. 74, the sipNose device provides greater repeatability than typical commercial devices. The SipNose device and a commercial device, the Otrimer delivery device, were repeatedly fired. For the SipNose device, the pressure before activation was, within 1%, the same each time (6.13±0.02 bar) whereas, for the Otrimer delivery device, the pressure decreased each time the device was used; the pressure before the last activation was less than 60% of the initial pressure (first activation, 6.14 bar, last activation, 3.57 bar).

Furthermore, for the SipNose device, the pressure was completely discharged for each activation (pressure after=0 each time; ratio current/first=1). For the Otrimer delivery device, on the other hand, only a small fraction of the pressure was discharged. The pressure difference was less than 5% of the pressure before activation for the first activation and decreased with activation number, being less than 1% for the fifth activation.

Some of the other types of delivery devices, which include pressurized metered dose inhalers (pMDIs), dry powder inhalers and nebulizers, can also suffer from poor repeatability.

In a pMDI, the delivery pressure will necessarily decrease with activation number, as a portion of the fixed initial pressure is discharged on each activation. Dry powder inhalers tend to have poor repeatability because the patient inhales to deliver the medication, which is inherently poorly controllable. Nasal sprays, such as the Otrmier delivery device, tend to have a fairly long "recovery time", which limits repeatability.

Nebulizers can have good repeatability. In a typical nebulizer, a gas at high pressure flows through the device, combines with an aerosol, and is then delivered to the patient. If a regulator is used to control the pressure of the gas flowing through the device, the repeatability of the nebulizer can be as good as the accuracy and reliability of the regulator.

The Respimat® Soft Mist inhaler from Boehringer Ingelheim is a carrier-free inhaler. It comprises a medicament cartridge with a stiff outer shell and a flexible inner bag which contains the medicament and a holder. The holder comprises a bottom part, into which the cartridge fits, which is rotatable relative to the upper part. Rotating the bottom part tensions a spring, which moves the cartridge downward toward the base of the device. This induces pressure in the region between the base and the cartridge and forces air through a hole in the base of the cartridge, compressing the flexible inner bag and causing the liquid medicament to rise through a capillary tube into a holding chamber.

Pressure on a triggering device releases the spring and activates the device. The released spring contracts back to its inactivated position, which pushes the cartridge and attached capillary tube upward into the holding chamber. A non-return valve prevents the medicament from returning to the flexible bag. The increased pressure on the medicament in the holding chamber forces the medicament through a nozzle, thereby atomizing it.

Unlike the SipNose device, the Respimat device is designed to produce a low-velocity, "soft" mist with a velocity of less than 30 cm/s, compared to the velocities of over 10 m/s for the SipNose device. For the Respimat device, a high-velocity mist is disadvantageous and is to be avoided.

In the Respimat device, the quality of the aerosol is controlled by the design of the nozzle, with the small particle size produced by a number of small openings in the nozzle.

Brain Absorption of Insulin

FIG. 75 demonstrates absorption of the desired substance into the brain as a function of time after administration. The substance in this experiment is Human Insulin (Lispro insulin, 5807 Da); the animal model is a rabbit. Administration was 10 U/Kg of Human Insulin via SipNose nasal administration. Brain concentrations were measured using insulin quantitative ELISA at 1 h, 2 h, and 3 h post administration.

Lispro Insulin is delivered to the brain with the SipNose device and can be specifically detected.

Example 2—Blood and Brain Absorption of Insulin

In FIG. 76A-C, the efficacy of delivery of insulin to the brain is compared for the SipNose device vs. IV administration. The substance was Lispro insulin (5,807 Da) administered to rabbits. Four rabbits were used; all animals were given 0.5 U/kg of Human Insulin. Administration was via IV for rabbits 1 and 3 and via SipNose nasal administration for rabbits 2 and 4. Brain concentrations were measured using insulin quantitative ELISA.

The results of the experiment are shown in FIGS. 76A-C. FIG. 76A shows the concentration of insulin in the blood for two animals that were given an IV administration (1 and 3) and two animals that were given nasal administration with the SipNose device (2 and 4). FIG. 76B shows the amount of insulin in the anterior part of the brain for the four animals and FIG. 76C shows the amount of insulin in the posterior part of the brain for the same four animals.

From FIG. 76A-C, the following conclusions can be drawn:
1. Lispro Insulin delivery to the brain with the SipNose device is highly efficient when compared to I/V administration
2. Insulin delivery to the brain with the SipNose direct-nose-to-brain approach results in Insulin in both anterior and posterior parts of the brain.

Efficacy of Delivery of Midazolam

A comparison was made of the efficacy of delivery of the anesthetic Midazolam, when used for pre-medication, between an embodiment of the SipNose device of the present invention and a prior-art device, the commercial nasal pump based on positive displacement (as the pump used for Alrin™ delivery) and the MAD Nasal from Wolfe Tory.

Comparison with nasal pump (using 5 mg/ml solution): For a pre-medication procedure with commercial nasal pump (positive displacement pump), in order to achieve the desired dose of 3 mg Midazolam, the delivery device was inserted into a nostril and an aliquot of Midazolam is delivered. The delivery device is then inserted into the opposite nostril and a second aliquot of Midazolam is delivered. This is repeated twice more with a 30 s intervals between each cycle, for a total of six aliquots of Midazolam, three in each nostril. As opposed to that, for a SipNose device delivery, a single dose of 0.6 ml was delivered to one nostril.

Comparison with MAD (using a 1 mg/ml solution): For a pre-medication procedure with MAD atomizer, in order to achieve the desired dose of 1.4 mg Midazolam, the delivery device was delivered to one nostril and an aliquot of Midazolam within a volume of 1.4 ml was delivered. For SipNose device delivery the Midazolam was delivered in 2 separate aliquots of 0.7 ml, one to each nostril.

In order to determine the efficacy of anesthetization a BIS EEG monitoring was used, where the BIS values for brain activity are calculated from the EEG activity. Awake, unsedated individuals typically have BIS values ≥97. Mildly sedated individuals typically have BIS values in the 80's, moderately sedated individuals typically have BIS values in the 70's, while fully sedated individuals typically have BIS values below about 70; BIS values between about 45 and about 60 are commonly used for general anesthesia during the maintenance phase of an operation.

Two comparisons were made between the commercial device and the present, SipNose, device. In the first, 3 mg of Midazolam was administered and the commercial device was a commercial nasal pump (positive displacement), in the second, 1.4 mg of Midazolam was administered and the commercial device was a MAD applicator.

As can be seen from Table 21, the SipNose device effectively sedated the patient in all 8 cases, while the commercial nasal pump was only effective for 3 out of 4 patients. In no case were there adverse events. The mean onset times are not significantly different for the SipNose device and the commercial device, since the range of variability is large.

The administration time was significantly shorter for the SipNose device, 1 s vs. 1 min.

The rate of sedation was greater with the SipNose device, with a minimum BIS of 74.5±9 for the SipNose device compared to a minimum BIS of 87.5±5.3 for the commercial device.

TABLE 21

Comparison of SipNose and Commercial Nasal Pump in sedation with Midazolam

|  | SipNose | Commercial Nasal Pump |
|---|---|---|
| Number of Patients | 8 | 4 |
| Number of Positive Sedations | 8 | 3 |
| Mean onset time (min) | 5.9 ± 4.6 | 6.7 ± 4.6 |
| Adverse events | 0 | 0 |
| Time to administer (s) | 1 | 60 |
| level of Maximum BIS | 97 | 97 |
| Level of minimum BIS | 74.5 ± 9 | 87.5 ± 5.3 |
| Minimum BIS excluding failure | — | 85 |

Figure 77:
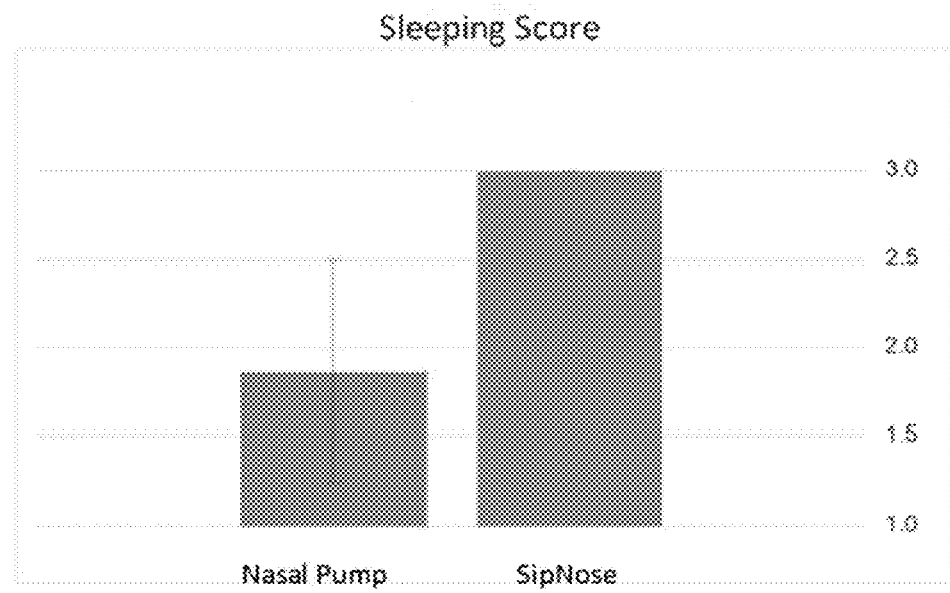
FIG. 77 shows sleeping score after administration of Midazolam.

If sleep scores are taken for the patients, where a 1 means the patients was not sleepy, 2 means that the patient is sleepy or calm, and 3, that the patient is sleeping, the SipNose device (FIG. 77) achieved a score of 3, with all patients sleeping, whereas the score for the commercial device was less than 2.

In the second comparison, the total dose of Midazolam was 1.4 mg in a total volume of carrier of 1.4 ml. For the SipNose device, it was administered in two aliquots of 0.7 ml, whereas it was administered in one aliquot for the commercial MAD Nasal atomizer from Wolfe Tory. Midozolam was administered to four patients, two with the SipNose device and two with the commercial MAD device.

As shown in Table 22, sedation is better with the SipNose device; sedation failed entirely for Patient 2 with the commercial device. For this lower dose, the onset time was significantly shorter for the SipNose device (3 and 5 min vs. 20 and 8 min).

Even for this lower dose, where the SipNose administration was in two aliquots and the commercial device administration was in a single aliquot, administration time was lower for the SipNose device, with each aliquot administered in 1 s, rather than the 7-10 s for administration of a single aliquot with the commercial device.

TABLE 22

Comparison of SipNose and Commercial Nasal Pump on sedation with Midazolam

|  | SipNose | | Commercial Nasal Pump | |
|---|---|---|---|---|
|  | Patient No. | | | |
|  | 1 | 2 | 1 | 2 |
| Positive Sedation | Yes | Yes | Limited | No |
| Onset time (min) | 5 | 3 | 20 | 8 |
| Adverse events | No | No | No | No |
| Time to administer (s) | 2 × 1 | 2 × 1 | 10 | 7 |
| Level of minimum BIS | 84 | 84 | 83 | 92 |

In addition to the BIS values, a sleeping score was found by observation of the patients. The sleeping score was 3 for SipNose administration and averaged 1.5 for the commercial nasal pump.

As can be seen from this example, the SipNose device is at least as good as the commercial device in terms of efficacy and onset time for the delivery of the small molecule Midazolam, with onset time being no greater for the SipNose device than for the commercial device. The SipNose device appears to be more reliable in inducing anesthesia, with no failures in 10 patients compared to 2 failures and one partial failure in 6 patients with the commercial devices.

Administration of a single aliquot is faster with the SipNose device, approximately 1 s vs. approximately 10 s for the commercial device.

In addition, larger does can be administered in a single aliquot with the SipNose device, reducing the number of aliquots needed for delivery of a total dose and thereby decreasing the chances of error in administration and the discomfort of the patient. The more rapid administration (1 s vs. 7-10 s or 1 min) will also reduce patient discomfort and reduce chances of error (e.g., releasing a patient before an aliquot is completely delivered).

Efficacy of Delivery of Midazolam

In this example, epileptic seizures were induced in rats by administration of 47.5-50 mg/kg of Pentylenetetrazol (PTZ) for 5 min before the start of treatment with Midazolam. The Midazolam was administered either via IV or using a SipNose device, via the nasal passages. There were two dosing levels, 0.6 mg/kg (FIG. 78) and 6 mg/kg (FIG. 79).

In all cases, the Racine grading standard was used to determine the severity of the seizures. PZT was at t=−5 min, the start of treatment was at time t=0.

Treatment consisted of saline (control, diamonds), Midazolam administered by IV (triangles) or Midazolam administered nasally by a SipNose device (squares).

0.6 mg/kg

Figure 78:
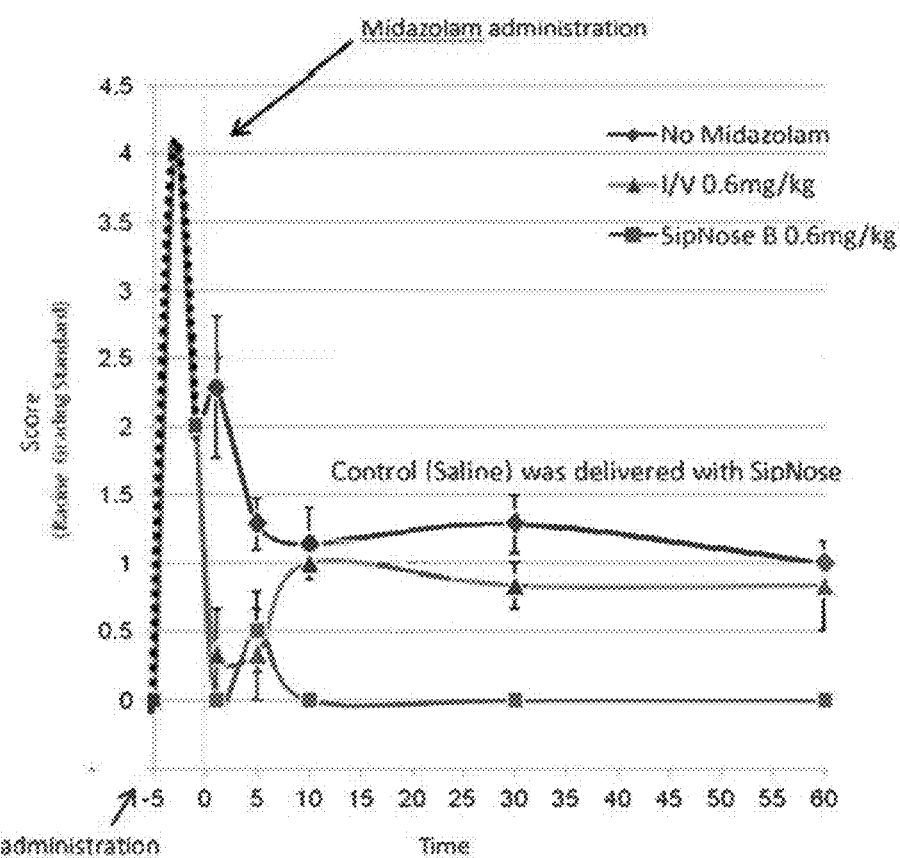
FIG. 78 shows the response of rats to administration of 0.6 mg/kg Midazolam.
Figure 79:
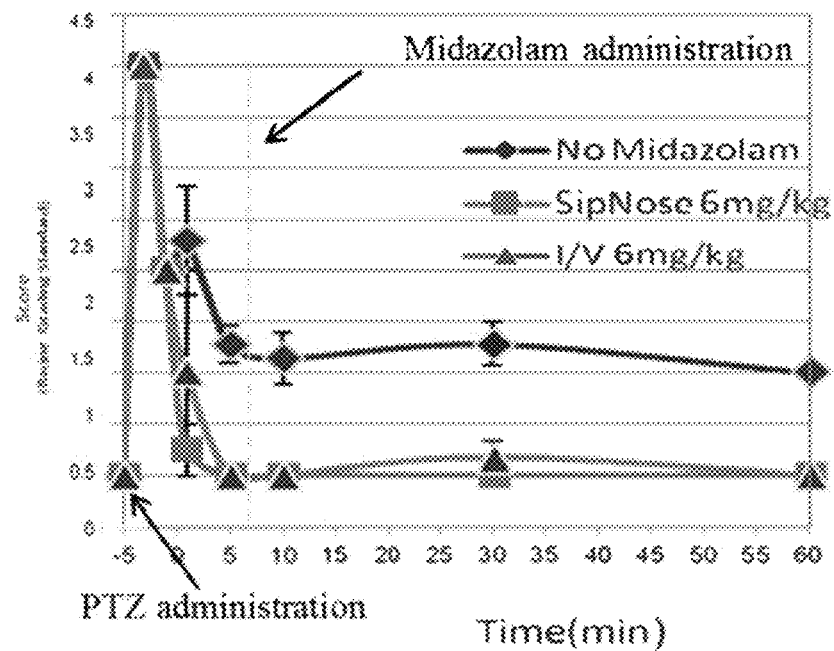
FIG. 79 shows the response of rats to administration of 6 mg/kg Midazolam.

As can be seen in FIG. 78, the seizure severity rose from 0 to 4 by time t=0. After time t=0, seizure severity decreased. For saline administration, the Racine severity stabilized by about time t=5 min; it remained between about 1 and about 1.5 for the entire time between about t=10 min and about t=60 min. After IV administration of Midazolam, it remained between about 0.5 and about 1, whereas after SipNose administration, it was zero, no seizures were seen, for the entire time period between about time t=10 min and time t=60 min.

6 mg/kg

As can be seen in FIG. 79, the seizure severity rose from 0 to 4 by time t=0. After time t=0, seizure severity decreased. For saline administration, the Racine severity stabilized by about time t=5 min; it remained between about 1 and about 1.5 for the entire time between about t=10 min and about t=60 min.

For this larger dose, the IV and SipNose responses were more alike; both remained below a Racine severity of 0.5. No seizures were seen (Racine score 0) for the entire time period between about time t=10 min and time t=60 min.

Dose-Response for Delivery of Midazolam

In this example, doses of Midazolam between about 0.6 mg/kg and about 6 mg/kg were administered to rats and the concentration of Midazolam in the brain was measured 60 minutes after administration.

Figure 80:
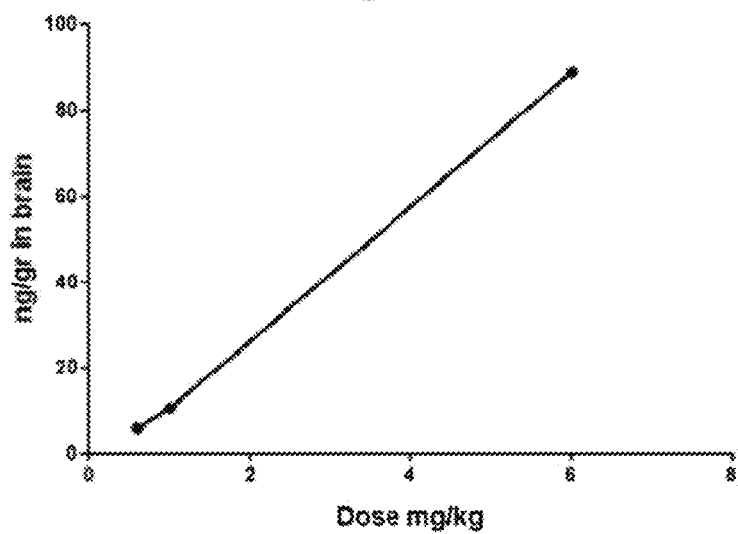
FIG. 80 shows the dose response curve.

As shown in FIG. 80, for doses between about 0.6 mg/kg and about 6 mg/kg, the dose-response curve is essentially linear.

In other cases, the dose-response curve may not be linear, even if the amount reaching the target location (e.g., the brain) increases linearly with increasing dose, since, for some drugs, a subjects' dose-response curve will be non-linear (e.g., no response below a threshold, response independent of dose for doses above a threshold, etc.).

Efficacy of Control of Epileptic Seizures with Midazolam

Figure 81:
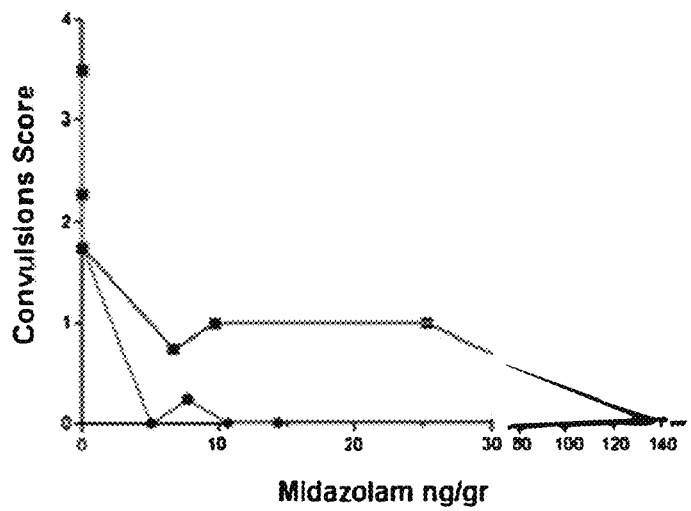
FIG. 81 shows the effect of brain concentrations of Midazolam on convulsions.

Epileptic seizures were induced in rats by administration of Pentylenetetrazol (PTZ) and the severity of the seizures was measured 60 minutes after administration of Mizadolam. Doses of Mizadolam varied from zero to 6 mg/kg with SipNose nasal delivery device and with an I/V administration. Brain concentrations of Midazolam were measured and a correlation between brain concentration and convulsions score is shown in FIG. 81. Brain concentrations varied from zero to 130 ng/gr brain tissue. Black squares represent the I/V administrated animals and black dots represent the SipNose administrated animals.

As can be seen from FIG. 81, the Racine severity (convulsion score) remained at about 1 until the IV administration of Mizadolam was about 25 ng/gm. The Racine severity then dropped slowly, not reaching zero until the IV administration of Mizadolam was about 130 ng/gm. In contrast, a SipNose concentration of Mizadolam of only about than 11 ng/gm was needed to completely prevent seizures (score=0).

As the examples disclosed hereinabove demonstrate, the SipNose device is stable with respect to minor changes in device parameters (e.g., pressure, volume, etc.); minor changes in device parameters do not significantly change the results.

Anti-Epileptic Treatment of Status Epilepticus (SE) with Midazolam in a Human

Case study of a patient age of 39 years old, suffering from epileptic seizures (SE) was treated with a dose of 2 mg Midazolam with sipNose delivery device to deliver Midazolam via the nasal cavity.

Figure 82A:
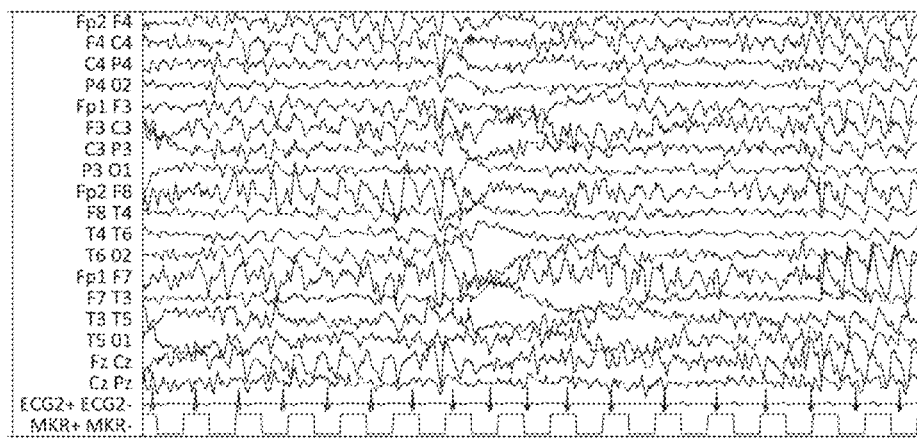
FIG. 82A-B illustrates the EEG recordings before the nasal administration of the drug with SipNose device.
Figure 82B:
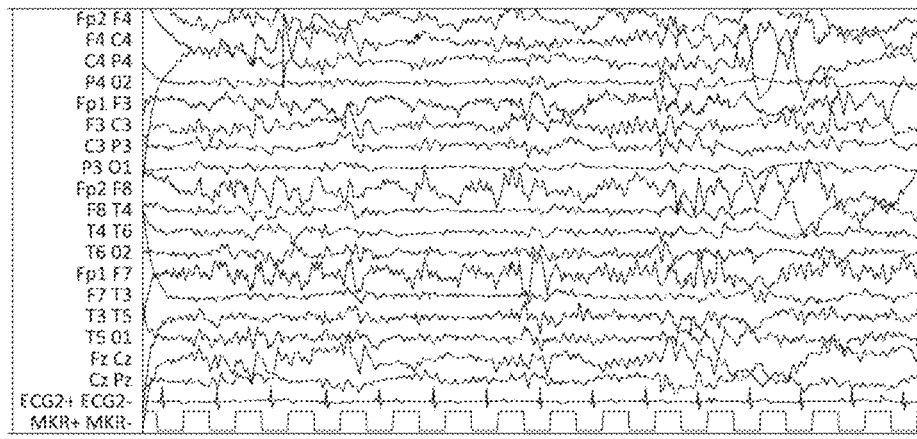

Administration of Midazolam was done by administrating of 1 ml of Midazolam to each nostril in a carrier volume of 1 ml. EEG recordings were measured before (FIGS. 82A and 82B) and 3 minutes following to the nasal administration of the drug with SipNose device. As can be seen from the recordings, brain signaling went back to normal with a short onset time following the administration of the drug.

Figure 83:
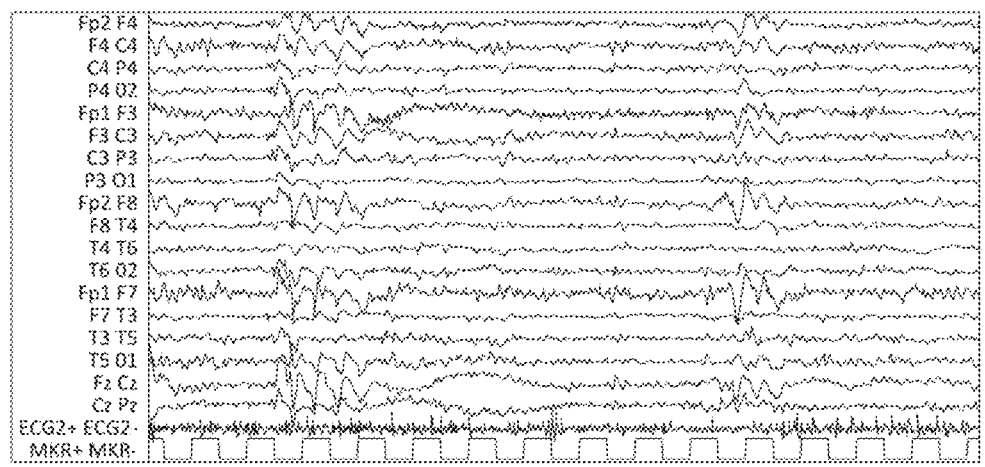
FIG. 83 illustrates the EEG recordings 3 minutes following to the nasal administration of the drug with SipNose device.

FIG. 83 illustrates the EEG recordings 3 minutes following to the nasal administration of the drug with SipNose device.

As can be seen, administration of the drug via the SipNose nasal delivery device results in reducing the repetitive un-normal brain activity during the seizures. Brain activity is back to normal 3 min following administration which reflects a fast onset and efficient delivery of the drug to its targets in the brain.

Figures 84A, 84B:
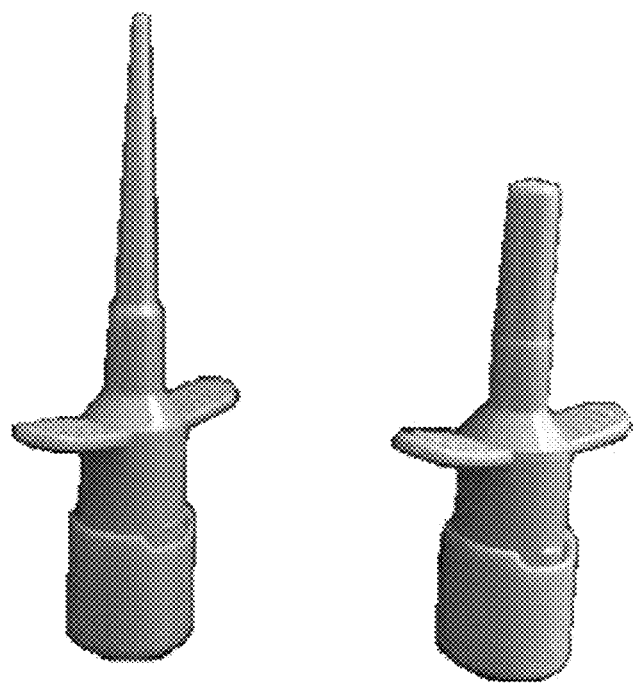
FIG. 84A-B show embodiments of SipNose devices.

Nasal Cavity Irritation and Toxicity for Intra-Nasal Administration of Midazolam Nasal cavity irritation and general toxicity were assessed for repeated intra-nasal applications of Midazolam to rabbits, using a SipNose intra-nasal delivery device. Six New Zealand White female rabbits were used, with the three experimental animals being given two 200 μL doses of Midazolam (5 mg/ml) per day, six hours apart. The three control animals were given four 200 μL doses of saline solution per day, at 3 hour intervals. All animals were dosed using a sipNose device adapted for administration to rabbits, as shown in FIG. 84. FIG. 84A shows a sipNose device configured for intranasal delivery to a rabbit's nose, while FIG. 84B shows a sipNose device configured for intranasal delivery to a human nose.

The daily dosing was repeated for 10 days, for 11 days' dosage in total. 24 hours after the last dosing, the animals were sacrificed. Table 23 shows a timeline for the study.

As shown in Table 23, the animals were observed for toxic/adverse symptoms: within the first 30 min post administration, with special attention during the first 4 hours and periodically during the day (3 times a day), following treatment. The animals were observed once daily until study termination. Shortly before sacrifice, blood was taken for testing.

TABLE 23

Test Schedule

| Study Day | Procedure | Body weight | Cinical signs | Food consumption | Ophthalmic examination |
|---|---|---|---|---|---|
| Acclimation | | ✓ | ✓ | | |
| 1 | Pre-dosing Intra-nasal dosing | Once a week | Daily (after dosing at least once during the first 30 min, periodically during the first 24 h, with special attention during the first 4 h | ✓ | ✓ |
| 2-10 | Intra-nasal dosing | | | | |
| 11 | Recovery (24-48 h) | | Once | ✓ | ✓ |
| 12 | Termination | ✓ | Before sacrifice | | |

Figure 85:
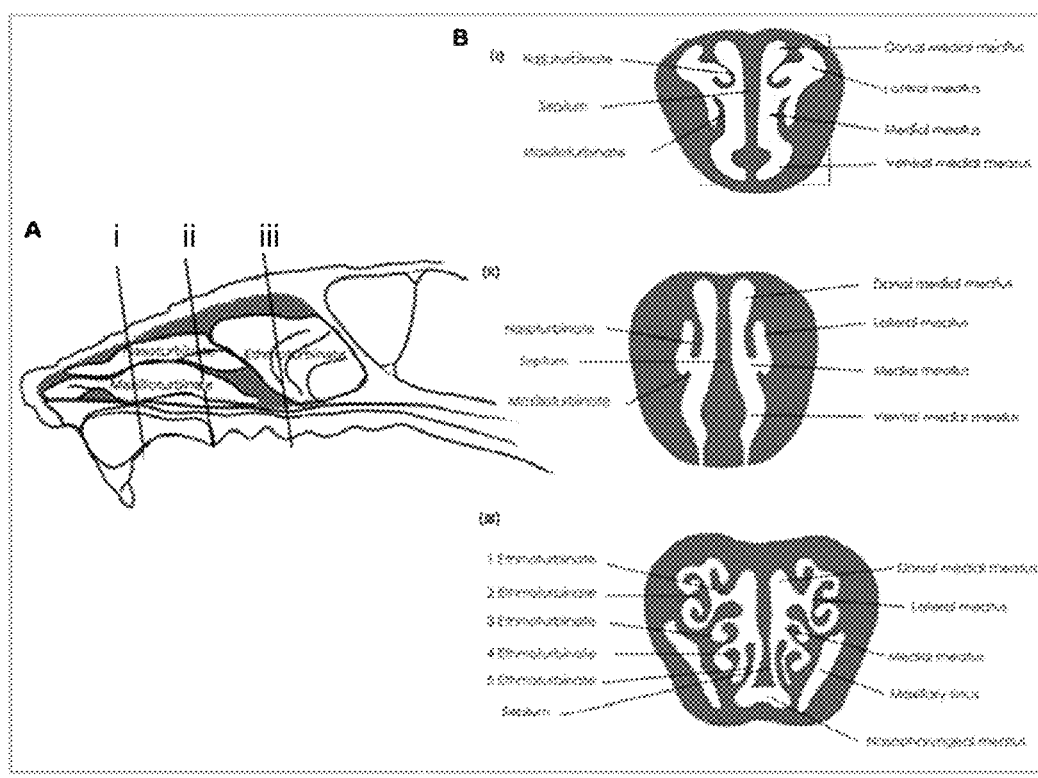
FIG. 85 shows locations for sectioning in a rat's brain.

After sacrifice, gross pathology was performed, examining major tissue and organ systems. Organs (nasal cavity (including olfactory epithelium), nasopharynx, paranasal sinus, trachea, lungs, larynx, brain (olfactory bulbs and hippocampus), heart, olfactory nerve, optic nerve and lacrimal glands) of all animals were harvested and examined. Three cross sections of the skull were taken: (1) in the nose from rostral, (2) behind the incisor teeth and (3) caudal, including the olfactory epithelium labyrinth, as shown in FIG. 85.

Brains were dissected in the olfactory regions and the hippocampus. Lungs were evaluated in both right and left lobes. Tissues were trimmed, embedded in paraffin, sectioned at no more than 5 microns thickness, and stained with Hematoxylin & Eosin (H&E).

In order to alleviate the discomfort an animal might endure during intra-nasal administration, prior to placement the sipNose device, Lidocaine was applied locally in the nasal area.

Figure 86A:
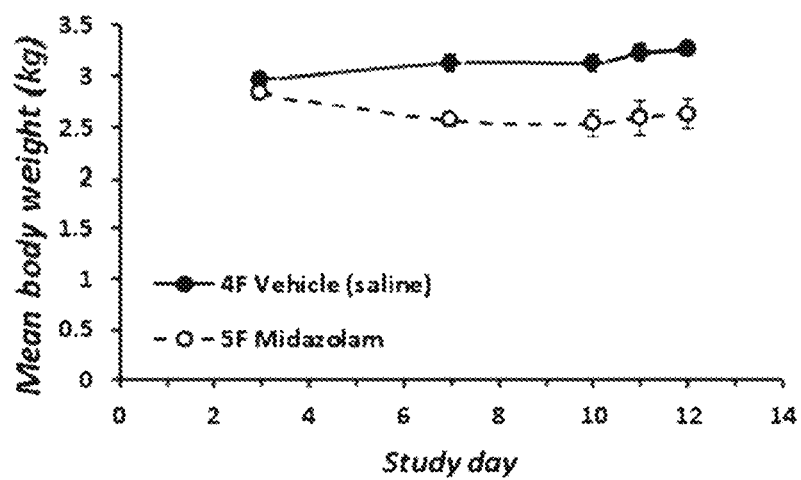
FIG. 86A-B shows the effect of midazolam on rats' body weight.
Figure 86B:
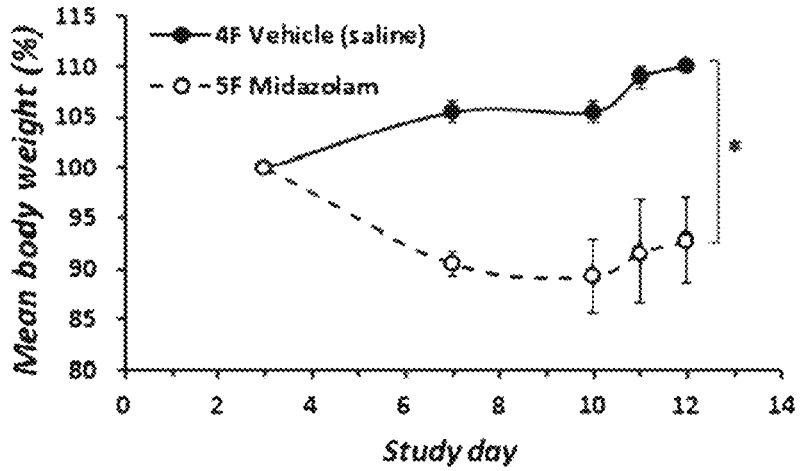
Figure 87A:
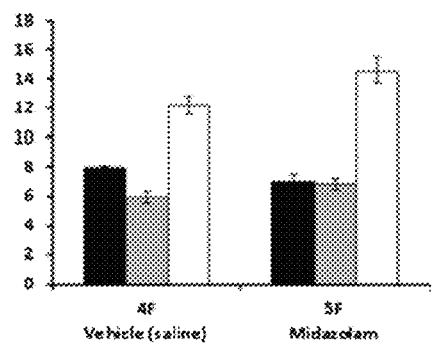
FIG. 87A-F shows the effect of midazolam on rats' blood hematology.
Figure 87B:
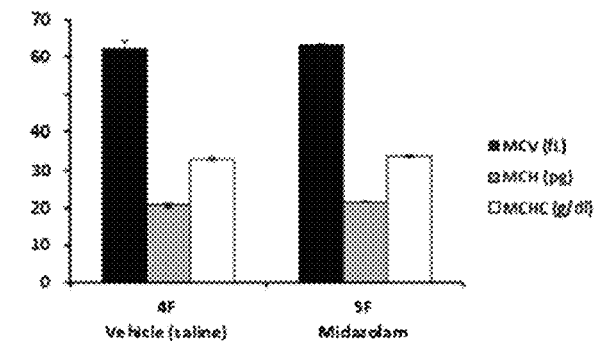
Figure 87C:
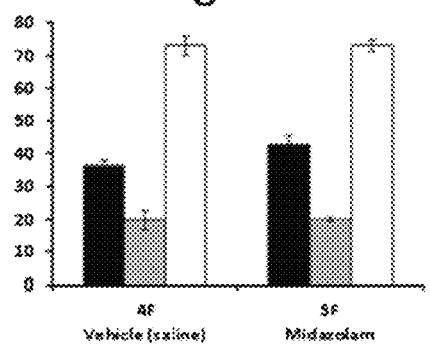
Figure 87D:
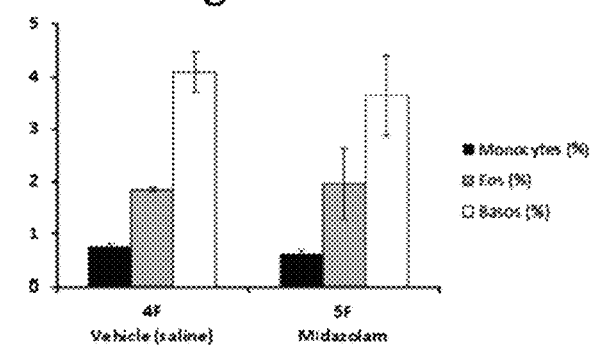
Figure 87E:
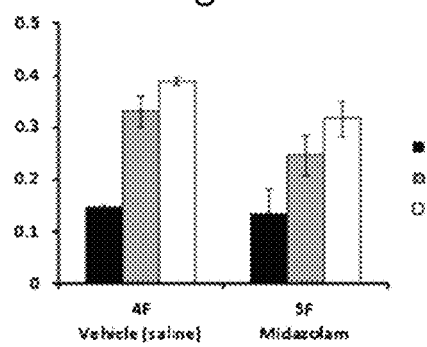
Figure 87F:
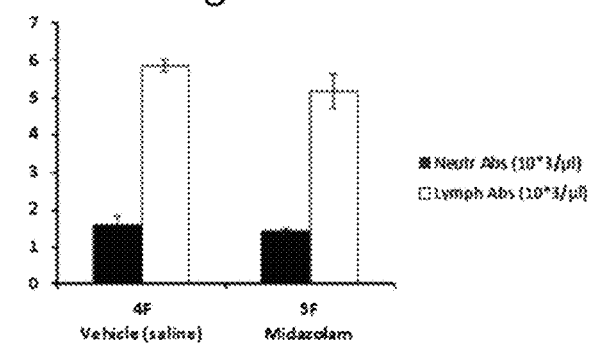
Figure 88A:
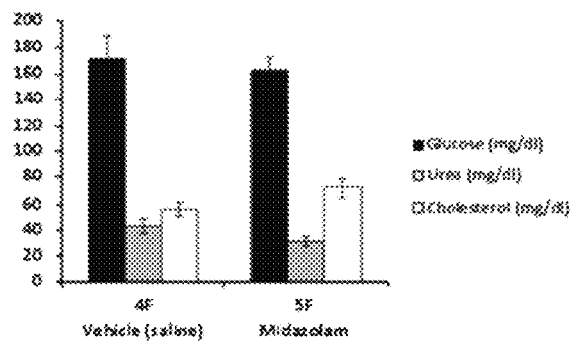
FIG. 88A-H shows the effect of midazolam on rats' blood chemistry.
Figure 88B:
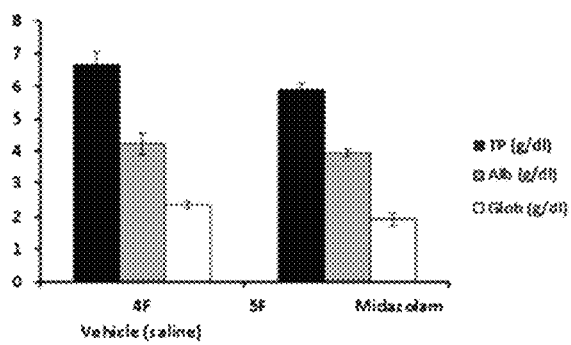
Figure 88C:
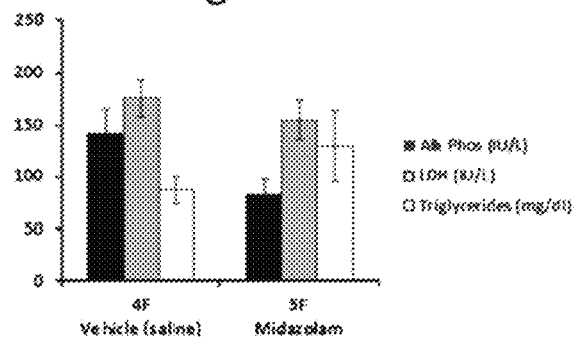
Figure 88D:
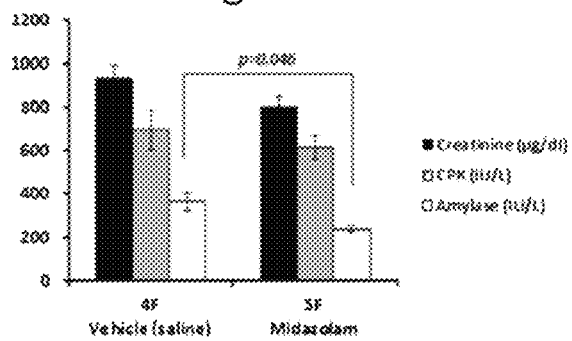
Figure 88E:
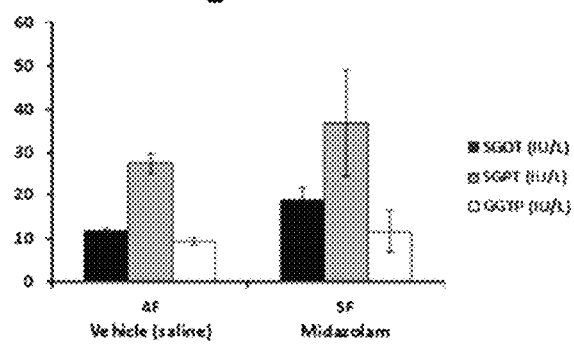
Figure 88F:
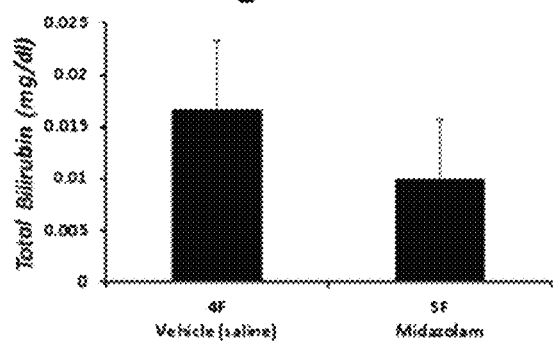
Figure 88G:
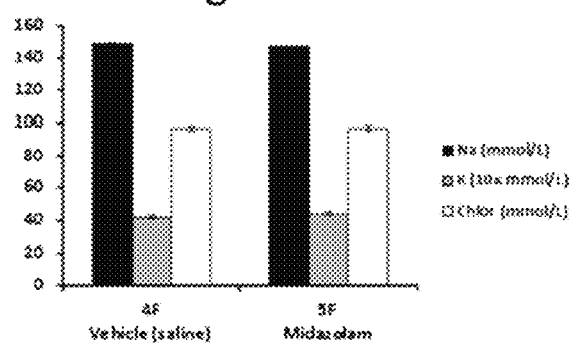
Figure 88H:
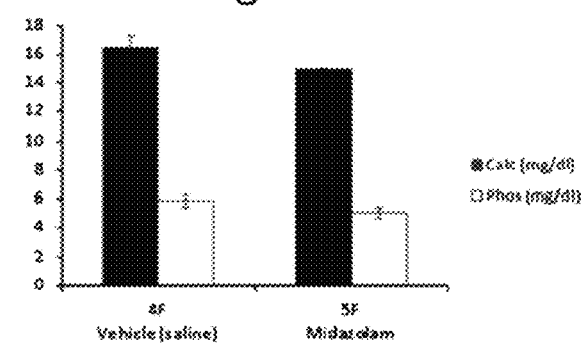

FIG. 86A-B shows the animals' body weight during the study, with the solid line being body weight for the control animals (saline-treated) and the dashed line being body weight for the Midazolam-treated animals. FIG. 86A shows mean body weight, while FIG. 86B shows percent change in body weight. The animals did not exhibit major changes in weight during the study.

FIG. 87A-F show the results of the blood hematology analysis. None of the parameters showed any difference between the control group and the study group, and all showed the normal expected blood histology.

FIG. 88A-H show the results of the blood chemistry analysis. Only the Amylase results (FIG. 89D, white bar at right) differed between the control group and the study group, with the amylzas being less in the Midazolam group (240±13.1 IU/L), than in the control group (365.3±+41.8 IU/L). However, all results, including the Amylase results, were within the normal range for the blood of rabbits.

Figure 89A:
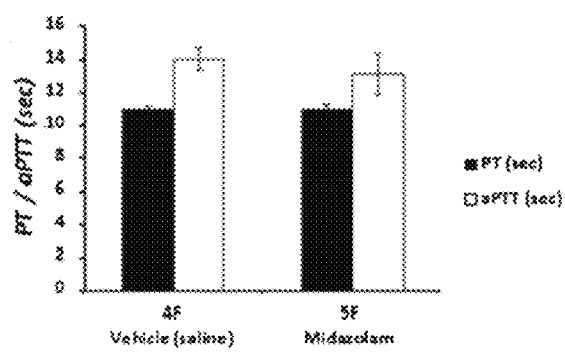
FIG. 89A-B shows the effect of midazolam on rats' blood coagulation.
Figure 89B:
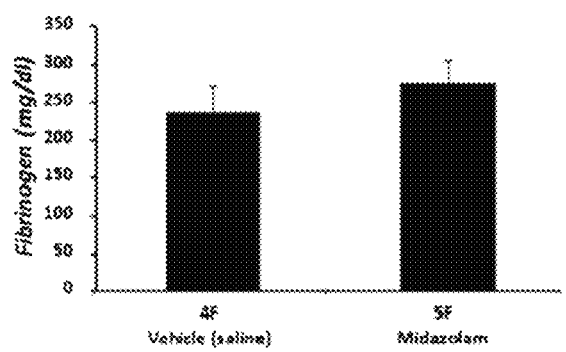

FIG. 89A-B show the results for the blood coagulation tests. No differences were detected between the blood coagulation parameters for the control and study groups and all parameters are in within the normal ranges.

No major histopathological abnormalities were found in any of the samples from either group. In all except two of the animals, no pathological changes were found. Some of the animals showed some minor abnormalities:

Animal #7913, from the control group (4F) showed hemorrhages in both rostral nose and within the nose sinus.

Animals #7775 and #7921, from the Midaxolam group (5F) showed few hemorrhages in the rostral nose. These changes were very mild and reversible.

In some animals, the lungs showed a diffuse hyperemia with a mild edema. These are agonal changes that are not a result of the different treatments.

In three animals, one from the saline group and two from the Midazolam group, a very mild bleeding was detected in the frontal nose space. This was a result of the administration to the animals' nasal cavity, as non-anesthetized animals sometime move during the administration and thus are superficially scratched by the tip of the sipNose device. All the pathological findings were mild and clinically not significant.

In all relevant safety parameters that were examined— clinical observations, histopathological evaluation, ophthalmic examination, haematology and blood analysis—no differences were found between the control and study groups and all showed parameters normal for rabbits.

This study supports the safety of repeated intranasal delivery of Midazolam with the SipNose device.

Effect of Intra-Nasal Delivery of Midazolam in Rats— Safety Study

Safety and possible adverse effects (toxicity) were assessed the safety and toxicity including adverse effects of Midazolam following intranasal administration via SipNose dedicated device to Sprague-Dawley (SD) rats.

A total of 78 SD rats (39 female and 39 male) were utilized. The animals were divided into four groups of 3 or 12 female rats and 3 or 12 male rats. At each of the times 6 hrs, 24 hrs, 7 days, and 14 days, three males and three females were sacrificed.

The test material was a commercially available injectable Midazolam.

The day of dosing was Day 1 and termination days were Day 1 (6 hrs), Day 2 (24 hrs), Day 8 and Day 15.

Groups were allocated according to Table 24 the study time line is shown in Table 25. Each test material or vehicle dose was administrated to three female and three male rats at each of the above times. The administration was performed intranasally (IN) via a SipNose device. The dose volume was 25-125 µl per naris (50-250 µl total per rat). Dosing was performed in an escalating fashion, each increase in dose depending on the outcome of the previous dose. The time between increasing doses was approximately half an hour.

TABLE 24

Study design and group allocation per test material

| Group | Animal ID | Total Animals (males + females) | No. of Animals each Time | Test Material | Dose (mg/kg)* | Time of Termination | Dose Volume (per naris) | Dose Volume (total) | Route of Administration |
|---|---|---|---|---|---|---|---|---|---|
| 1M + 1F | 1, 2, 3 + 19, 20, 21 | 3 + 3 | 3 + 3 | Naïve | 0 | — | NA | NA | NA |
| 2M + 2F | 4, 5, 6, 37, 38, 39, 40, 41, 42, 43, 44, 45 + 22, 23, 24, 82, 83, 84, 85, 86, 87, 88, 89, 90 | 12 + 12 | 3 + 3 | Saline | 0 | 6 h, 24 h, 7 days and 14 days | ~125 µl | ~250 µl+ | IN** |
| 5M + 5F | 7, 8, 9, 46, 47, 48, 49, 50, 51, 52, 53, 54 | 12 + 12 | 3 + 3 | Midazolam (Clinical Dose) | 0.0093 | 6 h, 24 h, 7 days and 14 days | ~25 µl | ~50 µl+ | IN** |
| 6M + 6F | 10, 11, 12, 55, 56, 57, 58, 59, 60, 61, 62, 63 | 12 + 12 | 3 + 3 | Midazolam (five times clinical dose) | 0.0405 | 6 h, 24 h, 7 days and 14 days | ~125 µl | ~250 µl+ | IN** |

*The clinical dose of Midazolam is 0.2 mg kg (i.e. 1.24 mg/kg in rats).
**Intra-nasal via SipNose dedicated device.
+Calculated for an approximately 200 g rat.

TABLE 25

Study Time Line

| Study Day | Procedure | Body Weight Checked | Clinical signs | Gross Pathology |
|---|---|---|---|---|
| Acclimation | | ✓ | | Gross pathology, |
| 1 | Pre-dosing | ✓ | ✓ | Blood collection and |
|  | Termination 6 hrs post-dosing | | ✓* | Plasma preparation, organ collection and |
| 2 | 24 hrs Termination | | | fixation for H&E staining |
| 3 | | | Daily | |
| 4 | | ✓ | | |
| 5 | | | | |
| 6 | | | | |
| 7 | | | | |
| 8 | Termination | ✓ | | |
| 9 | | | | |
| 10 | | ✓ | | |
| 11 | | | | |
| 12 | | | | |
| 13 | | | | |
| 14 | | | | |
| 15 | Termination | ✓ | | |

*Animals were examined after dosing at least once during the first 30 min, periodically during the first 24 h, with special attention during the first 4 h Dosing was performed in a staggered fashion, each increase in dose pending on the outcome of the previous dose. The lag time between the increasing doses was approximately half an hour. The maximum dose was five times the clinical dose in order to determine a maximum tolerated dose.

The test material and vehicle were administered IN once via a SipNose device at a dose volume of 50-250 µl to non-fasting animals. Prior to application of the test material, lidocaine was applied locally on the outer area of the nostril, in order to decrease the level of distress.

Animals were observed individually at least once during the first 30 minutes after dosing and daily thereafter, for a total of 1, 7, or 14 days (according to time of sacrifice for histological observation). All observations were systematically recorded and individual records were maintained for each animal.

Body weight was monitored one day after the animals' arrival, prior to administration of the test material and twice a week thereafter (days 4, 8, 10 and 15) for a total of 5 times.

Clinical signs were observed daily, at least once during the first 30 min after dosing, periodically during the first 24 h, with special attention during the first 4 h, and once daily thereafter.

Blood samples from groups 3 (M+F) and 4 (M+F) were collected into K3-EDTA tubes on ice, at 6 and 24 hr only. A blood volume of approximately 300 μl was taken each time.

Animals were sacrificed by carbon dioxide asphyxiation and gross pathology was performed examining the major tissue and organ systems. All animals were subjected to gross necropsy.

The following organs were collected from all animals at each termination point and fixed in 4% formaldehyde: Nasal cavity (including olfactory epithelium), nasopharynx, paranasal sinus, trachea, lungs, brain (cut in several areas including the olfactory bulb), heart and larynx.

The tissue samples from groups 1, 2, 3 and 4 (M+F) were embedded, sectioned and mounted on slides. The tissue sections were stained with Hematoxylin & Eosin (H&E).

Forty two rats were observed for histopathological findings: Three males and three females from groups 1, 2, and 3 and 24 rats (12M+12F) from group 4. Three cross sections of the skull and brain were taken: (1) in the nose from rostral area, (2) behind the incisor teeth and (3) in the caudal area including the olfactory epithelium labyrinth (FIG. 85). The brain was dissected in the olfactory regions, hippocampus, cerebellum and brain stem. The lungs were evaluated in both right and left lobes. The inflammatory status in the tissue samples were evaluated using the following parameters.

Grade of Inflammation:
  Grade 0: No inflammation
  Grade 1: Mild (few inflammatory cells, 10-20 per ×40 high-power field)
  Grade 2: moderate (more inflammatory cells, 20-50 per ×40 high-power field),
  Grade 3: severe (many inflammatory cells, more than 50 per ×40 high-power field).

No abnormal clinical signs were detected in any of the animals during the study.

The intranasal treatment, at both tested doses, led to no adverse effects or histopathological findings in any of the tissues that were examined—Nasal cavity, nasopharynx, paranasal sinus, trachea, lungs, brain, heart and larynx.

No death of neurons was detected in the brain in both the Saline and the Midazolam treated groups.

Figure 90A:
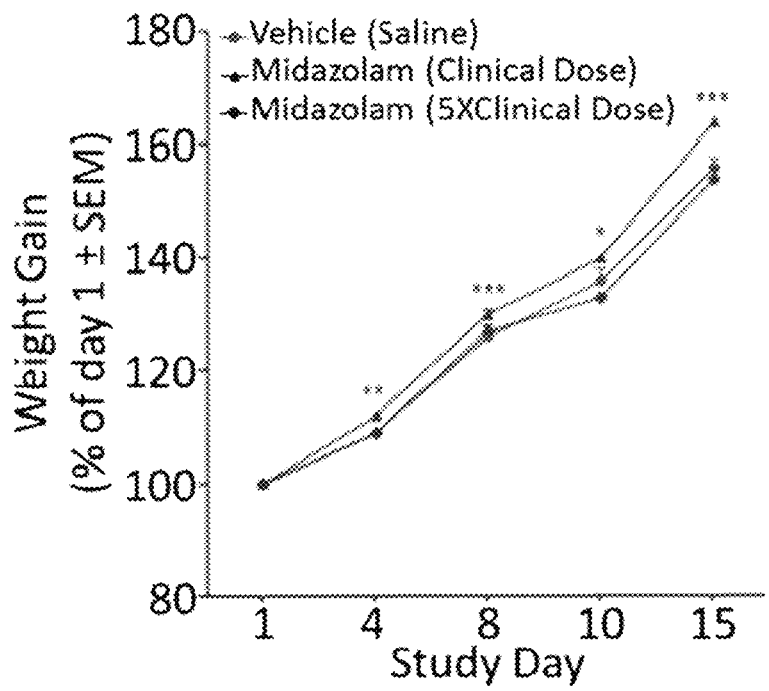
FIG. 90A-B shows the effect of midazolam on rats' body weight.
Figure 90B:
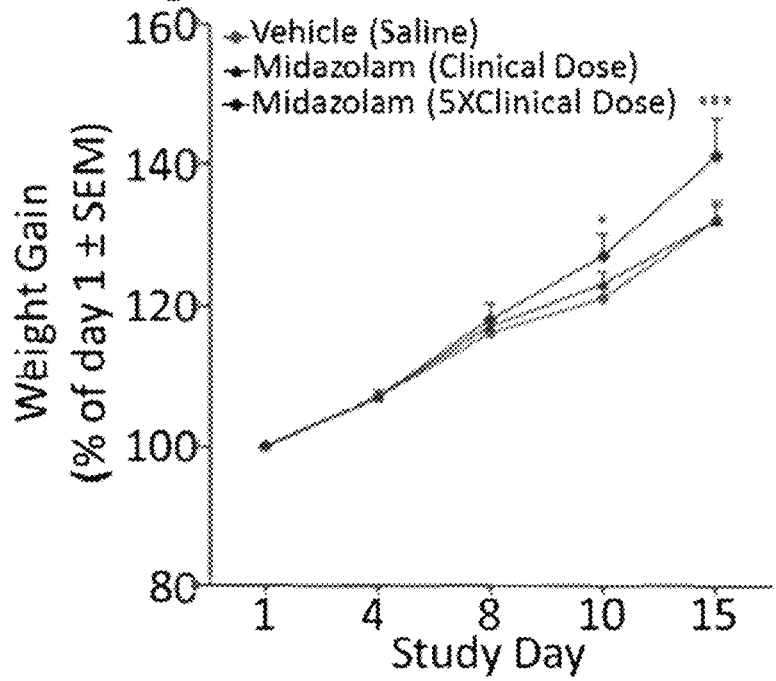
Figure 92:
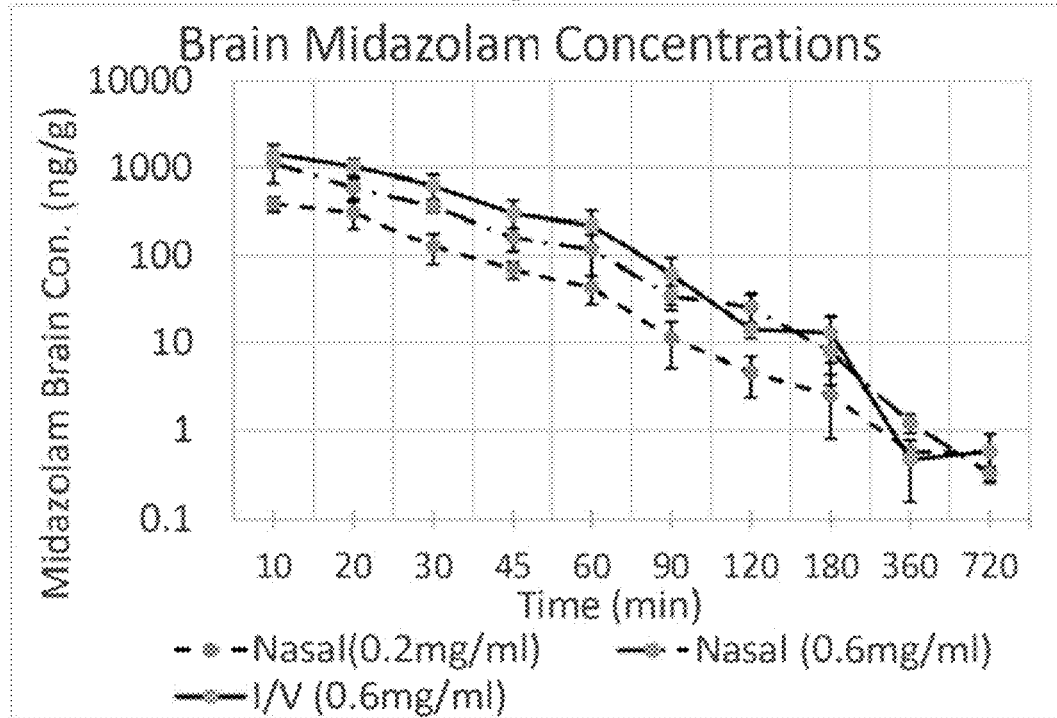
FIG. 92 shows Midazolam concentration in the brain of rats.

Body weight was increased as expected in all treatment groups as can be seen in FIG. 90A-B. In the male groups (FIG. 90A), at several times there was a statistically significant greater increase in weight with a clinical dose of Midazolam (circles, FIG. 92A) than for the control group (triangles, FIG. 90A) (*=p<0.05, =p<0.01, *=p<0.001). However, for the males, weight gain for animals receiving a dose five times the clinical dose (diamonds, FIG. 90A) was similar to that for the control group. In contrast, for the females, there was a statistically significant greater weight gain for animals receiving five times the clinical dose (diamonds, FIG. 90B) than the control group (triangles, FIG. 90B) on days 10 and 15, although weight gain for females receiving a clinical dose (circles, FIG. 90B) was similar to that for the controls. Although not consist between the groups, or within each sex this might indicate that Midazolam might improve the animals' appetite.

In all the observed animals, no pathological abnormalities were found in the brain, lungs, heart larynx and trachea of all the rats that were examined A very mild inflammation was observed in the most caudal cross section of the nose, involving the sinus and nose turbinate walls, in 12 out of the 42 animals examined (29%). In those lesions there was a lymphocytic infiltrate admixed with some hemorrhages and few erythrocytes. The lesions were observed both in the Saline treated groups 2M (#4, 6#) and 2F (#23, 24#), as well as in the Midazolam treated groups 3M (#8) and 4M (#12), 4F (#28, #29, #55, #59, #100, #102). Therefore these very minor changes were most probably not drug-related but rather a result of the insertion of the drug delivery nose piece to the animal's nose.

In both the Saline and the Midazolam groups no death of neurons was detected.

Figure 91:
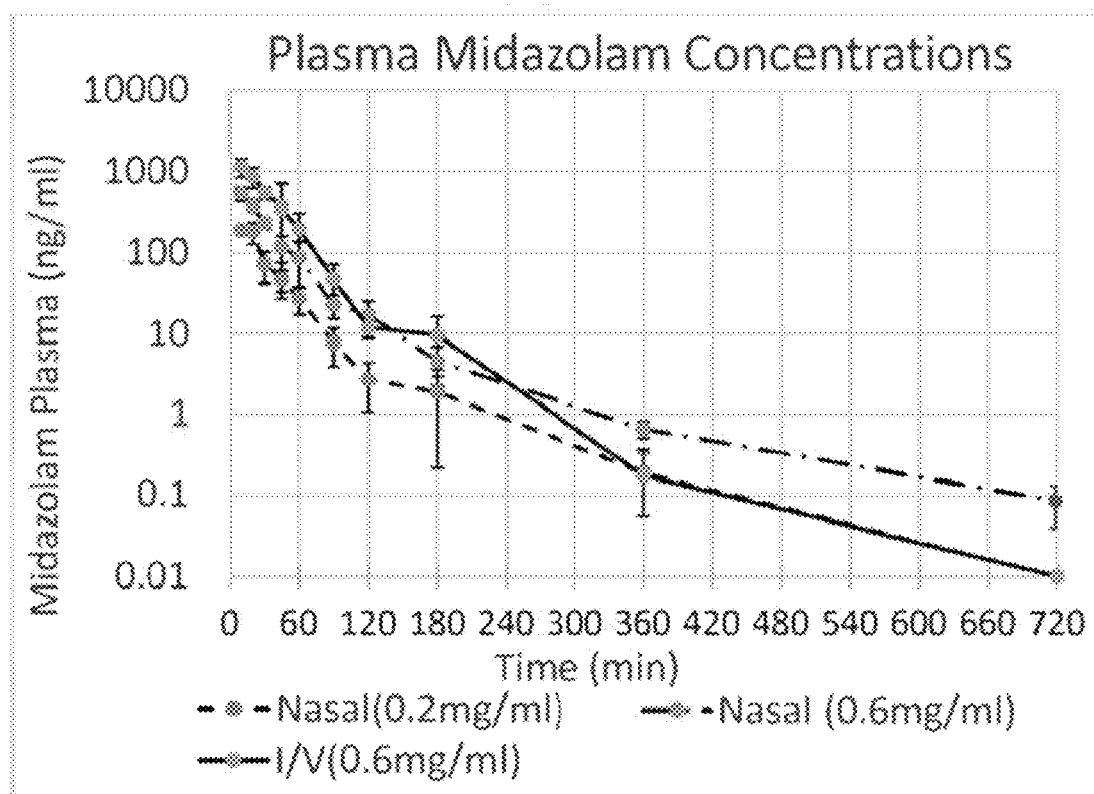
FIG. 91 shows Midazolam concentration in the blood of rats.

Midazolam Pharmacokinetic Study in Rat Model:

Concentration of Midazolam in the plasma and brain of rats were compared for intranasal administration via the SipNose delivery device and via IV administration. A standard drug formulation (Injectable Midazolam 5 mg/ml, Pfizer/Hospira brand) was used, with no reformulation or adaptation for nasal delivery. Two drug concentrations were used for the intranasal administration, 0.2 mg/kg (dashed line in FIGS. 91 and 92) and 0.6 mg/kg (dot-dash line in FIGS. 91 and 92), compared to the standard of care I/V administration of 0.6 mg/kg (solid line in FIGS. 91 and 92). Concentration was measured 10 times in the 12 hours of the study. For each measurement time, midazolam concentration was measured in the plasma and brain of five animals.

The results demonstrate high reproducibility in the absorption of Midazolam into the blood and brain after administration with the SipNose nasal delivery device. For both, absorption is comparable to that seen for I/V administration. Since a standard drug and formulation was used, with no reformulation or adaptation for nasal delivery, the high reproducibility can be attributed to the delivery method, since the SipNose technology allows very reproducible delivery to the nasal cavity, effective distribution at the target area in the nasal cavity, which has a large surface area to allow effective absorption. The results also show that the SipNose delivery method produces a desirable dose-response pattern, one that is a key element in therapeutic treatments. The very similar dose-response patterns for the two intranasal applications show the delivery method's flexibility in delivering differing volumes of drug without changing performance characteristics and effectiveness—identical devices providing identical deliveries were used for both doses, with the 0.6 mg/kg dose had three times the volume of the 0.2 mg/kg dose. There was no need to make any changes in the delivery device other than loading a different drug volume in going from one dose to another three times as large.

For the 0.6 mg/kg dose, intranasal delivery by the SipNose device showed a pharmacokinetic pattern very similar to that of standard of care (I/V) administration, with no reformulation of the drug to make it more suitable to nasal delivery. The 0.2 mg/kg dose showed a similar change in concentration with time, although the absolute concentration, not surprisingly, was smaller.

Those results indicate that the SipNose device provides an effective delivery technology.

Effectiveness, Safety and User Compliance for Midazolam as a Pre-Anesthetic Drug in Humans Midazolam was administered as a pre-anesthetic drug as a part of premeditation to subjects that needed to be anesthetized prior to the beginning a surgical procedure. Administration of the pre-anesthetic drug was done intranasally instead of the routine PO/IM (oral/intramuscular) route used by the anesthesiologist from the hospital.

Figure 93A:
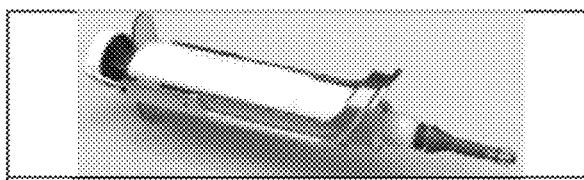
FIG. 93A-B illustrates a SipNose device and a commercial nasal pump.
Figure 93B:
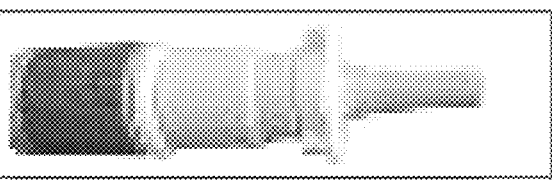
Figure 94A:
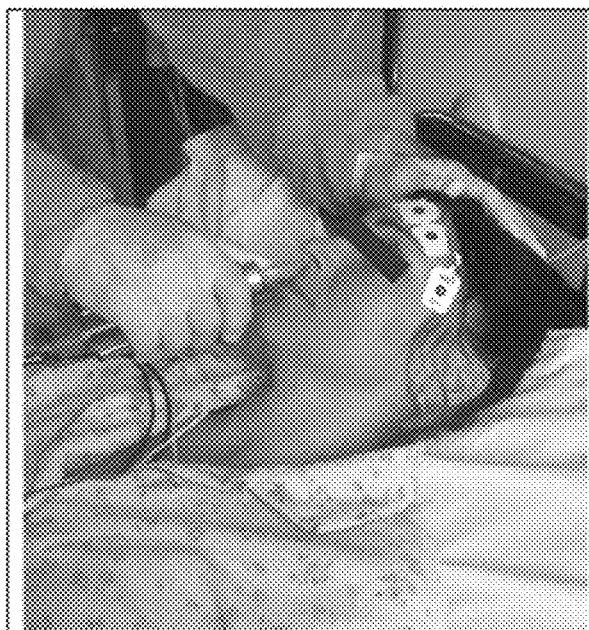
FIG. 94A-B illustrates anesthetizing a patient using a SipNose device and a commercial nasal pump.
Figure 94B:

The intranasal administration was given by one of the following medical devices: a SipNose nasal device (FIG. 93A) or a commercial nasal pump (FIG. 93B). A single dose of 1×600 microliter (μl) was given with the SipNose device, while 6×100 μl doses were given with a commercial nasal pump. An exemplary administration for the SipNose device is shown in FIG. 94A, while an exemplary administration for the commercial nasal pump is shown in FIG. 94B.

Eight low-risk patients (American Society of Anesthesiology physical status classification I or II) patients were included in each group. Clinical status of the patients, standard continuous monitoring of vital signs, and continuous bispectral index (BIS) monitoring was ongoing 5 minutes before intranasal administration and 30 minutes after.

The objective data consisted in minimum BIS value obtained after administration and time until minimum BIS. The subjective data consisted in physician feedback, swallowing of the drug appreciated by patient, sleeping score appreciated by physician.

Figure 95:
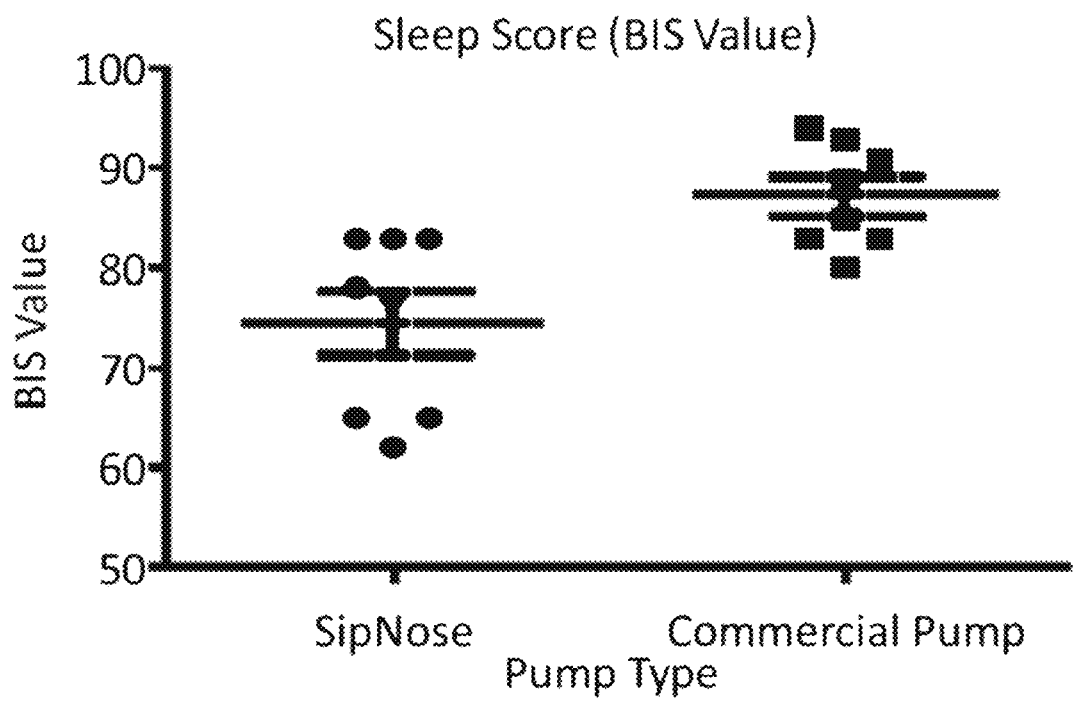
FIG. 95 illustrates sleeping score for midazolam administered using a SipNose device and a commercial nasal pump.

As shown in FIG. 95, the sedation obtained when midazolam was administered intranasally with SipNose was significantly better (p=0,0019) than with a commercial pump as shown by a BIS value of 74.50±3.196 for the SipNose group vs a BIS value of 87.25±1.840 for the commercial pump group.

Figure 96:
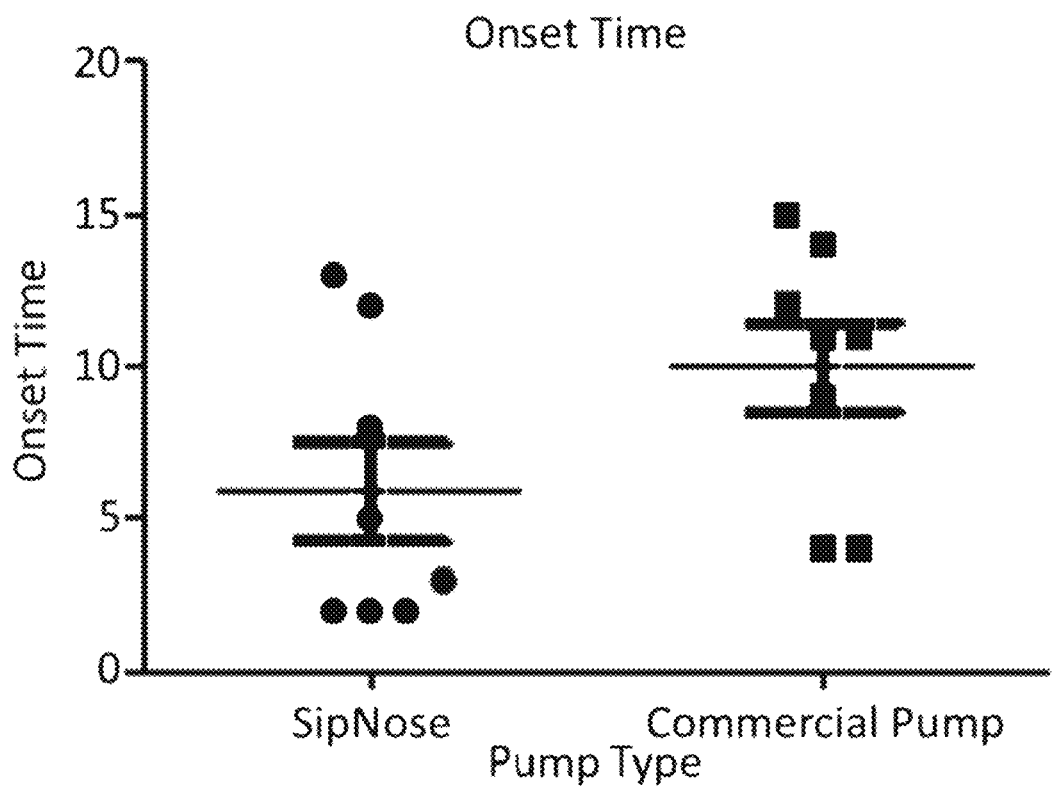
FIG. 96 illustrates onset time for midazolam administered using a SipNose device and a commercial nasal pump.

As shown in FIG. 96, the time until the minimum BIS value was reached was also superior (p=0.039) for the SipNose group—5.875±1.619 s vs 10.00±1.464 s for the commercial pump group.

Sedation Score was evaluated by physicians as a behavior tool to determine effectiveness of the dose that was given in each of the nasal administrations. Scoring was done according to the following criteria: 1=not Sleepy (not effective); 2=Sleepy/Calm (intermediate effect); 3=Sleeping (drug was effective).

Figure 97:
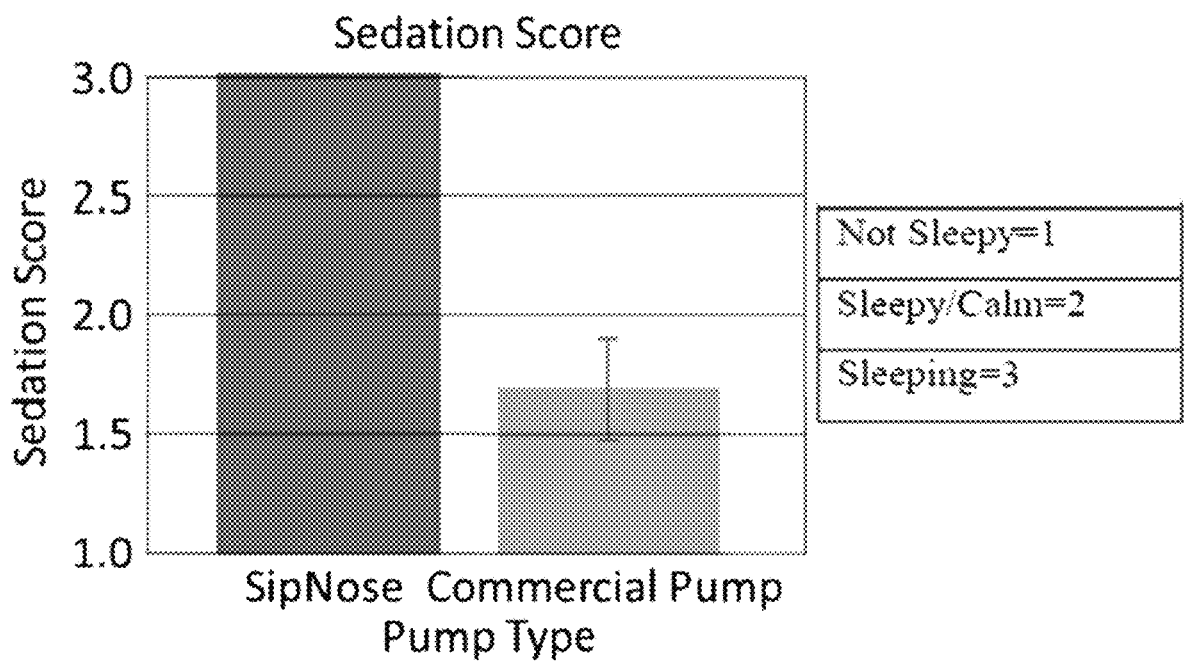
FIG. 97 illustrates sedation score for midazolam administered using a SipNose device and a commercial nasal pump.

As shown in FIG. 97 and Table 26, the SipNose device provided a significantly better sedation score—all of the SipNose group had a score of 3; the SipNose device was highly effective in delivering the Midazolam. On the other hand, the commercial pump score was below 2; 3 of the 8 patients in this group were not sleepy and only one was asleep.

TABLE 26

Comparison of Effectiveness of Sedation

| Effect | SipNose | Commercial Nasal Pump |
|---|---|---|
| Not Effective | — | 37.5% |
| Intermediate Effect | — | 50% |
| Highly Effective | 100% | 12.5% |

Patients were asked to score if they felt the drug in their throat and/or felt a bitter taste in the throat after the administration of the drug. Swallowing and bitter taste are major user compliance issues in nasal delivery that also reflect the administration potential efficacy, as, if a meaningful amount goes down the throat, it means that most of the drug did not reach the target area in the nasal cavity thus absorption of the drug will be poor.

The bitterness and swallowing were graded according to the following scale: 1=No swallowing/No bitter taste; 5=A meaningful amount was swallowed/Strong bitter taste.

The repeated administrations with the nasal pump were given with 30 s intervals between them to allow the drug to be absorbed in the nasal cavity before another dose was given.

With the SipNose device, one short administration of 0.6 ml was given.

Figure 98:
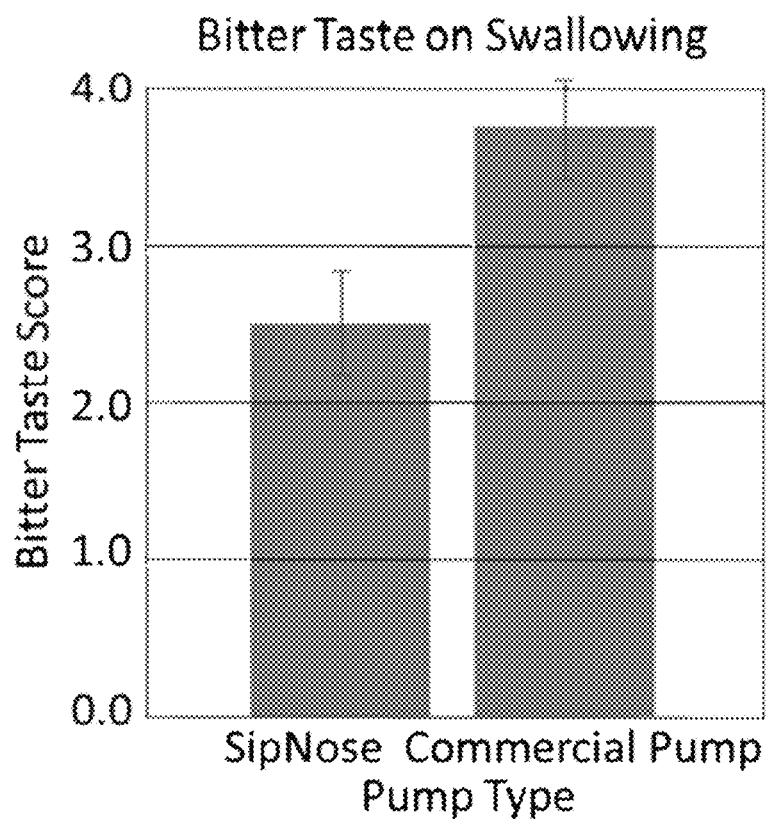
FIG. 98 illustrates bitter taste experienced for midazolam administered using a SipNose device and a commercial nasal pump.

As shown in FIG. 98, the dose of 0.6 ml that was given with the SipNose device was scored lower (about 2.5) than the 0.1 ml standard volume administration that was given with the nasal pump (about 4.7).

Figure 99:
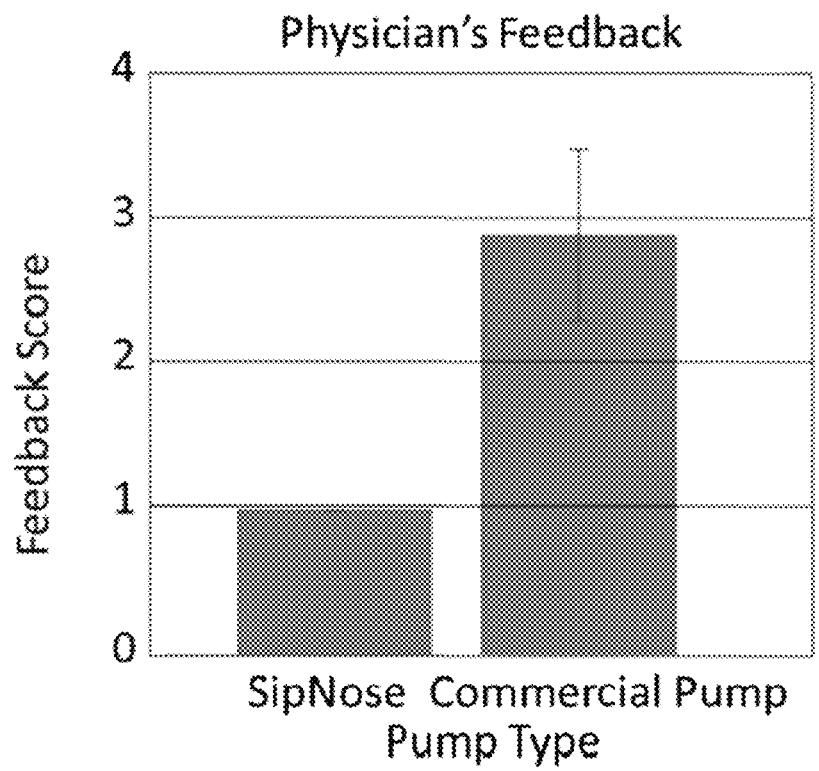
FIG. 99 illustrates physician satisfaction on using a SipNose device and a commercial nasal pump to administer midazolam.

The anesthesiologist in charge of the patients was asked to rate the overall experience with intranasal administration of midazolam. (1=very good; 5=Not satisfactory). As can be seen in FIG. 99 and Table 27, the SipNose device provided a much better overall experience for the anesthesiologist (a score of 1; 100% satisfactory for the SipNose device vs. a score of about 2.9; 75% less than completely satisfactory) for the commercial nasal pump).

TABLE 27

Physician Feedback

| Effect | SipNose | Commercial Nasal Pump |
|---|---|---|
| Not Satisfactory | — | 25% |
| Intermediate Satisfactory | — | 50% |
| Very good feedback | 100% | 25% |

The SipNose delivery is superior to the commercial nasal pump, in terms of quality of sedation, onset time, swallowing of the drug and physician satisfaction when the same doses of Midazolam were given to patients. Administration with the SipNose device showed higher consistency and more effective results than the commercial nasal pump. Onset time was lower with the SipNose device than the commercial nasal pump. Administration of a single dose of 1×600 μl is much more user friendly and the time of administration is reduced, thus increasing patient comfort and anesthesiologist compliance. None of the SipNose group patients complained about post administration discomfort. No adverse events or safety issues were reported in both administration procedures.

It should be noted that one of the SipNose patients was scared during administration by the force of the jet produced by the device.

Effect of Intra-Nasal Delivery of Topiramate in Rats—Safety Study

A study was performed to evaluate the safety and toxicity, including adverse effects, of Topiramate following intranasal administration via a SipNose device to Sprague-Dawley (SD) rats. A dose 8 times the therapeutic dose was administered in order to determine the maximal tolerated dose. Doses used in this study were chosen to assess the safety of the approved drug given via the nose with an embodiment of a sipNose device.

A total of 13 male Sprague-Dawley rats were utilized. The animals were divided into four treated groups of three rats and one group with one naïve control rat. The treatments are given in Table 28.

TABLE 28

Study design and group allocation

| Test No. | # of animals | Test Material | Dose Level (mg/animal)* | Termination time | # of doses per day | Dose per naris | Total Dose * | Route of Administration |
|---|---|---|---|---|---|---|---|---|
| 1M | 1 (14) | Naïve | 0 | — | | NA | NA | NA |
| 2M | 3 (1, 2, 13) | Oral Topiramate | 3 mg per naris; given at both nares, total of 6 mg | 24 h after second dosing | Twice a day; five hour interval | | 6 mg total | Oral |
| 3M | 3 (4, 5, 6) | Topiramate (Liquid formulation) | | | | 300 µl | 600 µl | IN** |
| 4M | 3 (7, 8, 9) | Topiramate (Dry powder Formulation 1) | | | | 3 mg | 6 mg | IN** |
| 5M | 3 (10, 11, 12) | Topiramate (Dry powder formulation 2) | | | | 3 mg | 6 mg | IN** |

*The clinical dose of Topiramate is up to 400 mg per day for Epilepsy. In Qsymia the clinical dose is up to 92 mg per day. The chosen dose was ~20 mg per naris per day (total of 40 mg twice a day = 80 mg daily dosage), for estimated 100 kg patients (that try losing weight). The 0.2 mg/kg (per navis) clinical dose is approximately 1.24 mg/kg in rats per naris (using the 6.2 ratio rats/humans). For ~250 gr rat the dose should thus be 0.31 mg per naris (0.62 mg total). Around ten times the clinical dose were chosen for the toxicity and irritation test.
**Intra-Nasal via a SipNose device.

The following tests were performed:
After sacrifice, gross pathology was performed, examining the nasal cavity (both sides, including the olfactory epithelium), the nasopharynx, paranasal sinus, trachea, lungs, brain (in several areas including the olfactory bulb), heart and larynx.
A histopathological evaluation of all groups of animals was made.
Blood was collected and plasma prepared 10, 30 and 90 min after the first and second administration and at termination.

As shown in Table 29, the test material was administered twice (with a five hour interval between administrations) to non-fasting rats, either orally (to Group 2M only) or intra-nasally (IN) via a SipNose device. IN application was carried out using solution at a dose volume of 300 µl per naris or as a powder (in two formulations). In all cases the total dose per rat was 6 mg of Topiramate. Prior to application of the test material, lidocaine was applied locally to the outer area of the nostril in order to decrease the level of distress.

TABLE 29

Test Schedule

| Study Day | Procedure | Body Weight | Blood collected | Clinical signs |
|---|---|---|---|---|
| Acclimation | | ✓ | | |
| 1 | Pre-dosing | ✓ | 10, 30 and 90 min post first and second administration and terminal bleeding | ✓ |
| | 6 hrs post-dosing | | | ✓* |
| | Termination | | | |
| 2 | 24 hrs Termination | ✓ | | |

*Animals were examined after dosing at least once during the first 30 minutes after dosing, with special attention during the first 4 h and prior to termination.

Animals were observed individually at least once during the first 30 minutes after dosing, with special attention during the first four hours and prior to termination. Observations included changes in skin and fur, eyes and mucous membranes, and also respiratory, circulatory, autonomic and central nervous systems, and somatomotor activity and behavior pattern.

Body weight was monitored one day after the animals' arrival, prior to administration of the test material and before termination.

Blood samples were collected into Li-Heparin tubes on ice, at 10, 30 and 90 min post first and second dosing. A blood volume of approximately 300 µl was obtained at each time point.

Animals were sacrificed via carbon dioxide asphyxiation and gross pathology was performed, examining the major tissue and organ systems.

The following organs were collected from all animals: Nasal cavity (including olfactory epithelium), nasopharynx, paranasal sinus, trachea, lungs, brain, heart and larynx.

Results

Figure 100:
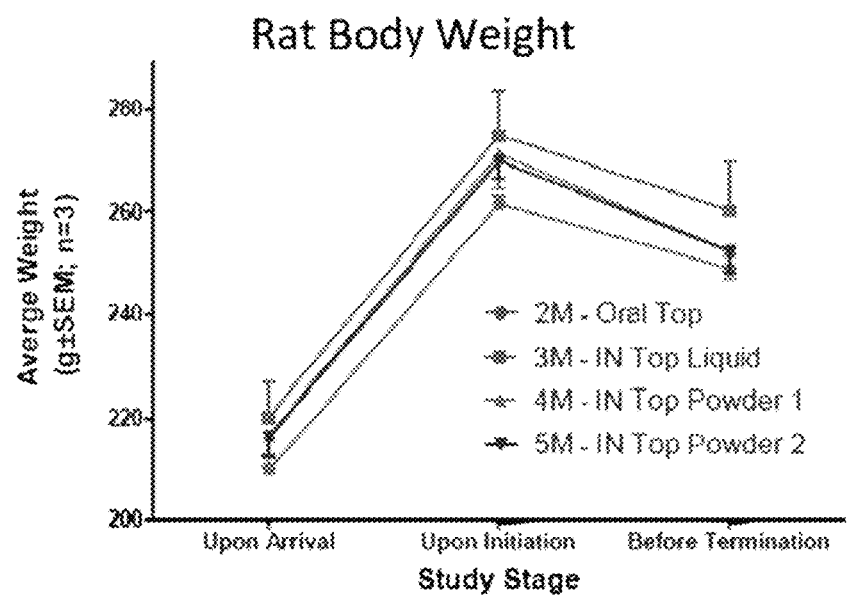
FIG. 100 illustrates the effect of Topiramate on rats' body weight during acclimation.
Figure 101:
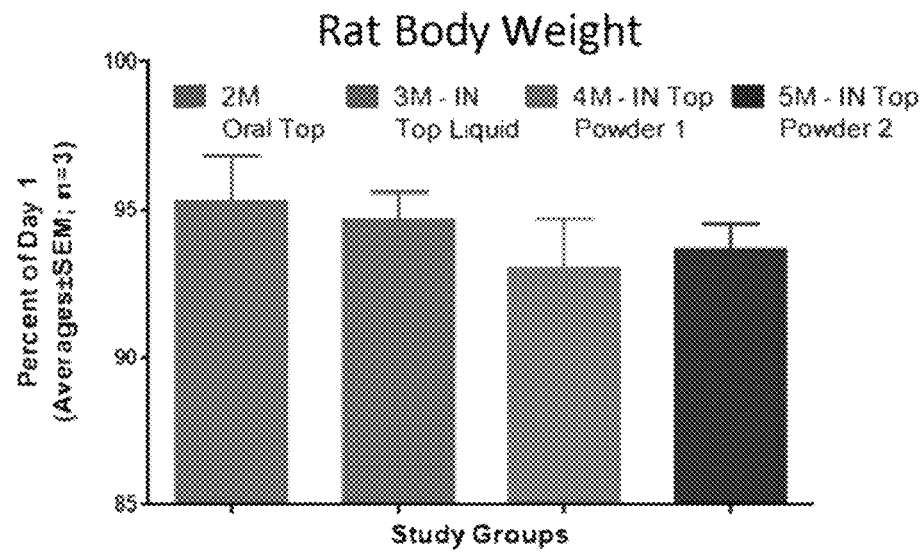
FIG. 101 illustrates the effect of Topiramate on rats' body weight from study initiation to study termination.

As can be seen in FIG. 100, all animals started the study at approximately the same weight and gained weight during acclimation. From study initiation to study termination, rats lost some weight, due to being studied for the whole day, but the change was relatively minor, as shown in FIG. 101.

Figure 102:
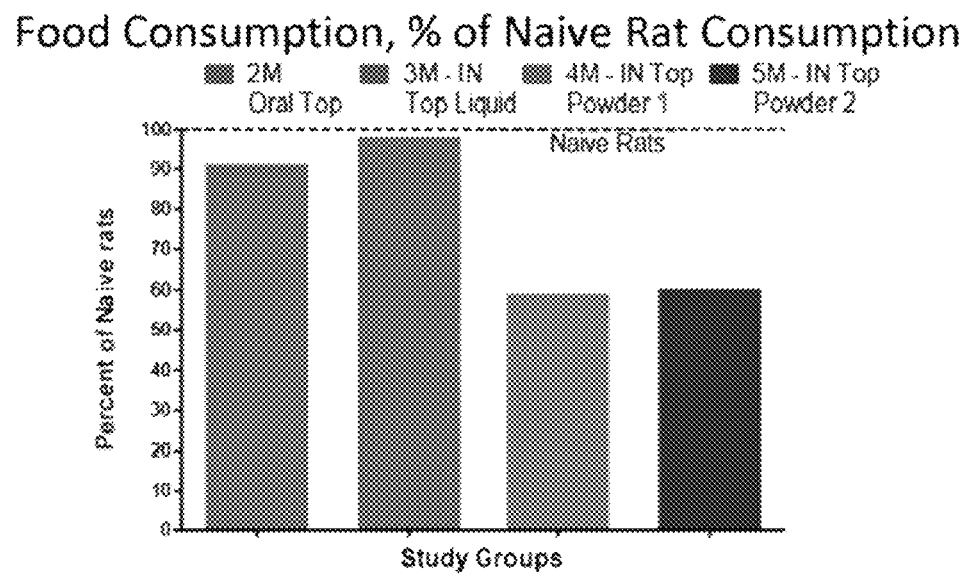
FIG. 102 illustrates the effect of Topiramate on rats' food consumption.

Food consumption (FC), as measured on Day 2 of the study, was reduced to around 60% of naïve rats FC in rats treated by Topiramate powder, as shown in FIG. 102, and to 91% and 98% respectively in rats treated orally or IN with Topiramate liquid.

Topiramate was administered to the relevant study groups twice, with a five hour interval between administrations. The plasma levels that were found 10, 30 and 90 minutes following the first and second administrations are depicted in FIG. 103A and FIG. 103B respectively.

Figure 103A:
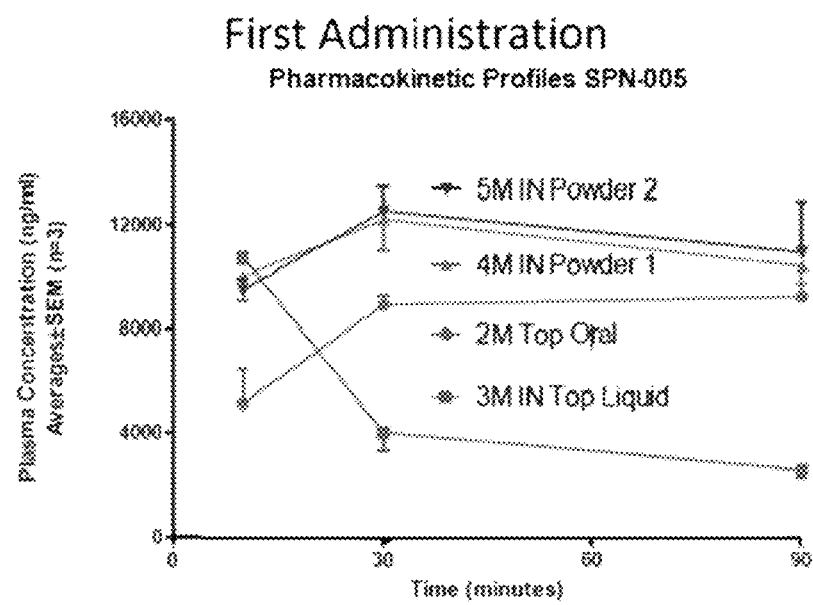
FIGS. 103A-B illustrate plasma concentrations of Topiramate in rats after 10, 30, and 90 minutes following the first and second administrations.
Figure 103B:
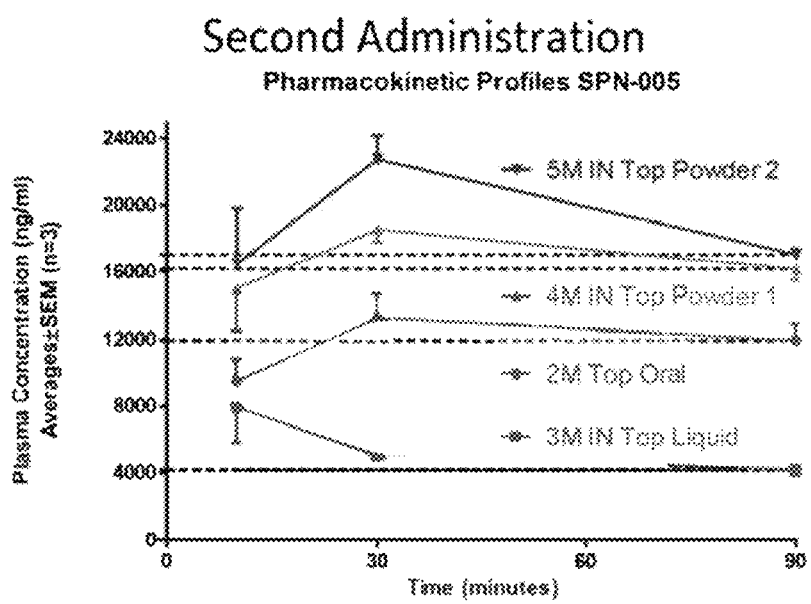

As can be seen in FIG. 103A, 10 minutes after administration all three IN applications showed similar levels, about twice the concentration found 10 minutes after oral administration, which reached close to the IN levels only at 90 minutes. The two powder formulations behaved similarly, however Topiramate concentrations after IN application in a liquid form declined rapidly with an estimated half-life of 45 minutes.

Ten minutes following the second administration, almost all groups exhibited higher values compared to those found 10 minutes after the first administration (2M: 84%; 4M: 50%; 5M 73%) and only group 3M (Topiramate in liquid form IN) exhibited 26% lower values. Ninety minutes after the second administration all groups reached exactly the same level that was achieved 90 minutes after the first administration with no significant accumulation.

Due the fact that only three time-points were assessed after the first Topiramate administration, strict pharmacokinetic evaluation of PK parameters could not be performed. The estimated values that could be obtained are summarized in Table 30.

TABLE 30

Estimated pharmacokinetic parameters

| Study Group | AUC (µg-min/ml) | Half-life (min) |
|---|---|---|
| 2M oral | 710 | NA* |
| 3M (liquid) | 611 | 45 |
| 4M (powder 1) | 4,938 | 259 |
| 5M (powder 2) | 5,894 | 304 |

Figure 104:
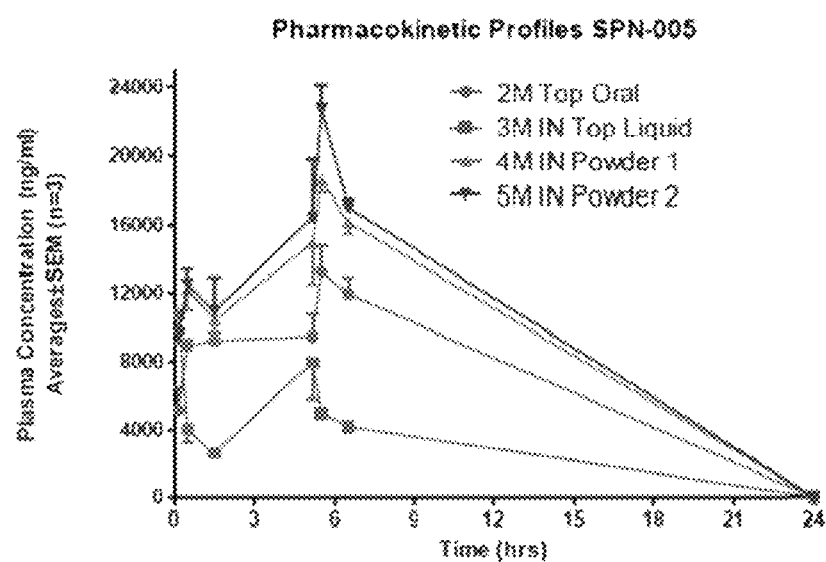
FIG. 104 illustrates plasma concentrations of Topiramate in rats after 18 hours following the second administration.

*No estimate was obtained, since at 90 min the concentration was still increasing As can be seen in FIG. 104, 18 hours after the second administration, plasma levels had dropped to pre-administration levels for all routes of administration.

The investigated organs: nasal cavity (including olfactory epithelium), nasopharynx, paranasal sinus, trachea, lungs, brain, heart and larynx of 13 animals, were harvested. Three cross sections of the skull were taken: (1) in the nose from rostral, (2) behind the incisor teeth and (3) caudal, including the olfactory epithelium labyrinth, as shown in FIG. 85.

Brains were dissected in the olfactory regions and the hippocampus, cerebellum and brain stem. Lungs were evaluated in both right and left lobes. All tissues were trimmed into block cassettes and sent to L.E.M for slide preparation and staining.

Most of the samples exhibited no pathological findings and only minor observations, mostly unrelated to the treatment, were revealed. In seven animals out of the 13 inspected, a very mild hemorrhage in the rostral node and/or the nose sinuses was found. This can be associated most probably to the blood sampling collected from the retro-orbital sinus during the study, since three of the seven animals were treated orally.

In one animal (#7) a focal tear in the respiratory epithelium in the nose cavity was found, which might be a result of a sudden movement of the animal during the nasal administration (as the animals were not anesthetized during the procedure and sometimes moved their heads during the procedure).

No pathological changes were detected in any of the other sites that were examined.

Ten minutes after the first Topiramate administration, all three IN applications showed similar plasma concentrations, about twice the concentration found 10 minutes after oral administration, which reached close to the IN levels only at 90 minutes. The two powder formulations behaved similarly. However, Topiramate concentrations after 1N application of a liquid form declined rapidly with an estimated half-life of 45 minutes. This indicates a unique fast elimination following this application route, since Topiramate is known to have a relatively long half-life in rats (e.g. showing stable ED50 for 8 hours after oral administration). The Areas under the pharmacokinetic curves (in units of µg-min/ml) exhibited similar relationships between the groups: 2M≈3M<<4M≈5M.

Except for the liquid application. Topiramate seemed to maintain reasonable concentrations during the five hour interval between doses. Indirect evidence can be seen in the fact that ten minutes following the second administration, all these groups exhibited considerably higher values compared to those found 10 minutes after the first administration (2M: 84%; 4M: 50%; 5M: 73%) and only group 3M (Topiramate in liquid form IN) exhibited a 26% lower value. Ninety minutes after the second administration, all groups reached exactly the same level as was achieved 90 minutes after the first administration, indicating that, under the conditions of this study, two administrations with a five hour interval between them led to no significant accumulation of Topiramate.

No drug-related pathological changes were detected during histology evaluation in any animal in any of the investigated tissues.

Effect of Intra-Nasal Delivery of Topiramate in Rats—Efficacy and Safety Study

The study investigated repeated intra-nasal delivery of Topiramate, using SipNose's novel device, in order to evaluate its effect on food consumption, body weight, and behavior and to measure the concentrations of the drug in the brain and plasma, in comparison to oral administration. Also, the safety of repeated dosing was examined.

The probability of appetite loss is a potential indicator for Topiramate. Food consumption was monitored during the experiment, and as the expectation was that food consumption will be reduced, care was taken in order to make sure it is not too dramatic or harmful to the animals.

A total of 38 rats were utilized. Thirty six (36) rats were divided into four groups of nine animals in each group. Two animals were used as the naïve, untreated group.

Topiramate was used in its original API form with no specific formulation. Topiramate was delivered to the nasal cavity either as a dry powder or as a solution of 10 mg/ml solubilized in Saline.

Figure 105:
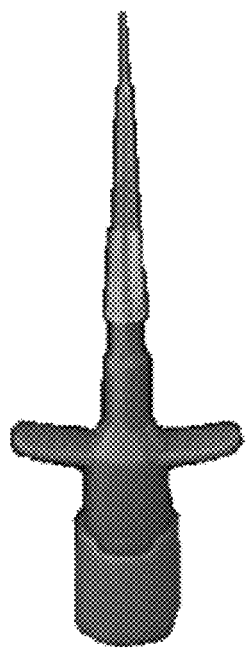
FIG. 105 illustrates a SipNose device.

Application was by means of a SipNose device (FIG. 105) configured for use in the nasal cavities of rats. In order to alleviate the discomfort animal might endured during IN administration, Lidocaine was locally applied on the nasal area, prior to placement of the SipNose's device.

One animal, animal #10 (Group 5M) was euthanized after exhibiting drastic weight loss (13% in one day) and apathy before the procedure on study Day 2. Gross pathology was performed and no significant findings were observed, except for a blood clot in the right nasal cavity, probably formed by the applicator.

The study was performed according to the parameters of Table 31, for group allocation, and Table 32, for the study time-line. Test material or vehicle (control) were administrated twice a day, 6 hours apart, to 9 rats in each group, at a dose of 0.78 mg (0.39 mg in each of the two nostrils), which is comparable to 25 mg per nostril (50 mg total) in humans. This provided a total of 1.56 mg per day per animal. For the liquid nasal samples, the administration was performed IN via SipNose's dedicated device at doses of 78 µL, from 10 mg/ml stock, or orally, after dilution to a dose volume of 200 µL. Food consumption was monitored two days before study initiation and daily during the study. Three (3) animals per group were sacrificed 45 minutes after the first dose of the first day, and six animals per group were sacrificed after 6 consecutive days of dosing, via CO2 asphyxiation.

TABLE 31

Study design and group allocation

| Group No. | # of Animals & animal #s | Treatment | Dose | Doses per day | Total drug per day | Route of Administration | Termination* |
|---|---|---|---|---|---|---|---|
| 1M | 1 (25) | Naïve | NA | — | NA | NA | End of last dosing day |
| 2M | 9 (1, 2, 3, 4, 5, 6, 27, 28, 29) | Liquid Topiramate, Oral | 0.78 mg (solubilised in saline to 200 µL) | 2 | 1.56 mg | Oral | 3 at end of first day (PK) 6 at end of last dosing day |
| 3M | 9 (19, 20, 21, 22, 23, 24, 36, 37, 38) | Liquid Topiramate SipNose | 0.78 mg (78 µL from 10 mg/ml stock) | 2 | 1.56 mg | IN | 3 at end of first day (PK) 6 at end of last dosing day |
| 4M | 9 (13, 14, 15, 16, 17, 18, 33, 34, 35) | Dry powder Topiramate SipNose | 0.78 mg (as dry powder) | 2 | 1.56 mg | IN | 3 at end of first day (PK) 6 at end of last dosing day |
| 5M | 9 (7, 8, 9, 26#, 11, 12, 30, 31, 32) | Saline, SipNose | 78 µL | 2 | NA | IN | 3 at end of first day (PK) 6 at end of last dosing day |

TABLE 32

Test Schedule

| Study Day | Procedure | Body weight | Clinical signs | Food consumption | Dosing | Necropsy and Gross pathology**: Blood samples* |
|---|---|---|---|---|---|---|
| Acclimation | | | | | | |
| −1 | | ✓ | | Daily | | |
| 1 | Dosing Post-dosing sacrifice | Daily | Daily | | Twice a day, 6 hours apart, at a dose of 0.78 mg/200 µL; 1.56 mg total per animal On Day 6, once only, 45 minutes before termination | 3 Animals were sacrificed for PK analysis of blood and brain (following perfusion with saline). PK analysis: 1 animal per cage - Blood and brain collection following perfusion with Saline. Tissue collection: 1 animal per cage - Nasal cavity (including olfactory epithelium), nasopharynx, paranasal sinus, trachea, lungs, brain, heart and larynx was collected at termination point following and fixed in 4% formaldehyde. H&E staining. Inflammatory status was evaluated according to a scoring scale, listed below**. |
| 2-6 | Dosing | | | | | |
| 6 | Dosing Termination | | | | | |

*blood was collected, at a volume of 400 µL, 45 minutes after first dosing of Day 1 and Day 6, prior to animal sacrifice. Additional bleeding was performed prior to dosing of Day 6.

Body weight was recorded upon arrival, 2 days before study initiation and once a day thereafter.

At the end of the study (termination), animals were sacrificed by CO2 asphyxiation or cardiac perfusion, and gross pathology was performed, examining major tissue and organ systems. Perfusion was performed under anesthesia with Isoflurane, using saline, for further PK examination of compounds in the brain.

Animals were sacrificed 45 minutes after the first administration of Day 1 and the last administration of Day 6, following blood sampling of 400 µL, if required, as described below. Three (3) rats, sacrificed after the first dosing day, were perfused with saline for PK analysis of blood and brain. Animals sacrificed on the last day of the study (after one dose only) were divided into 2 groups: one animal in each cage was bled and perfused with saline, after which the brain was collected and frozen in liquid nitrogen for PK analysis. The second animal in the cage was sacrificed by $CO_2$ asphyxiation and the nasal cavity (including the olfactory epithelium), nasopharynx, paranasal sinus, trachea, lungs, brain, heart and larynx were collected and fixed in 4% formaldehyde and Histopathological evaluation (H&E staining) was performed. Inflammatory status was evaluated. Slide preparation was followed by histopathological examination of the collected organs during scheduled termination and necropsy from all the animals. Tissues were trimmed, embedded in paraffin, sectioned at approximately five micron thickness and stained with Hematoxylin & Eosin (H&E).

Figure 106A:
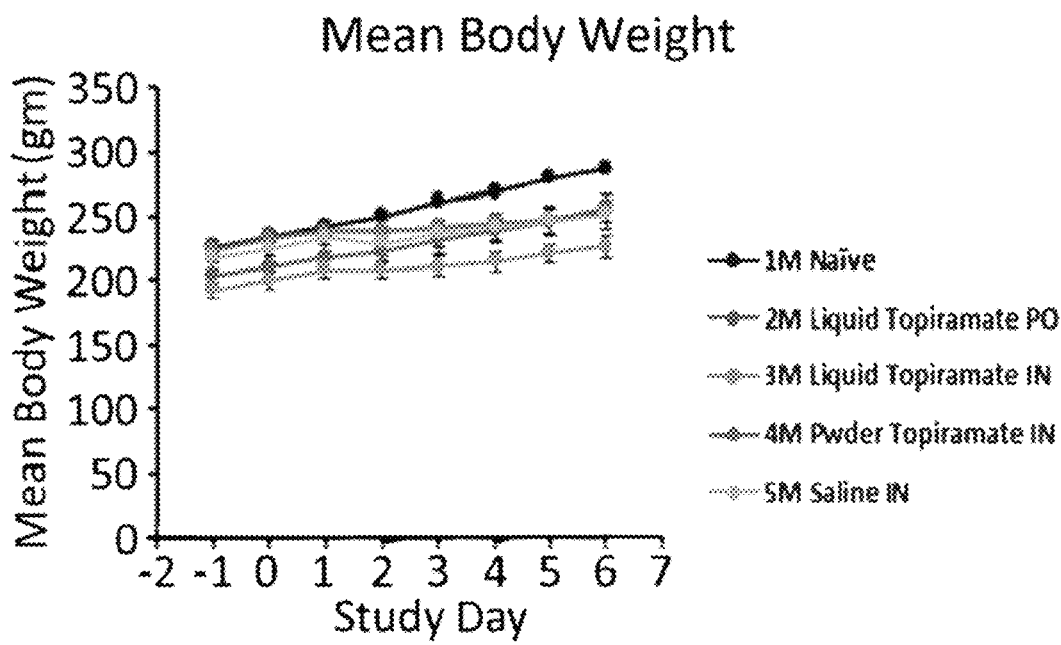
FIG. 106A-C illustrate the effect of Topiramate on rabbits' body weight.
Figure 106B:
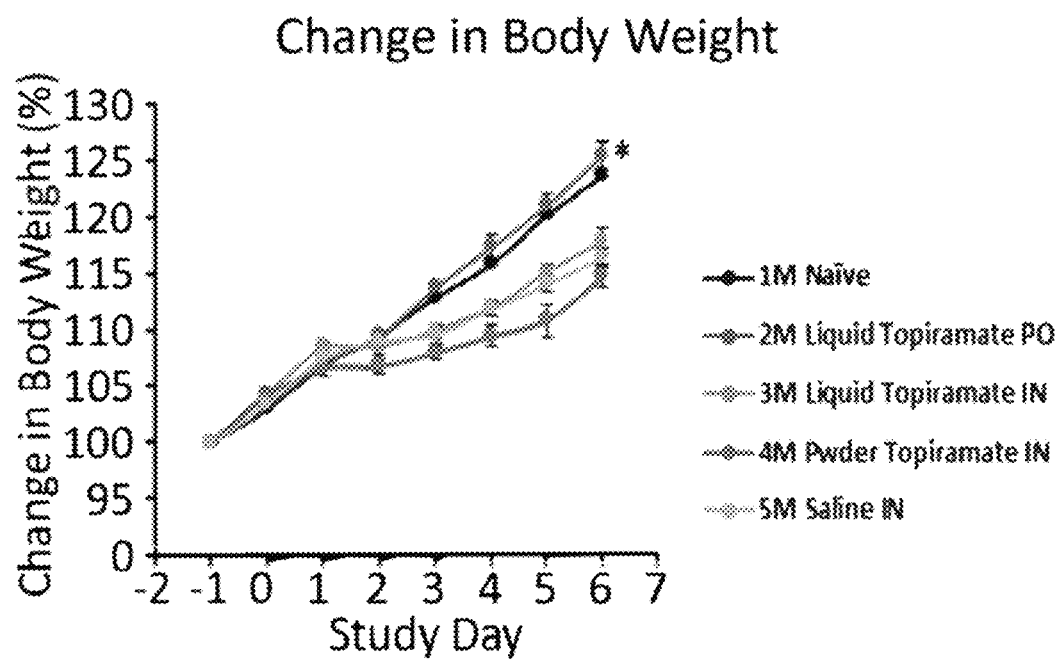
Figure 106C:
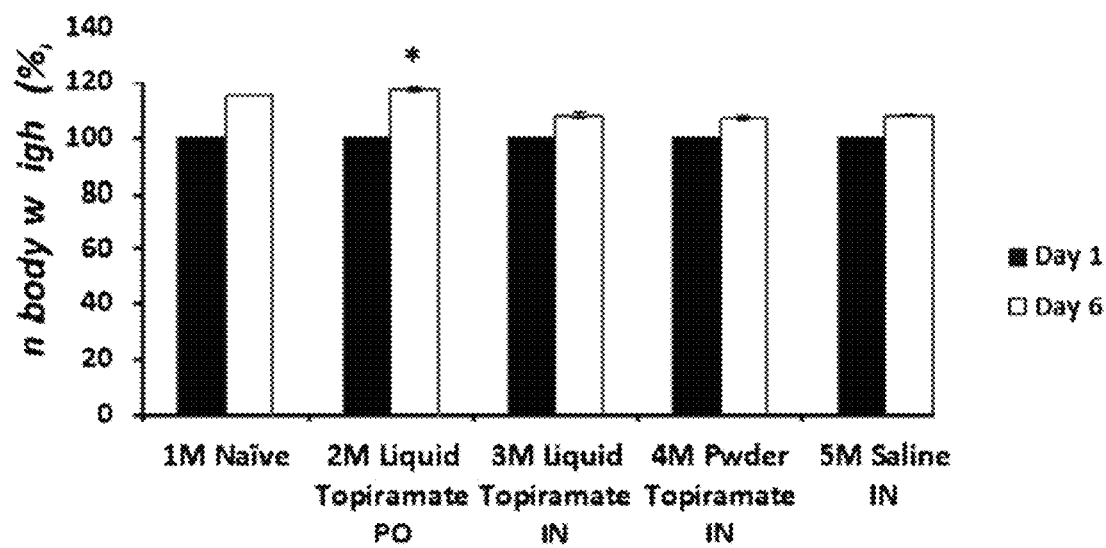

As shown in FIG. 106A-B, which show the mean body weight (FIG. 106A) and percent change in body weight (FIG. 106B) from the animals' arrival (Day −2) through the first dosing day (Day 1) to study termination (Day 6). When comparing this increase in body weight relative to the first day of the study (Day 1 of dosing), a statistically significant difference ($p<0.001$) was observed for Group 2M, treated orally with liquid Topiramate, compared to the other groups. As shown in FIG. 106C, which shows the mean±SEM of all animals in each group (n=3), all animals showed a statistically significant increase in body weight during the study. Group 2M displayed approximately 17% increase in body weight during the treatment phase, while the other treatment groups displayed a moderate increase of ~8%.

While body weight, as expected, increased throughout the study in all groups, a statistically significant increase was observed for Group 2M (liquid Topiramate, IN), which showed a 2-fold increase in body weight by the end of the treatment period (i.e. relative to study day 6), relative to all other treatment groups (FIG. 106A-C). Furthermore, an increase was observed in food consumption in this group, supporting the increase in body weight, similar to the vehicle group (5M). This suggests that the low dose that was given (IN and orally), in comparison to the higher doses that are given clinically orally to affect weight, is not effective when given orally. Also, it is important to note that the oral formulation that was given was the API Topiramate solubilized in saline, and not the commercially used oral formulation that is in use and developed for improved GI absorption.

Figure 107A:
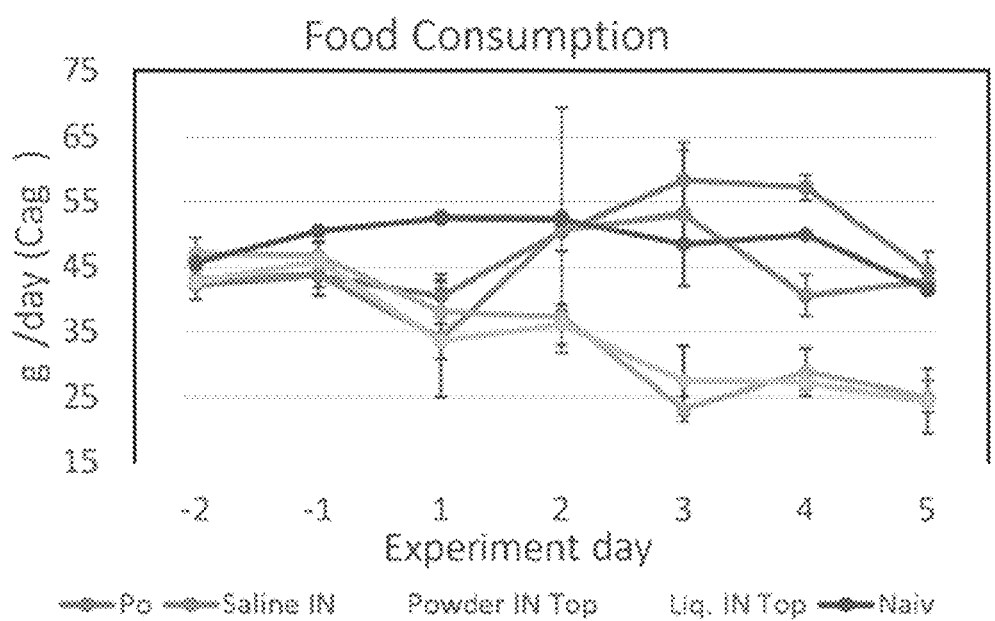
FIG. 107A-C illustrate the effect of Topiramate on rabbits' food consumption.
Figure 107B:
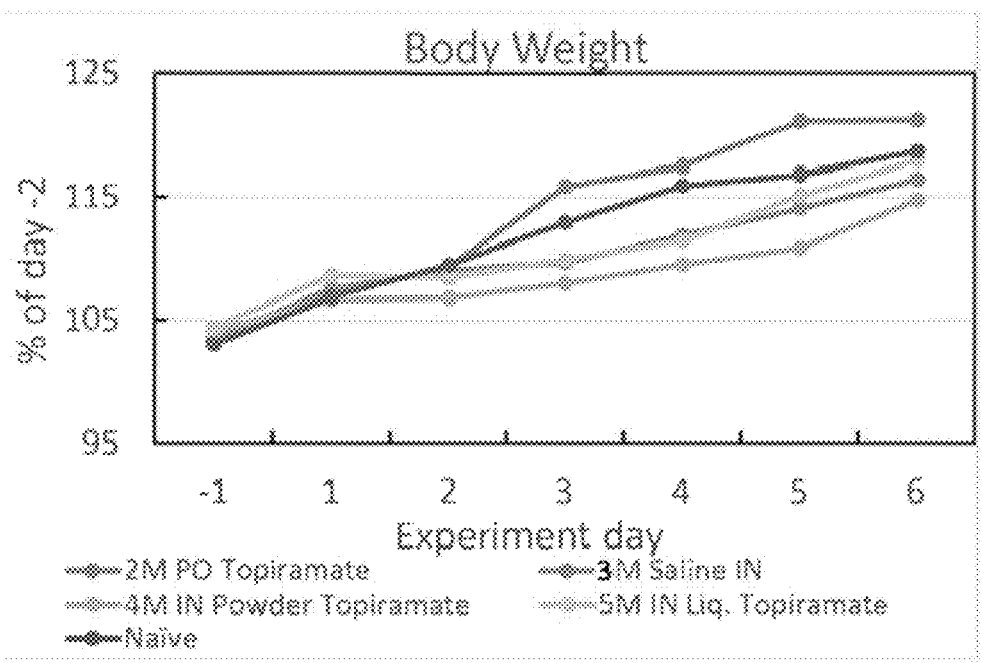
Figure 107C:
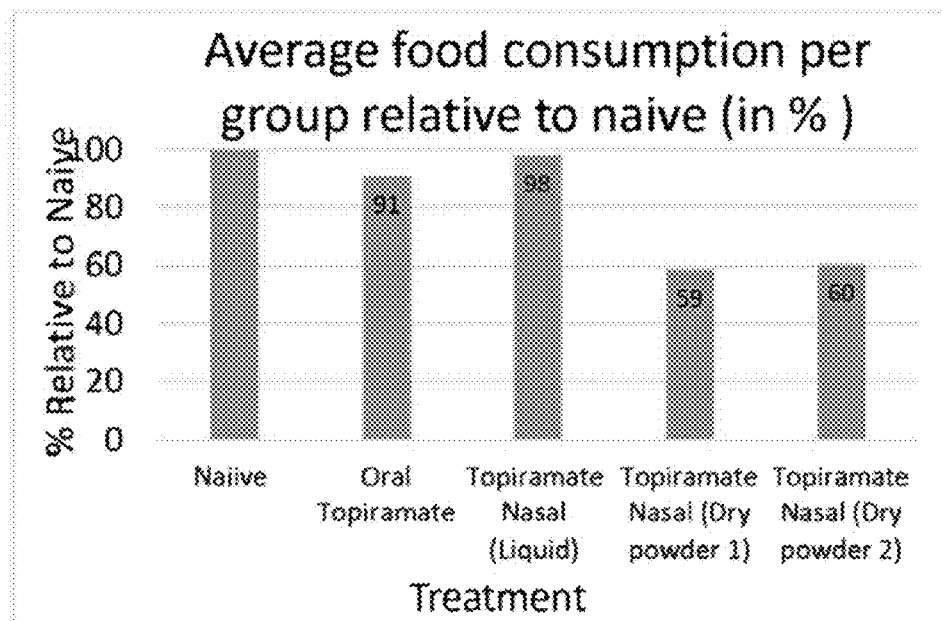

As shown in FIG. 107A-B, food consumption was evaluated daily for each group (3 cages, 2 animals per cage), starting two days before treatment. As shown in FIG. 107A, increased food consumption was observed for Groups 1M, 2M and 5M, while reduced food consumption was observed for Groups 3M and 4M. The difference was statistically significant ($p<0.005$) compared to group 5M on Study Day 2 (or −1). No significance was observed compared to Study Day 1, except for the increased appetite observed for groups 2M ($p<0.05$) and 5M (not significant).

As shown in FIG. 107B, body weight increased slightly for all the animals, with body weight increasing most for the group 2M animals, given Topiramate orally (PO Topiramate) and least for the group 4M animals, given powder Topiramate intranasally (IN Powder Topiramate). However, these results are not statistically significant, as they are within range of the results for the untreated (naïve) animal and the group 5M animals (IN saline).

Figure 108A:
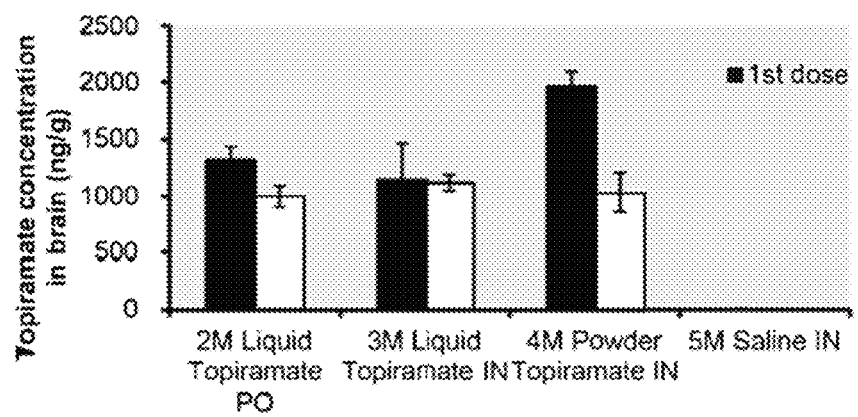
FIGS. 108A-B illustrate plasma and brain concentrations of Topiramate in rabbits.
Figure 108B:
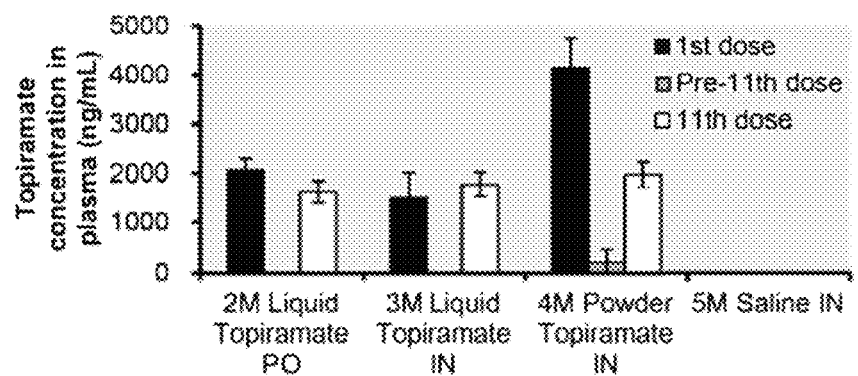
Figures 109A, 109B:
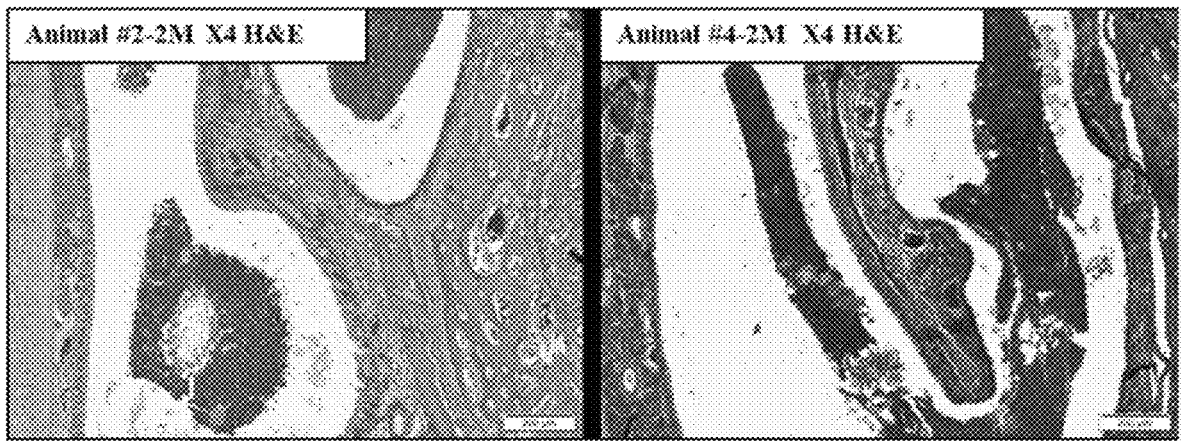
FIG. 109A-E shows histopathological images of rabbits treated with midazolam.
Figures 109C, 109D:
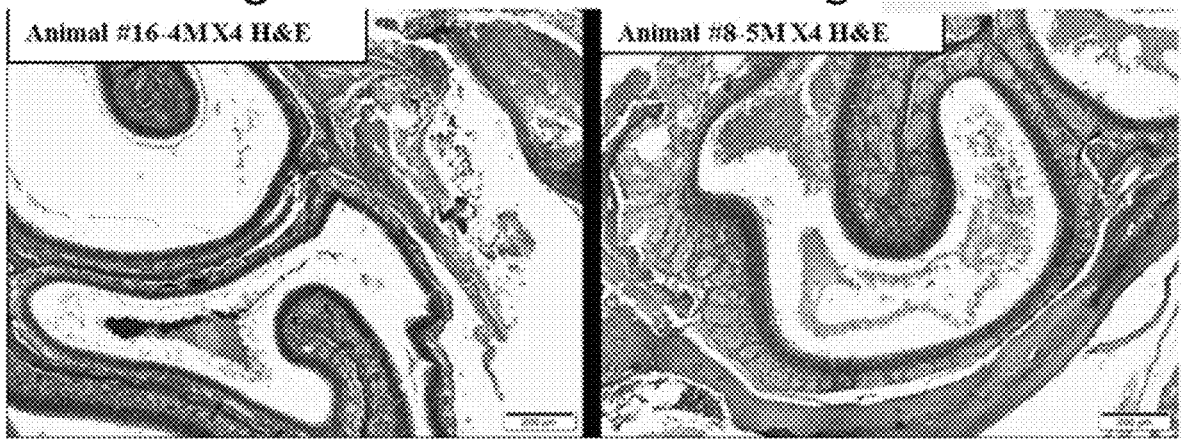
Figure 109E:
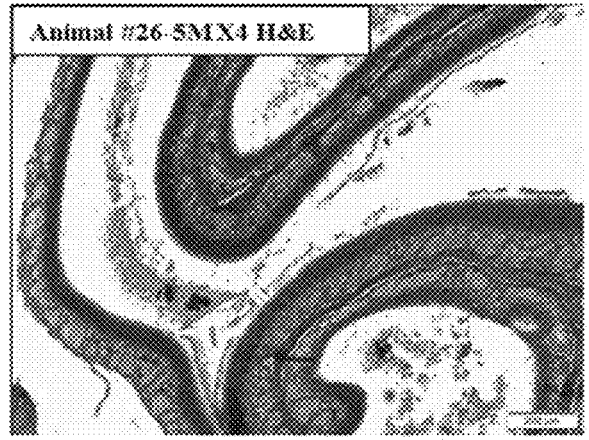

FIG. 108A-B shows Topiramate concentrations in plasma (FIG. 108A) and brain (FIG. 108B). Nasal delivery of the Topiramate API with the SipNose device resulted in pronounced Topiramate concentrations. A higher efficiency of intra-nasal administration of powder Topiramate (group 4M) over both IN liquid Topiramate (group 3M) and Topiramate liquid administered orally is seen. Topiramate concentration measured after the first administration was 4143±596.7 ng/mL for plasma and 1962134.4 ng/mL for brain. Interestingly, following the 11th administration plasma and brain concentrations were comparable between groups 3M, 4M and 5M (e.g., group 4M: blood: 1977±256.4 and brain: 1033±172.1 ng/mL). Concentrations following the 11th administration in group 4M were considerably lower than those following the first administration, reaching a level similar to the other treated groups.

Examination of Topiramate concentrations in plasma and brain revealed that IN Topiramate administration of powder or liquid is an optional route of administration when using the SipNose delivery device, and results in similar or higher blood and brain concentrations, when compared to 45 min following oral administration (FIG. 108A-B). As shown above, Topiramate blood concentrations reach a steady state about 45 min after both IN and oral administration.

Intra-nasal administration of powder Topiramate (Group 4M) provides a higher efficiency (higher blood and brain concentrations) than both oral and IN administered liquid Topiramate (Groups 2M and 3M, respectively). Topiramate plasma concentration that was measured after the first administration was twice as high (average of 4143±596.7 ng/mL) as the other two groups indicated (2070±228.1 and 1512±505.2 ng/mL, respectively). A similar trend was observed for brain concentrations. Interestingly, following the 11th administration, plasma concentrations (1977±256.4 ng/mL) as well as brain concentrations, were considerably lower than those following the first administration in the powder Topiramate intranasal group. A possible explanation is induction of CYP 3A4 activity leading to increased metabolism of the drug.

Both liquid and powder Topiramate were administered intranasally. Only liquid Topiramate was administered orally, as it is not feasible to administer Topiramate powder orally. After the first dose, intranasal administration of Topiramate liquid results in blood and brain concentrations of Topiramate which are similar to higher than the concentrations seen with orally-administered liquid Topiramate and intranasal administration of Topiramate powder results in blood and brain concentrations of Topiramate which are similar to those seen with orally-administered liquid Topiramate. After the eleventh dose, blood and brain concentrations of Topiramate were similar for all types of administration. No major histopathological findings were observed in all the samples of all the tissues that were examined. Some minor findings that were found are listed below:

FIG. 109A-E shows representative histopathological images of H&E slides. Animals #2 (FIG. 109A) and #4 (FIG. 109B), from group 2M, showed a moderate hemorrhage in the rostral nose, with some groups of erythrocytes admixed with fibrin in the lumen. In these two animals, there are also small hemorrhages under the mucosa. In animals #2 and #4 hemorrhages were also found under the respiratory epithelium of the nasal cavity. These findings cannot be related to the nasal delivery device and method as they appear specifically in the group receiving orally delivered drug.

Animal #16 (FIG. 189C), from group 4M, shows a moderate hemorrhage in the rostral nose. Animals #16, (FIG. 109D) #8 and #26 (FIG. 109E) showed a moderate hemorrhage in the rostral nose, with fibrin and some erythrocytes in the nose lumen, while other structures are intact. The above findings cannot be related to the nasal delivery device and method as are also appear in the oral delivered drug group.

At all other sites and for all other animals no pathological changes were detected.

Absorption into the Brain and Spinal Cord of for Oil-Based Substances

For most liquid drug formulations, the drugs are dissolved in, suspended in or mixed with water-based liquids. However, many of the *cannabis* derivatives that show promise as therapeutic agents, such as the cannabinoids, need to be dissolved in oil. Therefore, a study was done to investigate uptake to the brain of an oil-based formulation. For this study, Fluorescein was dissolved in oil and administered intranasally, via the SipNose device, to rats. Fluorescein was administered to the control animals intravenously.

FIG. 110A-C shows that, for Fluorescein dissolved in oil, there is considerably more uptake to the brain of the Fluorescein than for 1/V when the substance is administered intranasally using a SipNose device and that there is good persistence of the fluorescein in the brain. FIG. 110B also shows that the Fluorescein is distributed throughout the brain, rather than being concentrated in the cerebellum, as in the controls. There is also considerably less early deposition of Fluorescein in the spinal cord.

Thus, the SipNose device can provide efficient administration to the brain of oil-based drugs such as cannabinoids.

No major histopathological findings were observed in all the samples of all the tissues that were examined following the repeated dosing. Any mild findings that were seen in the histopathological examination cannot be related to the nasal delivery device and/or method as are also appear in the oral delivered drug group.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for delivering a predetermined amount $V_{sub}$ [ml or mg] of at least one substance, within at least one body cavity of a subject, said device comprising:
   at least one open-ended nosepiece enclosing said predetermined amount $V_{sub}$ of said at least one substance, said at least one open-ended nosepiece comprising at least one fluid discharging outlet port of diameter $D_{out}$ [mm] and configured for placement in proximity to said at least one body cavity;
   a base comprising at least one chamber configured to confine compressed pressurized gas at a predetermined compressed volume $V_{gas}$ [ml] and pressure $P_{gas}$ [barg] at a pre-determined pressure, $P_{gas}$;
   at least one valve in communication with said base and said at least one chamber, having at least two configurations:
   (i) an active configuration in which said at least one valve enables delivery of predetermined amount $V_{sub}$ of said at least one substance from said at least one open-ended nosepiece to said at least one body cavity by the release of said pressurized gas; and
   (ii) an inactive configuration, in which said at least one valve prevents delivery of said predetermined amount $V_{sub}$ of said at least one substance from said at least one open-ended nosepiece to said at least one body cavity;
   wherein said at least one valve is reconfigurable from said inactive configuration to said active configuration within a predetermined period of time, dt, in response to activation of said at least one valve;
   wherein said predetermined volume $V_{gas}$ of said pressurized gas is releasable upon reconfiguration of said at least one valve from said inactive configuration to said active configuration from said at least one chamber, enters said at least one open-ended nosepiece, entrains said at least one substance, and exits via said at least one fluid discharging outlet port into said at least one body cavity;
   wherein said at least one valve comprises at least one sealing member adapted to seal said at least one chamber containing said $V_{gas}$ of pressurized gas at said predetermined pressure $P_{gas}$ to prevent leakage thereof;
   wherein said base comprises an air chamber gate interconnected with said at least one sealing member; and
   wherein said at least one valve is reconfigurable from said inactive configuration to said active configuration by linear movement of said air chamber gate, such that said at least one sealing member is moved from its position and the sealing of said at least one chamber is removed, and such that said at least one valve is reconfigured from said inactive configuration to said active configuration to allow said $V_{gas}$ of said pressurized gas to exit said at least one chamber, enter said at least one open-ended nosepiece, and entrain said $V_{sub}$ of said at least one substance to be delivered to said at least one body cavity.

2. The device of claim 1, wherein at least one of the following is satisfied:
   (a) said predetermined amount Vsub of said at least one substance is at an effective amount for treatment of at least one condition selected from a group consisting of: obesity, binge eating disorder, pain management, epilepsy, eating disorders, psychiatric disorders, dementia, addiction, and sedation;
   (b) said pain management manages pain selected from a group consisting of: chronic pain; neuropathic pain; cancer pain, breakthrough pain, migraines and any combination thereof;
   (c) said predetermined amount $V_{sub}$ of said at least one substance is at an effective amount for emergency treatment of drug overdose;
   (d) said epilepsy treatment is selected from a group consisting of: a chronic treatment for prevention of epileptic seizures, a chronic treatment for reduction in occurrence of epileptic seizures, a chronic treatment for reduction of strength of epileptic seizures, a rescue treatment at the time of occurrence of an epileptic seizure, and any combination thereof;
   (e) said predetermined amount Vsub of said at least one substance is at an effective amount for treatment of brain cancer; said brain cancer selected from a group consisting of: Glioblastoma, secondary tumor, brain stem cancer and any combination thereof;
   (f) said treatment for brain cancer is selected from a group consisting of: direct treatment of a brain cancer in order to reduce a tumor; treatment of a patient with a non-brain cancer in order to prevent metastasis of the non-brain cancer to the brain; and any combination thereof; and (g) said predetermined amount Vsub is measurable as a volume [ml] or a mass [mg].

3. The device of claim 1, wherein at least one of the following is satisfied:

said at least one substance is selected from a group consisting of: Midazolam, Topiramate and at least one *cannabis* derivative, tetrahydrocannabinol (THC), cannabidiol (CBD), cannabinol (CBN), tetrahydrocannbivarin (THCV), natural or synthetic *cannabis* extract, Phentamine, glucagon-like peptide 1 (GLP-1), a GLP-1 analog, a GLP-1 derivative and any combination thereof;

said at least one substance is Naloxone;

said at least one substance is selected from a group consisting of: a chemotherapy drug, a biologic, an antibody, and any combination thereof;

said predetermined amount Vsub of said at least one substance is at an effective amount for vaccination;

said vaccination is configured to provide a vaccine selected from a group consisting of: anthrax vaccine, Hepatitis B vaccine, Tetanus vaccine, Influenza vaccine and any combination thereof;

said predetermined amount $V_{sub}$ of said at least one substance is at an effective amount for enhancement of an immune system;

at least one central nervous system disorder is treatable via said enhancement of the immune system;

said at least one central nervous system disorder is selected from a group consisting of: Alzheimer's disease, Parkinson's disease and any combination thereof;

said at least one substance is selected from a group consisting of: a pharmaceutical, a natural compound, a biologic, a hormone, a peptide, a protein, a virus, a cell, a stem cell and any combination thereof; and at least one odorant is deliverable at the time of delivery of said at least one substance; an odor of said at least one odorant is selected from a group consisting of: grapefruit, lemon, vanilla, green apple, banana, peppermint, fennel, patchouli, bergamot and any combination thereof; a component of said at least one odorant is selected from a group consisting of: a natural smell molecule, a synthetic smell molecule and any combination thereof; and before delivery, said odorant is held in a manner selected from a group consisting of: stored in said pressurized gas, stored in at least one of said at least one substance, stored in a device material, and any combination thereof.

4. The device claim 1, wherein at least one of the following is satisfied:

said delivery occurs at a pressure rate of $dP_{gas}/dt_{deliver}$; a volume rate of $dV_{gas}/dt_{deliver}$; and an amount rate of $dV_{sub}/dt_{deliver}$;

said at least one body cavity is selected from a group consisting of: a nasal cavity, the mouth, the throat, an ear, the vagina, the rectum, and the urethra;

said at least one substance is selected from a group consisting of a gas, a liquid, a powder, an aerosol, a slurry, a gel, a suspension and any combination thereof;

said device is configured to deliver a plurality of amounts of said at least one substance; each of said plurality of amounts separated in time from all other of said plurality of amounts, each of said plurality of amounts being predetermined; said predetermination selected from a group consisting of: each of said plurality of amounts being an unchangeable amount fixed before first use of the device; each of said plurality of amounts being a selectable adjustable amount and, after selection of a size for said amount, said selected amount being automatically deliverable; and said predetermined amount of said at least one substance is introducible into said device via a syringe.

5. The device of claim 1, wherein at least one of the following is satisfied:

said at least one valve is reconfigurable from said inactive configuration to said active configuration;

said at least one valve is single use;

said at least one valve is selected from a group consisting of a frangible membrane, a mechanical valve and any combination thereof.

6. The device of claim 1, wherein at least one of the following is satisfied:

a median particle size distribution, DV50, of a diameter of particles of said at least one substance, after exiting from said device, is about 100 μm;

a particle diameter larger than 90% of particles of said substance, DV90, is less than about 1000 μm;

a full width of a plume of aerosol comprising said at least one substance and said pressurized gas subtends an angle θ of about 25°;

particles in said plume of aerosol have velocities in a range of about 5 m/s to 50 m/s;

said pressurized gas comprises air, nitrogen, oxygen, carbon dioxide, helium, neon, xenon and any combination thereof;

during dispensing of said at least one substance, a mixture of said predetermined volume $V_{gas}$ of said pressurized gas with said predetermined amount $V_{sub}$ of said at least one substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume $V_{gas}$ of said pressurized gas, said predetermined amount $V_{sub}$ of said at least one substance, said predetermined pressure $P_{gas}$ of said pressurized gas, said predetermined orifice diameter D, and any combination thereof;

said at least one substance is stored under either an inert atmosphere or under vacuum to prevent reactions during storage;

a dose-response curve is substantially linear for brain concentration of said at least one substance when administered nasally via said device; and a dose-response curve for brain concentration of said at least one substance when administered nasally via said device selected from a group consisting of logarithmic, parabolic, exponential, sigmoid, power-law, and any combination thereof.

7. The device of claim 1, wherein at least one of the following is satisfied:

said at least one open-ended nosepiece is selected from a group consisting of: a container fluidly connectable to said device, a predetermined volume within said device and any combination thereof;

said at least one open-ended nosepiece comprises a port fluidly connectable to the exterior of said device, said port configured such that said at least one substance is insertable into said container via said port;

said device comprises a port cover configured to provide an air-tight closure for said at least one open-ended nosepiece, said port cover is selected from the group consisting of a port cover slideable along said device, a port cover rotatable around said device, a port cover rotatable around a hinge on the exterior of said device and any combination thereof; and said container is insertable into said device.

8. The device of claim 1, wherein said at least one open-ended nosepiece has a main longitudinal axis, said at least one open-ended nosepiece comprising a number n of compartments, said at least one open-ended nosepiece configured to contain at least a portion of said predetermined amount $V_{sub}$ of said at least one substance, said amount $V_{sub}$ of said at least one substance containable in at least one of said compartments; at least one of the following being satisfied:

the number n of said compartments is an integer greater than or equal to 1; at least one said compartment has cross-section with shape selected from a group consisting of: wedge shaped, circular, oval, elliptical, polygonal, annular, and any combination thereof;

for said number n of compartments being an integer greater than 1, at least two said compartments have different volumes;

for said number n of compartments being an integer greater than 1, at least two said compartments have the same volume;

for said number n of compartments being an integer greater than 1, at least two said compartments have different cross-sectional areas;

for said number n of compartments being an integer greater than 1, at least two said compartments have the same cross-sectional area;

for said number n of compartments being an integer greater than 1, at least two said compartments contain different substances;

for said number n of compartments being an integer greater than 1, at least two said compartments contain the same substance;

for said number n of compartments being an integer greater than 1, at least two said compartments are disposed coaxially around said main longitudinal axis of said at least one open-ended nosepiece;

for said number n of compartments being an integer greater than 1, at least two said compartments are disposed sequentially along said main longitudinal axis of said at least one open-ended nosepiece;

for said number n of compartments greater than 1, said plurality of substances mix during said dispensing; and for said number n of compartments greater than 1, said plurality of substances react during said dispensing.

9. The device of claim 1, wherein, when said at least one substance is delivered into a tube, at least one of the following is satisfied:

a distance travelled down the tube is L and L is substantially independent of said viscosity η of said at least one substance;

the distance travelled down the tube is L, where $L=a_{6a} P+b_{6a}$; the units of L are cm and the units of P are barg, coefficient $a_{6a}$ is in a range of about 0 to about 116 and coefficient $b_{6a}$ is in a range of about 0 to about 306;

the distance travelled down the tube is L, where $L=a_{6b} P^3-b_{6b} P^2+C_{6b} P$; the units of L are cm and the units of P are barg, coefficient $a_{6b}$ is in a range of about 6.5 to about 9.75, coefficient $b_{6b}$ is in a range of about −65 to about −97.5 and coefficient $c_{6b}$ is in a range of about 202 to about 303;

the distance travelled down the tube is L, where $L=a_{6c} P^{b6c}$; the units of L are cm and the units of P are barg, coefficient $a_{6c}$ is in a range of about 0 to about 902 and coefficient $b_{6c}$ is in a range of about 0 to about 3.72;

the distance travelled down the tube is L, where $L=a_{7a} V_{gas}+b_{7a}$; the units of L are cm and the units of P are barg, coefficient $a_{7a}$ is in a range of about 0 to about 10 and coefficient $b_{7a}$ is in a range of about 165 to about 282;

the distance travelled down the tube is L, where $L=b_{7b} V_{gas}(a_{7b}+V_{gas})$; the units of L are cm and the units of P are barg, coefficient $a_{7b}$ is in a range of about −0.26 to about 2.05 and coefficient $b_{7b}$ is in a range of about 235 to about 350; and the distance travelled down the tube is L, where $L=a_{7c} V_{gas}^{b7c}$; the units of L are cm and the units of P are barg, coefficient $a_{7c}$ is in a range of about 0 to about 320 and coefficient $b_{7c}$ is in a range of about 0 to about 0.96.

10. The device of claim 1, further comprising at least one nosepiece cover configured to sealably cover, at least in part, said at least one open-ended nosepiece.

11. The device of claim 10, wherein said at least one nosepiece cover and said at least one open-ended nosepiece are coupled to each other.

12. The device of claim 10, wherein a coupling between at least one nosepiece cover and said at least one open-ended nosepiece said is reversible.

13. The device of claim 10, wherein said at least one open-ended nosepiece is configured to be pierced.

14. The device of claim 10, wherein removal of said at least one nosepiece cover is obtained by sliding said at least one nosepiece cover along said device.

15. The device of claim 10, wherein said at least one nosepiece cover comprises at least one nosepiece puncturing member adapted to pierce said at least one open-ended nosepiece.

16. The device of claim 10, wherein said at least one open-ended nosepiece comprises at least one port throughout which said at least one substance exits said device, such that said at least one nosepiece cover seals said at least one port and removal thereof unseals the at least one port.

17. The device of claim 1, wherein said at least one chamber is a container adapted to hold said pressured gas at said $P_{gas}$ for about 5-about 150 minutes.

18. The device of claim 1, wherein said at least one sealing member is adapted to seal said predetermined amount $V_{sub}$ of said at least one substance in said at least one open-ended nosepiece and prevent leakage thereof.

19. The device of claim 18, wherein said at least one sealing member separates said at least one open-ended nosepiece and said at least one chamber.

20. The device of claim 1, wherein said at least one sealing member is said at least one valve.

21. The device of claim 1, wherein said at least one sealing member is at least one O-ring.

22. The device of claim 1, further comprising a safety latch, the safety latch adapted to prevent accidental operation of said device.

23. The device of claim 1, wherein said at least one fluid discharging outlet port is disposed in at least one position selected from a group consisting of: (a) along a circumference along a longitudinal axis of said device so as to deliver said predetermined amount $V_{sub}$ of said at least one substance to one or more sides of said at least one body cavity; (b) at a distal-most end of said at least one open-ended nosepiece; and any combination thereof.

24. The device of claim 1, additionally comprising at least one expandable portion, the at least one expandable portion adapted to inflate before activation of said device.

25. The device of claim 1, wherein at least one of the following is satisfied:
   a) the diameter is in a range of 0.2-6 mm;
   b) an amount rate $dV_{sub}/dt_{deliver}$ is greater than about 0.0001 ml/milliseconds or greater than about 0.0001 mg/ms;
   c) viscosity η of said at least one substance is in a range of about $1\times10^{-3}$ poise to about 1 poise;
   d) said predetermined amount $V_{sub}$ of said at least one substance reaches said at least one body cavity at a velocity greater than at least 11.9 m/s;
   e) said $V_{sub}$ is in a range of about 0.01-7 ml or in a range of about 0.01-1000 mg;
   f) said $P_{gas}$ is in a range of about 1-10 barg;
   g) the volume of said pressurized gas, when compressed, $V_{gas}$, is in a range of about 1-50 ml;
   h) said predetermined period of time is less than 500 milliseconds;
   i) a release time of said Vsub of said at least one substance and said $V_{gas}$ of said pressurized gas $dT_{deliver}$ is less than 500 milliseconds; or
   j) any combination thereof.

26. The device of claim 1, wherein said pressurized gas exits said at least one chamber peripherally with respect to said at least one sealing member.

27. The device of claim 1, wherein said at least one valve comprises a valve that is not reconfigurable from said active configuration to said inactive configuration.

28. The device of claim 1, wherein said at least one valve is reconfigurable from said inactive configuration to said active configuration responsive to compression of said base.

29. The device of claim 28, wherein said air chamber gate comprises at least one gate anchor; and said base comprises at least one groove in mechanical communication with said at least one gate anchor, such that when said at least one valve is reconfigurable from said inactive configuration to said active configuration said at least one gate anchor is pressed inwards, thereby (a) removing contact between said at least one gate anchor and said at least one groove, (b) linearly moving said air chamber gate proximally, (c) removing said at least one sealing member from its position, and (d) opening a gap between said air chamber gate and a distal-most end of said at least one chamber to allow said pressurized gas to exit said at least one chamber through said gap.

30. A method of delivering a predetermined volume $V_{sub}$ [ml] of at least one substance within at least one body cavity of a subject, comprising:
   providing a device comprising:
      at least one open-ended nosepiece enclosing said predetermined volume $V_{sub}$ of said at least one substance, wherein said at least one open-ended nosepiece comprises at least one fluid discharging outlet port having diameter $D_{out}$ [mm], said at least one open-ended nosepiece being configured for placement in proximity to said at least one body cavity;
      a base comprising at least one chamber configured to confine pressurized gas at a predetermined compressed volume $V_{gas}$ [ml] and pressure $P_{gas}$ [barg] at a predetermined pressure, $P_{gas}$;
      at least one valve in communication with said base, having at least two configurations:
         (i) an active configuration in which said at least one valve enables delivery of said predetermined volume $V_{sub}$ of said at least one substance from said at least one open-ended nosepiece to said at least one body cavity by the release of said pressurized gas; and
         (ii) an inactive configuration, in which said at least one valve prevents delivery of said predetermined volume $V_{sub}$ of said at least one substance from said at least one open-ended nosepiece to said at least one body cavity;
      said at least one valve is reconfigurable from said inactive configuration to said active configuration within a predetermined period of time, dt, in response to activation of said at least one valve;
   placing said at least one open-ended nosepiece in proximity to said at least one body cavity;
   reconfiguring said at least one valve from said inactive configuration to said active configuration thereby releasing said pressurized gas from said at least one chamber and entraining said at least one substance in said predetermined volume $V_{gas}$ of said pressurized gas, and releasing said predetermined volume $V_{sub}$ of said at least one substance and said predetermined volume $V_{gas}$ of said pressurized gas through said at least one discharging outlet port to said at least one body cavity within a predetermined time $dt_{deliver}$;
   wherein said predetermined volume $V_{gas}$ of said pressurized gas at pressure $P_{gas}$ is released upon activation of said base and said at least one valve from said at least one chamber erupts via said at least one fluid discharging outlet port into said at least one body cavity;
   providing said at least one valve with at least one sealing member adapted to seal said at least one chamber containing said predetermined volume Vgas of pressurized gas at said predetermined pressure and prevent leakage thereof;
   providing said base with an air chamber gate interconnected with said at least one sealing member;
   wherein said step of reconfiguring said at least one valve from said inactive configuration to said active configuration is performed by linear movement of said chamber gate, such that said at least one sealing member is moved from its position and the sealing of said at least one chamber is removed, and such that said at least one valve is reconfigured from said inactive configuration to said active configuration thus allowing said Vgas of said pressurized gas to exit said at least one chamber, enter said at least one open-ended nosepiece and entrain said Vsub of said at least one substance to be delivered to said at least one body cavity.

31. The method of claim 30, additionally comprising at least one of the following steps:
   selecting said predetermined volume $V_{sub}$ of said at least one substance to be at an effective amount for treatment of at least one condition selected from a group consisting of: obesity, binge eating disorder, pain management, epilepsy, eating disorders, psychiatric disorders, dementia, and sedation;
   selecting said predetermined volume $V_{sub}$ of said at least one substance to be at an effective amount for treatment of pain management selected from a group consisting of: chronic pain; neuropathic pain; cancer pain, breakthrough pain, migraines and any combination thereof;

selecting said predetermined volume $V_{sub}$ of said at least one substance to be at an effective amount for emergency treatment of drug overdose;

selecting said predetermined volume $V_{sub}$ of at least one substance to be an effective amount for treatment of epilepsy treatment selected from a group consisting of: a chronic treatment for prevention of epileptic seizures, a chronic treatment for reduction in occurrence of epileptic seizures, a chronic treatment for reduction of strength of epileptic seizures; a rescue treatment at the time of occurrence of an epileptic seizure, and any combination thereof;

providing said predetermined volume $V_{sub}$ of said at least one substance to be at an effective amount for treatment of brain cancer; said brain cancer selected from a group consisting of: Glioblastoma, secondary tumor, brain stem cancer and any combination thereof;

selecting said treatment for brain cancer from a group consisting of: direct treatment of a brain cancer in order to reduce a tumor; treatment of a patient with a non-brain cancer in order to prevent metastasis of the non-brain cancer to the brain; and any combination thereof; and measuring said predetermined volume $V_{sub}$ as a volume [ml] or a mass [mg].

32. The method of claim 30, additionally comprising at least one of the following steps:

selecting said at least one substance from a group consisting of: Midazolam, Topiramate and at least one *cannabis* derivative, tetrahydrocannabinol (THC), cannabidiol (CBD), cannabinol (CBN), tetrahydrocannaivarin (THCV), natural or synthetic *cannabis* extract, Phentamine, glucagon-like peptide 1 (GLP-1), a GLP-1 analog, a GLP-1 derivative and any combination thereof;

selecting said at least one substance to be Naloxone;

selecting said at least one substance from a group consisting of: a chemotherapy drug, a biologic, an antibody, and any combination thereof;

selecting said predetermined amount Vsub of said at least one substance to be at an effective amount for vaccination;

selecting a vaccine to provide said vaccination from a group consisting of:

anthrax vaccine, Hepatitis B vaccine, Tetanus vaccine, Influenza vaccine and any combination thereof;

selecting said predetermined amount Vsub of said at least one substance to be an effective amount for enhancement of an immune system;

treating at least one central nervous system disorder via enhancement of the immune system;

selecting said at least one central nervous system disorder from a group consisting of: Alzheimer's disease, Parkinson's disease and any combination thereof;

selecting said at least one substance from a group consisting of: a pharmaceutical, a natural compound, a biologic, a hormone, a peptide, a protein, a virus, a cell, a stem cell and any combination thereof; and delivering at least one odorant at the time of delivery of said at least one substance; an odor of said at least one odorant is selected from a group consisting of: grapefruit, lemon, vanilla, green apple, banana, peppermint, fennel, patchouli, bergamot and any combination thereof; a component of said at least one odorant is selected from a group consisting of: a natural smell molecule, a synthetic smell molecule and any combination thereof; and before delivery, said odorant is held in a manner selected from a group consisting of: stored in said pressurized gas, stored in at least one of said at least one substance, stored in a device material, and any combination thereof.

33. The method claim 30, additionally comprising at least one of the following steps:

delivering at a pressure rate of $dP_{gas}/dt_{deliver}$; a volume rate of $dV_{gas}/dt_{deliver}$; and an amount rate of $dV_{sub}/dt_{deliver}$;

selecting said at least one body cavity from a group consisting of: a nasal cavity, the mouth, the throat, an ear, the vagina, the rectum, and the urethra; and selecting said at least one substance from a group consisting of a gas, a liquid, a powder, an aerosol, a slurry, a gel, a suspension and any combination thereof delivering a plurality of amounts of said at least one substance; each of said plurality of amounts separated in time from all other of said plurality of amounts, each of said plurality of amounts being predetermined; said predetermination selected from a group consisting of: each of said plurality of amounts being an unchangeable amount fixed before first use of the device; each of said plurality of amounts being a selectable adjustable amount and, after selection of a size for said amount, said selected amount being automatically deliverable; and introducing said predetermined amount of said at least one substance into said device via a syringe.

34. The method of claim 30, additionally comprising at least one of the following steps:

reconfiguring said at least one valve from said active configuration to said inactive configuration;

providing said at least one valve as a single use valve; and selecting said at least one valve is selected from a group consisting of a frangible membrane, a mechanical valve and any combination thereof.

35. The method of claim 30, wherein at least one of the following is satisfied:

a median particle size distribution, DV50, of a diameter of particles of said at least one substance, after exit from said device, is about 100 µm;

a particle diameter larger than 90% of particles of said substance, DV90, is less than about 1000 µm;

a full width of a plume of aerosol comprising said at least one substance and said pressurized gas subtends an angle θ of about 25°;

particles in said plume of aerosol have velocities in a range of about 5 m/s to 50 m/s;

said pressurized gas comprises air, nitrogen, oxygen, carbon dioxide, helium, neon, xenon and any combination thereof;

during dispensing of said at least one substance, a mixture of said predetermined volume $V_{gas}$ of said pressurized gas with said predetermined amount $V_{sub}$ of said at least one substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume $V_{gas}$ of said pressurized gas, said predetermined amount $V_{sub}$ of said at least one substance, said predetermined pressure $P_{gas}$ of said pressurized gas, said predetermined orifice diameter D, and any combination thereof;

said at least one substance is stored under either an inert atmosphere or under vacuum to prevent reactions during storage;

a dose-response curve is substantially linear for brain concentration of said at least one substance when administered nasally via said device; and a dose-response curve for brain concentration of said at least one substance when administered nasally via said device selected from a group consisting of logarithmic, parabolic, exponential, sigmoid, power-law, and any combination thereof.

36. The method of claim 30, additionally comprising at least one of the following steps:

selecting said at least one open-ended nosepiece from a group consisting of: a container fluidly connectable to said device, a predetermined volume within said device and any combination thereof providing said at least one open-ended nosepiece with a port fluidly connectable to the exterior of said device, said port configured such that said at least one substance is insertable into said container via said port;

providing said device with a port cover, said port cover providing an air-tight closure for said at least one open-ended nosepiece by at least one member of a group consisting of: sliding said port cover along said device, rotating said port cover around said device, rotating said port cover around a hinge on the exterior of said device and any combination thereof; and inserting said container into said device.

37. The method of claim 30, wherein said at least one open-ended nosepiece has a main longitudinal axis, said at least one open-ended nosepiece comprising a number n of compartments, said at least one open-ended nosepiece configured to contain at least a portion of said predetermined amount $V_{sub}$ of said at least one substance, said amount $V_{sub}$ of said at least one substance containable in at least one of said compartments; at least one of the following being satisfied:

the number n of said compartments is an integer greater than or equal to 1; at least one said compartment has cross-section with shape selected from a group consisting of: wedge shaped, circular, oval, elliptical, polygonal, annular, and any combination thereof;

for said number n of compartments being an integer greater than 1, at least two said compartments have different volumes;

for said number n of compartments being an integer greater than 1, at least two said compartments have the same volume;

for said number n of compartments being an integer greater than 1, at least two said compartments have different cross-sectional areas;

for said number n of compartments being an integer greater than 1, at least two said compartments have the same cross-sectional area;

for said number n of compartments being an integer greater than 1, at least two said compartments contain different substances;

for said number n of compartments being an integer greater than 1, at least two said compartments contain the same substance;

for said number n of compartments being an integer greater than 1, at least two said compartments are disposed coaxially around said main longitudinal axis of said at least one open-ended nosepiece;

for said number n of compartments being an integer greater than 1, at least two said compartments are disposed sequentially along said main longitudinal axis of said at least one open-ended nosepiece;

for said number n of compartments greater than 1, said plurality of substances mix during said dispensing; and for said number n of compartments greater than 1, said plurality of substances react during said dispensing.

38. The method of claim 30, wherein, when said at least one substance is delivered into a tube, at least one of the following is satisfied:

a distance travelled down the tube is L and L is substantially independent of said viscosity η of said at least one substance;

the distance travelled down the tube is L, where $L=a_{6a} P+b_{6a}$; the units of L are cm and the units of P are barg, $a_{6a}$ is in a range of about 0 to about 116 and $b_{6a}$ is in a range of about 0 to about 306;

the distance travelled down the tube is L, where $L=a_{6b} P^3 b_{6b} P^2+c_{6b} P$; the units of L are cm and the units of P are barg, $a_{6b}$ is in a range of about 6.5 to about 9.75, $b_{6b}$ is in a range of about −65 to about −97.5 and $c_{6b}$ is in a range of about 202 to about 303;

the distance travelled down the tube is L, where $L=a_{6c} P^{b6c}$; the units of L are cm and the units of P are barg, $a_{6c}$ is in a range of about 0 to about 902 and $b_{6c}$ is in a range of about 0 to about 3.72;

the distance travelled down the tube is L, where $L=a_{7a} V_{gas} b_{7a}$; the units of L are cm and the units of P are barg, $a_{7a}$ is in a range of about 0 to about 10 and $b_{7a}$ is in a range of about 165 to about 282;

the distance travelled down the tube is L, where $L=b_{7b} V_{gas}/(a7b+V_{gas})$; the units of L are cm and the units of Pare barg, $a_{7b}$ is in a range of about −0.26 to about 2.05 and $b_{7b}$ is in a range of about 235 to about 350; and the distance travelled down the tube is L, where $L=a_{7c} v_{gas}^{b7c}$; the units of L are cm and the units of P are barg, $a_{7c}$ is in a range of about 0 to about 320 and $b_{7c}$ is in a range of about 0 to about 0.96.

39. The method of claim 30, further comprising coupling said at least one open-ended nosepiece to said base.

40. The method of claim 30, further comprising either pre-pressurizing said fluid-tight chamber with said gas to said predetermined pressure; or pressurizing said fluid-tight chamber with said gas to said predetermined pressure before reconfiguring said at least one valve from said inactive configuration to said active configuration.

41. The method of claim 30, further comprising either pre-emplacing said at least one substance in said at least one open-ended nosepiece; or emplacing said at least one substance in said at least one open-ended nosepiece before reconfiguring said at least one valve from said inactive configuration to said active configuration.

42. The method of claim 30, further comprising providing at least one nosepiece cover configured to, at least in part, sealably cover said at least one open-ended nosepiece.

43. The method of claim 42, further comprising coupling, at least partially, said at least one nosepiece cover to said at least one nosepiece.

44. The method of claim 43, further comprising piercing said at least one open-ended nosepiece.

45. The method of claim 43, further comprising providing said at least one nosepiece cover with at least one nosepiece puncturing member adapted to pierce said open-ended nosepiece.

46. The method of claim 30, further comprising sealing, by said at least one sealing member, said $V_{sub}$ of said at least one substance in said at least one open-ended nosepiece and prevent leakage thereof.

47. The method of claim 46, wherein said at least one sealing member separates said at least one open-ended nosepiece and said at least one chamber.

48. The method of claim 30, wherein said at least one sealing member is said at least one valve.

49. The method of claim 30, wherein said at least one sealing member is at least one O-ring.

50. The method of claim 30, further comprising providing a safety latch, the safety latch adapted to prevent accidental operation of said device.

51. The method of claim 30, further comprising positioning said at least one fluid discharging outlet port in at least one position selected from a group consisting of: (a) along a circumference along a longitudinal axis of said device so as to deliver said predetermined volume $V_{sub}$ of said at least one substance to one or more sides of said at least one body cavity; (b) at a distal-most end of said at least one open-ended nosepiece; and any combination thereof.

52. The method of claim 30, additionally comprising step of providing at least one expandable portion, adapted to inflate before activation of said device.

53. The method of claim 30, wherein said step of releasing said predetermined volume $V_{sub}$ of said at least one substance and said predetermined volume $V_{gas}$ of said pressurized gas additionally comprises mixing the same.

54. The method of claim 30, wherein at least one of the following is satisfied:
a) the diameter is in a range of 0.2-6 mm;
b) an amount rate $dV_{sub}/dt_{deliver}$ is greater than about 0.0001 ml/ms or greater than about 0.0001 mg/ms;
c) viscosity η of said at least one substance is in a range of about $1\times10^{-3}$ poise to about 1 poise;
d) said predetermined amount $V_{sub}$ of said at least one substance reaches said at least one body cavity at a velocity greater than at least 11.9 m/s;
e) said $V_{sub}$ is in a range of about 0.01-7 ml or in a range of about 0.01-1000 mg;
f) said $P_{gas}$ is in a range of about 1-10 barg;
g) the volume of said pressurized gas, when compressed, $V_{gas}$, is in a range of about 1-50 ml;
h) said predetermined period of time is less than 500 milliseconds;
i) a release time of said Vsub of said at least one substance and said $V_{gas}$ of said pressurized gas $dT_{deliver}$ is less than 500 milliseconds; or
j) any combination thereof.

55. The method of claim 30, wherein said pressurized gas exits said at least one chamber peripherally with respect to said at least one sealing member.

56. The method of claim 30, wherein said at least one valve comprises a valve that is not reconfigurable from said active configuration to said inactive configuration.

57. The method of claim 30, wherein reconfiguring at least one valve from said inactive configuration to said active configuration comprises pressing said base.

58. The method of claim 57, wherein said air chamber gate comprises at least one gate anchor and said base comprises at least one groove in communication with said least one gate anchor, such that when said at least one valve is reconfigurable from said inactive configuration to said active configuration said at least one gate anchor is pressed inwards, thereby (a) removing contact between said at least one gate anchor and said at least one groove, (b) linearly moving said air chamber gate proximally, (c) removing said at least one sealing member from its position, and (d) opening a gap between said air chamber gate and a distal-most end of said at least one chamber to allow said pressurized gas to exit said at least one chamber through said gap.

* * * * *